US008609892B2

(12) United States Patent
Conner et al.

(10) Patent No.: US 8,609,892 B2
(45) Date of Patent: Dec. 17, 2013

(54) GLUCAGON RECEPTOR ANTAGONISTS, PREPARATION AND THERAPEUTIC USES

(75) Inventors: Scott Eugene Conner, Indianapolis, IN (US); Guoxin Zhu, Carmel, IN (US); Jianke Li, Hamden, CT (US)

(73) Assignee: Eli Lilly and Company, Indianapolis, IN (US)

( * ) Notice: Subject to any disclaimer, the term of this patent is extended or adjusted under 35 U.S.C. 154(b) by 506 days.

(21) Appl. No.: 13/013,280

(22) Filed: Jan. 25, 2011

(65) Prior Publication Data

US 2011/0124648 A1     May 26, 2011

Related U.S. Application Data

(63) Continuation of application No. 12/868,773, filed on Aug. 26, 2010, now abandoned, which is a continuation of application No. 11/570,449, filed as application No. PCT/US2005/019901 on Jun. 8, 2005, now Pat. No. 7,816,557.

(60) Provisional application No. 60/579,362, filed on Jun. 14, 2004.

(51) Int. Cl.
*C07C 323/60* (2006.01)
*C07C 235/42* (2006.01)
*C07D 213/62* (2006.01)
*A61K 31/197* (2006.01)

(52) U.S. Cl.
USPC ........................................................ 562/450

(58) Field of Classification Search
None
See application file for complete search history.

(56) References Cited

U.S. PATENT DOCUMENTS

| 5,811,459 | A | 9/1998 | Breault et al. |
| 6,489,333 | B2 | 12/2002 | Pitts et al. |
| 7,696,248 | B2 | 4/2010 | Li et al. |
| 7,816,557 | B2 | 10/2010 | Conner et al. |
| 7,863,329 | B2 | 1/2011 | Li et al. |
| 2003/0065031 | A1 | 4/2003 | Madsen et al. |
| 2008/0125468 | A1 | 5/2008 | Chappel et al. |
| 2008/0300289 | A1 | 12/2008 | Chappel et al. |
| 2008/0319074 | A1 | 12/2008 | Chappel et al. |
| 2009/0156655 | A1 | 6/2009 | Conner et al. |
| 2010/0137417 | A1 | 6/2010 | Chappel et al. |

FOREIGN PATENT DOCUMENTS

| EP | 0288305 A | 10/1998 |
| WO | 03048109 A1 | 6/2003 |
| WO | 2004056763 A | 7/2004 |
| WO | 2005102067 A | 9/2006 |

OTHER PUBLICATIONS

Brown et al., Hydroxacetophenone-derived antagonists of the peptidoleukotrienes, Journal Med. Chem., 32(4), pp. 807-826, 1989.
Beasley, H.L., et al., Development of a Panel of Immunoassays for Monitory DDT, Its Metabolites, and Analogs in Food and Environmental Matrixes, Journal of Agricultural and Food Chemistry, 46(8), pp. 3339-3352; compound HAPTEN VI, 1998.
Kundu B et al., Identification of novel alpha-glucosidase inhibitors by screening libraries based on N-[4-(Benzyloxy) benzoyl] Alanine derivatives, Chemical Abstracts Service, 5(7), pp. 545-550, 2002.
Kurukulasuriya et al., "Biaryl amide glucagon receptor antagonists" Bioorganic & Medicinal Chemistry Letters, vol. 14, No. 9, pp. 2047-2050, 2004.

*Primary Examiner* — Yevegeny Valenrod
(74) *Attorney, Agent, or Firm* — Dan L. Wood

(57) ABSTRACT

The present invention discloses novel compounds of Formula I, or pharmaceutically acceptable salts thereof, which have glucagon receptor antagonist or inverse agonist activity, as well as methods for preparing such compounds. In another embodiment, the invention discloses pharmaceutical compositions comprising compounds of Formula I as well as methods of using them to treat diabetic and other glucagon related metabolic disorders, and the like.

18 Claims, No Drawings

GLUCAGON RECEPTOR ANTAGONISTS, PREPARATION AND THERAPEUTIC USES

This application is a continuation of U.S. application Ser. No. 12/868,773, filed Aug. 26, 2010, which was a continuation of U.S. application Ser. No. 11/570,449, filed Dec. 12, 2006, which was the national stage application under 35 U.S.C. 371 of International Application No. PCT/US2005/019901, filed Jun. 8, 2005, which claims the benefit of U.S. Provisional Patent Application No. 60/579,362 filed Jun. 14, 2004.

This invention relates to compounds that are antagonists or inverse agonists of the glucagon receptor, and to pharmaceutical compositions thereof, and the uses of these compounds and compositions in the treatment of the human or animal body. The present compounds show a high affinity and selective binding for the glucagon receptor, and as such are useful in the treatment of disorders responsive to the modulation of glucagon receptors, such as diabetic and other glucagon related metabolic disorders, and the like.

Glucagon is a key hormonal agent that, in cooperation with insulin, mediates homeostatic regulation of the amount of glucose in the blood. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Both glucagon and insulin are peptide hormones. Glucagon is produced in the alpha islet cells of the pancreas and insulin is produced in the beta islet cells. Glucagon exerts its action by binding to and activating its receptor, which is a member of the Glucagon-Secretin branch of the 7-transmembrane G-protein coupled receptor family. The receptor functions by activating the adenylyl cyclase second messenger system resulting in an increase in cAMP levels. The glucagon receptor, or naturally occurring variants of the receptor, may possess intrinsic constitutive activity, invitro, as well as in vivo (i.e. activity in the absence of an agonist). Compounds acting as inverse agonists can inhibit this activity.

Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, i.e. substances that inhibit or prevent constitutive, or glucagon-induced, glucagon receptor mediated responses.

Several publications disclose peptides that are stated to act as glucagon antagonists. Peptide antagonists of peptide hormones are often potent; however they are generally known not to be orally available because of degradation by physiological enzymes and poor distribution in vivo. Therefore, orally available non-peptide antagonists of peptide hormones are generally preferred.

A number of publications have appeared in recent years reporting non-peptide agents that act at the glucagon receptor. In spite of the number of treatments for diseases that involve glucagon, the current therapies suffer from one or more inadequacies, including poor or incomplete efficacy, unacceptable side effects, and contraindications for certain patient populations. Thus, there remains a need for an improved treatment using alternative or improved pharmaceutical agents that modulate glucagon receptor activity and treat the diseases that could benefit from glucagon receptor modulation. The present invention provides such a contribution to the art based on the finding that a novel class of compounds has a high affinity, selective, and potent inhibitory activity at the glucagon receptor. The present invention is distinct in the particular structures and their activities.

SUMMARY OF THE INVENTION

The present invention provides a compound structurally represented by Formula I:

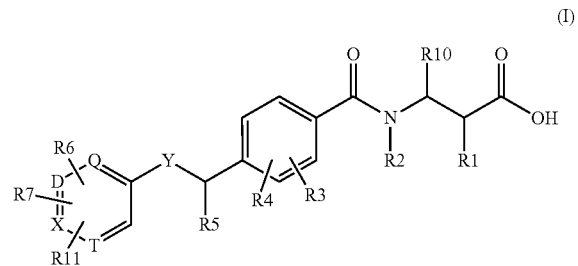

or a pharmaceutically acceptable salt thereof wherein:

Y is —O— or —S—;

Q, D, X, and T independently represent carbon (substituted with hydrogen or the optional substituents as indicated herein), or nitrogen (optionally substituted with oxygen), provided that no more than two of Q, D, X, and T are nitrogen;

R1 is —H, —OH, or -halogen;

R2 is —H or —($C_1$-$C_3$) alkyl (optionally substituted with 1 to 3 halogens);

R3 and R4 are independently
—H, -halogen, —CN, —OH, —($C_1$-$C_7$) alkoxy, —($C_1$-$C_7$) alkyl (optionally substituted with 1 to 3 halogens), or —($C_2$-$C_7$) alkenyl;

R5 is selected from the group consisting of
—H, —($C_1$-$C_{12}$) alkyl (optionally substituted with 1 to 3 halogens), —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, —($C_2$-$C_{12}$)alkenyl, —($C_3$-$C_{12}$)cycloalkenyl, -heterocycloalkyl, -aryl-($C_2$-$C_{10}$)alkenyl, -heteroaryl-($C_2$-$C_{10}$)alkenyl, —($C_2$-$C_{12}$) alkynyl, —($C_3$-$C_{12}$)cycloalkynyl, -aryl-($C_2$-$C_{12}$)alkynyl, and -heteroaryl-($C_2$-$C_{12}$)alkynyl, and wherein —($C_1$-$C_{12}$)alkyl, —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, -heterocycloalkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —(C$_2$-C$_{12}$)alkynyl, —(C$_3$-C$_{12}$) cycloalkynyl, -aryl-(C$_2$-C$_{12}$)alkynyl, -heteroaryl-(C$_2$-C$_{12}$)alkynyl, are each optionally substituted with from one to three substituents each independently selected from the group consisting of -hydrogen, -hydroxy, -cyano, -nitro, -halo, -oxo, —(C$_1$-C$_7$)alkyl (optionally substituted with 1 to 3 halogens), —(C$_1$-C$_7$)alkyl-COOR12, —(C$_1$-C$_7$)alkoxy, —(C$_3$-C$_7$)cycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R6 and R7 are independently at each occurrence selected from the group consisting of
—H, -halogen, -hydroxy, —CN, —(C$_1$-C$_7$) alkoxy, —(C$_2$-C$_7$)alkenyl, —(C$_1$-C$_{10}$)alkyl (optionally substituted with 1 to 3 halogens), —(C$_3$-C$_{12}$)cycloalkyl, tert-butoxyiminomethyl, 1,3-dioxan-2-yl, hydroxymethyl, formyl, hydroxyiminomethyl, morpholino-4-yl-methyl, 4-methylpentyloxy, and pentyloxy;

provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;

wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence selected from the group consisting of
-hydrogen, -hydroxy, —CN, -nitro, -halo, —(C$_1$-C$_7$)alkyl (optionally substituted with 1 to 3 halogens), —(C$_1$-C$_7$) alkoxy, —(C$_3$-C$_7$)cycloalkyl, -aryl, -aryl-(C$_1$-C$_7$)alkyl, -heteroaryl, -heteroaryl-(C$_1$-C$_7$)alkyl, -aryloxy, —C(O)R12, —C(O)OR12, —OC(O)R12, —OS(O)$_2$R12, —N(R12)$_2$, —NR12C(O)R12, —NR12SO$_2$R12, —SR12, —S(O)R12, —S(O)$_2$R12, —O(C$_2$-C$_7$)alkenyl, and —S(O)$_2$N(R12)$_2$; and wherein —(C$_1$-C$_7$)alkyl, —(C$_1$-C$_7$)alkoxy, —(C$_3$-C$_7$)cycloalkyl, -aryl, -aryl-(C$_1$-C$_7$)alkyl, -heteroaryl, -heteroaryl-(C$_1$-C$_7$)alkyl, -aryloxy, and —O(C$_2$-C$_7$)alkenyl are each optionally substituted with from one to three substituents independently selected from the group consisting of -hydrogen, -hydroxy, -cyano, -nitro, -halo, -oxo, —(C$_1$-C$_7$)alkyl, —(C$_1$-C$_7$)alkyl-C(O)OR12, —(C$_1$-C$_7$)alkoxyl, —(C$_3$-C$_7$)cycloalkyl, -heterocycloalkyl, —C(O)R12, —C(O)OR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R10 is selected from the group consisting of
—H, halogen, —(C$_1$-C$_{12}$)alkyl (optionally substituted with 1 to 3 halogens), -cycloalkyl, -aryl, -aryl-(C$_1$-C$_7$)alkyl, -heteroaryl, -heteroaryl —(C$_1$-C$_7$)alkyl, —(C$_2$-C$_{12}$)alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$) alkynyl, —(C$_3$-C$_{12}$)cycloalkynyl, -aryl-(C$_2$-C$_{12}$) alkynyl, and -heteroaryl-(C$_2$-C$_{12}$)alkynyl;

R11 is independently at each occurrence selected from the group consisting of
—H, -halogen,

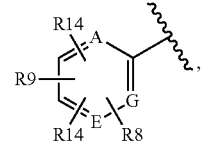

wherein the zig-zag mark shows the point of attachment to the parent molecule, wherein A, G, and E independently represent carbon (substituted with hydrogen or the optional substituents as indicated herein) or nitrogen, provided that no more than two of A, G, and E are nitrogen;
provided however that wherein A is nitrogen, then R8, R9, and R14 are not attached to A, and provided that wherein G is nitrogen, then R8, R9, and R14 are not attached to G, and provided that wherein E is nitrogen, then R8, R9, and R14 are not attached to E,

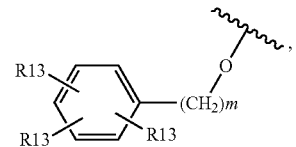

wherein the zig-zag mark shows the point of attachment to the parent molecule, wherein m is an integer of 0, 1, 2, or 3, and when m is 0, then (CH$_2$)$_m$ is a bond, and

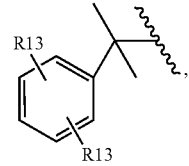

wherein the zig-zag mark shows the point of attachment to the parent molecule,
provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;

R12 is independently at each occurrence selected from the group consisting of
-hydrogen, —(C$_1$-C$_7$) alkyl (optionally substituted with 1 to 3 halogens), and -aryl;

R13 is independently at each occurrence selected from the group consisting of
-hydrogen, -halogen, —(C$_1$-C$_7$) alkyl (optionally substituted with 1 to 3 halogens), phenyl, and —(C$_2$-C$_7$)alkenyl; and R14 is independently at each occurrence
—H, halogen, or —(C$_1$-C$_7$) alkyl (optionally substituted with 1 to 3 halogens).

The present invention provides compounds that are useful as glucagon receptor antagonists or inverse agonists. The present invention further provides compounds that are selective antagonists or inverse agonists of the glucagon receptor over the GLP-1 receptor. The present invention further provides a pharmaceutical composition which comprises a compound of Formula I, or a pharmaceutical salt thereof, and a pharmaceutically acceptable carrier, diluent, or excipient.

Due to their interaction with the glucagon receptor, the present compounds are useful in the treatment of a wide range of conditions and disorders in which an interaction with the glucagon receptor is beneficial. These disorders and conditions are defined herein as "diabetic and other glucagon related metabolic disorders". One of skill in the art is able to identify "diabetic and other glucagon related metabolic disorders" by the involvement of glucagon receptor mediated signaling either in the pathophysiology of the disorder, or in the homeostatic response to the disorder. Thus, the compounds may find use for example to prevent, treat, or alleviate, diseases or conditions or associated symptoms or sequelae, of the endocrinological system, the central nervous system, the peripheral nervous system, the cardiovascular system, the pulmonary system, and the gastrointestinal system, while reducing and or eliminating one or more of the unwanted side effects associated with the current treatments. "Diabetic and other glucagon related metabolic disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrythmia, premature death, anti-apoptosis, wound healing, impaired glucose tolerance (IGT), insulin resistance syndromes, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting the glucagon receptor; for use in inhibiting a glucagon receptor mediated cellular response in a mammal; for use in reducing the glycemic level in a mammal; for use in treating a disease arising from excessive glucagon; for use in treating diabetic and other glucagon related metabolic disorders in a mammal; and for use in treating diabetes, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting the glucagon receptor; for the manufacture of a medicament for inhibiting a glucagon receptor mediated cellular response in a mammal; for the manufacture of a medicament for reducing the glycemic level in a mammal; for the manufacture of a medicament for treating a disease arising from excessive glucagon; for the manufacture of a medicament for treating diabetic and other glucagon related metabolic disorders in a mammal; and for the manufacture of a medicament for preventing or treating diabetes, obesity, hyperglycemia, atherosclerosis, ischemic heart disease, stroke, neuropathy, and improper wound healing.

The present invention further provides a method of treating conditions resulting from excessive glucagon in a mammal; a method of inhibiting the glucagon receptor in a mammal; a method of inhibiting a glucagon receptor mediated cellular response in a mammal; a method of reducing the glycemic level in a mammal; a method of treating diabetic and other glucagon related metabolic disorders in a mammal; a method of preventing or treating diabetes, obesity, hyperglycemia, atherosclerosis, ischemic heart disease, stroke, neuropathy, and improper wound healing; said methods comprising administering to a mammal in need of such treatment a glucagon receptor-inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting the glucagon receptor; adapted for use in inhibiting glucagon receptor mediated cellular responses; adapted for use in reducing the glycemic level in a mammal; adapted for use in treating diabetic and other glucagon related metabolic disorders in a mammal; and adapted for use in preventing or treating diabetes, obesity, hyperglycemia, atherosclerosis, ischemic heart disease, stroke, neuropathy, and wound healing.

The compound or salt of the present invention further provides a diagnostic agent for identifying patients having a defect in the glucagon receptor, as a therapy to increase gastric acid secretions, and to reverse intestinal hypomobility due to glucagon administration. The invention also provides a method for the treatment of disorders or diseases, wherein a glucagon antagonistic action is beneficial, the method comprising administering to a subject in need thereof an effective amount of a compound according to the invention. In another embodiment of the invention, the present compounds are used for the preparation of a medicament for the treatment of any glucagon-mediated conditions and diseases. In another embodiment of the invention, the present compounds are used for the preparation of a medicament for the treatment of hyperglycemia. In yet another embodiment of the invention, the present compounds are used for the preparation of a medicament for lowering blood glucose in a mammal. The present compounds are effective in lowering the blood glucose, both in the fasting and the postprandial stage. In still another embodiment of the invention, the present compounds are used for the preparation of a pharmaceutical composition for the treatment of IGT. In a further embodiment of the invention, the present compounds are used for the preparation of a pharmaceutical composition for the treatment of type 2 diabetes. In yet a further embodiment of the invention the present compounds are used for the preparation of a pharmaceutical composition for the delaying or prevention of the progression from IGT to type 2 diabetes. In yet another embodiment of the invention the present compounds are used for the preparation of a pharmaceutical composition for the delaying or prevention of the progression from non-insulin requiring type 2 diabetes to insulin requiring type 2 diabetes. In a further embodiment of the invention the present compounds are used for the preparation of a pharmaceutical composition for the treatment of type 1 diabetes. Such treatment is normally accompanied by insulin therapy. In yet a further embodiment of the invention the present compounds are used for the preparation of a pharmaceutical composition for the treatment of obesity. In still a further embodiment of the invention the present compounds are used for the preparation of a pharmaceutical composition for the treatment of disorders of the lipid metabolism. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise.

DETAILED DESCRIPTION OF THE INVENTION

General terms used in the description of compounds, compositions, and methods herein described, bear their usual meanings. Throughout the instant application, the following terms have the indicated meanings:

"GLP-1" means glucagon-like peptide 1. The term "glucagon receptor" means one or more receptors that interact specifically with glucagon to result in a biological signal. The term "GLP-1 receptor" means one or more receptors that interact specifically with glucagon-like peptide 1 to result in a biological signal.

The term "glucagon receptor antagonist" means a compound of the present invention with the ability to block cAMP production in response glucagon. The term "glucagon receptor inverse agonist" means a compound of the present invention with the ability to inhibit the constitutive activity of glucagon receptor. The term "selective" antagonist or inverse agonist means a compound having greater affinity for the glucagon receptor as compared to the affinity for the GLP-1 receptor.

In the general formulae of the present document, the general chemical terms have their usual meanings. For example;

"Halogen" or "halo" means fluoro, chloro, bromo and iodo.

The term "alkyl," unless otherwise indicated, refers to those alkyl groups of a designated number of carbon atoms of either a straight or branched saturated configuration. "$(C_1-C_3)$ alkyl" are one to three carbon atoms, such as methyl, ethyl, propyl, n-propyl, isopropyl, and the like and branched or isomeric forms thereof, and optionally may be substituted with one to three halogens or a designated number of substituents as set forth in the embodiments recited herein, "$(C_1-C_7)$ alkyl" are one to seven carbon atoms such as methyl, ethyl, propyl, n-propyl, isopropyl, n-butyl, isobutyl, sec-butyl and tert-butyl, pentyl, isopentyl, hexyl, heptyl, and the like, and branched or isomeric forms thereof, and optionally may be substituted with one to three halogens or a designated number of substituents as set forth in the embodiments recited herein, and "$(C_1-C_{10})$ alkyl" are one to ten carbon atoms, such as methyl, ethyl, propyl, butyl, pentyl, hexyl, heptyl, nonyl, decyl, and the like, and branched or isomeric forms thereof, and optionally may be substituted with one to three halogens or a designated number of substituents as set forth in the embodiments recited herein. "$(C_1-C_{12})$ alkyl" are one to twelve carbon atoms, such as methyl, ethyl, propyl, butyl, pentyl, hexyl, heptyl, nonyl, decyl, and the like, and branched or isomeric forms thereof, and optionally may be substituted with one to three halogens or a designated number of substituents as set forth in the embodiments recited herein.

The term "$(C_3-C_{12})$ cycloalkyl" refers to a saturated or partially saturated carbocycle containing one or more rings of from 3 to 12 carbon atoms, typically 3 to 7 carbon atoms optionally substituted with up to three halogens. Examples of $(C_3-C_{12})$ cycloalkyl include but are not limited to cyclopropyl, cyclobutyl, cyclopentyl, cyclohexyl and cycloheptyl, and the like. "$(C_3-C_7)$ cycloalkyl" means a ring with three to seven carbon atoms such as cyclopropyl, cyclobutyl, cyclopentyl and cyclohexyl, cycloheptyl, and the like, optionally substituted with up to three halogens.

The term "$(C_1-C_7)$ alkoxy" represents an alkyl group of one to seven carbon atoms attached through an oxygen bridge, such as methoxy, ethoxy, propoxy, isopropoxy, butoxy, tert-butoxy, pentoxy, and the like, and may be optionally substituted with three halogens or a designated number of substituents as set forth in the embodiments recited herein.

The terms "$(C_2-C_7)$ alkenyl", "$(C_2-C_{10})$ alkenyl", "$(C_2-C_{10})$ alkylenyl", "$(C_2-C_{12})$ alkenyl", or "$(C_2-C_{12})$ alkylenyl" means hydrocarbon chains of the indicated number of carbon atoms of either a straight or branched configuration having at least one carbon-carbon double bond which may occur at any point along the chain, such as ethenyl, propenyl, butenyl, pentenyl, vinyl, alkyl, 2-butenyl and the like, and may be optionally substituted with one to three halogens or a designated number of substituents as set forth in the embodiments recited herein.

The term "$(C_3-C_{12})$ cycloalkenyl" refers to a partially saturated carbocycle containing one or more rings of from 3 to 12 carbon atoms, typically 3 to 7 carbon atoms optionally substituted with up to three halogens.

The term "$(C_2-C_{12})$ alkynyl" means a hydrocarbon chain of two to twelve carbon atoms of either a straight or branched configuration and having at least one carbon-carbon triple bond, which may occur at any point along the chain. Example of alkynyl is acetylene. Alkynyl as defined above may be optionally substituted with up to three halogens or the designated number of substituents as set forth in the embodiments recited herein.

The term "$(C_3-C_{12})$ cycloalkynyl" refers to a carbocycle containing one or more rings of from 3 to 12 carbon atoms, typically 3 to 7 carbon atoms, having at least one carbon-carbon triple bond which may occur at any point along the chain or ring, optionally substituted with up to three halogens. Cycloalkynyl as defined above may be optionally substituted with the designated number of substituents as set forth in the embodiments recited herein.

The term "aryl" includes carbocyclic aromatic ring systems (e.g. phenyl), fused polycyclic aromatic ring systems (e.g. naphthyl and anthracenyl), and aromatic ring systems fused to carbocyclic non-aromatic ring systems (e.g., 1,2,3,4-tetrahydronaphthyl). "Aryl" as defined above may be optionally substituted with a designated number of substituents as set forth in the embodiments recited herein.

The term "aryloxy" refers to an aryl group which is linked to the parent molecule through an oxygen bridge.

The term "heteroaryl" group, as used herein, is an aryl ring system having at least one heteroatom such as nitrogen, sulfur, or oxygen, and includes monocyclic, bicyclic, or tricyclic aromatic rings of 5 to 14 carbon atoms containing one or more heteroatoms selected from the group consisting of O, N, and S. The "heteroaryl" as defined above may be optionally substituted with a designated number of substituents as set forth in the embodiments recited herein. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline, and the like.

The term "arylalkyl" refers to an aryl group which is linked to the parent molecule through an alkyl moiety, and "arylalkyl" may be further optionally substituted with a designated number of substituents as set forth in the embodiments recited herein.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N, or S.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The term "a glucagon receptor mediated cellular response" includes various responses by mammalian cells to glucagon stimulation or glucagon receptor activity. For example "glucagon receptor mediated cellular responses," include but are not limited to, release of glucose from liver, or other cells, in response to glucagon stimulation or glucagon receptor activity. One of ordinary skill in the art can readily identify other cellular responses mediated by glucagon receptor activity, for example by observing a change in the responsive cellular endpoint after contacting the cell with an effective dose of glucagon.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

In one embodiment, the present invention provides compounds of Formula I as described in detail herein. While all of the compounds of the present invention are useful, certain of the compounds are particularly interesting and are preferred. The following listing sets out several groups of preferred compounds. It will be understood that each of the listings may be combined with other listings to create additional groups of preferred embodiments.
1. wherein Y is —O—,
2. wherein Y is —S—,
3. wherein D, Q, X, and T are carbon (substituted with hydrogen or the optional substituents as indicated herein),
4. wherein R1, R2, R3, R4 and R10 are hydrogen,
5. wherein X is carbon and R11 is attached to X,
6. wherein D is carbon and R11 is attached to D,
7. wherein X is carbon and R11 is attached to X and R11 is

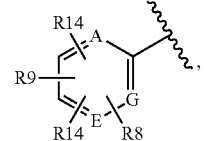

wherein the zig-zag mark shows the point of attachment to the parent molecule, and wherein A, G, and E independently represent carbon (substituted with hydrogen or the optional substituents as indicated herein) or nitrogen, provided that no more than two of A, G, and E are nitrogen;
8. wherein X is carbon and R11 is attached to X and R11 is

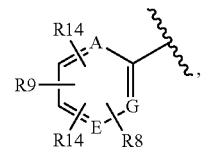

wherein the zig-zag mark shows the point of attachment to the parent molecule, and wherein A, G, and E independently represent carbon (substituted with hydrogen or the optional substituents as indicated herein) or nitrogen, provided that no more than two of A, G, and E are nitrogen, and R8 and R9 are independently at each occurrence selected from the group consisting of -hydrogen, -hydroxy, —CN, -nitro, -halo, —($C_1$-$C_7$)alkyl (optionally substituted with 1 to 3 halogens), —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —C(O)OR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$, 9. wherein X is carbon and R11 is attached to X and R11 is

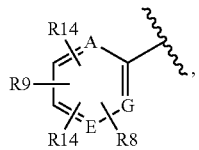

wherein the zig-zag mark shows the point of attachment to the parent molecule, and wherein A, G, and E independently represent carbon (substituted with hydrogen or the optional substituents as indicated herein) or nitrogen, provided that no more than two of A, G, and E are nitrogen, and R8 and R9 are independently at each occurrence selected from the group consisting of -hydrogen, -hydroxy, —CN, -nitro, -halo, —($C_1$-$C_7$)alkyl (optionally substituted with 1 to 3 halogens), —($C_1$-$C_7$)alkoxy, and —($C_3$-$C_7$)cycloalkyl, 10. wherein X is carbon and R11 is attached to X and R11 is

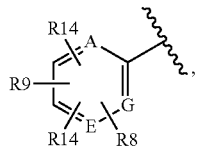

wherein the zig-zag mark shows the point of attachment to the parent molecule, and wherein A, G, and E are carbon (substituted with hydrogen or the optional substituents as indicated herein), 11. wherein X is carbon and R11 is attached to X and R11 is

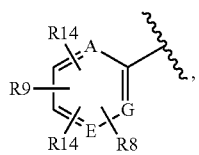

wherein the zig-zag mark shows the point of attachment to the parent molecule, and wherein A, G, and E are carbon (substituted with hydrogen or the optional substituents as indicated herein), and R8 and R9 are independently at each occurrence selected from the group consisting of -hydrogen, -hydroxy, —CN, -nitro, -halo, —($C_1$-$C_7$)alkyl (optionally substituted with 1 to 3 halogens), —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —C(O)OR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$, 12. wherein X is carbon and R11 is attached to X and R11 is

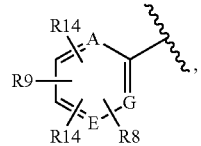

wherein the zig-zag mark shows the point of attachment to the parent molecule, and wherein A, G, and E are carbon (substituted with hydrogen or the optional substituents as indicated herein), and R8 and R9 are independently at each occurrence selected from the group consisting of -hydrogen, -hydroxy, —CN, -nitro, -halo, —($C_1$-$C_7$)alkyl (optionally substituted with 1 to 3 halogens), —($C_1$-$C_7$)alkoxy, and —($C_3$-$C_7$)cycloalkyl, 13. wherein one of D, X, Q or T is nitrogen,
14. wherein D is nitrogen,
15. wherein X is nitrogen,
16. wherein Q is nitrogen,
17. wherein T is nitrogen,
18. wherein two of D, X, Q and T are nitrogen,
19. wherein D and T are nitrogen,
20. wherein Q and X are nitrogen,
21. wherein R1 is hydrogen,
22. wherein R1 is —OH,
23. wherein R1 is halogen,
24. wherein R2 is hydrogen,
25. wherein R2 is —($C_1$-$C_3$) alkyl (optionally substituted with 1 to 3 halogens),
26. wherein R3 is hydrogen,
27. wherein R3 is halogen,
28. wherein R4 is hydrogen,
29. wherein R4 is halogen,
30. wherein R3 is selected from the group consisting of —($C_1$-$C_7$) alkoxy, —($C_1$-$C_7$) alkyl (optionally substituted with 1 to 3 halogens), and —($C_2$-$C_7$) alkenyl,
31. wherein R4 is selected from the group consisting of —($C_1$-$C_7$) alkoxy, —($C_1$-$C_7$) alkyl (optionally substituted with 1 to 3 halogens), and —($C_2$-$C_7$) alkenyl,
32. R5 is selected from the group consisting of
    —H, —($C_1$-$C_{12}$) alkyl (optionally substituted with 1 to 3 halogens), —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, —($C_2$-$C_{12}$) alkenyl, —($C_3$-$C_{12}$)cycloalkenyl, -heterocycloalkyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, and -heteroaryl-($C_2$-$C_{12}$)alkynyl,
33. R5 is selected from the group consisting of
    —H, —($C_1$-$C_{12}$) alkyl (optionally substituted with 1 to 3 halogens), —($C_3$-$C_{12}$)cycloalkyl, -phenyl, -phenyl-phenyl-($C_1$-$C_{12}$)alkyl, —($C_2$-$C_{12}$)alkenyl, —($C_3$-$C_{12}$)cycloalkenyl, -heterocycloalkyl, —($C_2$-$C_{12}$) alkynyl, and —($C_3$-$C_{12}$)cycloalkynyl,
34. R5 is selected from the group consisting of —($C_1$-$C_{12}$) alkyl (optionally substituted with 1 to 3 halogens), and —($C_3$-$C_{12}$)cycloalkyl,
35. wherein R6 and R7 are methyl,
36. wherein R6 and R7 form a six membered ring with the atoms to which they are attached, and the ring so formed may optionally contain up to two oxygens, and further the ring so formed may optionally be substituted with up to four halogens, 37. wherein R8 is attached in the para position and is tertbutyl or trifloromethyl, 38. R10 is selected from the group consisting of —H, halogen, —(C$_1$-C$_{12}$)alkyl (optionally substituted with 1 to 3 halogens), —(C$_3$-C$_{12}$)cycloalkyl, —(C$_2$-C$_{12}$)alkenyl, —(C$_3$-C$_{12}$)cycloalkenyl, —(C$_2$-C$_{12}$)alkynyl, —(C$_3$-C$_{12}$)cycloalkynyl, -aryl-(C$_2$-C$_{12}$)alkynyl, and -heteroaryl-(C$_2$-C$_{12}$)alkynyl, 39. R10 is selected from the group consisting of —H, halogen, or —(C$_1$-C$_{12}$)alkyl (optionally substituted with 1 to 3 halogens, Another embodiment is a compound of Formula I or a pharmaceutically acceptable salt thereof wherein:

Y is —O— or —S—;

Q, D, X, and T independently represent carbon or nitrogen, provided that no more than two of Q, D, X, and T are nitrogen;

R1 is —H, —OH, or -halogen;

R2 is —H or —(C$_1$-C$_3$) alkyl;

R3 and R4 are independently at each occurrence selected from the group consisting of
—H, -halogen, —CN, —OH, —(C$_1$-C$_7$) alkoxy, —(C$_1$-C$_7$) alkyl, —(C$_2$-C$_7$) alkenyl;

R5 is selected from the group consisting of
—H, —(C$_1$-C$_{12}$) alkyl, —(C$_3$-C$_{12}$)cycloalkyl, -phenyl, -phenyl-phenyl-(C$_1$-C$_{12}$)alkyl, -aryl, -aryl-(C$_1$-C$_{12}$) alkyl, -heteroaryl, -heteroaryl-(C$_1$-C$_{12}$)alkyl, —(C$_2$-C$_{12}$)alkenyl, —(C$_3$-C$_{12}$)cycloalkenyl, -heterocycloalkyl, -aryl-(C$_2$-C$_{10}$)alkenyl, -heteroaryl-(C$_2$-C$_{10}$)alkenyl, —(C$_2$-C$_{12}$)alkynyl, —(C$_3$-C$_{12}$)cycloalkynyl, -aryl-(C$_2$-C$_{12}$)alkynyl, and -heteroaryl-(C$_2$-C$_{12}$)alkynyl, and wherein —(C$_1$-C$_{12}$)alkyl, —(C$_3$-C$_{12}$)cycloalkyl, -phenyl, -phenyl-phenyl-(C$_1$-C$_{12}$)alkyl, -aryl, -aryl-(C$_1$-C$_{12}$)alkyl, -heteroaryl, -heteroaryl-(C$_1$-C$_{12}$)alkyl, -heterocycloalkyl, —(C$_2$-C$_{12}$)alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$)alkynyl, —(C$_3$-C$_{12}$) cycloalkynyl, -aryl-(C$_2$-C$_{12}$)alkynyl, and -heteroaryl-(C$_2$-C$_{12}$)alkynyl, are each optionally substituted with from one to three substituents each independently selected from the group consisting of -hydrogen, -hydroxy, -cyano, -nitro, -halo, -oxo, —(C$_1$-C$_7$)alkyl, —(C$_1$-C$_7$)alkyl-COOR12, —(C$_1$-C$_7$)alkoxy, —(C$_3$-C$_7$)cycloalkyl, -aryloxy, -aryl, -aryl-(C$_1$-C$_7$)alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R6 and R7 are independently at each occurrence selected from the group consisting of
—H, -halogen, -hydroxy, —CN, —(C$_1$-C$_7$) alkoxy, —(C$_2$-C$_7$)alkenyl, and —(C$_1$-C$_7$)alkyl, provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;

wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence selected from the group consisting of
-hydrogen, -hydroxy, —CN, -nitro, -halo, —(C$_1$-C$_7$)alkyl, —(C$_1$-C$_7$)alkoxy, —(C$_3$-C$_7$)cycloalkyl, -aryl, -aryl-(C$_1$-C$_7$)alkyl, -heteroaryl, -heteroaryl-(C$_1$-C$_7$)alkyl, -aryloxy, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$; and wherein —(C$_1$-C$_7$)alkyl, —(C$_1$-C$_7$)alkoxy, —(C$_3$-C$_7$)cycloalkyl, -aryl, -aryl-(C$_1$-C$_7$)alkyl, -heteroaryl, -heteroaryl-(C$_1$-C$_7$)alkyl, -aryloxy, are each optionally substituted with from one to three substituents independently selected from the group consisting of -hydrogen, -hydroxy, -cyano, -nitro, -halo, -oxo, —(C$_1$-C$_7$)alkyl, —(C$_1$-C$_7$)alkyl-COOR12, —(C$_1$-C$_7$)alkoxyl, —(C$_3$-C$_7$)cycloalkyl, -aryloxy, -aryl, -aryl-(C$_1$-C$_7$)alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R10 is selected from the group consisting of
—H, —(C$_1$-C$_{12}$)alkyl, -cycloalkyl, -aryl, -aryl-(C$_1$-C$_7$) alkyl, -heteroaryl, -heteroaryl-(C$_1$-C$_7$)alkyl, —(C$_2$-C$_{12}$) alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$)alkynyl, —(C$_3$-C$_{12}$)cycloalkynyl, -aryl-(C$_2$-C$_{12}$)alkynyl, and -heteroaryl-(C$_2$-C$_{12}$)alkynyl, and wherein —(C$_1$-C$_{12}$) alkyl, -cycloalkyl, -aryl, -aryl-(C$_1$-C$_7$)alkyl, -heteroaryl, -heteroaryl —(C$_1$-C$_7$)alkyl, —(C$_2$-C$_{12}$)alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$)alkynyl, —(C$_3$-C$_{12}$)cycloalkynyl, -aryl-(C$_2$-C$_{12}$)alkynyl, and -heteroaryl-(C$_2$-C$_{12}$)alkynyl, are each optionally substituted with from one to three substituents each independently selected from the group consisting of -hydrogen, -hydroxy, -cyano, -nitro, -halo, -oxo, —(C$_1$-C$_7$)alkyl, —(C$_1$-C$_7$) alkyl-COOR12, —(C$_1$-C$_7$)alkoxyl, —(C$_3$-C$_7$)cycloalkyl, -aryloxy, -aryl, -aryl-C$_1$-C$_7$ alkyl, -heteroaryl, -heterocycloalkyl, —C(O)R12, —COOR12, —OC(O) R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R11 is independently at each occurrence selected from the group consisting of
—H,

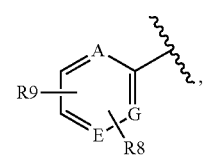

wherein the zig-zag mark shows the point of attachment to the parent molecule, wherein A, G, and E independently represent carbon or nitrogen, provided that no more than two of A, G, and E are nitrogen;

provided however that wherein A is nitrogen, then R8 or R9 are not attached to A, and provided that wherein G is nitrogen, then R8 or R9 are not attached to G, and provided that wherein E is nitrogen, then R8 or R9 are not attached to E;

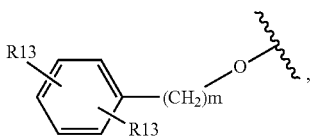

wherein the zig-zag mark shows the point of attachment to the parent molecule, wherein m is an integer of 0, 1, 2, or 3, and when m is 0 m is a bond,
provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;

R12 is independently at each occurrence selected from the group consisting of
-hydrogen, —($C_1$-$C_7$) alkyl, and -aryl, R13 is independently at each occurrence selected from the group consisting of -hydrogen, -halogen, —($C_1$-$C_7$) alkyl, and —($C_2$-$C_7$)alkenyl.

Another preferred embodiment is a compound of Formula I, or a pharmaceutically acceptable salt thereof, wherein:
Y is —O— or —S—;
Q, D, X, and T independently represent carbon (substituted with hydrogen or the optional substituents as indicated herein) or nitrogen, provided that no more than two of Q, D, X, and T are nitrogen;
R1 is —H, —OH, or -halogen;
R2 is —H or —($C_1$-$C_3$) alkyl (optionally substituted with 1 to 3 halogens);
R3 and R4 are independently
—H, -halogen, —CN, —($C_1$-$C_7$) alkoxy, —($C_1$-$C_7$) alkyl (optionally substituted with 1 to 3 halogens), or —($C_2$-$C_7$) alkenyl;
R5 is selected from the group consisting of
—($C_1$-$C_{12}$) alkyl (optionally substituted with 1 to 3 halogens), —($C_3$-$C_{12}$)cycloalkyl, -phenyl, -phenyl-phenyl-($C_1$-$C_{12}$)alkyl, —($C_2$-$C_{12}$)alkenyl, —($C_3$-$C_{12}$)cycloalkenyl, -heterocycloalkyl, —($C_2$-$C_{12}$) alkynyl, and —($C_3$-$C_{12}$)cycloalkynyl, and wherein —($C_1$-$C_{12}$)alkyl, —($C_3$-$C_{12}$)cycloalkyl, -phenyl, -phenyl-phenyl-($C_1$-$C_{12}$)alkyl, -heterocycloalkyl, —($C_2$-$C_{12}$)alkenyl, —($C_3$-$C_{12}$)cycloalkenyl, —($C_2$-$C_{12}$)alkynyl, and —($C_3$-$C_{12}$)cycloalkynyl, are each optionally substituted with from one to three substituents each independently selected from the group consisting of -hydrogen, -hydroxy, -cyano, -nitro, -halo, -oxo, —($C_1$-$C_7$)alkyl (optionally substituted with 1 to 3 halogens);

R6 and R7 are independently at each occurrence selected from the group consisting of
—H, -halogen, -hydroxy, —CN, —($C_1$-$C_7$) alkoxy, —($C_2$-$C_7$)alkenyl, —($C_1$-$C_{10}$)alkyl (optionally substituted with 1 to 3 halogens), —($C_3$-$C_{12}$)cycloalkyl, tert-butoxyiminomethyl, 1,3-dioxan-2-yl, hydroxymethyl, formyl, hydroxyiminomethyl, morphylino-4-yl-methyl, 4-methylpentyloxy, and pentyloxy;
provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;

wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence selected from the group consisting of
-hydrogen, -hydroxy, —CN, -nitro, -halo, —($C_1$-$C_7$) alkyl(optionally substituted with 1 to 3 halogens), —($C_1$-$C_7$)alkoxy, —($C_3$-$C_7$)cycloalkyl, —C(O)R12, —C(O)OR12, —OC(O)R12, —OS(O)$_2$R12, —N(R12)$_2$, —NR12C(O) R12, —NR12SO$_2$R12, —SR12, —S(O)R12, —S(O)$_2$R12, —O($C_2$-$C_7$)alkenyl, and —S(O)$_2$N(R12)$_2$; and wherein —($C_1$-$C_7$) alkyl, —($C_1$-$C_7$)alkoxy, —($C_3$-$C_7$)cycloalkyl, and —O($C_2$-$C_7$)alkenyl are each optionally substituted with from one to three substituents independently selected from the group consisting of -hydrogen, -hydroxy, -cyano, -nitro, -halo, -oxo, and —($C_1$-$C_7$) alkyl;

R10 is selected from the group consisting of
—H, halogen, and —($C_1$-$C_{12}$)alkyl (optionally substituted with 1 to 3 halogens);

R11 is independently at each occurrence selected from the group consisting of
—H, -halogen,

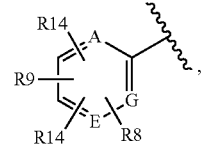

wherein the zig-zag mark shows the point of attachment to the parent molecule, wherein A, G, and E independently represent carbon (substituted with hydrogen or the optional substituents as indicated herein) or nitrogen, provided that no more than two of A, G, and E are nitrogen;
provided however that wherein A is nitrogen, then R8, R9, and R14 are not attached to A, and provided that wherein G is nitrogen, then R8, R9, and R14 are not attached to G, and provided that wherein E is nitrogen, then R8, R9, and R14 are not attached to E,

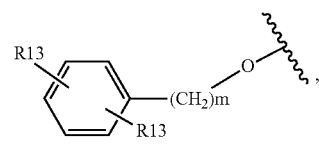

wherein the zig-zag mark shows the point of attachment to the parent molecule, wherein m is an integer of 0, 1, 2, or 3, and when m is 0 then (CH$_2$)$_m$ is a bond, and

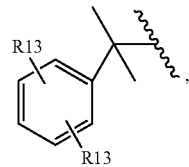

wherein the zig-zag mark shows the point of attachment to the parent molecule, provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;

R12 is independently at each occurrence selected from the group consisting of

-hydrogen, and —($C_1$-$C_7$) alkyl (optionally substituted with 1 to 3 halogens);

R13 is independently at each occurrence selected from the group consisting of

-hydrogen, -halogen, —($C_1$-$C_7$) alkyl (optionally substituted with 1 to 3 halogens), phenyl, and —($C_2$-$C_7$) alkenyl; and R14 is independently at each occurrence —H, halogen, or —($C_1$-$C_7$) alkyl (optionally substituted with 1 to 3 halogens).

Another preferred embodiment is a compound of Formula I, or a pharmaceutically acceptable salt thereof, wherein:

Y is —O— or —S—;

Q, D, X, and T independently represent carbon (substituted with hydrogen or the optional substituents as indicated herein);

R1 is —H, —OH, or -halogen;

R2 is —H;

R3 and R4 are independently —H, -halogen, or —($C_1$-$C_7$) alkyl (optionally substituted with 1 to 3 halogens);

R5 is selected from the group consisting of

—($C_1$-$C_{12}$) alkyl (optionally substituted with 1 to 3 halogens), and —($C_3$-$C_{12}$)cycloalkyl (optionally substituted with 1 to 3 halogens);

R6 and R7 are independently at each occurrence selected from the group consisting of —H, -halogen, -hydroxy, —CN, —($C_1$-$C_7$) alkoxy, —($C_2$-$C_7$)alkenyl, —($C_1$-$C_{10}$)alkyl (optionally substituted with 1 to 3 halogens), —($C_3$-$C_{12}$)cycloalkyl, tert-butoxyiminomethyl, 1,3-dioxan-2-yl, hydroxymethyl, formyl, hydroxyiminomethyl, morphylino-4-yl-methyl, 4-methylpentyloxy, and pentyloxy;

provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;

R8 and R9 are independently at each occurrence selected from the group consisting of -hydrogen, -halogen, —($C_1$-$C_7$)alkyl (optionally substituted with 1 to 3 halogens), —($C_1$-$C_7$)alkoxy, —($C_3$-$C_7$) cycloalkyl, —C(O)R12, —COOR12, —OC(O)R12, —OS(O)$_2$R12, —SR12, —S(O)R12, —S(O)$_2$R12, and —O($C_2$-$C_7$)alkenyl;

R10 is —H;

R11 is independently at each occurrence selected from the group consisting of

—H, -halogen, and

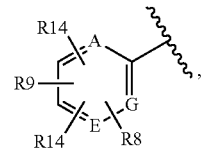

wherein the zig-zag mark shows the point of attachment to the parent molecule, wherein A, G, and E independently represent carbon (substituted with hydrogen or the optional substituents as indicated herein), provided however that wherein A is nitrogen, then R8, R9, and R14 are not attached to A, and provided that wherein G is nitrogen, then R8, R9, and R14 are not attached to G, and provided that wherein E is nitrogen, then R8, R9, and R14 are not attached to E;

R12 is independently at each occurrence selected from the group consisting of

-hydrogen, and —($C_1$-$C_7$) alkyl (optionally substituted with 1 to 3 halogens);

R13 is independently at each occurrence selected from the group consisting of

-hydrogen, -halogen, —($C_1$-$C_7$) alkyl (optionally substituted with 1 to 3 halogens), and —($C_2$-$C_7$)alkenyl; and R14 is independently at each occurrence —H, halogen, or —($C_1$-$C_7$) alkyl (optionally substituted with 1 to 3 halogens).

As used herein, the term "stereoisomer" refers to a compound made up of the same atoms bonded by the same bonds but having different three-dimensional structures called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The compounds of the present invention may be chiral, and it is intended that any enantiomers, whether pure, partially purified, or racemic mixtures, are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of Formula I. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister)

refers to that configuration of a chiral center with a counter-clockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ━━▬ " refers to a bond that protrudes forward out of the plane of the page. The designation " ◂◂◂◂◂ " refers to a bond that protrudes backward out of the plane of the page. The designation " ∿∿∿ " refers to a bond wherein the stereochemistry is not defined.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I, can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen, "*Stereochemistry of Organic Compounds*," (Wiley-Interscience 1994), and European Patent Application No. EP-A-838448, published Apr. 29, 1998. Examples of resolutions include recrystallization techniques or chiral chromatography. Unless otherwise indicated, a compound indicated to be "isomer 1" will be the first isomer eluted from the chiral separation column and "isomer 2" will be the second.

In general, the term "pharmaceutical" when used as an adjective means substantially non-toxic to living organisms. For example, the term "pharmaceutical salt" as used herein, refers to salts of the compounds of Formula I, which are substantially non-toxic to living organisms. See, e.g., Berge, S. M, Bighley, L. D., and Monkhouse, D. C., "Pharmaceutical Salts," *J. Pharm. Sci.*, 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts such as lysine, arginine and ornithine. Typical pharmaceutical salts include those salts prepared by reaction of the compounds of Formula I, with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I, prepared by reaction of a compound of Formula I, with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, ethanesulfonic acid, methanesulfonic acid, oxalic acid, p-bromophenylsulfonic acid, carbonic acid, succinic acid, citric acid, tartaric acid, benzoic acid, acetic acid and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The skilled artisan would appreciate that some compounds of Formula I, may be acidic in nature and accordingly react with any of a number of inorganic and organic bases to form pharmaceutical base addition salts. The term "base addition salt" refers to a salt of a compound of Formula I, prepared by reaction of a compound of Formula I, with a mineral or organic base. For exemplification of pharmaceutical base addition salts see, e.g., Berge, S. M, Bighley, L. D., and Monkhouse, D. C., *J. Pharm. Sci.*, 66:1, 1977. Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I. The potassium and sodium salt forms are particularly preferred. The present invention also contemplates pharmaceutical base addition salts of compounds of Formula I.

The pharmaceutical salts of the invention are typically formed by reacting a compound of Formula I, with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods. All pharmaceutically acceptable salts are contemplated in the present invention. The compound or salt of the present invention may form a solvate with low molecular weight solvents. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28} Pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069

In another embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28} Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide for example metormin.

In yet another embodiment of the invention the present compounds are administered in combination with a meglitinide for example repaglinide or nateglinide.

In still another embodiment of the invention the present compounds are administered in combination with a thiazolidinedione insulin sensitizer for example troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer for example such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/23153, WO 63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor for example voglibose, emiglitate, miglitol or acarbose.

In another embodiment of the invention the present compounds are administered in combination with an agent acting on the ATP-dependent potassium channel of the β-cells for example tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further embodiment of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant). In another embodiment the antiobesity agent is dexamphetamine or amphetamine. In another embodiment the antiobesity agent is leptin. In another embodiment the antiobesity agent is fenfluramine or exfenfluramine. In still another embodiment the antiobesity agent is sibutramine. In a further embodiment the antiobesity agent is orlistat. In another embodiment the antiobesity agent is mazindol or phentermine. In still another embodiment the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, SCE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "MS" refers to mass spectrometry, Observed Mass indicates [M+H] unless indicated otherwise. "MS (FD)" refers to field desorption mass spectrometry, "MS (IS)" refers to ion spray mass spectrometry, "MS (FIA)" refers to flow injection analysis mass spectrometry, "MS (FAB)" refers to fast atom bombardment mass spectrometry, "MS (EI)" refers to electron impact mass spectrometry, "MS (ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature. "DEAD" refers to diethylazodicrboxylate. "PPh$_3$" refers to triphenylphosphine. "ADDP" refers to 1,1'-(azodicarbonyl)dipiperidine. "PPBu$_3$" refers to tributylphosphine. "OTF" refers to triflate. "LAH" refers to lithium aluminum hydride. "DIBAL-H" refers to diisobutylaluminum hydride. "KOtBu" refers to potassium t-butoxide. "THF" refers to tetrahydrofuran. "TBP" refers to tributylphosphine. "EDCI" refers to 1-(3-dimethylaminopropyl)-3-ethylcarbodiamide hydrochloride. "DMAP" refers to dimethylaminopyridine. "HNMe(OMe)" refers to N,N, dimethylhydroxyamine. "CDMT" refers to 2-chloro-4,6-dimethoxy-[1,3,5]triazine. "NMM" refers to N-methyl morpholine. "DCM" refers to dichloromethane. "DMSO" refers to dimethylsulfoxide. "ET$_3$N" refers to triethylamine. "DMF" refers to dimethylformamide. "Et" in a formula refers to ethyl, for example Et$_2$O refers to diethylether, and EtOAc refers to ethylacetate. "PyBOP" refers to bromo-tris-pyrrolidino-phosphonium hexafluorophosphate. "Me" refers to methyl as in MeOH which is methanol. "Pd/C" refers to 10% palladium on carbon. Unless otherwise indicated, isomer 1 refers to the first isomer to be eluted in a chiral separation and isomer 2 refers to the second isomer to be eluted in a chiral separation.

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

GENERAL SCHEMES

Compounds of the present invention have been formed as specifically described in the examples. Further, many compounds are prepared as more generally using a) alkylation of a alcohol, phenol or thiophenol with a halide, b) a Mitsunobu protocol (O. Mitsunobu, 1981 Synthesis, p1); c) and other methods known to the skilled artisan. Alternative synthesis methods may also be effective and known to the skilled artisan. Unless otherwise indicated, all variables, such as Y', R1' to R15', etc., are as defined for analogous variables (R1 to R15, etc.) in the summary of the invention, and otherwise as defined herein.

For example, an intermediate like A is alkylated with an alkylating agent B in the presence of a base (e.g. NaH, K$_2$CO$_3$, Cs$_2$CO$_3$ etc.). Hydrolysis in the presence of aqueous NaOH or LiOH gave the acid product.

Scheme 1

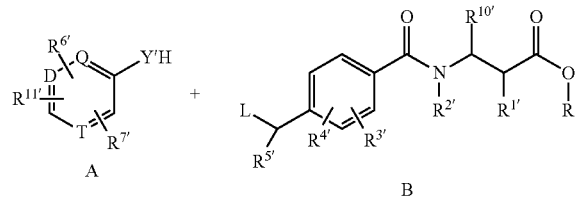

L = halide, mesylate, tosylate etc.

1) base 2) hydrolysis

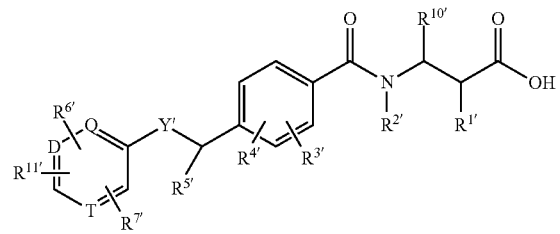

Alternatively, an intermediate like A is coupled with an alcohol C under Mitsunobu reaction condition (DEAD/PPh$_3$, ADDP/PBu$_3$ etc.). Hydrolysis in the presence of aqueous NaOH or LiOH gave the acid product:

Scheme 2

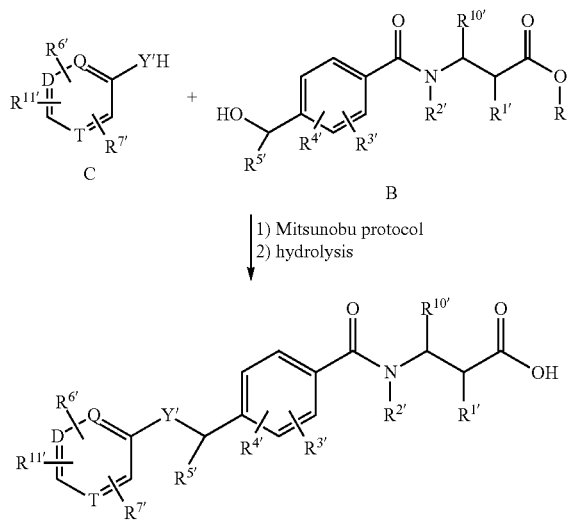

Under certain circumstances, the synthetic sequence can be altered, where an intermediate like D is coupled with an aryl boronic acid or ester under Suzuki reaction conditions (Pd catalyst, base). Hydrolysis in the presence of aqueous NaOH or LiOH gave the acid product:

Scheme 3

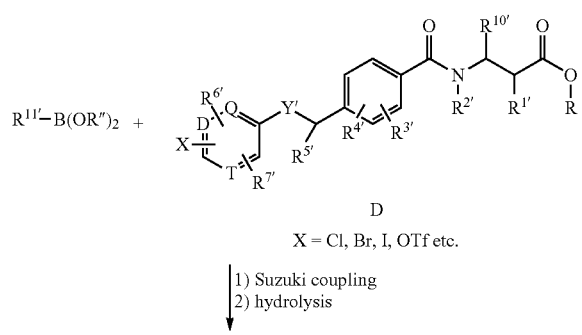

X = Cl, Br, I, OTf etc.

1) Suzuki coupling
2) hydrolysis

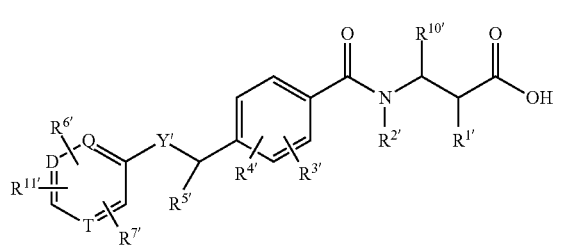

The alcohol intermediates A and C can be made by A) reduction of the ketone with or without chiral auxiliary or B) alkylation of aldehyde with an organometallic reagent, e.g. Grignard reagent.

Scheme 4

Method A

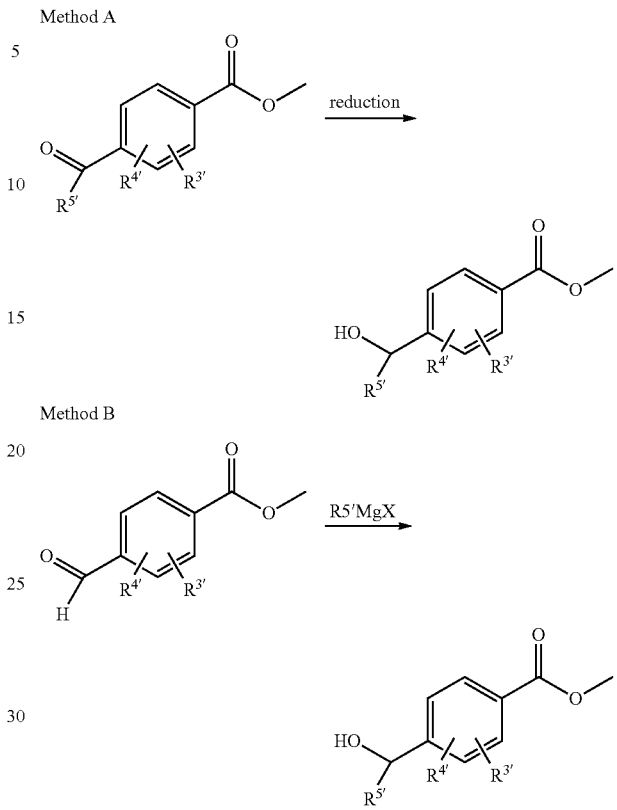

Method B

The biaryl phenol analogs can be made by a palladium catalyzed cross coupling reaction:

Scheme 5

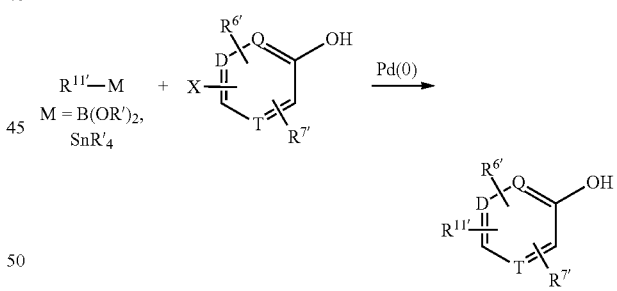

The enantiomeric purified products are prepared either through A) chiral chromatography or B) Mitsunobu coupling between a phenol or thiophenol and a chiral alcohol that can be prepared using the methods known to the art.

PREPARATIONS AND EXAMPLES

The Examples provided herein are illustrative of the invention claimed herein and are not intended to limit the scope of the claimed invention in any way. Names of the preparations and examples are derived using ChemDraw.

Infrared spectra are recorded on a Perkin Elmer 781 spectrometer. 1H NMR spectra are recorded on a Varian 400 MHz spectrometer at ambient temperature. Data are reported as follows: chemical shift in ppm from internal standard tetramethylsilane on the (scale, multiplicity (b=broad, s=singlet, d=doublet, t=triplet, q=quartet, qn=quintet and in =multiplet), integration, coupling constant (Hz) and assignment. $^{13}$C NMR are recorded on a Varian 400 MHz spectrometer at ambient temperature. Chemical shifts are reported in ppm from tetramethylsilane on the (scale, with the solvent resonance employed as the internal standard (CDCl3 at 77.0 ppm and DMSO-d6 at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

Preparation 1

Racemic 4-(1-Hydroxy-propyl)-benzoic acid methyl ester

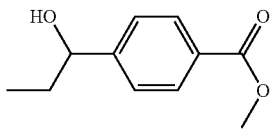

To a solution of 4-formyl-benzoic acid methyl ester (3.0 g, 18.3 mmol) in THF (10 mL) at 0° C. is added ethylmagnesium bromide (2M, 10 mL). After stirring at room temperature for 2 hours, it is quenched with saturated ammonium chloride, extracted with EtOAc. The organic is concentrated to give the titled compound as colorless oil: 2.2 g (62%).

The following compounds are made in a similar manner:

Preparation 2

Racemic 4-(1-Hydroxy-butyl)-benzoic acid methyl ester

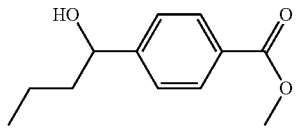

This compound is made from 4-formyl-benzoic acid methyl ester and n-propylmagnesium chloride following the general method exemplified in Preparation 1.

Preparation 3

Racemic 4-(1-Hydroxy-2-methyl-propyl)-benzoic acid methyl ester

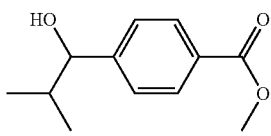

This compound is made from 4-formyl-benzoic acid methyl ester and isopropylmagnesium chloride following the general method exemplified in Preparation 1.

Preparation 4

Racemic 4-(1-Hydroxy-pentyl)-benzoic acid methyl ester

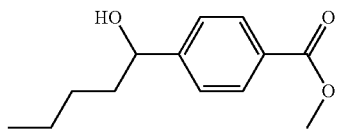 [SMILES: CCCCC(O)c1ccc(C(=O)OC)cc1]

This compound is made from 4-formyl-benzoic acid methyl ester and n-butyl magnesium chloride following the general method exemplified in Preparation 1.

Preparation 5

Racemic 4-(1-Hydroxy-3-methyl-butyl)-benzoic acid methyl ester

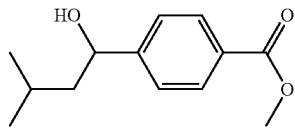 [SMILES: COC(=O)c1ccc(C(O)CC(C)C)cc1]

This compound is made from 4-formyl-benzoic acid methyl ester and isobutylmagnesium chloride following the general method exemplified in Preparation 1.

Preparation 6

Racemic 4-(1-Hydroxy-hexyl)-benzoic acid methyl ester

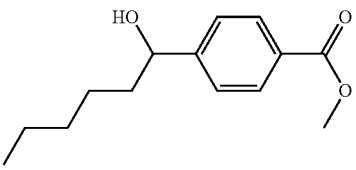

This compound is made from 4-formyl-benzoic acid methyl ester and n-pentylmagnesium chloride following the general method exemplified in Preparation 1.

Preparation 7

Racemic 4-(1-Hydroxy-heptyl)-benzoic acid methyl ester

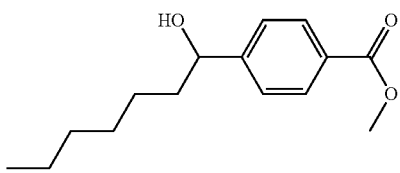 [SMILES: CCCCCCC(O)c1ccc(C(=O)OC)cc1]

This compound is made from 4-formyl-benzoic acid methyl ester and n-hexylmagnesium chloride following the general method of Preparation 1.

Preparation 8

Racemic 4-(1-Hydroxy-4,4-dimethyl-pentyl)-benzoic acid methyl ester

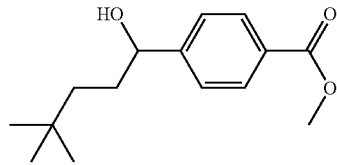 [SMILES: COC(=O)c1ccc(C(O)CCC(C)(C)C)cc1]

This compound is made from 4-formyl-benzoic acid methyl ester and 4,4-dimethylpentylmagnesium bromide following the general method of Preparation 1.

Preparation 9

Racemic 4-(1-Hydroxy-butyl)-benzoic acid methyl ester

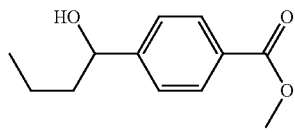

Step A. N-Methoxy-N-methyl-terephthalamic acid methyl ester

To a solution of Terephthalic acid monomethyl ester (5.4 g, 30 mmol) and 2-chloro-4,6-dimethoxy-[1,3,5]triazine (7.9 g, 45 mmol) in THF (300 mL) is added N-methyl morpholine (4.95 mL, 45 mmol), the mixture is stirred at room temperature overnight. Additional N-methyl morpholine (4.95 mL, 45 mmol) is added, followed by the addition of O, N-dimethyl-hydroxylamine HCl salt (3.51 g, 45 mmol). The reaction mixture is stirred overnight, and filtered through celite. The filtrate was concentrated and purified by column chromatography on silica gel (hexane/ethyl acetate) giving the title compound (6.8 g).

Step B. 4-Butyryl-benzoic acid methyl ester

To a solution of N-methoxy-N-methyl-terephthalamic acid methyl ester (4.56 g, 20.4 mmol) in THF (100 mL) is added PrMgCl (2.0M, 30.6 mmol) at 0° C., the reaction is warmed to room temperature, stirred overnight, quenched by NH$_4$Cl aqueous solution, extracted with ethyl acetate. The combined organic layers are washed with brine, dried over sodium sulfate, concentrate. Column chromatography on silica gel gives the title compound (1 g, 23.7%).

Step C. Racemic 4-(1-Hydroxy-butyl)-benzoic acid methyl ester

To a solution of 4-butyryl-benzoic acid methyl ester (400 mg, 1.94 mmol) in ethanol (5 mL) and THF (4 mL) is added sodium borohydride (110 mg, 2.9 mmol), the mixture is stirred at room temperature for 2 h. The reaction mixture is quenched by acetic acid (0.5 mL) and water (10 mL), extracted with ethyl acetate. Combined organic layers are washed with brine and dried over sodium sulfate. Concentration and column chromatography on silica gel gives the title compound (370 mg).

Preparation 10

Racemic 3-[4-(1-Hydroxy-nonyl)-benzoylamino]-propionic acid methyl ester

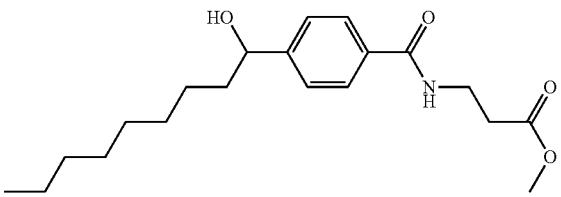 [SMILES: CCCCCCCCC(O)c1ccc(C(=O)NCCC(=O)OC)cc1]

Step A. 3-(4-Formyl-benzoylamino)-propionic acid methyl ester

4-Formyl-benzoic acid, CDMT, and 4-methylmorpholine are combined in anhydrous DCM under nitrogen. The reaction is allowed to stir under nitrogen at room temperature overnight. The amine is then added to the reaction mixture, and allowed to stir at room temperature. Some water (<10% volume) is added to help solubility. The reaction is monitored by HPLC, and upon complete consumption of the acid, the reaction is diluted with DCM. The reaction is diluted with water and rinsed with 1N HCl. Upon acidification, a white solid precipitated from the biphasic mixture. The solid was isolated by filtration and dried under vacuum to afford the titled compound.

Step B. Racemic 3-[4-(1-Hydroxy-nonyl)-benzoylamino]-propionic acid methyl ester To a solution of 3-(4-formyl-benzoylamino)-propionic acid methyl ester (1.2 g, 5 mmol) in THF (10 mL) at 0° C. is added ethylmagnesium bromide (2M, 1.1 mL). After stirring at room temperature for 2 hours, it is quenched with saturated ammonium chloride, extracted with EtOAc. The organic is concentrated to give the titled compound as colorless oil: 270 mg (15%).

The following compound is made in a substantially similar manner:

Preparation 11

Racemic 3-[4-(4,4,4-Trifluoro-1-hydroxy-butyl)-benzoylamino]-propionic acid methyl ester

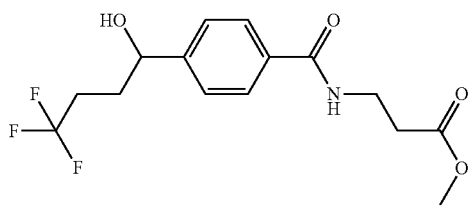 [SMILES: COC(=O)CCNC(=O)c1ccc(C(O)CCC(F)(F)F)cc1]

This compound is made by the general method exemplified in Preparation 10 using 3,3,3-trifluoropropylmagnesium bromide.

Preparation 12

Racemic 3-[4-(1-Hydroxy-4,4-dimethyl-pentyl)-benzoylamino]-propionic acid methyl ester

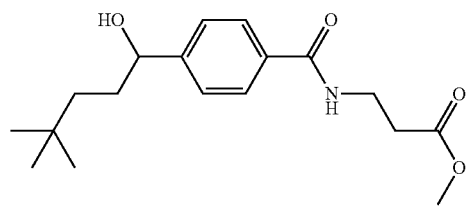 [SMILES: COC(=O)CCNC(=O)c1ccc(C(O)CCC(C)(C)C)cc1]

This compound is made by the general method exemplified in Preparation 10 using 2,2-dimethylbutylmagnesium bromide.

Preparation 13

Racemic 3-[4-(1-Hydroxy-butyl)-benzoylamino]-propionic acid methyl ester

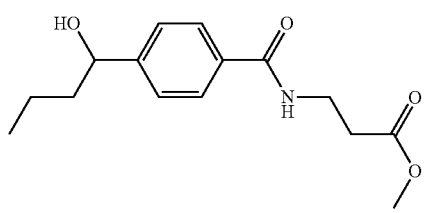 [SMILES: CCCC(O)c1ccc(C(=O)NCCC(=O)OC)cc1]

This compound is made by the general method exemplified in Preparation 10 using n-propylmagnesium bromide.

Preparation 14

Racemic 3-[4-(1-Hydroxy-3-methyl-butyl)-benzoylamino]-propionic acid methyl ester

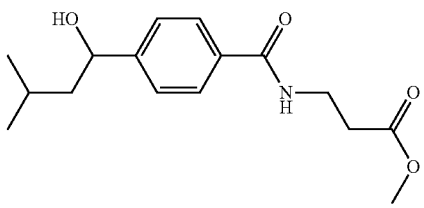 [SMILES: COC(=O)CCNC(=O)c1ccc(C(O)CC(C)C)cc1]

This compound is made by the general methods as exemplified in Preparation 10 using isobutyl magnesium bromide as reagent.

Preparation 15

Racemic 3-[4-(1-Hydroxy-heptyl)-benzoylamino]-propionic acid methyl ester

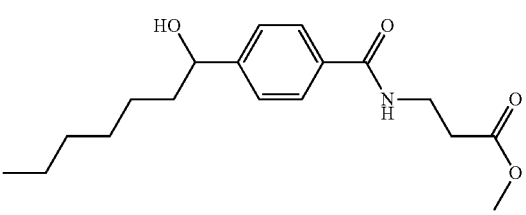 [SMILES: CCCCCCC(O)c1ccc(C(=O)NCCC(=O)OC)cc1]

This compound is made by the general methods as exemplified in Preparation 10 using hexyl magnesium bromide as reagent.

Preparation 16

4'-Trifluoromethyl-biphenyl-4-ol

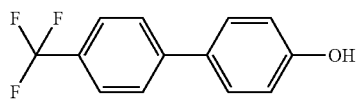 [SMILES: Oc1ccc(-c2ccc(C(F)(F)F)cc2)cc1]

4-Bromophenol (5 g, 28.9 mmol), 4-trifluoromethyl phenyl boronic acid (6.59 g, 34.7 mmol), potassium carbonate (12 g, 86.7 mmol) and palladium acetate (0.324 g, 1.445 mmol) are placed in water (50 mL), and the resulting mixture is stirred at room temperature over night under open air. The mixture is filtered through celite and extracted with ethyl acetate (3×200 ml). The combined organic layers are washed with water, 1N HCl, water, brine, dried (MgSO$_4$), concentrated and chromatographed to yield the title compound as a white solid (6.0 g, 87%).

The following compound is made in a substantially similar manner:

Preparation 17

4'-tert-Butyl-biphenyl-4-ol

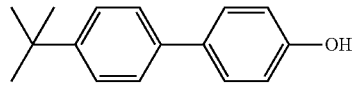

This compound is made by the general method exemplified in Preparation 16 using 4-tert-butyl phenyl boronic acid as reagent.

Preparation 18

4-(5-Trifluoromethyl-pyridin-2-yl)-phenol

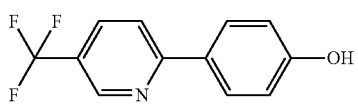 [SMILES: Oc1ccc(-c2ccc(C(F)(F)F)cn2)cc1]

Step A.
2-(4-Benzyloxy-phenyl)-5-trifluoromethyl-pyridine

A mixture of 2-chloro-5-trifluoromethylpyridine (1.81 g, 10 mmol), 4-benzyloxyphenyl boronic acid (2.74 g, 12 mmol) and CsF (5.32 g, 35 mmol) in dioxane (40 mL) is degassed and filled with nitrogen. PdCl$_2$ (dppf) (200 mg) is added under nitrogen, the reaction mixture is heated at 105° C. overnight. The mixture is cooled to room temperature, diluted with ethyl acetate (100 mL), filtered through a pad of Celite. The filtrate is concentrated and the residue is purified by column chromatography on silica gel giving the title compound (2.55 g, 77.4%).

Step B. 4-(5-Trifluoromethyl-pyridin-2-yl)-phenol

To a solution of 2-(4-Benzyloxy-phenyl)-5-trifluoromethyl-pyridine (2.55 g) in ethanol (100 mL) and THF (25 mL) is added Pd/C (5%, 0.253 g), the mixture is stirred under 60 psi of hydrogen overnight. The catalyst is filtered off, concentration of the filtrate gave the title compound (1.25 g, 67.5%).

Preparation 19

Racemic 4-(1-Hydroxy-3,3-dimethyl-butyl)-benzoic acid methyl ester

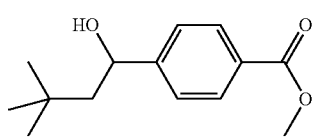

This compound is made from 4-formyl-benzoic acid methyl ester and 3,3-dimethyl-butanemagnesium bromide following the general method exemplified in Preparation 1.

Preparation 20

Racemic 4-(Cyclopropyl-hydroxy-methyl)-benzoic acid methyl ester

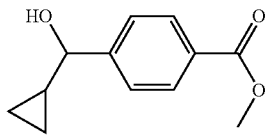

This compound is made from 4-formyl-benzoic acid methyl ester and Cyclopropyl magnesium bromide following the general method exemplified in Preparation 1.

Preparation 21

Racemic 3-Fluoro-4-(1-hydroxy-3-methyl-butyl)-benzoic acid methyl ester

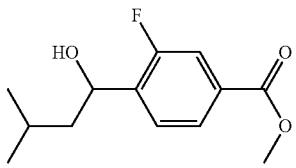 [SMILES: COC(=O)c1ccc(C(O)CC(C)C)c(F)c1]

This compound is made from 3-Fluoro-4-formyl-benzoic acid methyl ester and isobutylmagnesium bromide following the general method exemplified in Preparation 1.

Preparation 22

Racemic 3-Fluoro-4-(1-hydroxy-heptyl)-benzoic acid methyl ester

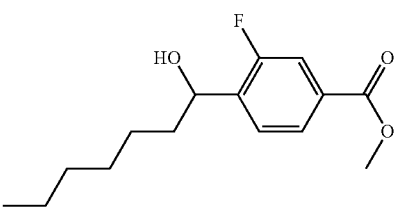 [SMILES: CCCCCCC(O)c1ccc(C(=O)OC)cc1F]

This compound is made from 3-Fluoro-4-formyl-benzoic acid methyl ester and hexylmagnesium bromide following the general method exemplified in Preparation 1.

Preparation 23

4-Bromo-3-[1,3]dioxan-2-yl-phenol

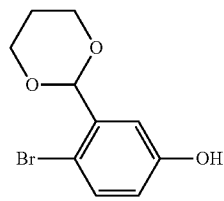 [SMILES: Oc1ccc(Br)c(C2OCCCO2)c1]

To the solution of 2-bromo-5-methoxy-benzaldehyde (10 g, 46.5 mmol) at −78° C. is added BBr$_3$ (25 g, 93.75 mmol) and allowed to warm to room temperature. After 2 h, the reaction is quenched with water and extracted with ethyl acetate. The combined organic layers are washed with water, brine, dried over MgSO$_4$, concentrated and purified by column chromatography to afford 3.6 g of 2-bromo-5-hydroxy-benzaldehyde. To the solution of 2-bromo-5-hydroxy-benzaldehyde (1.45 g, 7.2 mmol in benzene (30 ml) and THF (6 ml) is added 1,3-propanediol (2.74 g, 36 mmol) and TsOH (37 mg, 0.22 mmol). The mixture is refluxed for 24. After cooling down, the solvent is evaporated. The residue is loaded on silica and purified by column chromatography to afford the titled compound (2.3 g) as brown oil.

Preparation 24

6-Chloro-5-methyl-pyridin-3-ol

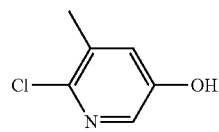

2-Chloro-3-methyl-5-nitro-pyridine (2 g, 11.6 mmol) and SnCl$_2$.(H$_2$O)$_2$ (7.86 g, 34.8 mmol) are refluxed in MeOH overnight. After cooled down, the mixture is diluted with ethyl acetate, washed with water, brine, dried over MgSO$_4$, concentrated and purified by column chromatography to afford 6-chloro-5-methyl-pyridin-3-ylamine (1.7 g). To the solution of 6-chloro-5-methyl-pyridin-3-ylamine (1.7 g, 11.6 mmol) in 1N HCl is added the solution of NaNO$_2$ (960 mg, 13.92 mmol) in water (10 ml) slowly at 0° C. After the addition, the solution is stirred for 20 min and then heated to 90° C. for 30 min. The solution is cooled down, quenched with K$_2$CO$_3$, extracted with ether, dried over MgSO$_4$, and purified by column chromatography to afford the titled compound (560 mg) as a yellow solid.

Preparation 25

4'-Isopropyl-2-methyl-biphenyl-4-ol

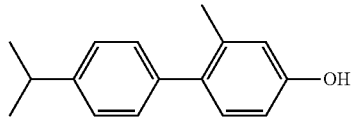 [SMILES: Cc1cc(O)ccc1-c1ccc(C(C)C)cc1]

4-Bromo-3-methylphenol (1.87 g, 10 mmol), 4-isopropyl phenyl boronic acid (2.0 g, 12 mmol), potassium carbonate (4.1 g, 30 mmol) and palladium acetate (0.112 g, 0.5 mmol) are placed in water (100 mL). And the resulting mixture is stirred at room temperature over night under open air. The mixture is filtered through Celite and extracted with ethyl acetate (3×200 ml). The combined organic layers are washed with water, 1N HCl, water, brine, dried (MgSO$_4$), concentrated and chromatographed to yield the title compound as a white solid (1.9 g).

Preparation 26

2-Bromo-5-hydroxy-benzaldehyde

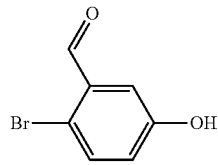

To 2-bromo-5-methoxy-benzaldehyde (10 g, 31.25 mmol) in dichloromethane (30 ml) at −78° C. is added BBr$_3$ (25 g, 93.75 mmol) and allowed to warm to room temperature. After 2 h, the reaction is quenched with water and extracted with ethyl acetate. The combined organic layers are washed with water, brine, dried and purified by the column chromatography to afford 3.6 g of the titled compound.

Preparation 27

2-Bromo-5-hydroxy-benzaldehyde O-tert-butyl-oxime

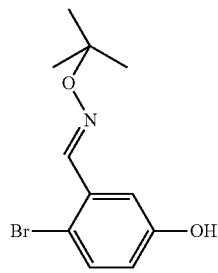

To the solution of 2-bromo-5-hydroxy-benzaldehyde (402 mg, 2 mmol) in methanol (10 ml) is added O-tert-butyl-hydroxylamine hydrochloride (125 mg, 10 mmol). The mixture is stirred at room temperature overnight. The resulting mixture is diluted with ethyl acetate, washed with brine, dried over $MgSO_4$, and evaporated to afford the titled compound (360 mg) as colorless oil.

Preparation 28

4-Bromo-3,5-dimethyl-benzenethiol

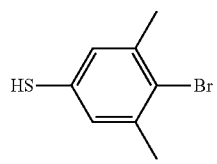

Step A. Dimethyl-thiocarbamic acid O-(4-bromo-3,5-dimethyl-phenyl) ester

4-Bromo-3,5-dimethyl-phenol (10.0 g, 50.01 mmol) is dissolved into dry dioxane (200 mL) and combined with 4-dimethylamino pyridine (1.0 g, 5.2 mmol), triethylamine (12.77 mL, 100.1 mmol), and dimethylamino-thiocarbomoyl chloride (7.69 g, 62.51 mmol). The reaction is heated to reflux under nitrogen. The reaction is monitored by TLC until all of the phenol is consumed, approximately 20 h. After cooling to room temperature, the reaction is diluted with ethyl acetate (200 mL). Water (75 mL) is added and the two layers are separated. The organic layer is washed with brine (75 mL) then dried-over anhydrous sodium sulfate. The solvent is removed and the residue is purified by column chromatography, (6.4 g or 55% yield).

Step B. Dimethyl-thiocarbamic acid S-(4-bromo-3,5-dimethyl-phenyl) ester

Dimethyl-thiocarbamic acid O-(4-bromo-3,5-dimethyl-phenyl) ester (6.4 g, 22.3 mmol) is diluted with 50 mL of tetradecane and heated to reflux under nitrogen. The reaction is monitored by TLC until all the conversion was complete, approximately 20 h. The reaction is allowed to cool to room temperature and then loaded onto silica gel column and purified using flash column chromatography, yielding 5.78 g, or 90% of the target product.

Step C. 4-Bromo-3,5-dimethyl-benzenethiol

Dimethyl-thiocarbamic acid S-(4-bromo-3,5-dimethyl-phenyl) ester (5.78 g, 20.14 mmol) is diluted with methanol (50 mL) and sodium methoxide (4.75 mL of 4.25M in methanol, 20.14 mmol) is added. The reaction is heated to reflux under nitrogen and monitored by TLC. After complete conversion, 20 hours, the reaction is allowed to cool to room temperature. The reaction is neutralized with 1N hydrochloric acid (7.5 mL) and diluted with ethyl acetate (150 mL). The two phases are separated and the organic layer is washed with water (75 mL), then brine (75 mL). The organic layer is dried over anhydrous sodium sulfate, concentrated and loaded onto silica gel column. The title compound is purified using flash column chromatography, yielding 4.0 g, or 92%.

Preparation 29

(R,S) 4-(5,5,5-Trifluoro-1-hydroxy-pentyl)-benzoic acid methyl ester

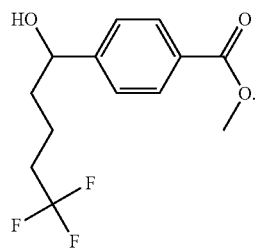

This compound is made following the general method exemplified in Preparation 1 using 4-formyl-benzoic acid methyl ester and 1,1,1-trifluoro-butane-4-magnesium bromide.

Preparation 30

(R,S) 3-[4-(Cyclohexyl-hydroxy-methyl)-benzoylamino]-propionic acid, methyl ester

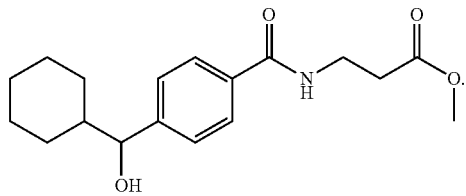 [SMILES: COC(=O)CCNC(=O)c1ccc(C(O)C2CCCCC2)cc1]

This compound is made by the general method exemplified in Preparation 10 using 3-(4-formyl-benzoylamino)-propionic acid methyl ester and cyclohexylmagnesium bromide.

Preparation 31

(R,S) 3-[4-(1-Hydroxy-5-methyl-hexyl)-benzoylamino]-propionic acid methyl ester

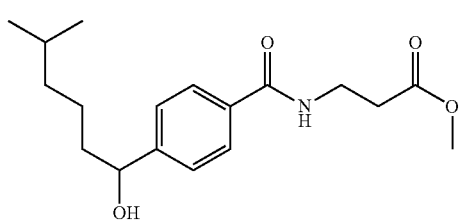 [SMILES: COC(=O)CCNC(=O)c1ccc(C(O)CCCC(C)C)cc1]

This compound is made by the general method exemplified in Preparation 10 using 3-(4-formyl-benzoylamino)-propionic acid methyl ester and 4-methylpentane-1-magnesium-bromide.

Preparation 32

4'-tert-Butyl-2,6-dimethyl-biphenyl-4-ol

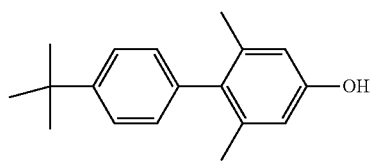 [SMILES: Cc1cc(O)cc(C)c1-c1ccc(C(C)(C)C)cc1]

This compound is made by the general method as exemplified in Preparation 16 using 4-bromo-3,5-dimethyl-phenol and 4-tert-butyl phenyl boronic acid as reagents.

Preparation 33

2,6-Dimethyl-4'-trifluoromethyl-biphenyl-4-ol

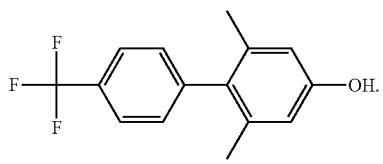 [SMILES: Cc1cc(O)cc(C)c1-c1ccc(C(F)(F)F)cc1]

This compound is made by the general method as exemplified in Preparation 16 using 4-bromo-3,5-dimethyl-phenol and 4-trifluoromethyl phenyl boronic acid as reagents.

Preparation 34

5-Methyl-6-(4-trifluoromethyl-phenyl)-pyridin-3-ol

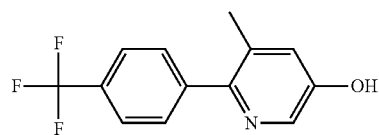 [SMILES: Cc1cc(O)cnc1-c1ccc(C(F)(F)F)cc1]

Step A. 3-Methyl-5-nitro-2-(4-trifluoromethyl-phenyl)-pyridine

To a solution of 2-chloro-3-methyl-5-nitro-pyridine (5.0 g, 28.73 mmol) in toluene (50 mL) is added palladium tetrakis triphenylphosphine (1.66 g, 1.44 mmol), 4-trifluoromethyl phenyl boronic acid (10.92 g, 57.46 mmol), and potassium fluoride (3.34 g, 57.46 mmol). The reaction is purged with nitrogen three times and heated to reflux under nitrogen. At reflux, water (25 mL) is added to the reaction and the reaction is allowed to reflux under nitrogen. The reaction is monitored by HPLC, and upon completion, allowed to cool to room temperature. The reaction is diluted with ethyl acetate and Celite is added, followed by water. This mixture is then filtered through a pad of Celite. The solution is poured into a separatory funnel and the organic layer is washed with water and brine. The organic layer is dried over anhydrous sodium sulfate and concentrated. The product is purified by flash column chromatography (5.6 g, 19.71 mmol).

Step B. 5-Methyl-6-(4-trifluoromethyl-phenyl)-pyridin-3-ylamine

To a solution of the 3-methyl-5-nitro-2-(4-trifluoromethyl-phenyl)-pyridine (3.5 g, 10.56 mmol) in ethanol (50 mL) is added palladium (10%) on carbon (0.700 g, 20% by wt.). The reaction is charged to 15 psi under a hydrogen atmosphere and allowed to stir for 4 hours. The reaction is diluted with ethyl acetate and Celite is added, followed by water. This mixture is then filtered through a pad of celite. The solution is concentrated, diluted with ethyl acetate, poured into a separatory funnel and the organic layer is washed with water and brine. The organic layer is dried over anhydrous sodium sulfate and concentrated. The product is used directly in the next step (2.74 g, 10.87 mmol).

Step C.
5-Methyl-6-(4-trifluoromethyl-phenyl)-pyridin-3-ol

5-Methyl-6-(4-trifluoromethyl-phenyl)-pyridin-3-ylamine (2.74 g, 10.87 mmol) is suspended in hydrochloric acid (21.74 mL, 5N) and the solution is cooled to −15° C. in a brine/ice bath. Sodium nitrate (0.9 g, 13.04 mmol) in water (10 mL) is added slowly to the mixture. The reaction is allowed to stir at −15° C. for ten minutes after complete addition. Hexafluorophosphoric acid (5 mL, 21.74 mmol of a 60% wt. solution in water) is added slowly to the mixture. The resulting slurry is filtered, rinsed with cold water, methanol, and diethyl ether, and dried under vacuum. This solid is added in small portions to a round bottom containing acetic acid (10 mL) at 105° C. This solution is cooled to room temperature then treated with sodium hydroxide (25 mL, 5N) for 30 min. The pH of this solution is adjusted to 6 with hydrochloric acid, extracted with ethyl acetate, washed with brine, dried over anhydrous sodium sulfate, then filtered and concentrated to provide the title product (2.2 g, 8.69 mmol).

Preparation 35

6-(4-tert-Butyl-phenyl)-5-methyl-pyridin-3-ol

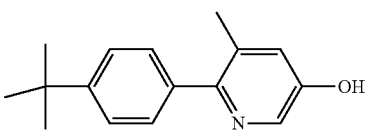

This compound is made by the general method exemplified in Preparation 16 using 2-chloro-3-methyl-5-nitro-pyridine and 4-tbutyl phenyl boronic acid.

Example 1

Racemic 3-{4-[1-(4'-Trifluoromethyl-biphenyl-4-yloxy)-propyl]-benzoylamino}-propionic acid

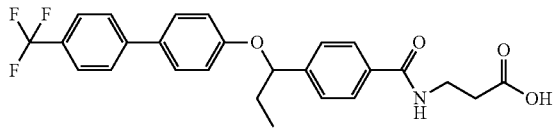 [SMILES: CCC(Oc1ccc(-c2ccc(C(F)(F)F)cc2)cc1)c1ccc(C(=O)NCCC(=O)O)cc1]

Step A. 4-[1-(4'-Trifluoromethyl-biphenyl-4-yloxy)-propyl]-benzoic acid

To a solution of 4-(1-hydroxy-propyl)-benzoic acid methyl ester (300 mg, 1.55 mmol) in toluene (10 mL) is added 1,1'-(azodicarbonyl)dipiperidine (ADDP, 585 mg, 2.32 mmol) at 0° C., followed by the addition of tributylphosphine (0.58 mL, 2.32 mmol) and 4'-trifluoromethyl-biphenyl-4-ol (442 mg, 1.86 mmol). The reaction mixture is warmed up to room temperature and stirred overnight. The mixture is loaded on silica gel, eluted with hexanes with a gradient from 0% of ethyl acetate to 50% of ethyl acetate giving 4-[1-(4'-trifluoromethyl-biphenyl-4-yloxy)-propyl]-benzoic acid methyl ester. The ester product is taken into ethanol (2 mL), treated with sodium hydroxide (5N aqueous, 1 mL) for 3 hours at room temperature. The mixture is concentrated, diluted with ethyl acetate, acidified with 5 N HCl (1.1 mL), extracted with ethyl acetate. The organic layers are dried and concentrated giving 4-[1-(4'-trifluoromethyl-biphenyl-4-yloxy)-propyl]-benzoic acid (570 mg).

Step B. Racemic methyl 3-(4-{1-[6-(4-Trifluoromethyl-phenyl)-pyridin-3-yl]-heptyloxy}-benzoylamino)-propionate To a mixture of 4-[1-(4'-Trifluoromethyl-biphenyl-4-yloxy)-propyl]-benzoic acid (270 mg, 0.68 mmol) in methylene chloride (7 mL) are added triethyl amine (0.28 mL, 2.03 mmol), DMAP (5.0 mg), 3-amino-propionic acid methyl ester (141 mg, 1.01 mmol) and EDCI (389 mg, 2.03 mmol) at room temperature. The reaction mixture is stirred at room temperature overnight, loaded on silica gel, eluted with eluted with hexanes with a gradient from 0% of ethyl acetate to 100% of ethyl acetate giving 3-{4-[1-(4'-trifluoromethyl-biphenyl-4-yloxy)-propyl]-benzoylamino}-propionic acid methyl ester (215 mg).

Step C. Racemic 3-{4-[1-(4'-Trifluoromethyl-biphenyl-4-yloxy)-propyl]-benzoylamino}-propionic acid To a mixture of 3-{4-[1-(4'-Trifluoromethyl-biphenyl-4-yloxy)-propyl]-benzoylamino}-propionic acid methyl ester (60 mg, 0.12 mmol) in methanol (2 mL) is added sodium hydroxide (5 N aqueous, 0.5 mL) and stirred for 5 hours. The reaction mixture is concentrated and acidified by 5 N HCl (0.5 mL), extracted with ethyl acetate. Combined organic layers are washed with water and brine, dried over sodium sulfate. Concentration gives the title compound (54 mg). MS (ES): 472.2 [M+H]+.

Example 2

Racemic 3-{4-[3-Methyl-1-(4'-trifluoromethyl-biphenyl-4-yloxy)-butyl]-benzoylamino}-propionic acid

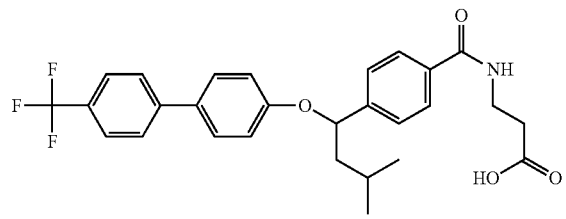 [SMILES: CC(C)CC(Oc1ccc(-c2ccc(C(F)(F)F)cc2)cc1)c1ccc(C(=O)NCCC(=O)O)cc1]

This compound is made by the general method exemplified in Example 1 using 4-(1-hydroxy-3-methylbutyl)-benzoic acid methyl ester and 4'-trifluoromethyl-biphenyl-4-ol as starting materials. MS (ES): 500.2 [M+H]+.

Example 3

Racemic 3-{4-[1-(4-tert-Butyl-phenoxy)-3-methyl-butyl]-benzoylamino}-propionic acid

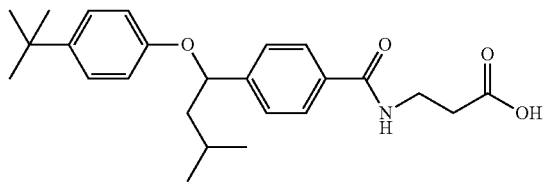 [SMILES: CC(C)CC(Oc1ccc(C(C)(C)C)cc1)c1ccc(C(=O)NCCC(=O)O)cc1]

This compound is made by the general method exemplified in Example 1 using 4-(1-hydroxy-3-methylbutyl)-benzoic acid methyl ester and 4-tert-butyl-phenol as starting materials. MS (ES): 412.3 [M+H]+.

Example 4

Racemic 3-{4-[1-(4'-tert-Butyl-biphenyl-4-yloxy)-4,4,4-trifluoro-butyl]-benzoylamino}-propionic acid

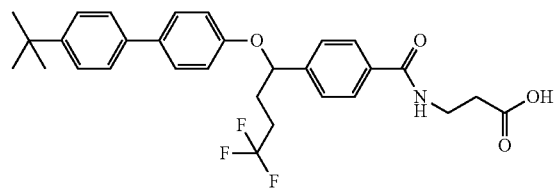 [SMILES: CC(C)(C)c1ccc(-c2ccc(OC(CCC(F)(F)F)c3ccc(C(=O)NCCC(=O)O)cc3)cc2)cc1]

This compound is made by the general method exemplified in Example 1 using 4-(1-hydroxy-4,4,4-trifluorobutyl)-benzoic acid methyl ester and 4'-tert-butyl-biphenyl-4-ol as starting materials. MS (ES): 526.2 [M+H]⁺.

Example 5

Racemic 3-{4-[4,4,4-Trifluoro-1-(4'-trifluoromethyl-biphenyl-4-yloxy)-butyl]-benzoylamino}-propionic acid

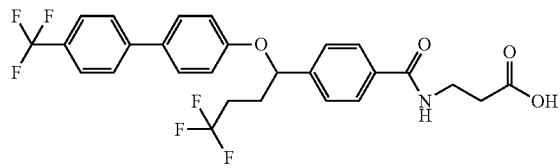 [SMILES: O=C(O)CCNC(=O)c1ccc(C(CCC(F)(F)F)Oc2ccc(-c3ccc(C(F)(F)F)cc3)cc2)cc1]

This compound is made by the general method exemplified in Example 1 using 4-(1-hydroxy-4,4,4-trifluorobutyl)-benzoic acid methyl ester and 4'-trifluoromethyl-biphenyl-4-ol as starting materials. MS (ES): 538.3 [M+H]⁺.

Example 6

Racemic 3-{4-[(4-Bromo-phenyl)-(4'-tert-butyl-biphenyl-4-yloxy)-methyl]-benzoylamino}-propionic acid

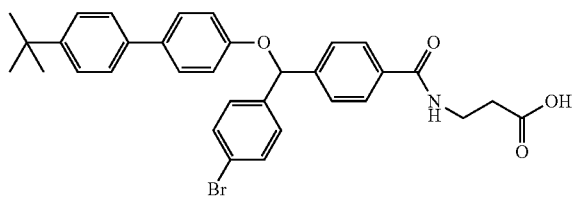 [SMILES: CC(C)(C)c1ccc(-c2ccc(OC(c3ccc(Br)cc3)c3ccc(C(=O)NCCC(=O)O)cc3)cc2)cc1]

This compound is made by the general method exemplified in Example 1 using 4-(1-hydroxy-1-(4-bromophenyl)-methyl)-benzoic acid methyl ester and 4'-tbutyl-biphenyl-4-ol as starting materials. MS (ES): 585.0.

Example 7

Racemic 3-{4-[2-Methyl-1-(4'-trifluoromethyl-biphenyl-4-yloxy)-propyl]-benzoylamino}-propionic acid

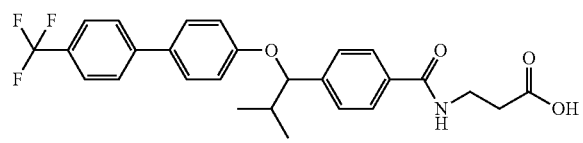 [SMILES: CC(C)C(Oc1ccc(-c2ccc(C(F)(F)F)cc2)cc1)c1ccc(C(=O)NCCC(=O)O)cc1]

This compound is made by the general method exemplified in Example 1 using 4-(1-hydroxy-2-methylpropyl)-benzoic acid methyl ester and 4'-trifluoromethyl-biphenyl-4-ol as starting materials. MS (ES): 486.2 [M+H]⁺.

Example 8

Racemic 3-{4-[1-(4'-tert-Butyl-biphenyl-4-yloxy)-propyl]-benzoylamino}-propionic acid

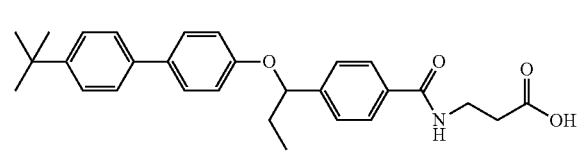 [SMILES: CCC(Oc1ccc(-c2ccc(C(C)(C)C)cc2)cc1)c1ccc(C(=O)NCCC(=O)O)cc1]

This compound is made by the general method exemplified in Example 1 using 4-(1-hydroxy-propyl)-benzoic acid methyl ester and 4'-tert-butyl-biphenyl-4-ol as starting materials. MS (ES): 458.3 [M−H]⁻.

Example 9

Racemic 3-{4-[1-(4'-tert-Butyl-biphenyl-4-yloxy)-heptyl]-benzoylamino}-propionic acid

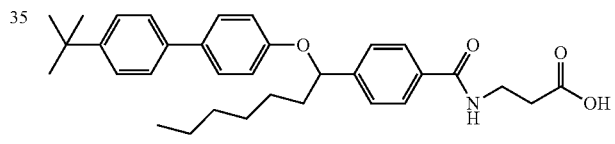

This compound is made by the general method exemplified in Example 1 using 4-(1-hydroxy-heptyl)-benzoic acid methyl ester and 4'-tert-butyl-biphenyl-4-ol as starting materials. MS (ES): 516.3 [M+H]⁺.

Example 10

Racemic 3-{4-[1-(4'-tert-Butyl-biphenyl-4-yloxy)-3-methyl-butyl]-benzoylamino}-propionic acid

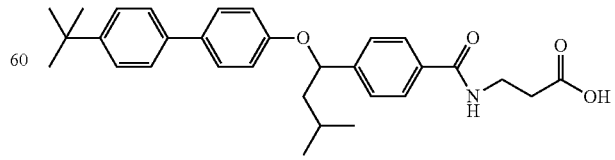

This compound is made by the general method exemplified in Example 1 using 4-(1-hydroxy-3-methylbutyl)-benzoic acid methyl ester and 4'-tbutyl-biphenyl-4-ol as starting materials. MS (ES): 488.3 [M+H]⁺.

Example 11

Racemic 3-{4-[1-(4-Cyclohexyl-phenoxy)-hexyl]-benzoylamino}-propionic acid

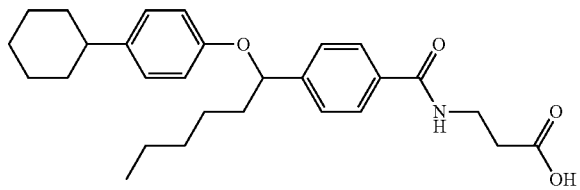 [SMILES: CCCCCC(Oc1ccc(C2CCCCC2)cc1)c1ccc(C(=O)NCCC(=O)O)cc1]

This compound is made by the general method exemplified in Example 1 using 4-(1-hydroxy-hexyl)-benzoic acid methyl ester and 4-cyclohexylphenol as starting materials. MS (ES): 452.3 [M+H]⁺.

Example 12

Racemic 3-{4-[1-(4-Benzyloxy-phenoxy)-hexyl]-benzoylamino}-propionic acid

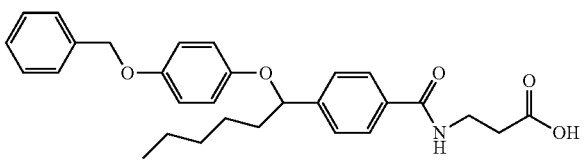 [SMILES: CCCCCC(Oc1ccc(OCc2ccccc2)cc1)c1ccc(C(=O)NCCC(=O)O)cc1]

This compound is made by the general method exemplified in Example 1 using 4-(1-hydroxy-hexyl)-benzoic acid methyl ester and 4-benzyloxyphenol as starting materials. MS (ES): 476.2 [M+H]⁺.

Example 13

Racemic 3-[4-(1-Phenoxy-hexyl)-benzoylamino]-propionic acid

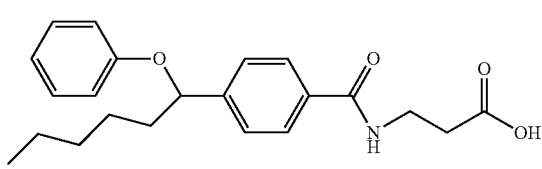 [SMILES: CCCCCC(Oc1ccccc1)c1ccc(C(=O)NCCC(=O)O)cc1]

This compound is made by the general method exemplified in Example 1 using 4-(1-hydroxy-hexyl)-benzoic acid methyl ester and phenol as starting materials. MS (ES): 370.3 [M+H]⁺.

Example 14

Racemic 3-{4-[1-(4'-Trifluoromethyl-biphenyl-4-yloxy)-heptyl]-benzoylamino}-propionic acid

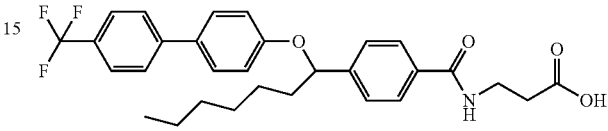

This compound is made by the general method exemplified in Example 1 using 4-(1-hydroxy-heptyl)-benzoic acid methyl ester and 4'-trifluoromethyl-biphenyl-4-ol as starting materials. MS (ES): 528.2 [M+H]⁺.

Example 15

Racemic 3-{4-[1-(4'-Trifluoromethyl-biphenyl-4-ylsulfanyl)-heptyl]-benzoylamino}-propionic acid

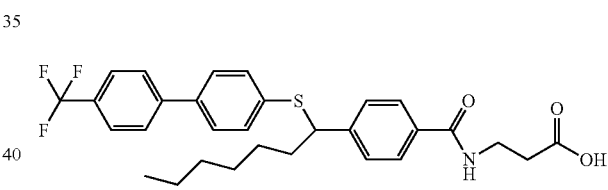

This compound is made by the general method exemplified in Example 1 using 4-(1-hydroxy-heptyl)-benzoic acid methyl ester and 4'-trifluoromethyl-biphenyl-4-mercaptol as starting materials. MS (ES): 542.2 [M−H]⁻.

Example 16

Racemic 3-{4-[1-(4'-Trifluoromethyl-biphenyl-4-yloxy)-pentyl]-benzoylamino}-propionic acid

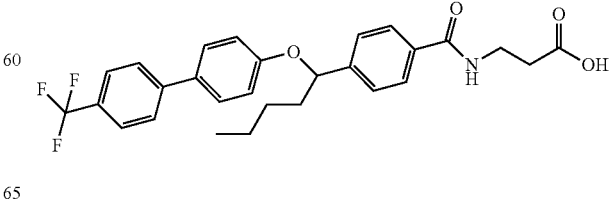

This compound is made by the general method exemplified in Example 1 using 4-(1-hydroxy-pentyl)-benzoic acid methyl ester and 4'-trifluoromethyl-biphenyl-4-ol as starting materials. MS (ES): 498.2 [M–H]⁻.

Example 17

Racemic 3-{4-[1-(4'-tert-Butyl-biphenyl-4-yloxy)-pentyl]-benzoylamino}-propionic acid

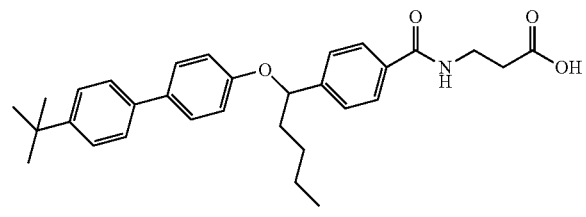 [SMILES: CCCCC(Oc1ccc(-c2ccc(C(C)(C)C)cc2)cc1)c1ccc(C(=O)NCCC(=O)O)cc1]

This compound is made by the general method exemplified in Example 1 using 4-(1-hydroxy-pentyl)-benzoic acid methyl ester and 4'-tbutyl-biphenyl-4-ol as starting materials. MS (ES): 486.3 [M–H]⁻.

Example 18

Racemic 3-{4-[1-(4'-Trifluoromethyl-biphenyl-4-yloxy)-butyl]-benzoylamino}-propionic acid

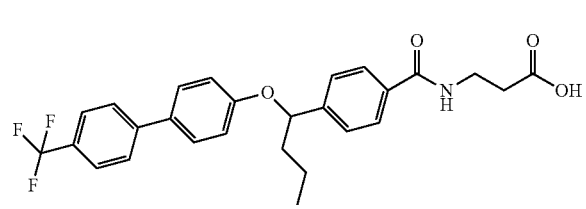 [SMILES: CCCC(Oc1ccc(-c2ccc(C(F)(F)F)cc2)cc1)c1ccc(C(=O)NCCC(=O)O)cc1]

This compound is made by the general method exemplified in Example 1 using 4-(1-hydroxy-butyl)-benzoic acid methyl ester and 4'-trifluoromethyl-biphenyl-4-ol as starting materials. MS (ES): 486.2 [M+H]⁺.

Example 19

Racemic 3-{4-[1-(4'-tert-Butyl-biphenyl-4-yloxy)-butyl]-benzoylamino}-propionic acid

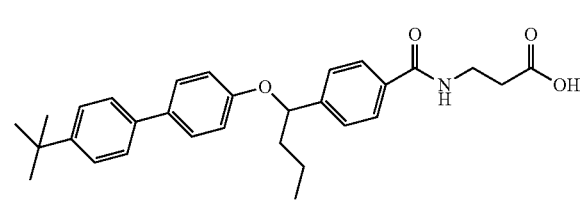 [SMILES: CCCC(Oc1ccc(-c2ccc(C(C)(C)C)cc2)cc1)c1ccc(C(=O)NCCC(=O)O)cc1]

This compound is made by the general method exemplified in Example 1 using 4-(1-hydroxy-butyl)-benzoic acid methyl ester and 4'-tert-butyl-biphenyl-4-ol as starting materials. MS (ES): 475.2 [M+H]⁺.

Example 20

Racemic 3-{4-[3-Methyl-1-(4'-trifluoromethyl-biphenyl-4-ylsulfanyl)-butyl]-benzoylamino}-propionic acid

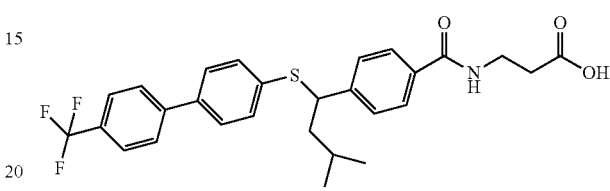

This compound is made by the general method exemplified in Example 1 using 4-(1-hydroxy-3-methylbutyl)-benzoic acid methyl ester and 4'-trifluoromethyl-biphenyl-4-mercaptol as starting materials. MS (ES): 515.3 [M–H]⁻.

Example 21

Racemic 3-{4-[1-(4'-Trifluoromethyl-biphenyl-4-yloxy)-nonyl]-benzoylamino}-propionic acid

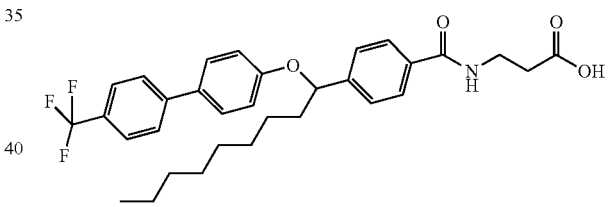

This compound is made by the general method exemplified in Example 1 using 4-(1-hydroxy-nonyl)-benzoic acid methyl ester and 4'-trifluoromethyl-biphenyl-4-mercaptol as starting materials. MS (ES): 554.2 [M–H]⁻.

Example 22

Racemic 3-(4-{3-Methyl-1-[4-(6-trifluoromethyl-pyridin-3-yl)-phenoxy]-butyl}-benzoylamino)-propionic acid

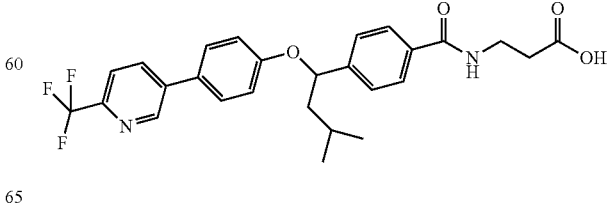

This compound is made by the general method exemplified in Example 1 using 4-(1-hydroxy-3-methylbutyl)-benzoic acid methyl ester and 4-(6-Trifluoromethyl-pyridin-3-yl)-phenol as starting materials. MS (ES): 500.3 [M−H]⁻.

Example 23

Racemic 3-(4-{2-Methyl-1-[4-(6-trifluoromethyl-pyridin-3-yl)-phenoxy]-propyl}-benzoylamino)-propionic acid

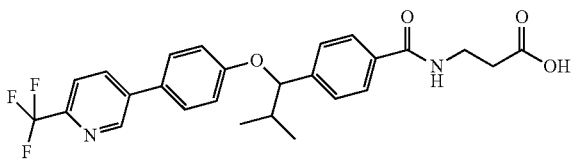 [SMILES: CC(C)C(Oc1ccc(-c2ccc(C(F)(F)F)nc2)cc1)c1ccc(C(=O)NCCC(=O)O)cc1]

This compound is made by the general method exemplified in Example 1 using 4-(1-hydroxy-2-methylpropyl)-benzoic acid methyl ester and 4-(6-Trifluoromethyl-pyridin-3-yl)-phenol as starting materials. MS (ES): 487.3 [M+H]⁺.

Example 24

Racemic 3-(4-{1-[4'-trifluoromethoxy-biphenyl-4-ylsulfanyl]-3-methyl-butyl}-benzoylamino)-propionic acid

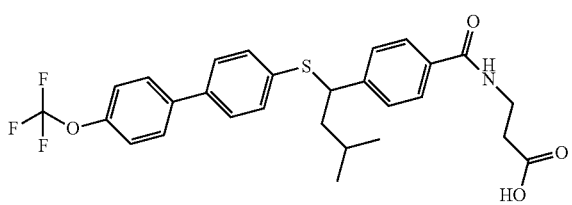 [SMILES: CC(C)CC(Sc1ccc(-c2ccc(OC(F)(F)F)cc2)cc1)c1ccc(C(=O)NCCC(=O)O)cc1]

Step A. 4-[1-(4-Bromo-phenylsulfanyl)-3-methyl-butyl]-benzoic acid

To a solution of 4-(1-hydroxy-3-methyl-butyl)-benzoic acid methyl ester (1240 mg, 5.59 mmol) in toluene (10 mL) is added 1,1'-(azodicarbonyl)dipiperidine (ADDP, 2114 mg, 8.38 mmol) at 0° C., followed by the additions of tributylphosphine (2.09 mL, 8.38 mmol) and 4-bromo-thiophenol (1267 mg, 6.7 mmol). The reaction mixture is warmed up to room temperature and stirred overnight. The mixture is loaded on silica gel, eluted with hexanes with a gradient from 0% of ethyl acetate to 50% of ethyl acetate giving 4-[1-(4-bromo-phenylsulfanyl)-3-methyl-butyl]-benzoic acid methyl ester. 393 mg of the ester product is taken into ethanol (2 mL), treated with sodium hydroxide (5N aqueous, 1 mL) for 3 h at room temperature. The mixture is concentrated, diluted with ethyl acetate, acidified with 5 N HCl (1.1 mL), extracted with ethyl acetate. The organic layers are dried and concentrated giving 4-[1-(4-bromo-phenylsulfanyl)-3-methyl-butyl]-benzoic acid (379 mg).

Step B. Racemic 3-{4-[1-(4-Bromo-phenylsulfanyl)-3-methyl-butyl]-benzoylamino}-propionic acid methyl ester To a mixture of 4-[1-(4-bromo-phenylsulfanyl)-3-methyl-butyl]-benzoic acid (379 mg, 1 mmol) in methylene chloride (10 mL) are added triethyl amine (0.42 mL, 3 mmol), DMAP (5.0 mg), 3-amino-propionic acid methyl ester (209 mg, 1.5 mmol) and EDCI (577 mg, 3.0 mmol) at room temperature. The reaction mixture is stirred at room temperature overnight, loaded on silica gel, eluted with eluted with hexanes with a gradient from 0% of ethyl acetate to 100% of ethyl acetate giving 3-{4-[1-(4-Bromo-phenylsulfanyl)-3-methyl-butyl]-benzoylamino}-propionic acid methyl ester (350 mg).

Step C. Racemic 3-{4-[3-Methyl-1-(4'-trifluoromethoxy-biphenyl-4-ylsulfanyl)-butyl]-benzoylamino}-propionic acid methyl ester 3-{4-[1-(4-bromo-phenylsulfanyl)-3-methyl-butyl]-benzoylamino}-propionic acid methyl ester (350 mg, 0.75 mmol), potassium carbonate (311 mg, 2.25 mmol), 4-triflouromethoxylphenyl boronic acid (311 mg, 1.5 mmol) and tetrakis-(triphenylphosphine)palladium (87 mg, 0.075 mmol) are place in a flask. After the reaction is purged with N₂ for several times, THF/H₂O (20 ml/5 ml) is added. The resulting solution is refluxed overnight, loaded on silica gel, eluted with hexane and ethyl acetate to give 3-{4-[3-Methyl-1-(4'-trifluoromethoxy-biphenyl-4-ylsulfanyl)-butyl]-benzoylamino}-propionic acid methyl ester (294 mg) as a yellow solid.

Step D. Racemic 3-(4-{1-[4'-(1-Fluoro-ethoxy)-biphenyl-4-ylsulfanyl]-3-methyl-butyl}-benzoylamino)-propionic acid To a mixture of 3-{4-[3-Methyl-1-(4'-trifluoromethoxy-biphenyl-4-ylsulfanyl)-butyl]-benzoylamino}-propionic acid methyl ester (20 mg) in methanol (2 mL) is added sodium hydroxide (5 N aqueous, 0.5 mL) and stirred for 5 h. The reaction mixture is concentrated and acidified by 5 N HCl (0.5 mL), extracted with ethyl acetate. Combined organic layers are washed with water and brine, dried over sodium sulfate. Concentration gives the title compound (18 mg). MS (ES): 531.2 [M−H]⁻.

The following compounds are made in a substantially similar manner:

Example 25

Racemic 3-{4-[1-(3',4'-dimethyl-biphenyl-4-ylsulfanyl)-3-methyl-butyl]-benzoylamino}-propionic acid

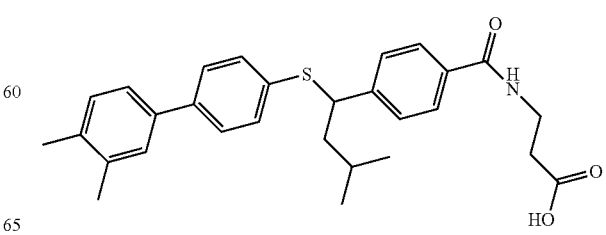

This compound is made by the general method as exemplified in Example 24 using 3,4-dimethylphenyl boronic acid as starting material in step C. MS (ES): 477.2 [M+H]⁺.

Example 26

Racemic 3-{4-[1-(4'-cyano-biphenyl-4-ylsulfanyl)-3-methyl-butyl]-benzoylamino}-propionic acid

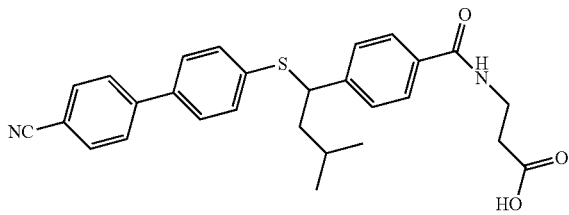 [SMILES: CC(C)CC(Sc1ccc(-c2ccc(C#N)cc2)cc1)c1ccc(C(=O)NCCC(=O)O)cc1]

This compound is made by the general method as exemplified in Example 24 using 4-cyanophenyl boronic acid as starting material in step C. MS (ES): 472.2 [M+H]⁺.

Example 27

Racemic 3-{4-[1-(4'-Isobutyl-biphenyl-4-ylsulfanyl)-3-methyl-butyl]-benzoylamino}-propionic acid

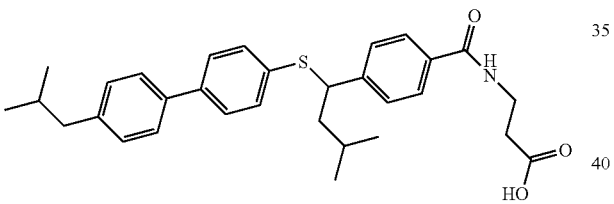

This compound is made by the general method as exemplified in Example 24 using 4-isobutylphenyl boronic acid in step C. MS (ES): 505.2 [M+H]⁺.

Example 28

Racemic 3-(4-{1-[4-(6-Methoxy-pyridin-3-yl)-phenylsulfanyl]-3-methyl-butyl}-benzoylamino)-propionic acid

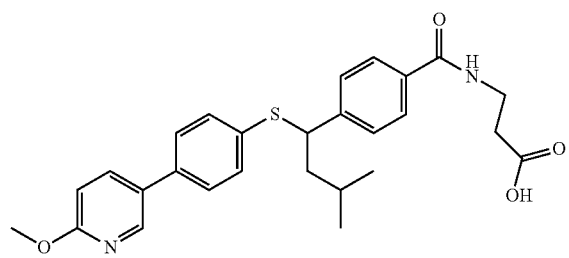 [SMILES: COc1ccc(-c2ccc(SC(CC(C)C)c3ccc(C(=O)NCCC(=O)O)cc3)cc2)cn1]

This compound is made by the general method as exemplified in Example 24 using 4-methoxy-pyridin-3-yl boronic acid as starting material in step C. MS (ES): 480.2 [M+H]⁺.

Example 29

Racemic 3-{4-[1-(4'-Ethyl-biphenyl-4-yloxy)-heptyl]-benzoylamino}-propionic acid

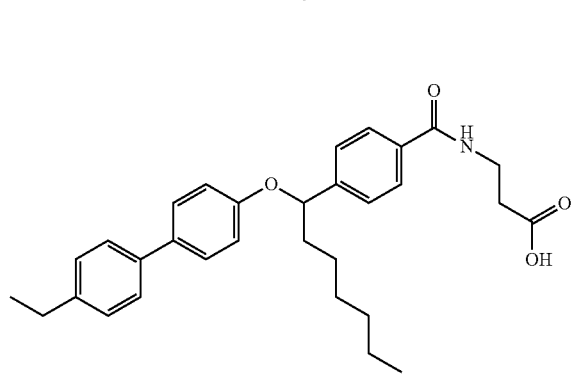 [SMILES: CCCCCCC(Oc1ccc(-c2ccc(CC)cc2)cc1)c1ccc(C(=O)NCCC(=O)O)cc1]

This compound is made by the general method as exemplified in Example 24 using 4-(1-hydroxy-heptyl)-benzoic acid methyl ester and 4-bromophenol as reagents in step A and 4-ethylphenyl boronic acid in step C. MS (ES): 488.3 [M+H]⁺.

Example 30

3-{4-[1-(4-Benzyloxy-phenoxy)-hexyl]-benzoylamino}-propionic acid, Isomer 1

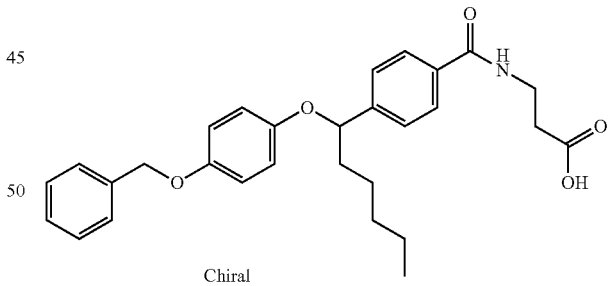

Chiral

Chiral Separation:

The racemic 3-{4-[1-(4-Benzyloxy-phenoxy)-hexyl]-benzoylamino}-propionic acid methyl ester was resolved on a Chiralpak AD column (4.6×150 mm). Eluted with Isopropyl Alcohol/Heptane (30/70) and concentrated the fractions to provide a purified enantiomer ester (isomer 1,100% ee). Hydrolysis of the purified enantiomer of the ester provided the title compound as a white solid. MS (ES): 476.3 [M+H]⁺.

The following enantiomerically purified compounds were obtained by substantially similar chiral separation using Chiralpak AD column (4.6×150 mm) or Chiralcel OJ column (4.6×250 mm):

Example 31

3-{4-[1-(4-Benzyloxy-phenoxy)-hexyl]-benzoylamino}-propionic acid, Isomer 2

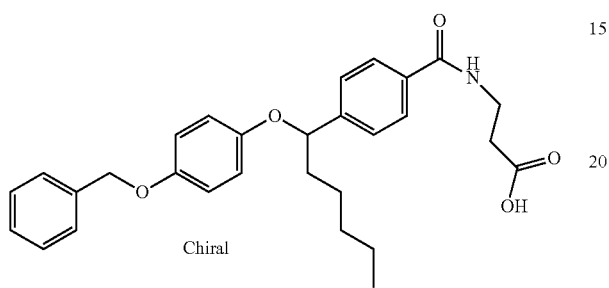

This compound is made by the general method as exemplified in Example 30 by resolving racemic 3-{4-[1-(4-Benzyloxy-phenoxy)-hexyl]-benzoylamino}-propionic acid methyl ester on Chiralpak AD column (4.6×150 mm). MS (ES): 476.3 [M+H]$^+$.

Example 32

3-{4-[3-Methyl-1-(4'-trifluoromethyl-biphenyl-4-yloxy)-butyl]-benzoylamino}-propionic acid, Isomer 1 and

Example 33

3-{4-[3-Methyl-1-(4'-trifluoromethyl-biphenyl-4-yloxy)-butyl]-benzoylamino}-propionic acid, Isomer 2

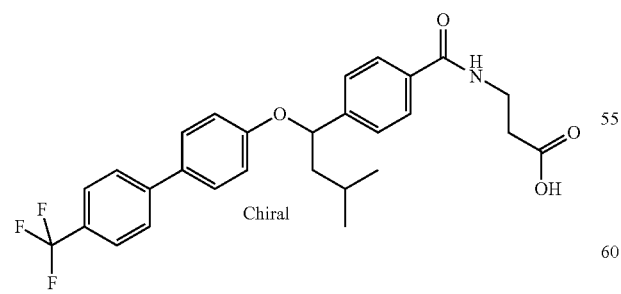

These compounds are made by the general method as exemplified in Example 30 by resolving racemic 3-{4-[3-methyl-1-(4'-trifluoromethyl-biphenyl-4-yloxy)-butyl]-benzoylamino}-propionic acid methyl ester on Chiralpak AD column (4.6×150 mm). Isomer 1 MS (ES): 500.3 [M+H]$^+$. Isomer 2 MS (ES): 500.3 [M+H]$^+$.

Example 34

3-{4-[1-(4'-Trifluoromethyl-biphenyl-4-yloxy)-propyl]-benzoylamino}-propionic acid, Isomer 1 and

Example 35

3-{4-[1-(4'-Trifluoromethyl-biphenyl-4-yloxy)-propyl]-benzoylamino}-propionic acid, Isomer 2

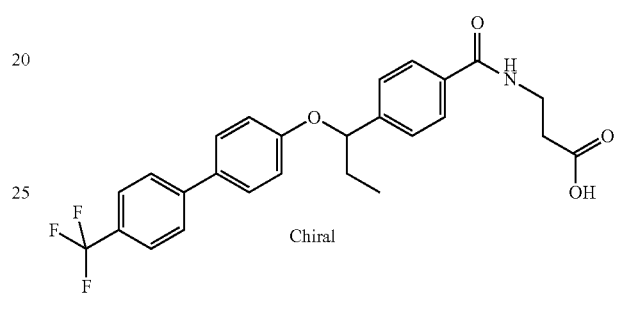

These compounds are made by the general method as exemplified in Example 30 by resolving racemic 3-{4-[1-(4'-trifluoromethyl-biphenyl-4-yloxy)-propyl]-benzoylamino}-propionic acid methyl ester on Chiralpak AD column (4.6×150 mm). Isomer 1 MS (ES): 470.2 [M−H]$^-$. Isomer 2 MS (ES): 470.2 [M−H]$^-$.

Example 36

3-{4-[1-(4'-tert-Butyl-biphenyl-4-yloxy)-propyl]-benzoylamino}-propionic acid, Isomer 1 and

Example 37

3-{4-[1-(4'-tert-Butyl-biphenyl-4-yloxy)-propyl]-benzoylamino}-propionic acid, Isomer 2

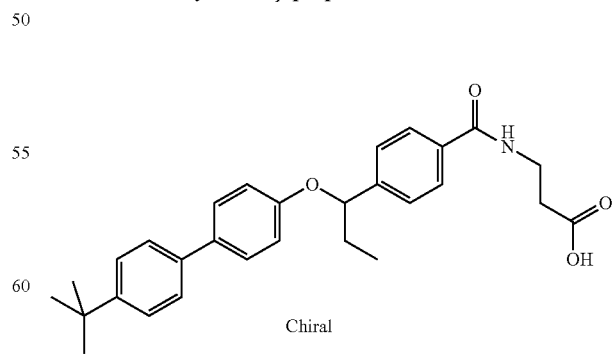

These compounds are made by the general method as exemplified in Example 30 by resolving racemic 3-{4-[1-(4'-tert-butyl-biphenyl-4-yloxy)-propyl]-benzoylamino}-propionic acid methyl ester on Chiralpak AD column (4.6×150 mm). Isomer 1 MS (ES): 458.3 [M−H]⁻. Isomer 2 MS (ES): 458.3 [M−H]⁻.

umn (4.6×150 mm). Isomer 1 MS (ES): 488.3 [M+H]⁺. Isomer 2 MS (ES): 488.3 [M+H]⁺.

Example 38

3-{4-[1-(4'-tert-Butyl-biphenyl-4-yloxy)-heptyl]-benzoylamino}-propionic acid, Isomer 1 and Example 39

3-{4-[1-(4'-tert-Butyl-biphenyl-4-yloxy)-heptyl]-benzoylamino}-propionic acid, Isomer 2

Example 42

3-{4-[1-(4'-Trifluoromethyl-biphenyl-4-ylsulfanyl)-heptyl]-benzoylamino}-propionic acid, Isomer 1 and Example 43

3-{4-[1-(4'-Trifluoromethyl-biphenyl-4-ylsulfanyl)-heptyl]-benzoylamino}-propionic acid, Isomer 2

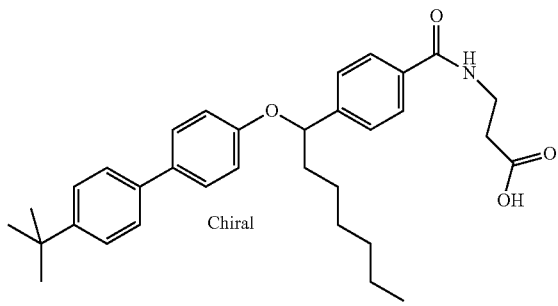 [SMILES: CCCCCCC(Oc1ccc(-c2ccc(C(C)(C)C)cc2)cc1)c1ccc(C(=O)NCCC(=O)O)cc1]

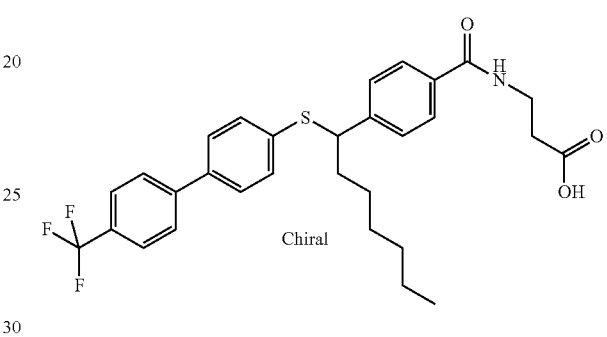

These compounds are made by the general method as exemplified in Example 30 by resolving racemic 3-{4-[1-(4'-tert-butyl-biphenyl-4-yloxy)-heptyl]-benzoylamino}-propionic acid methyl ester on Chiralpak AD column (4.6×150 mm). Isomer 1 MS (ES): 516.3 [M+H]⁺. Isomer 2 MS (ES): 516.3 [M+H]⁺.

These compounds are made by the general method as exemplified in Example 30 by resolving racemic 3-{4-[1-(4'-Trifluoromethyl-biphenyl-4-ylsulfanyl)-heptyl]-benzoylamino}-propionic acid methyl ester on Chiralcel OD column (4.6×150 mm). Isomer 1 MS (ES): 543.2 [M−H]⁻. Isomer 2 MS (ES): 543.2 [M−H]⁻.

Example 40

3-{4-[1-(4'-tert-Butyl-biphenyl-4-yloxy)-3-methyl-butyl]-benzoylamino}-propionic acid, Isomer 1 and Example 41

3-{4-[1-(4'-tert-Butyl-biphenyl-4-yloxy)-3-methyl-butyl]-benzoylamino}-propionic acid, Isomer 2

Example 44

3-{4-[1-(4'-tert-Butyl-biphenyl-4-yloxy)-pentyl]-benzoylamino}-propionic acid, Isomer 1 and Example 45

3-{4-[1-(4'-tert-Butyl-biphenyl-4-yloxy)-pentyl]-benzoylamino}-propionic acid, Isomer 2

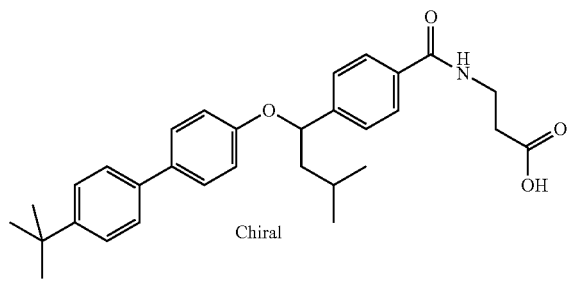 [SMILES: CC(C)CC(Oc1ccc(-c2ccc(C(C)(C)C)cc2)cc1)c1ccc(C(=O)NCCC(=O)O)cc1]

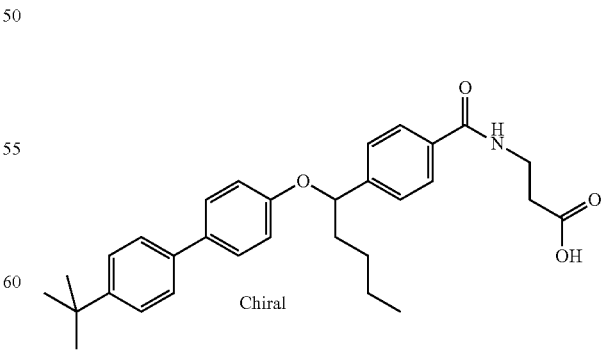

These compounds are made by the general method as exemplified in Example 30 by resolving racemic 3-{4-[1-(4'-tert-butyl-biphenyl-4-yloxy)-3-methyl-butyl]-benzoylamino}-propionic acid methyl ester on Chiralpak AD col- These compounds are made by the general method as exemplified in Example 30 by resolving racemic 3-{4-[1-(4'-tert-Butyl-biphenyl-4-yloxy)-pentyl]benzoylamino}-propionic acid methyl ester on Chiralpak AD column (4.6×150 mm). Isomer 1 MS (ES): 489.44 [M+H]+. Isomer 2 MS (ES): 489.44 [M+H]+.

Example 46

3-{4-[2-Methyl-1-(4'-trifluoromethyl-biphenyl-4-yloxy)-propyl]-benzoylamino}-propionic acid, Isomer 1 and

Example 47

3-{4-[2-Methyl-1-(4'-trifluoromethyl-biphenyl-4-yloxy)-propyl]-benzoylamino}-propionic acid, Isomer 2

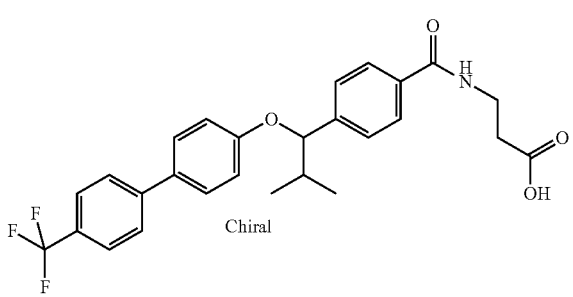 [SMILES: CC(C)C(Oc1ccc(-c2ccc(C(F)(F)F)cc2)cc1)c1ccc(C(=O)NCCC(=O)O)cc1]

These compounds are made by the general method as exemplified in Example 30 by resolving racemic 3-{4-[2-Methyl-1-(4'-trifluoromethyl-biphenyl-4-yloxy)-propyl]-benzoylamino}-propionic acid methyl ester on Chiralpak AD column (4.6×150 mm). Isomer 1 MS (ES): 486.2 [M+H]+, Isomer 2 MS (ES): 486.2 [M+H]+.

Example 48

3-{4-[1-(4'-Trifluoromethyl-biphenyl-4-yloxy)-pentyl]-benzoylamino}-propionic acid, Isomer 1 and

Example 49

3-{4-[1-(4'-Trifluoromethyl-biphenyl-4-yloxy)-pentyl]-benzoylamino}-propionic acid, Isomer 2

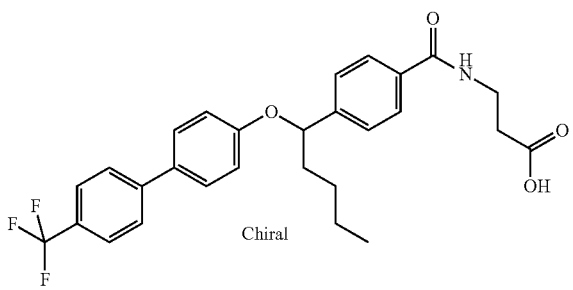 [SMILES: CCCCC(Oc1ccc(-c2ccc(C(F)(F)F)cc2)cc1)c1ccc(C(=O)NCCC(=O)O)cc1]

This compound is made by the general method as exemplified in Example 30 by resolving racemic 3-{4-[1-(4'-trifluoromethyl-biphenyl-4-yloxy)-pentyl]-benzoylamino}- propionic acid methyl ester on Chiralcel OJ column (4.6×150 mm). Isomer 1 MS (ES): 501.2 [M+H]+. Isomer 2 MS (ES): 501.2 [M+H]+.

Example 50

3-{4-[1-(4'-Trifluoromethyl-biphenyl-4-yloxy)-butyl]-benzoylamino}-propionic acid, Isomer 1 and

Example 51

3-{4-[1-(4'-Trifluoromethyl-biphenyl-4-yloxy)-butyl]-benzoylamino}-propionic acid, Isomer 2

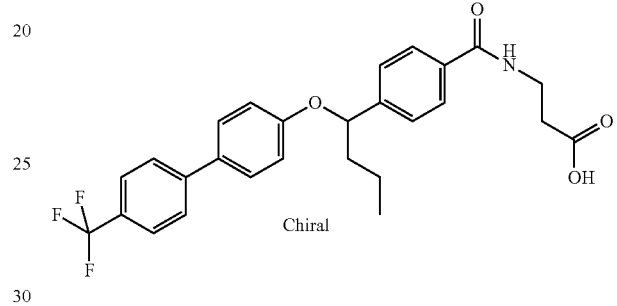

These compounds are made by the general method as exemplified in Example 30 by resolving racemic 3-{4-[1-(4'-trifluoromethyl-biphenyl-4-yloxy)-butyl]-benzoylamino}-propionic acid methyl ester on Chiralcel OJ column (4.6×150 mm). Isomer 1 MS (ES): 486.2 [M+H]+. Isomer 2 MS (ES): 486.2 [M+H]+.

Example 52

3-{4-[1-(4'-tert-Butyl-biphenyl-4-yloxy)-butyl]-benzoylamino}-propionic acid, Isomer 1 and

Example 53

3-{4-[1-(4'-tert-Butyl-biphenyl-4-yloxy)-butyl]-benzoylamino}-propionic acid, Isomer 2

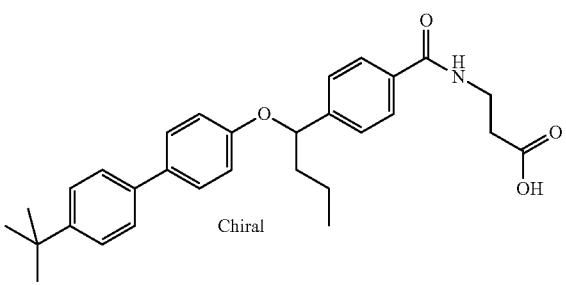 [SMILES: CCCC(Oc1ccc(-c2ccc(C(C)(C)C)cc2)cc1)c1ccc(C(=O)NCCC(=O)O)cc1]

These compounds are made by the general method as exemplified in Example 30 by resolving racemic 3-{4-[1-(4'-tert-butyl-biphenyl-4-yloxy)-butyl]-benzoylamino}-propionic acid methyl ester on Chiralpak AD column (4.6×150 mm). Isomer 1 MS (ES): 475.2 [M+H]⁺. Isomer 2 MS (ES): 475.2 [M+H]⁺.

Example 54

3-(4-{1-[4'-(1-Fluoro-1-methyl-ethyl)-biphenyl-4-ylsulfanyl]-3-methyl-butyl}-benzoylamino)-propionic acid, Isomer 1 and Example 55

3-(4-{1-[4'-(1-Fluoro-1-methyl-ethyl)-biphenyl-4-ylsulfanyl]-3-methyl-butyl}-benzoylamino)-propionic acid, Isomer 2

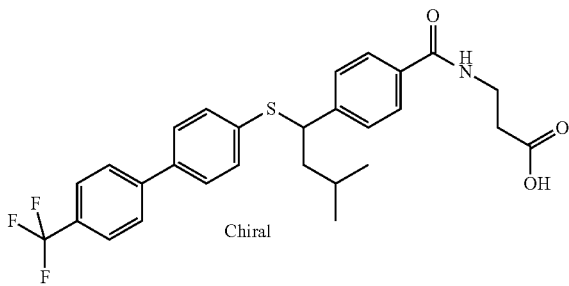 [SMILES: CC(C)CC(Sc1ccc(-c2ccc(C(F)(F)F)cc2)cc1)c1ccc(C(=O)NCCC(=O)O)cc1]

These compounds are made by the general method as exemplified in Example 30 by resolving racemic 3-(4-{1-[4'-(1-fluoro-1-methyl-ethyl)-biphenyl-4-ylsulfanyl]-3-methyl-butyl}-benzoylamino)-propionic acid methyl ester on Chiralpak AD column (4.6×150 mm). Isomer 1 MS (ES): 517.3 [M+H]⁺. Isomer 2 MS (ES): 517.3 [M+H]⁺.

Example 56

3-(4-{3-Methyl-1-[4-(6-trifluoromethyl-pyridin-3-yl)-phenoxy]-butyl}-benzoylamino)-propionic acid, Isomer 1 and Example 57

3-(4-{3-Methyl-1-[4-(6-trifluoromethyl-pyridin-3-yl)-phenoxy]-butyl}-benzoylamino)-propionic acid, Isomer 2

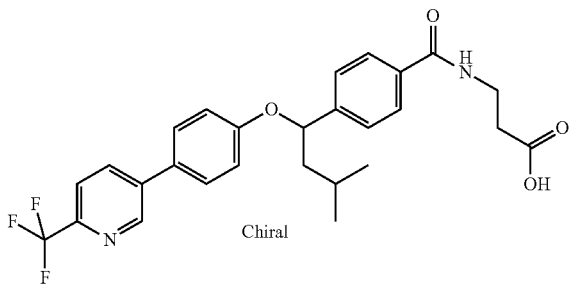 [SMILES: CC(C)CC(Oc1ccc(-c2ccc(C(F)(F)F)nc2)cc1)c1ccc(C(=O)NCCC(=O)O)cc1]

These compounds are made by the general method as exemplified in Example 30 by resolving racemic 3-(4-{3-methyl-1-[4-(6-trifluoromethyl-pyridin-3-yl)-phenoxy]-butyl}-benzoylamino)-propionic acid methyl ester on Chiralpak AD column (4.6×150 mm). Isomer 1 MS (ES): 501.2 [M+H]⁺. Isomer 2 MS (ES): 501.2 [M+H]⁺.

Example 58

3-{4-[1-(4'-Trifluoromethyl-biphenyl-4-yloxy)-nonyl]-benzoylamino}-propionic acid, Isomer 1 and Example 59

3-{4-[1-(4'-Trifluoromethyl-biphenyl-4-yloxy)-nonyl]-benzoylamino}-propionic acid, Isomer 2

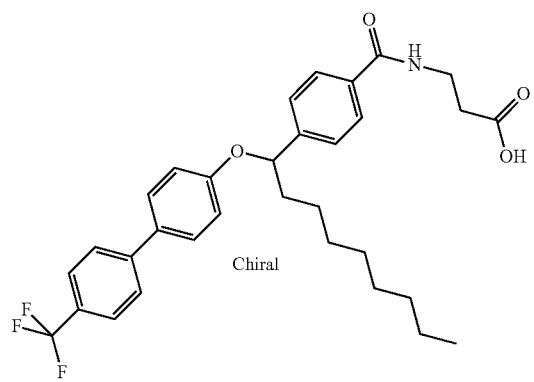 [SMILES: CCCCCCCCC(Oc1ccc(-c2ccc(C(F)(F)F)cc2)cc1)c1ccc(C(=O)NCCC(=O)O)cc1]

These compounds are made by the general method as exemplified in Example 30 by resolving racemic 3-{4-[1-(4'-trifluoromethyl-biphenyl-4-yloxy)-nonyl]-benzoylamino}-propionic acid methyl ester on Chiralpak AD column (4.6×150 mm). Isomer 1 MS (ES): 554.2 [M−H]⁻. Isomer 2 MS (ES): 554.2 [M−H]⁻.

Example 60

3-{4-[1-(4'-Ethyl-biphenyl-4-yloxy)-heptyl]-benzoylamino}-propionic acid, Isomer 1 and Example 61

3-{4-[1-(4'-Ethyl-biphenyl-4-yloxy)-heptyl]-benzoylamino}-propionic acid, Isomer 2

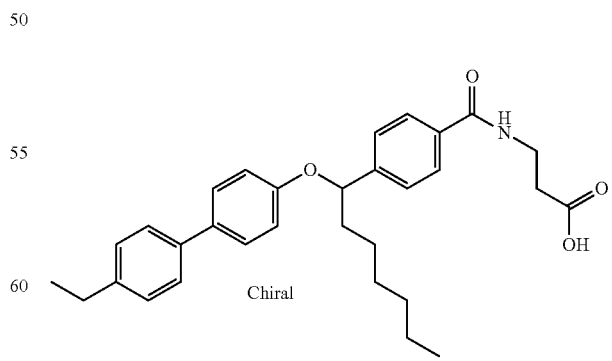

These compounds are made by the general method as exemplified in Example 30 by resolving racemic 3-{4-[1-(4'-ethyl-biphenyl-4-yloxy)-heptyl]-benzoylamino}-propionic

Example 62

3-(4-{1-[6-(4-tert-Butyl-phenyl)-pyridin-3-yloxy]-4,
4-dimethyl-pentyl}-benzoylamino)-propionic acid,
Isomer 1

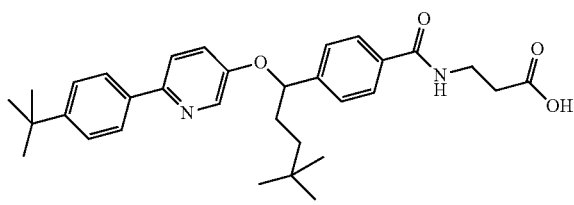 [SMILES: CC(C)(C)CCC(Oc1ccc(-c2ccc(C(C)(C)C)cc2)nc1)c1ccc(C(=O)NCCC(=O)O)cc1]

Step A. 3-(4-Formyl-benzoylamino)-propionic acid methyl ester 4-formyl-benzoic acid (20 g, 133 mmol), CDMT (24 g, 137 mmol), and 4-methyl-morpholine (15.4 mL, 140 mmol) are combined in anhydrous dichloromethane (DCM) (300 mL) under nitrogen. The reaction is allowed to stir under nitrogen at room temperature overnight. Beta-alanine methyl ester hydrochloride (20.4 g, (147 mmol) is then added to the reaction mixture, followed by 4-methylmorpholine (15.4 mL, 140 mmol), and allowed to stir at room temperature. Some water (<10% volume) is added to help solubility. The reaction is monitored by HPLC, and upon complete consumption of the acid, the reaction is diluted with DCM. The reaction is diluted with water and extracted with 1N HCl. The organic layer is washed with water and brine, followed by drying over anhydrous sodium sulfate. The solution is filtered and concentrated and further purified using flash column chromatography (30 g, 128 mmol).

Step B. 3-[4-(1-Hydroxy-4,4-dimethyl-pentyl)-benzoylamino]-propionic acid methyl ester A solution of 3-(4-Formyl-benzoylamino)-propionic acid methyl ester (4.8 g, 20.43 mmol) is dissolved in the anhydrous tetrahydrofuran (THF) (75 mL) and cooled to 0° C. under nitrogen. 2,2-Dimethyl-butyl magnesium bromide (16.3 mL, 1.5M solution in THF, 24.5 mmol) is then added slowly to the solution by addition funnel. The reaction is allowed to stir at 0° C. for 1 hour and the ice bath is removed. The reaction is monitored by TLC or HPLC to determine complete consumption of the aldehyde. The reaction is cooled back down to 0° C. and 1.0N hydrogen chloride solution is dropped in to quench. The solids are dissolved with enough water and the solution is diluted with ether. The two phases are separated and the organic layer is washed with brine, dried over anhydrous sodium sulfate and concentrated. The alcohol (1.6 g, 4.98 mmol) is purified by column chromatography.

Step C. 3-{4-[1-(6-Chloro-pyridin-3-yloxy)-4,4-dimethyl-pentyl]-benzoylamino}-propionic acid methyl ester 3-[4-(1-Hydroxy-4,4-dimethyl-pentyl)-benzoylamino]-propionic acid methyl ester (546 mg, 1.7 mmol) and 6-chloro-pyridin-3-ol (270 mg, 2.09 mmol) are combined in anhydrous toluene (10 mL), degassed, filled with nitrogen for 3 times, and cooled in an ice bath. Tributylphosphine (TBP) (630 uL, 2.55 mmol) is added to the reaction mixture under nitrogen at 0° C., followed by addition of 1,1'-(azodicarbonyl)-dipiperidine (ADDP) (643 mg, 2.55 mmol). The reaction mixture is allowed to warm to room temperature and stirred over night, the mixture is loaded on silica gel column. Chromatography gave the title compound (722 mg, 1.67 mmol).

Step D. 3-(4-{1-[6-(4-tert-Butyl-phenyl)-pyridin-3-yloxy]-4,4-dimethyl-pentyl}-benzoylamino)-propionic acid methyl ester To a solution of 3-{4-[1-(6-chloro-pyridin-3-yloxy)-4,4-dimethyl-pentyl]-benzoylamino}-propionic acid methyl ester (84 mg, 0.19 mmol) in toluene:water (1:1) (2 mL) is added palladium tetrakis triphenylphosphine (22.47 mg, 0.1 mol %), 4-tert-butylphenylboronic acid (58 mg, 0.39 mmol). The reaction is purged with nitrogen and heated to reflux and the potassium fluoride (23 mg, 0.39 mmol) is added. The reaction is monitored by HPLC, and upon completion, allowed to cool to room temperature. The reaction is diluted with ethyl acetate and then Celite is added, followed by water. This mixture is then filtered through a pad of Celite. The solution is separated in a separatory funnel and the organic layer is washed with 0.1N sodium hydroxide, water, and brine. The organic layer is dried over anhydrous sodium sulfate and concentrated. The 5-(4-{1-[6-(4-tert-butyl-phenyl)-pyridin-3-yloxy]-4,4-dimethyl-pentyl}-phenyl)-5-oxo-pentanoic acid methyl ester (80 mg, 0.15 mmol) is purified by flash column chromatography.

Step E. Chiral Separation

The racemic 3-(4-{1-[6-(4-tert-butyl-phenyl)-pyridin-3-yloxy]-4,4-dimethyl-pentyl}-phenyl)-5-oxo-pentanoic acid methyl ester is resolved on a Chiralpak AD-H column (4.6×150 mm). Fluted with Isopropyl Alcohol/Heptane (30/70) and concentrated the fractions to provide a purified enantiomer ester (isomer 1, 98.6% ee).

Step F. 3-(4-{1-[6-(4-tert-Butyl-phenyl)-pyridin-3-yloxy]-4,4-dimethyl-pentyl}-benzoylamino)-propionic acid 3-(4-{1-[6-(4-tert-Butyl-phenyl)-pyridin-3-yloxy]-4,4-dimethyl-pentyl}-benzoylamino)-propionic acid methyl ester (isomer 1, 80 mg, 0.15 mmol) is dissolved in the tetrahydrofuran (1 mL) and sodium hydroxide solution (5 M, 1.0 mL, 5 mmol) is added. The reaction is monitored by HPLC, and upon complete conversion, the reaction is neutralized with 5N HCl, diluted with diethyl ether and water. The two phases are separated, and the organic layer is washed, dried,

--- acid methyl ester on Chiralpak AD column (4.6×150 mm). Isomer 1 MS (ES): 488.3 [M+H]+. Isomer 2 MS (ES): 488.3 [M+H]+.

Example 63

Racemic 3-(4-{1-[6-(4-Trifluoromethyl-phenyl)-pyridin-3-yloxy]-heptyl}-benzoylamino)-propionic acid

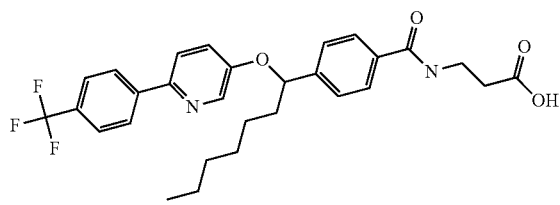 [SMILES: CCCCCCC(Oc1ccc(-c2ccc(C(F)(F)F)cc2)nc1)c1ccc(C(=O)NCCC(=O)O)cc1]

This compound is made by the general method as exemplified in Example 62 using pentylmagnesium chloride in step B and 4-trifluoromethyl phenyl boronic acid in step D as starting materials, without chiral separation in step E. MS (ES): 527.3 [M−H]⁻, the structure was also confirmed by proton NMR.

Example 64

Racemic 3-(4-{4,4,4-Trifluoro-1-[6-(4-trifluoromethyl-phenyl)-pyridin-3-yloxy]-butyl}-benzoylamino)-propionic acid

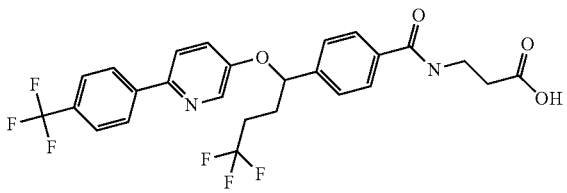 [SMILES: O=C(O)CCNC(=O)c1ccc(C(CCC(F)(F)F)Oc2ccc(-c3ccc(C(F)(F)F)cc3)nc2)cc1]

This compound is made by the general method as exemplified in Example 62 using 3,3,3-trifluoropropylmagnesium bromide in step B and 4-trifluoromethyl phenyl boronic acid in step D as starting materials, without chiral separation in step E. MS (ES): 539.2 [M−H]⁻, the structure was also confirmed by proton NMR.

Example 65

Racemic 3-(4-{3-Methyl-1-[6-(4-trifluoromethyl-phenyl)-pyridin-3-yloxy]-butyl}-benzoylamino)-propionic acid

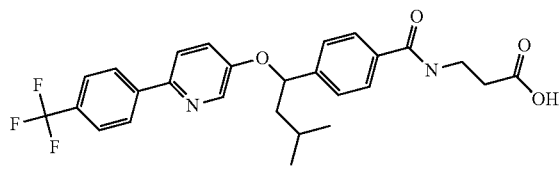 [SMILES: CC(C)CC(Oc1ccc(-c2ccc(C(F)(F)F)cc2)nc1)c1ccc(C(=O)NCCC(=O)O)cc1]

This compound is made by the general method as exemplified in Example 62 using isobutylmagnesium chloride in step B and 4-trifluoromethyl phenyl boronic acid in step D as starting materials, and without chiral separation in step E. MS (ES): 499.3 [M−H]⁻, the structure was also confirmed by proton NMR.

Example 66

Racemic 3-(4-{4,4-Dimethyl-1-[6-(4-trifluoromethyl-phenyl)-pyridin-3-yloxy]-pentyl}-benzoylamino)-propionic acid

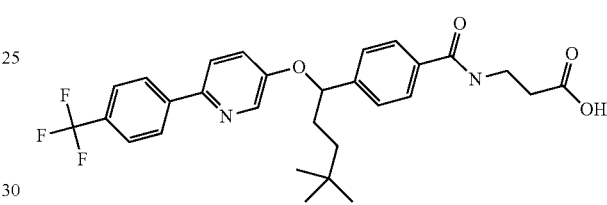

This compound is made by the general method as exemplified in Example 62 using 3,3-dimethylbutyl magnesium bromide in step B and 4-trifluoromethyl phenyl boronic acid in step D as starting materials without chiral separation in step E. MS (ES): 527.2 [M−H]⁻, the structure was also confirmed by proton NMR.

Example 67

Racemic 3-(4-{1-[6-(4-Trifluoromethyl-phenyl)-pyridin-3-yl]-butoxy}-benzoylamino)-propionic acid

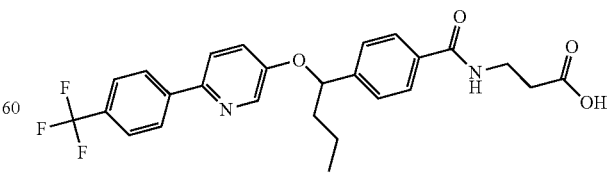

This compound is made by the general method as exemplified in Example 62 using pentylmagnesium chloride in step B and 4-trifluoromethyl phenyl boronic acid in step D as

Example 68

Racemic 3-(4-{1-[6-(4-tert-Butyl-phenyl)-pyridin-3-yloxy]-4,4,4-trifluoro-butyl}-benzoylamino)-propionic acid

This compound is made by the general method as exemplified in Example 62 using 3,3,3-trifluoropropylmagnesium chloride in step B and 4-tert-butylphenyl boronic acid in step D as starting materials. MS (ES): 527.3 [M–H]⁻, the structure was also confirmed by proton NMR.

Example 69

Racemic 3-(4-{1-[6-(4-tert-Butyl-phenyl)-pyridin-3-yloxy]-3-methyl-butyl}-benzoylamino)-propionic acid

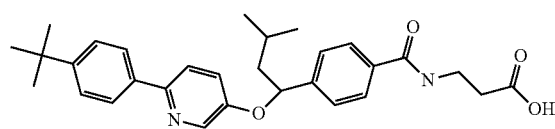 [SMILES: CC(C)CC(Oc1ccc(-c2ccc(C(C)(C)C)cc2)nc1)c1ccc(C(=O)NCCC(=O)O)cc1]

This compound is made by the general method as exemplified in Example 62 using isobutylmagnesium chloride in step B and 4-tert-butylphenyl boronic acid in step D as starting materials. MS (ES): 487.3 [M–H]⁻, the structure was also confirmed by proton NMR.

Example 70

3-(4-{1-[6-(4-tert-Butyl-phenyl)-pyridin-3-yloxy]-4,4-dimethyl-pentyl}-benzoylamino)-propionic acid, enantiomer 2

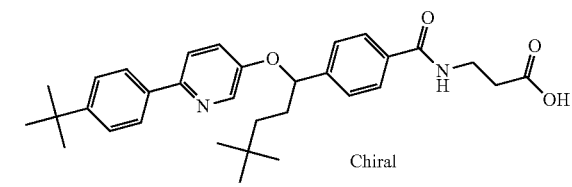 [SMILES: CC(C)(C)CCC(Oc1ccc(-c2ccc(C(C)(C)C)cc2)nc1)c1ccc(C(=O)NCCC(=O)O)cc1]

The racemic 3-(4-{1-[6-(4-tert-butyl-phenyl)-pyridin-3-yloxy]-4,4-dimethyl-pentyl}-benzoylamino)-propionic acid methyl ester (80 mg, 0.15 mmol) is resolved on a Chiralpak AD-H column (0.46×15 cm) with a flow rate of 0.6 mL/min. and detection at 260 nm. Elute with isopropyl alcohol in heptane and concentrate the fractions to provide a purified enantiomer ester (isomer 2, 99.9% ee). Hydrolysis of the enantiomer of the ester provided the title compound as a white solid. MS (ES): 517.3 [M+H]⁺, 515.2 [M–H]⁻, the structure was also confirmed by proton NMR.

Example 71

3-(4-{1-[6-(4-Trifluoromethyl-phenyl)-pyridin-3-yloxy]-heptyl}-benzoylamino)-propionic acid, Isomer 1 and

Example 72

3-(4-{1-[6-(4-Trifluoromethyl-phenyl)-pyridin-3-yloxy]-heptyl}-benzoylamino)-propionic acid, Isomer 2

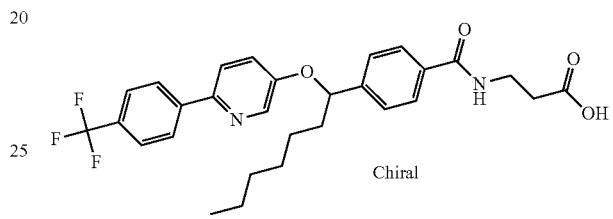

These compounds are made by the general method as exemplified in Example 70 by resolving racemic 3-(4-{1-[6-(4-trifluoromethyl-phenyl)-pyridin-3-yloxy]-heptyl}-benzoylamino)-propionic acid methyl ester on a Chiralpak AD-H column (4.6×150 mm) with a flow rate of 0.6 mL/min. and detection at 260 nm. Elute with acetonitrile in 3 A alcohol (isomer 2, 99.9% ee). Isomer 1 MS (ES): 527.2 [M–H]⁻, the structure was also confirmed by proton NMR; Isomer 2 MS (ES): 527.2 [M–H]⁻, the structure was also confirmed by proton NMR.

Example 73

3-(4-{4,4,4-Trifluoro-1-[6-(4-trifluoromethyl-phenyl)-pyridin-3-yloxy]-butyl}-benzoylamino)-propionic acid, Isomer 1 and

Example 74

3-(4-{4,4,4-Trifluoro-1-[6-(4-trifluoromethyl-phenyl)-pyridin-3-yloxy]-butyl}-benzoylamino)-propionic acid, Isomer 2

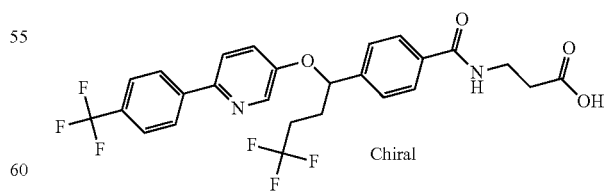

These compounds are made by the general method as exemplified in Example 70 by resolving racemic 3-(4-{4,4,4-trifluoro-1-[6-(4-trifluoromethyl-phenyl)-pyridin-3-yloxy]-butyl}-benzoylamino)-propionic acid methyl ester on a Chiralpak AD-H column (4.6×150 mm) with a flow rate of 0.6 mL/min. and detection at 260 nm. Elute with acetonitrile in 3 A alcohol (isomer 2, 99.8% ee). Isomer 1 MS (ES): 539.2 [M−H]⁻, the structure was also confirmed by proton NMR; Isomer 2 MS (ES): 539.2 [M−H]⁻, the structure was also confirmed by proton NMR.

Example 75

3-(4-{1-[6-(4-tert-Butyl-phenyl)-pyridin-3-yloxy]-butyl}-benzoylamino)-propionic acid, Isomer 1 and Example 76

3-(4-{1-[6-(4-tert-Butyl-phenyl)-pyridin-3-yloxy]-butyl}-benzoylamino)-propionic acid, Isomer 2

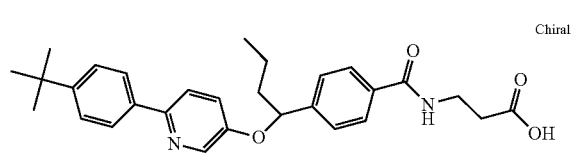 [SMILES: CCCC(Oc1ccc(-c2ccc(C(C)(C)C)cc2)nc1)c1ccc(C(=O)NCCC(=O)O)cc1]

These compounds are made by the general method as exemplified in Example 70 by resolving racemic 3-(4-{1-[6-(4-tert-butyl-phenyl)-pyridin-3-yloxy]-butyl}-benzoylamino)-propionic acid methyl ester on a Chiralpak AD-H column (0.46×15 cm) with a flow rate of 0.6 mL/min. and detection at 260 nm. Eluted with isopropyl alcohol in heptane (isomer 2, >99% ee). MS (ES): 473.2 [M−H]⁻, the structure was also confirmed by proton NMR; MS (ES): 473.2 [M−H]⁻, the structure was also confirmed by proton NMR.

Example 77

Racemic 3-(4-{1-[6-(4-Isobutyl-phenyl)-pyridin-3-yloxy]-butyl}-benzoylamino)-propionic acid

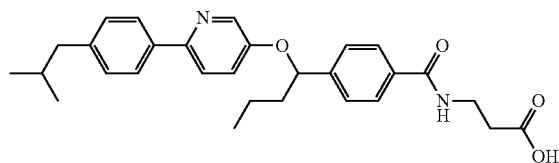 [SMILES: CCCC(Oc1ccc(-c2ccc(CC(C)C)cc2)nc1)c1ccc(C(=O)NCCC(=O)O)cc1]

This compound is made by the general method as exemplified in Example 62 using propylmagnesium chloride in step B and 4-isobutylphenyl boronic acid in step D as starting materials, without chiral separation in step E. MS (ES): 473.4 [M−H]⁻, the structure was also confirmed by proton NMR.

Example 78

Racemic 3-{4-[1-(3'-Trifluoromethyl-biphenyl-4-ylsulfanyl)-heptyl]-benzoylamino}-propionic acid

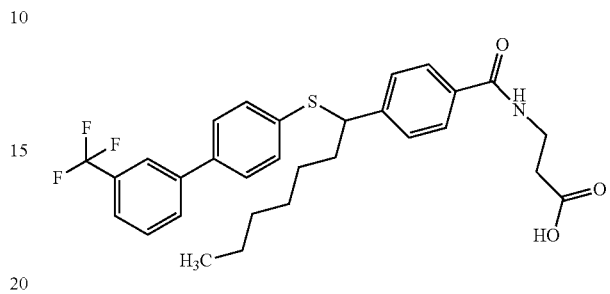

Step A. 4-[1-(4-Bromo-phenylsulfanyl)-3-methyl-butyl]benzoic acid

To a solution of 4-(1-hydroxy-3-methyl-heptyl)-benzoic acid methyl ester (1760 mg, 7.04 mmol) in toluene (70 mL) is added 1,1'-(azodicarbonyl)dipiperidine (ADDP, 2664 mg, 10.56 mmol) at 0° C., followed by the additions of tributylphosphine (2.63 mL, 8.38 mmol) and 4-bromo-benzenethiol (1597 mg, 8.45 mmol). The reaction mixture is warmed up to room temperature and stirred overnight. The mixture is loaded on silica gel, eluted with hexanes with a gradient from 0% of ethyl acetate to 50% of ethyl acetate giving 4-[1-(4-bromo-phenylsulfanyl)-heptyl]-benzoic acid methyl ester. 1700 mg of the ester product is taken into ethanol (5 mL), treated with sodium hydroxide (5N aqueous, 2 mL) for 3 h at room temperature. The mixture is concentrated, diluted with ethyl acetate, acidified with 5 N HCl (2 mL), and extracted with ethyl acetate. The organic layers are dried and concentrated giving 4-[1-(4-bromo-phenylsulfanyl)-3-methyl-heptyl]-benzoic acid (1700 mg).

Step B. Racemic 3-{4-[1-(4-Bromo-phenylsulfanyl)-3-methyl-heptyl]-benzoylamino}-propionic acid methyl ester To a mixture of 4-[1-(4-bromo-phenylsulfanyl)-3-methyl-heptyl]benzoic acid (1700 mg, 4.18 mmol) in methylene chloride (42 mL) are added triethyl amine (1.75 mL, 12.53 mmol), DMAP (5.0 mg), 3-amino-propionic acid methyl ester (875 mg, 6.27 mmol) and EDCI (2408 mg, 12.53 mmol) at room temperature. The reaction mixture is stirred at room temperature overnight, loaded on silica gel, eluted with eluted with hexanes with a gradient from 0% of ethyl acetate to 100% of ethyl acetate giving 3-{4-[1-(4-bromo-phenylsulfanyl)-3-methyl-heptyl]-benzoylamino}-propionic acid methyl ester (1.640 mg).

Step C. Racemic 3-{4-[3-Methyl-1-(4'-trifluoromethoxy-biphenyl-4-ylsulfanyl)-heptyl]-benzoylamino}-propionic acid 3-{4-[1-(4-bromo-phenylsulfanyl)-3-methyl-heptyl]-benzoylamino}-propionic acid methyl ester (100 mg, 0.2 mmol), potassium carbonate (83 mg, 0.6 mmol), 3-trifluoromethoxyphenyl boronic acid (76 mg, 0.4 mmol) and tetrakis-(triphenylphosphine)palladium (23 mg, 0.02 mmol) are placed in a flask. After the reaction is purged with $N_2$ for several times, THF/$H_2O$ (20 ml/5 ml) is added. The resulting solution is refluxed overnight, concentrated, diluted with ethyl acetate, acidified with 1 N HCl (0.6 mL), extracted with ethyl acetate. The organic layers are dried and purified with reverse phase HPLC to afford the title compound (58 mg). MS (ES): 544.1 $[M+H]^+$.

Example 79

Racemic 3-{4-[1-(4'-Acetyl-biphenyl-4-ylsulfanyl)-heptyl]-benzoylamino}-propionic acid

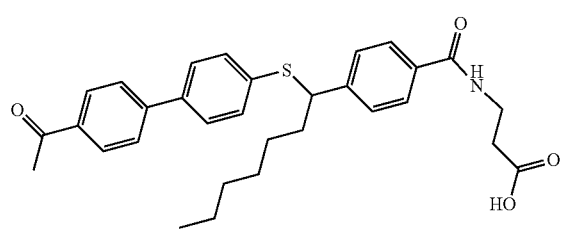 [SMILES: CCCCCCC(Sc1ccc(-c2ccc(C(C)=O)cc2)cc1)c1ccc(C(=O)NCCC(=O)O)cc1]

This compound is made in a substantially similar manner as Example 78 using 4-acetylphenyl boronic acid as reagent in step C. MS (ES): 518.3 $[M+H]^+$.

Example 80

Racemic 3-{4-[1-(3',4'-dimethyl-biphenyl-4-ylsulfanyl)-heptyl]-benzoylamino}-propionic acid

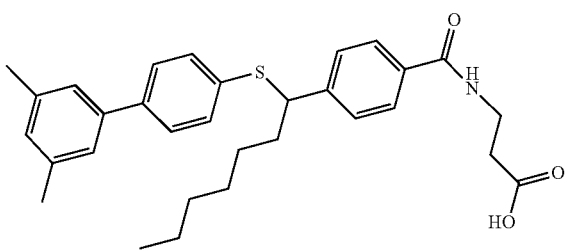 [SMILES: CCCCCCC(Sc1ccc(-c2cc(C)cc(C)c2)cc1)c1ccc(C(=O)NCCC(=O)O)cc1]

This compound is made in a substantially similar manner as Example 78 using 3,4-dimethylphenyl boronic acid as reagent in step C. MS (ES): 504.3 $[M+H]^+$.

Example 81

Racemic 3-{4-[1-(4'-methylsulfonyl-biphenyl-4-ylsulfanyl)-heptyl]-benzoylamino}-propionic acid

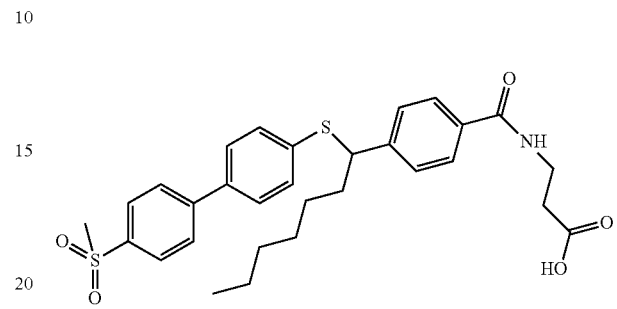

This compound is made in a substantially similar manner as Example 78 using 4-methylsulfonylphenyl boronic acid as reagent in step C. MS (ES): 554.3 $[M+H]^+$.

Example 82

Racemic 3-{4-[1-(2',3'-dimethyl-biphenyl-4-ylsulfanyl)-heptyl]-benzoylamino}-propionic acid

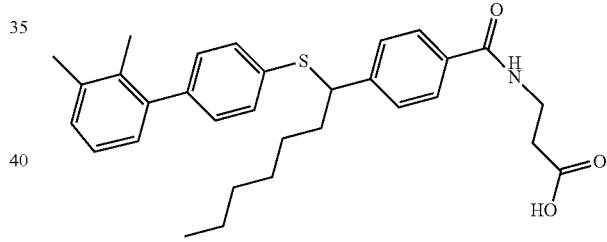

This compound is made in a substantially similar manner as Example 78 using 2,3-dimethylphenyl boronic acid as reagent in step C. MS (ES): 504.2 $[M+H]^+$.

Example 83

Racemic 3-{4-[1-(2',6'-dimethyl-biphenyl-4-ylsulfanyl)-heptyl]-benzoylamino}-propionic acid

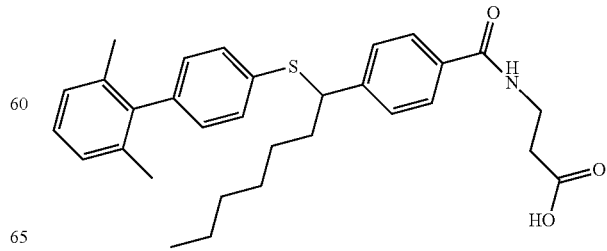

This compound is made in a substantially similar manner as Example 78 using 2,6-dimethylphenyl boronic acid as reagent in step C. MS (ES): 504.2 [M+H]⁺.

Example 84

Racemic 3-{4-[1-(3'-isopropyl-biphenyl-4-ylsulfanyl)-heptyl]-benzoylamino}-propionic acid

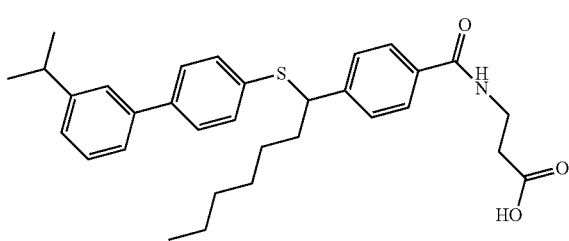 [SMILES: CCCCCCC(Sc1ccc(-c2cccc(C(C)C)c2)cc1)c1ccc(C(=O)NCCC(=O)O)cc1]

This compound is made in a substantially similar manner as Example 78 using 3-isopropylphenyl boronic acid as reagent in step C. MS (ES): 518.3 [M+H]⁺.

Example 85

Racemic 3-{4-[1-(3'-acetyl-biphenyl-4-ylsulfanyl)-heptyl]-benzoylamino}-propionic acid

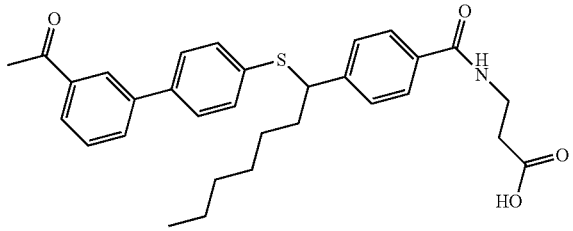 [SMILES: CCCCCCC(Sc1ccc(-c2cccc(C(C)=O)c2)cc1)c1ccc(C(=O)NCCC(=O)O)cc1]

This compound is made in a substantially similar manner as Example 78 using 3-acetylphenyl boronic acid as reagent in step C. MS (ES): 518.3 [M+H]⁺.

Example 86

Racemic 3-{4-[1-(4'-pentyl-biphenyl-4-ylsulfanyl)-heptyl]-benzoylamino}-propionic acid

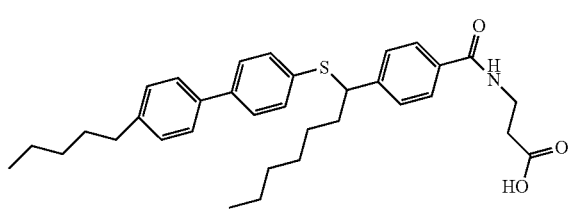 [SMILES: CCCCCCC(Sc1ccc(-c2ccc(CCCCC)cc2)cc1)c1ccc(C(=O)NCCC(=O)O)cc1]

This compound is made in a substantially similar manner as Example 78 using 4-pentylphenyl boronic acid as reagent in step C. MS (ES): 546.3 [M+H]⁺.

Example 87

Racemic 3-{4-[1-(4'-cyclohexyl-biphenyl-4-ylsulfanyl)-heptyl]-benzoylamino}-propionic acid

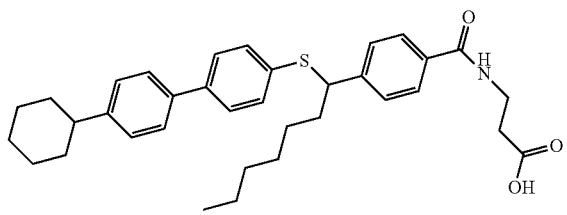 [SMILES: CCCCCCC(Sc1ccc(-c2ccc(C3CCCCC3)cc2)cc1)c1ccc(C(=O)NCCC(=O)O)cc1]

This compound is made in a substantially similar manner as Example 78 using 4-cyclohexylphenyl boronic acid as reagent in step C. MS (ES): 558.3 [M+H]⁺.

Example 88

Racemic 3-{4-[1-(4-Allyloxy-phenoxy)-heptyl]-benzoylamino}-propionic acid

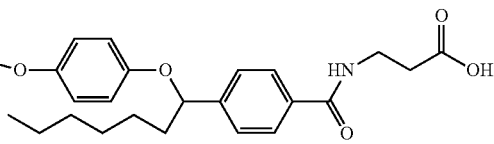

This compound is made in a substantially similar manner as Example 1 using 4-(1-hydroxy-heptyl)-benzoic acid methyl ester and 4-allyloxy-phenol as reagents in step A. MS (ES): 438.3 [M−H]⁻.

Example 89

Racemic 3-{4-[1-(2,2,3,3-Tetrafluoro-2,3-dihydro-benzo[1,4]dioxin-6-yloxy)-heptyl]-benzoylamino}-propionic acid

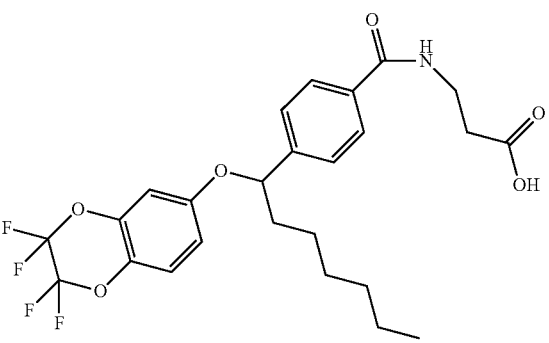 [SMILES: CCCCCCC(Oc1ccc2c(c1)OC(F)(F)C(F)(F)O2)c1ccc(C(=O)NCCC(=O)O)cc1]

This compound is made in a substantially similar manner as Example 1 using 4-(1-hydroxy-heptyl)-benzoic acid methyl ester and 2,2,3,3-tetrafluoro-2,3-dihydro-benzo[1,4]dioxin-6-ol as reagents in step A. MS (ES): 514.2 [M+H]⁺.

Example 90

Racemic 3-(4-{1-[4-(4-Trifluoromethyl-phenoxy)-phenoxy]-heptyl}-benzoylamino)-propionic acid

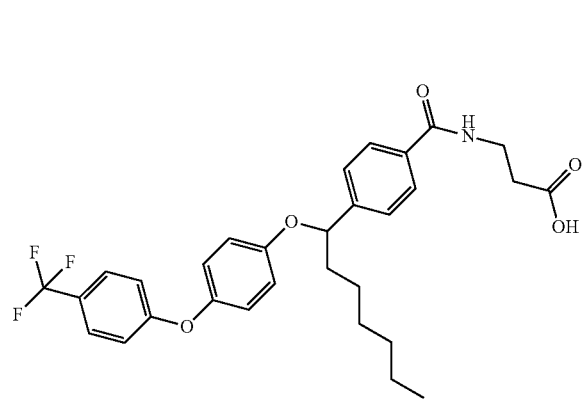 [SMILES: CCCCCCC(Oc1ccc(Oc2ccc(C(F)(F)F)cc2)cc1)c1ccc(C(=O)NCCC(=O)O)cc1]

This compound is made in a substantially similar manner as Example 1 using 4-(1-hydroxy-heptyl)-benzoic acid methyl ester and 4-(4-trifluoromethyl-phenoxy)-phenol as reagents in step A. MS (ES): 544.2 [M+H]⁺.

Example 91

Racemic 3-{4-[1-(4-Pentyl-phenoxy)-heptyl]-benzoylamino}-propionic acid

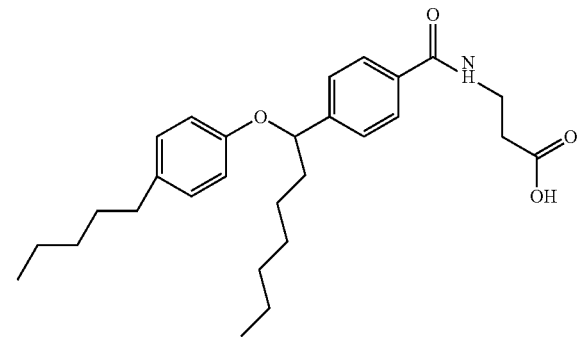 [SMILES: CCCCCCC(Oc1ccc(CCCCC)cc1)c1ccc(C(=O)NCCC(=O)O)cc1]

This compound is made in a substantially similar manner as Example 1 using 4-(1-hydroxy-heptyl)-benzoic acid methyl ester and 4-pentylphenol as reagents in step A. MS (ES): 454.2 [M+H]⁺.

Example 92

Racemic 3-(4-{1-[4-(4-tert-Butyl-benzyloxy)-phenoxy]-heptyl}-benzoylamino)-propionic acid

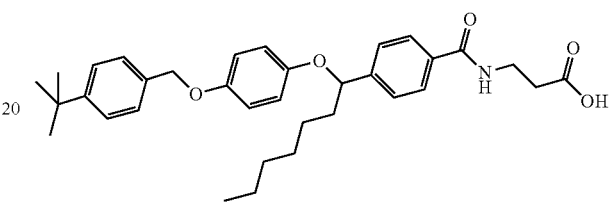

Step 1.

Racemic 3-{4-[1-(4-Allyloxy-phenoxy)-heptyl]-benzoylamino}-propionic acid methyl ester (1.59 g, 3.51 mmol) and triphenyl-phosphine tetrakis palladium (203 mg, 0.18 mmol) are combined with anhydrous tetrahydrofuran (10 mL) in a round bottom flask under nitrogen. Diethyl amine (712 uL, 7.02 mmol) is added and the reaction is allowed to stir under nitrogen at room temperature. The reaction is monitored by HPLC, and upon complete conversion, the reaction is quenched with water. The reaction is diluted with diethyl ether and rinsed with 1N HCl, water, and brine. The ether layer is dried over anhydrous sodium sulfate and concentrated. Racemic 3-{4-[1-(4-Allyloxy-phenoxy)-heptyl]-benzoylamino}-propionic acid methyl ester (1.47 g, 3.50 mmol) is obtained pure after column chromatography.

Step 2.

To 3-{4-[1-(4-Hydroxy-phenoxy)-heptyl]-benzoylamino}-propionic acid methyl ester (70 mg, 0.17 mmol) in anhydrous dimethyl formamide (1.0 mL) is added cesium carbonate (110 mg, 0.34 mmol) in one portion. The mixture is allowed to stir under nitrogen at room temperature and 4-tert-butyl-benzyl bromide is added. The reaction is allowed to stir at room temperature for several hours and is monitored by HPLC. Upon complete consumption of starting material, the reaction is carefully quenched with water, extracted with ethyl acetate, washed, dried, and concentrated. 3-(4-{1-[4-(4-tert-Butyl-benzyloxy)-phenoxy]-heptyl}-benzoylamino)-propionic acid methyl ester is purified by column chromatography.

Step 3.

The 3-(4-{1-[4-(4-tert-Butyl-benzyloxy)-phenoxy]-heptyl}-benzoylamino)-propionic acid methyl ester is dissolved in the THF (1.0 mL) and 5N NaOH (1.0 mL) is added. The mixture is heated to reflux under nitrogen and monitored by HPLC. Upon complete conversion, the reaction is neutralized with 5N HCl (1.0 mL), diluted with diethyl ether and water. The two phases are separated and the organic layer is washed, dried, and concentrated to provide the title compound (80 mg, 0.15 mmol). MS (ES): 544.2 [M−H]⁻.

Example 93

Racemic 3-(4-{1-[4-(3,5-bistrifluoromethyl-benzyloxy)-phenoxy]-heptyl}-benzoylamino)-propionic acid

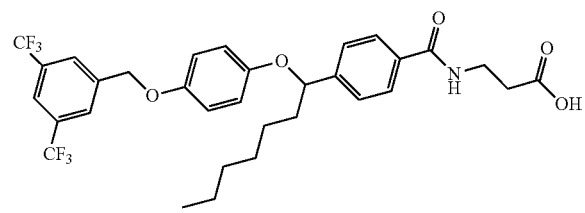 [SMILES: CCCCCCC(Oc1ccc(OCc2cc(C(F)(F)F)cc(C(F)(F)F)c2)cc1)c1ccc(C(=O)NCCC(=O)O)cc1]

This compound is made in a manner substantially similar to Example 92 using 3,5-bistrifluoromethyl-benzyl bromide. MS (ES): 624.2 [M−H]⁻.

Example 94

Racemic 3-(4-{1-[4-(4-isopropyl-benzyloxy)-phenoxy]-heptyl}-benzoylamino)-propionic acid

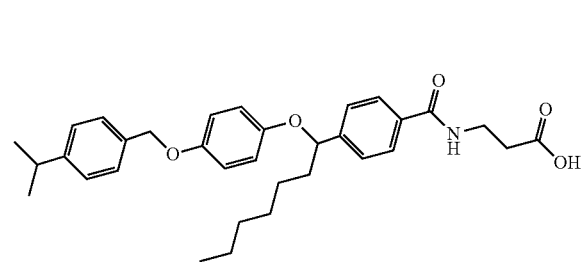 [SMILES: CCCCCCC(Oc1ccc(OCc2ccc(C(C)C)cc2)cc1)c1ccc(C(=O)NCCC(=O)O)cc1]

This compound is made in a manner substantially similar to Example 92 using 4-isopropylbenzyl bromide. MS (ES): 530.2 [M−H]⁻.

Example 95

Racemic 3-(4-{1-[4-(4-chloro-benzyloxy)-phenoxy]-heptyl}-benzoylamino)-propionic acid

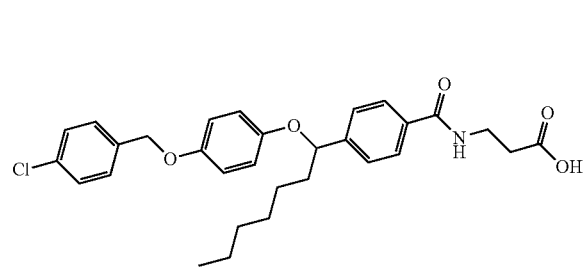 [SMILES: CCCCCCC(Oc1ccc(OCc2ccc(Cl)cc2)cc1)c1ccc(C(=O)NCCC(=O)O)cc1]

This compound is made in a manner substantially similar to Example 92 using 4-chlorobenzyl bromide. MS (ES): 522.2 [M−H]⁻.

Example 96

Racemic 3-(4-{1-[4-(4-ethyl-benzyloxy)-phenoxy]-heptyl}-benzoylamino)-propionic acid

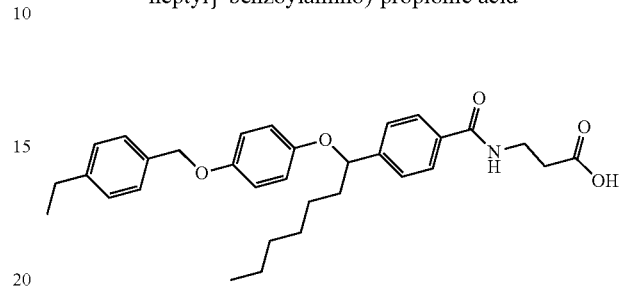

This compound is made in a manner substantially similar to Example 92 using 4-ethylbenzyl bromide. MS (ES): 516.3 [M−H]⁻.

Example 97

Racemic 3-(4-{1-[4-(4-bromo-benzyloxy)-phenoxy]-heptyl}-benzoylamino)-propionic acid

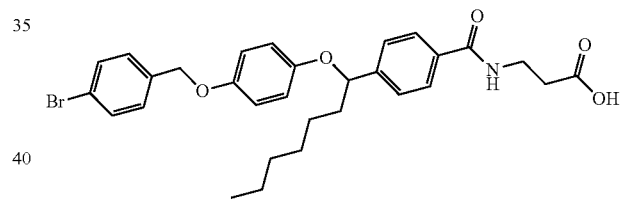

This compound is made in a manner substantially similar to Example 92 using 4-bromobenzyl bromide. MS (ES): 566.2 [M−H]⁻.

Example 98

Racemic 3-(4-{1-[4-(4-fluoro-benzyloxy)-phenoxy]-heptyl}-benzoylamino)-propionic acid

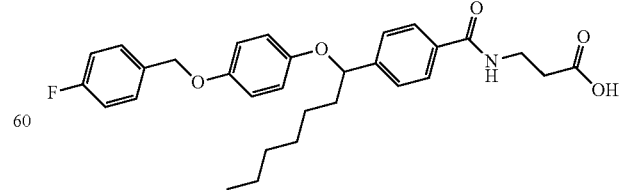

This compound is made in a manner substantially similar to Example 92 using 4-fluorobenzyl bromide. MS (ES): 506.2 [M−H]⁻.

Example 99

Racemic 3-(4-{1-[4-(4-trifluoromethyl-benzyloxy)-phenoxy]-heptyl}-benzoylamino)-propionic acid

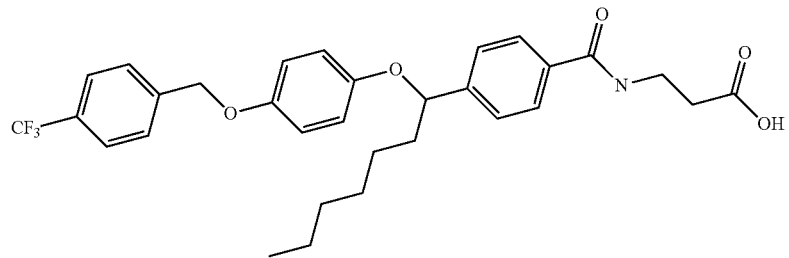 [SMILES: CCCCCCC(Oc1ccc(OCc2ccc(C(F)(F)F)cc2)cc1)c1ccc(C(=O)NCCC(=O)O)cc1]

This compound is made in a manner substantially similar to Example 92 using 4-trifluoromethylbenzyl bromide. MS (ES): 556.3 [M−H]⁻.

Example 100

Racemic 3-(4-{1-[4-(4-phenyl-benzyloxy)-phenoxy]-heptyl}-benzoylamino)-propionic acid

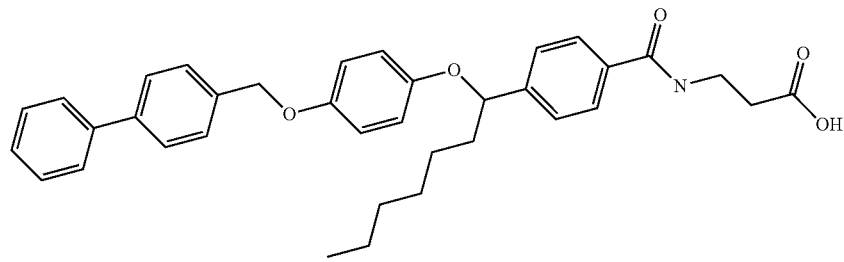 [SMILES: CCCCCCC(Oc1ccc(OCc2ccc(-c3ccccc3)cc2)cc1)c1ccc(C(=O)NCCC(=O)O)cc1]

This compound is made in a manner substantially similar to Example 92 using 4-phenylbenzyl bromide. MS (ES): 564.3 [M−H]⁻.

Example 101

Racemic 3-(4-{1-[4-(3-chloro-benzyloxy)-phenoxy]-heptyl}-benzoylamino)-propionic acid

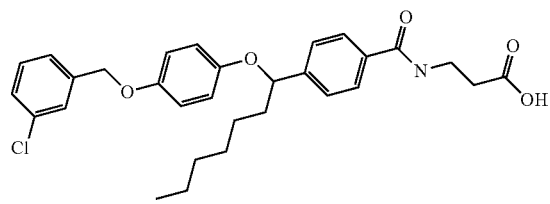 [SMILES: CCCCCCC(Oc1ccc(OCc2cccc(Cl)c2)cc1)c1ccc(C(=O)NCCC(=O)O)cc1]

This compound is made in a manner substantially similar to Example 92 using 3-chlorobenzyl bromide. MS (ES): 522.2 [M−H]⁻.

Example 102

Racemic 3-(4-{1-[4-(3,4-dimethyl-benzyloxy)-phenoxy]-heptyl}-benzoylamino)-propionic acid

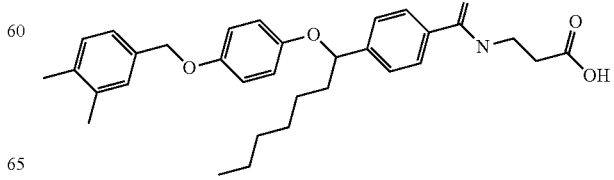

This compound is made in a manner substantially similar to Example 92 using 3,4-dimethylbenzyl bromide as reagent. MS (ES): 516.3 [M−H]⁻.

Example 103

Racemic 3-(4-{1-[4-(4-isopropoxyphenoxy]-heptyl}-benzoylamino)-propionic acid

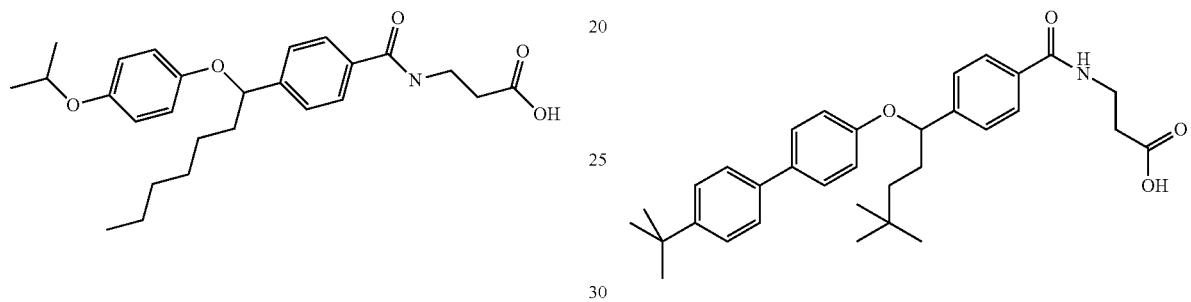

This compound is made in a manner substantially similar to Example 92 using 4-isopropyl iodide. MS (ES): 440.2 [M−H]⁻

.

Example 104

Racemic 3-{4-[1-(3',5'-bistrifluoromethyl-biphenyl-4-yloxy)-heptyl]-benzoylamino}-propionic acid This compound is made by the general method as exemplified in Example 24 using 4-(1-hydroxy-heptyl)-benzoic acid methyl ester and 4-bromophenol as reagents in Step A and 3,5-bitrifluoromethylphenyl boronic acid in Step C as starting materials. MS (ES): 594.2 [M−H]⁻.

Example 105

Racemic 3-{4-[1-(4'-tert-Butyl-biphenyl-4-yloxy)-4,4-dimethyl-pentyl]-benzoylamino}-propionic acid This compound is made by the general method as exemplified in Example 1 using 4'-tert-butyl-biphenyl-4-ol and 4-(1-hydroxy-4,4-dimethyl-pentyl)-benzoic acid methyl ester in step A as starting materials. MS (ES): 516.3 [M+H]⁺.

Example 106

Racemic 3-{4-[1-(4'-trifluoromethyl-biphenyl-4-yloxy)-4,4-dimethyl-pentyl]-benzoylamino}-propionic acid

This compound is made by the general method as exemplified in Example 1 using 4'-trifluoromethyl-biphenyl-4-ol and 4-(1-hydroxy-4,4-dimethyl-pentyl)-benzoic acid methyl ester in step A as starting materials. MS (ES): 526.2 [M−H]⁻.

Example 107

Racemic 3-{4-[1-(4'-tert-Butyl-biphenyl-4-yloxy)-2-methyl-propyl]-benzoylamino}-propionic acid

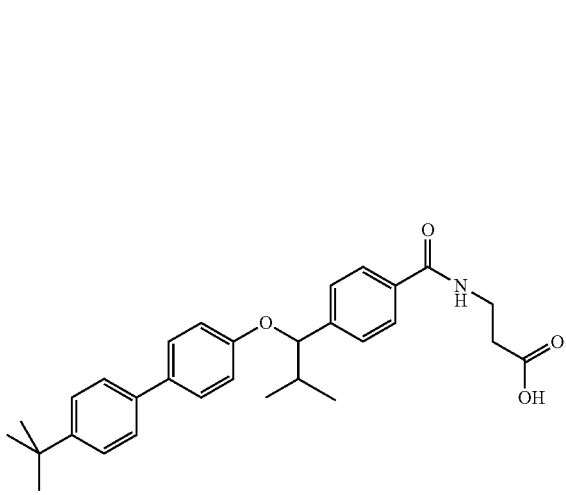 [SMILES: CC(C)C(Oc1ccc(-c2ccc(C(C)(C)C)cc2)cc1)c1ccc(C(=O)NCCC(=O)O)cc1]

This compound is made by the general method as exemplified in Example 1 using 4'-tert-butyl-biphenyl-4-ol and 4-(1-hydroxy-2-methyl-propyl)-benzoic acid methyl ester in step A as starting materials. MS (ES): 474.2 [M+H]⁺.

Example 108

Racemic 3-{4-[1-(4'-trifluoromethyl-biphenyl-4-yloxy)-hexyl]-benzoylamino}-propionic acid

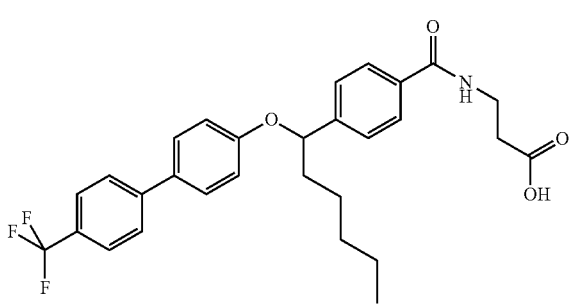 [SMILES: CCCCCC(Oc1ccc(-c2ccc(C(F)(F)F)cc2)cc1)c1ccc(C(=O)NCCC(=O)O)cc1]

This compound is made by the general method as exemplified in Example 1 using 4'-trifluoromethyl-biphenyl-4-ol and 4-(1-hydroxyhexyl)-benzoic acid methyl ester in step A as starting materials. MS (ES): 512.3 [M−H]⁻.

Example 109

3-{4-[1-(3',5'-bistrifluoromethyl-biphenyl-4-yloxy)-heptyl]-benzoylamino}-propionic acid, Isomer 1

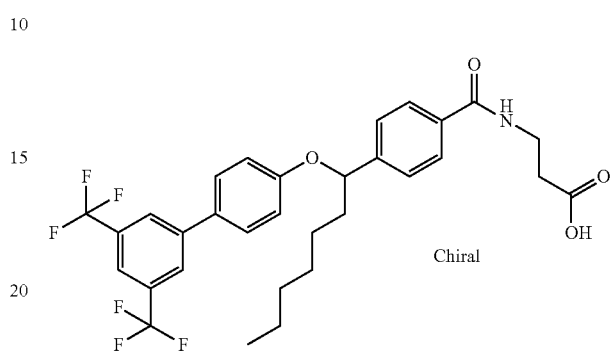

Chiral Separation:

The racemic 3-{4-[1-(4-benzyloxy-phenoxy)-hexyl]-benzoylamino}-propionic acid methyl ester is resolved on a Chiralpak AD-H column (4.6×150 mm). Elute with Isopropyl Alcohol/Heptane (15/85) and concentrate the fractions to provide a purified enantiomer ester (isomer 1, >99% ee). Hydrolysis of the purified enantiomer of the ester provided the title compound as a white solid. MS (ES): 594.2 [M−H]⁻.

Example 110

3-{4-[1-(3',5'-bistrifluoromethyl-biphenyl-4-yloxy)-heptyl]-benzoylamino}-propionic acid, Isomer 2

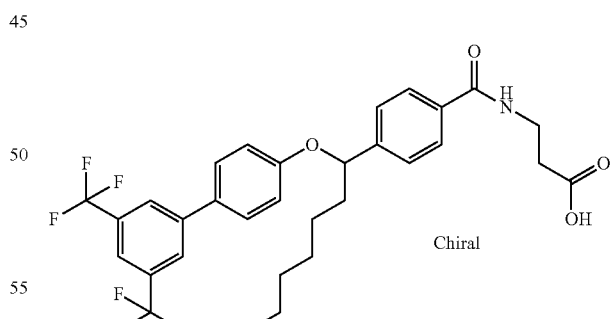

This compound is made by the general method as exemplified in Example 109 by resolving racemic 3-{4-[1-(3',5'-bistrifluoromethyl-biphenyl-4-yloxy)-heptyl]-benzoylamino}-propionic acid methyl ester on Chiralpak AD-H column (4.6×150 mm) eluted with Isopropyl Alcohol/Heptane (15/85). MS (ES): 594.2 [M−H]⁻.

Example 111

3-{4-[1-(4-tert-Butyl-phenoxy)-3-methyl-butyl]-benzoylamino}-propionic acid, Isomer 1 and Example 112

3-{4-[1-(4-tert-Butyl-phenoxy)-3-methyl-butyl]-benzoylamino}-propionic acid, Isomer 2

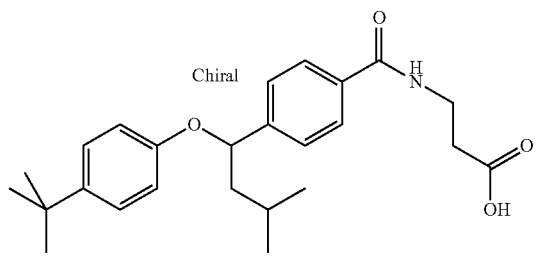 [SMILES: CC(C)CC(Oc1ccc(C(C)(C)C)cc1)c1ccc(C(=O)NCCC(=O)O)cc1]

These compounds are made by the general method as exemplified in Example 109 by resolving racemic 3-{4-[1-(4-tert-butyl-phenoxy)-3-methyl-butyl]-benzoylamino}-propionic acid methyl ester on Chiralpak AD-H column (4.6×150 mm) eluted with Methanol (100%). Isomer 1 MS (ES): 412.3 [M+H]⁺; Isomer 2 MS (ES): 412.3 [M+H]⁺.

Example 113

3-{4-[1-(4'-tertbutyl-biphenyl-4-yloxy)-2-methyl-propyl]-benzoylamino}-propionic acid, Isomer 1 or Example 114

3-{4-[1-(4'-tertbutyl-biphenyl-4-yloxy)-2-methyl-propyl]-benzoylamino}-propionic acid, Isomer 2

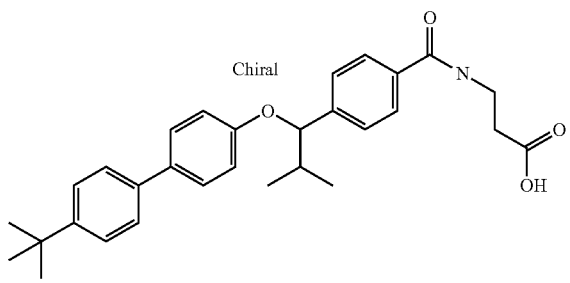 [SMILES: CC(C)C(Oc1ccc(-c2ccc(C(C)(C)C)cc2)cc1)c1ccc(C(=O)NCCC(=O)O)cc1]

These compounds are made by the general method as exemplified in Example 109 by resolving racemic 3-{4-[1-(4'-tertbutyl-biphenyl-4-yloxy)-2-methyl-propyl]-benzoylamino}-propionic acid methyl ester on Chiralpak AD-H column (4.6×150 mm) eluted with Isopropyl Alcohol/Heptane (50/50). Isomer 1 MS (ES): 474.2 [M+H]⁺. Isomer 2 MS (ES): 474.2 [M+H]⁺.

Example 115

3-{4-[1-(4'-trifluoromethyl-biphenyl-4-yloxy)-4,4-dimethyl-pentyl]-benzoylamino}-propionic acid, Isomer 1 and Example 116

3-{4-[1-(4'-trifluoromethyl-biphenyl-4-yloxy)-4,4-dimethyl-pentyl]-benzoylamino}-propionic acid, Isomer 2

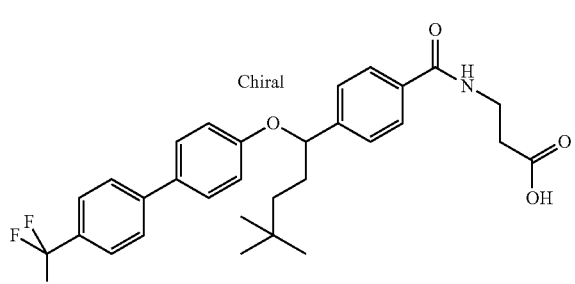

These compounds are made by the general method as exemplified in Example 109 by resolving racemic 3-{4-[1-(4'-trifluoromethyl-biphenyl-4-yloxy)-4,4-dimethyl-pentyl]-benzoylamino}-propionic acid methyl ester on Chiralpak AD-H column (4.6×150 mm) eluted with Propyl Alcohol (100%). Isomer 1 MS (ES): 526.2 [M−H]⁻. Isomer 2 MS (ES): 526.2 [M−H]⁻.

Example 117

3-{4-[1-(4'-Trifluoromethoxy-biphenyl-4-yloxy)-heptyl]-benzoylamino}-propionic acid, Isomer 1

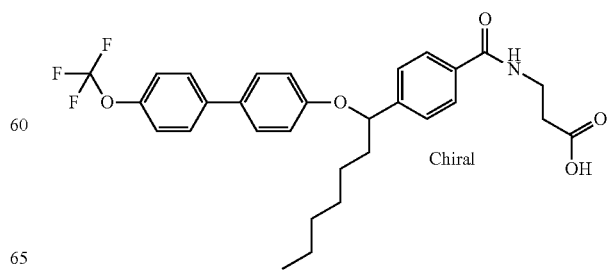

Step A. Racemic 4-[1-(4-Bromo-phenoxyl)-heptyl]-benzoic acid

To a solution of 4-(1-hydroxy-heptyl)-benzoic acid methyl ester (1800 mg, 7.2 mmol) in toluene (72 mL) is added 1,1'-(azodicarbonyl)dipiperidine (ADDP, 2725 mg, 10.8 mmol) at 0° C., followed by the additions of tributylphosphine (2.69 mL, 10.8 mmol) and 4-bromo-phenol (1503 mg, 8.64 mmol). The reaction mixture is warmed up to room temperature and stirred overnight. The mixture is loaded on silica gel, eluted with hexanes with a gradient from 0% of ethyl acetate to 50% of ethyl acetate giving 4-[1-(4-bromo-phenoxyl)-heptyl]-benzoic acid methyl ester. 1900 mg of the ester product is taken into ethanol (5 mL), treated with sodium hydroxide (5N aqueous, 2 mL) for 3 h at room temperature. The mixture is concentrated, diluted with ethyl acetate, acidified with 5 N HCl (2 mL), and extracted with ethyl acetate. The organic layers are dried and concentrated giving 4-[1-(4-bromo-phenoxyl)-heptyl]-benzoic acid (1800 mg).

Step B. Racemic 3-{4-[1-(4-Bromo-phenoxyl)-heptyl]-benzoylamino}-propionic acid methyl ester To a mixture of 4-[1-(4-bromo-phenoxyl)-heptyl]-benzoic acid (1700 mg, 4.35 mmol) in methylene chloride (43 mL) are added triethyl amine (1.82 mL, 13.4 mmol), DMAP (5.0 mg), 3-amino-propionic acid methyl ester (910 mg, 6.52 mmol) and EDCI (2507 mg, 13.04 mmol) at room temperature. The reaction mixture is stirred at room temperature overnight, loaded on silica gel, eluted with eluted with hexanes with a gradient from 0% of ethyl acetate to 100% of ethyl acetate giving racemic 3-{4-[1-(4-bromo-phenoxyl)-heptyl]-benzoylamino}-propionic acid methyl ester (1660 mg).

Step C. 3-{4-[1-(4-Bromo-phenoxyl)-heptyl]-benzoylamino}-propionic acid methyl ester, isomers 1 and 2

The racemic 3-{4-[1-(4-bromo-phenoxyl)-heptyl]-benzoylamino}-propionic acid methyl ester was resolved on a Chiralpak AD-H column (4.6×150 mm). Elute with Isopropyl Alcohol/Heptane (50/50) and concentrated the fractions to provide a purified enantiomer ester (isomer 1, 99.5% ee, isomer 2, 94.6% ee).

Step D. 3-{4-[1-(4'-Trifluoromethoxy-biphenyl-4-yloxy)-heptyl]-benzoylamino}-propionic acid methyl ester, isomer 1

3-{4-[1-(4-Bromo-phenoxyl)-heptyl]-benzoylamino}-propionic acid methyl ester (isomer 1, 100 mg, 0.21 mmol), potassium carbonate (85 mg, 0.63 mmol), 4-triflouromethoxyphenyl boronic acid (86 mg, 0.42 mmol) and tetrakis-(triphenylphosphine)palladium (24 mg, 0.021 mmol) are place in a flask. After the reaction is purged with $N_2$ for several times, THF/$H_2O$ (20 ml/5 ml) is added. The resulting solution is refluxed overnight, concentrated and acidified by 1 N HCl (0.6 mL), extracted with ethyl acetate. Combined organic layers are washed with water and brine, dried over sodium sulfate, purified by reverse phase HPLC to give the title compound (40 mg). MS (ES): 526.2 [M–H]$^-$.

Example 118

3-{4-[1-(4'-Trifluoromethoxy-biphenyl-4-yloxy)-heptyl]-benzoylamino}-propionic acid, Isomer 2

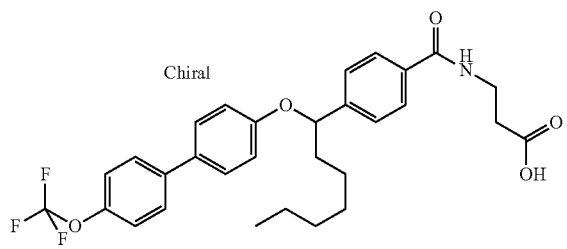 [SMILES: CCCCCCC(Oc1ccc(-c2ccc(OC(F)(F)F)cc2)cc1)c1ccc(C(=O)NCCC(=O)O)cc1]

This compound is made in a substantially similar manner as Example 117 using isomer 2 of 3-{4-[1-(4-bromo-phenoxyl)-heptyl]-benzoylamino}-propionic acid methyl ester as starting material in step D. MS (ES): 526.2 [M–H]$^-$.

Example 119

3-{4-[1-(4'-Trifluoromethyl-biphenyl-4-yloxy)-heptyl]-benzoylamino}-propionic acid, Isomer 1 or

Example 120

3-{4-[1-(4'-Trifluoromethyl-biphenyl-4-yloxy)-heptyl]-benzoylamino}-propionic acid, Isomer 2

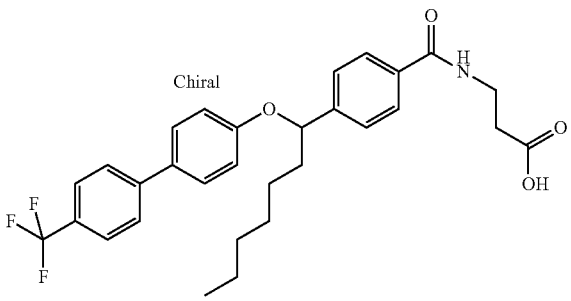 [SMILES: CCCCCCC(Oc1ccc(-c2ccc(C(F)(F)F)cc2)cc1)c1ccc(C(=O)NCCC(=O)O)cc1]

These compounds are made by the general method as exemplified in Example 117 using isomer 2 of 3-{4-[1-(4-bromo-phenoxyl)-heptyl]-benzoylamino}-propionic acid methyl ester and trifluoromethylphenyl boronic acid as starting materials in step D. Isomer 1 MS (ES): 528.3 [M+H]+; Isomer 2 MS (ES): 528.3 [M+H]+.

Example 121

3-{4-[1-(2,2,3,3-Tetrafluoro-2,3-dihydro-benzo[1,4]dioxin-6-yloxy)-heptyl]-benzoylamino}-propionic acid, Isomer 1 and Example 122

3-{4-[1-(2,2,3,3-Tetrafluoro-2,3-dihydro-benzo[1,4]dioxin-6-yloxy)-heptyl]-benzoylamino}-propionic acid, Isomer 2

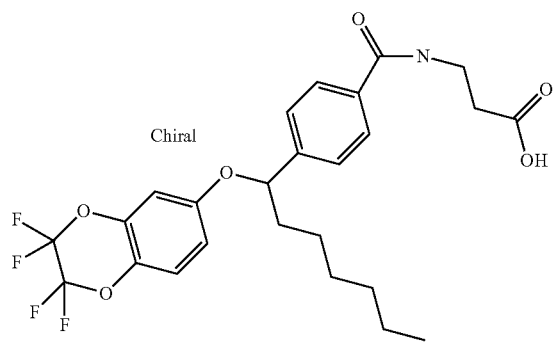 [SMILES: CCCCCCC(Oc1ccc2c(c1)OC(F)(F)C(F)(F)O2)c1ccc(C(=O)NCCC(=O)O)cc1]

This compound is made by the general method as exemplified in Example 109 by resolving racemic 3-{4-[1-(2,2,3,3-tetrafluoro-2,3-dihydro-benzo[1,4]dioxin-6-yloxy)-heptyl]-benzoylamino}-propionic acid methyl ester on Chiralpak AD-H column (4.6×150 mm) eluted with Propyl Alcohol/Heptane (15/85). Isomer 1 MS (ES): 512.3 [M–H]−; Isomer 2 MS (ES): 514.2 [M+H]+.

Example 123

3-(4-{1-[4-(4-Trifluoromethyl-phenoxy)-phenoxy]-heptyl}-benzoylamino)-propionic acid, Isomer 1 and Example 124

3-(4-{1-[4-(4-Trifluoromethyl-phenoxy)-phenoxy]-heptyl}-benzoylamino)-propionic acid, Isomer 2

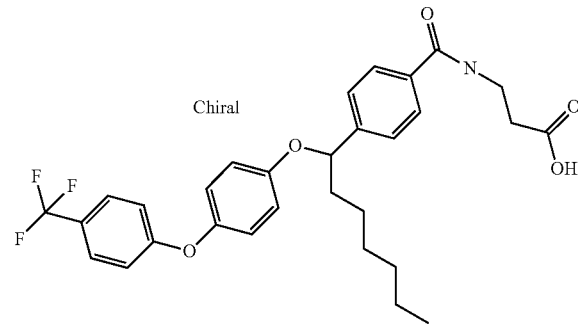 [SMILES: CCCCCCC(Oc1ccc(Oc2ccc(C(F)(F)F)cc2)cc1)c1ccc(C(=O)NCCC(=O)O)cc1]

These compounds are made by the general method as exemplified in Example 109 by resolving racemic 3-(4-{1-[4-(4-trifluoromethyl-phenoxy)-phenoxy]-heptyl}-benzoylamino)-propionic acid methyl ester on Chiralpak AD-H column (4.6×150 mm) eluted with Propyl Alcohol/Heptane (15/85). Isomer 1 MS (ES): 542.3 [M–H]−. Isomer 2 MS (ES): 542.3 [M–H]−.

Example 125

3-{4-[1-(4'-Trifluoromethyl-biphenyl-4-yloxy)-hexyl]-benzoylamino}-propionic acid, Isomer 1 and Example 126

3-{4-[1-(4'-Trifluoromethyl-biphenyl-4-yloxy)-hexyl]-benzoylamino}-propionic acid, Isomer 2

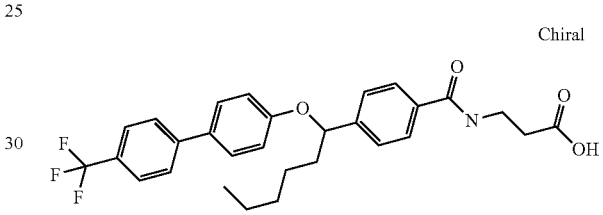

These compounds are made by the general method as exemplified in Example 109 by resolving racemic 3-{4-[1-(4'-trifluoromethyl-biphenyl-4-yloxy)-hexyl]-benzoylamino}-propionic acid methyl ester on Chiralcel OJ-H column (4.6×150 mm) eluted with MeOH (100%). Isomer 1 MS (ES): 512.3 [M–H]−. Isomer 2 MS (ES): 512.3 [M–H]−.

Example 127

3-(4-{1-[4'-isopropyl-biphenyl-4-ylsulfanyl]-butyl}-benzoylamino)-propionic acid, Isomer 1

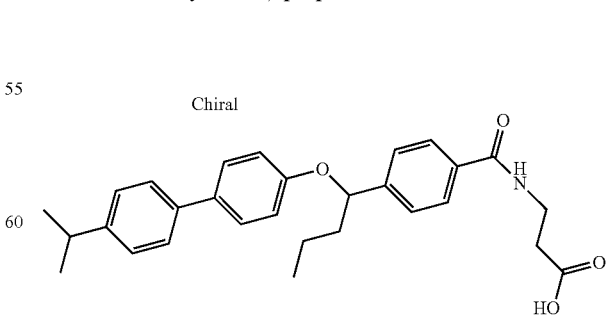

This compound is made in a substantially similar manner as Example 117 using 4-(1-hydroxy-butyl)-benzoic acid methyl ester as starting material in step A and 4-isopropyphenylboronic acid as reagent in step D. MS (ES): 460.2 [M+H]⁺.

Example 128

Racemic 3-{4-[1-(2,6-Dimethyl-4'-trifluoromethoxy-biphenyl-4-yloxy)-heptyl]-benzoylamino}-propionic acid

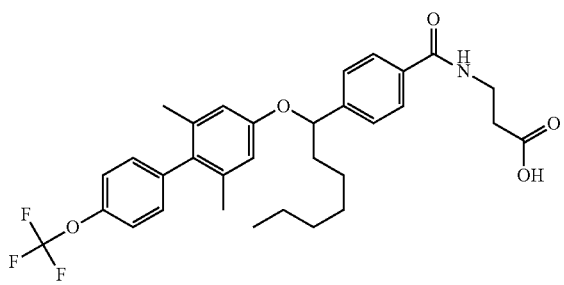 [SMILES: CCCCCCC(Oc1cc(C)c(-c2ccc(OC(F)(F)F)cc2)c(C)c1)c1ccc(C(=O)NCCC(=O)O)cc1]

Step A. Racemic 4-[1-(4-Bromo-3,5-dimethyl-phenoxyl)-heptyl]-benzoic acid

To a solution of 4-(1-hydroxy-heptyl)-benzoic acid methyl ester (1000 mg, 4.0 mmol) in toluene (40 mL) is added 1,1'-(azodicarbonyl)dipiperidine (ADDP, 1514 mg, 6.0 mmol) at 0° C., followed by the additions of tributylphosphine (1.49 mL, 6.0 mmol) and 4-bromo-3,5-dimethyl-phenol (965 mg, 4.8 mmol). The reaction mixture is warmed up to room temperature and stirred overnight. The mixture is loaded on silica gel, eluted with hexanes with a gradient from 0% of ethyl acetate to 50% of ethyl acetate giving 4-[1-(4-bromo-phenoxyl)-heptyl]-benzoic acid methyl ester. The ester product (1800 mg) is taken into ethanol (5 mL), treated with sodium hydroxide (5N aqueous, 5 mL) for 3 h at room temperature. The mixture is concentrated, diluted with ethyl acetate, acidified with 5 N HCl (5 mL), extract with ethyl acetate. The organic layers are dried and concentrated giving 4-[1-(4-bromo-3,5-dimethyl-phenoxyl)-heptyl]-benzoic acid (1790 mg).

Step B. Racemic 3-{4-[1-(4-Bromo-3,5-dimethyl-phenoxyl)-heptyl]-benzoylamino}-propionic acid methyl ester To a mixture of 4-[1-(4-bromo-3,5-dimethyl-phenoxyl)-heptyl]-benzoic acid (1790 mg, 4.27 mmol) in methylene chloride (43 mL) are added triethyl amine (1.79 mL, 12.82 mmol), DMAP (5.0 mg), 3-amino-propionic acid methyl ester (895 mg, 6.4 mmol) and EDCI (2463 mg, 12.8 mmol) at room temperature. The reaction mixture is stirred at room temperature overnight, loaded on silica gel, eluted with eluted with hexanes with a gradient from 0% of ethyl acetate to 100% of ethyl acetate giving racemic 3-{4-[1-(4-bromo-3,5-dimethyl-phenoxyl)-heptyl]-benzoylamino}-propionic acid methyl ester (945 mg).

Step C. Racemic 3-{4-[1-(2,6-Dimethyl-4'-trifluoromethoxy-biphenyl-4-yloxy)-heptyl]-benzoylamino}-propionic acid 3-{4-[1-(4-Bromo-3,5-dimethyl-phenoxyl)-heptyl]-benzoylamino}-propionic acid methyl ester (isomer 1, 100 mg, 0.2 mmol), potassium fluoride (35 mg, 0.6 mmol), 4-trifluoromethoxylphenyl boronic acid (83 mg, 0.4 mmol) and tetrakis(triphenylphosphine)palladium (23 mg, 0.02 mmol) are place in a flask. After the reaction is purged with N₂ for several times, Toluene/H₂O (20 ml/5 ml) is added. The resulting solution is refluxed overnight, loaded on silica gel, eluted with hexane and ethyl acetate to give 3-{4-[1-(2,6-Dimethyl-4'-trifluoromethoxy-biphenyl-4-yloxy)-heptyl]-benzoylamino}-propionic acid, (105 mg).

Step D. 3-{4-[1-(2,6-Dimethyl-4'-trifluoromethoxy-biphenyl-4-yloxy)-heptyl]-benzoylamino}-propionic acid To a mixture of 3-{4-[1-(2,6-Dimethyl-4'-trifluoromethoxy-biphenyl-4-yloxy)-heptyl]-benzoylamino}-propionic acid methyl ester (105 mg) in methanol (2 mL) is added sodium hydroxide (5 N aqueous, 0.5 mL) and stirred for 5 h. The reaction mixture is concentrated and acidified by 5 N HCl (0.5 mL), extracted with ethyl acetate. Combined organic layers are washed with water and brine, dried over sodium sulfate. Concentration gives the title compound (114 mg). MS (ES): 572.3 [M+H]⁺.

Example 129

Racemic 3-{4-[1-(2,6-Dimethyl-4'-trifluoromethyl-biphenyl-4-yloxy)-heptyl]-benzoylamino}-propionic acid

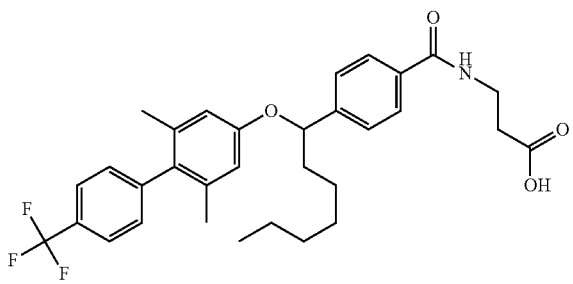 [SMILES: CCCCCCC(Oc1cc(C)c(-c2ccc(C(F)(F)F)cc2)c(C)c1)c1ccc(C(=O)NCCC(=O)O)cc1]

This compound is made in a substantially similar manner as Example 128 using 4-trifluoromethylphenyl boronic acid as reagent in step C. MS (ES): 554.2 [M−H]⁻.

Example 130

Racemic 3-{4-[1-(2,6-Dimethyl-4'-tertbutyl-biphenyl-4-yloxy)-heptyl]-benzoylamino}-propionic acid

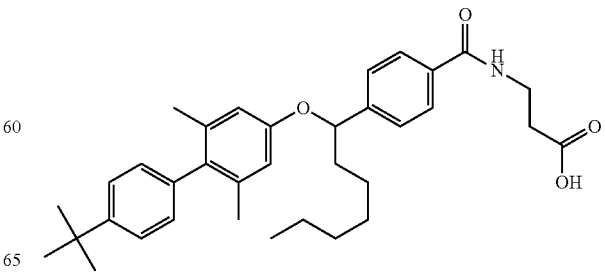

This compound is made in a substantially similar manner as Example 128 using 4-tertbutylphenyl boronic acid as reagent in step C. MS (ES): 542.3 [M–H]⁻.

Example 131

3-{4-[1-(4'-tert-Butyl-biphenyl-4-yloxy)-3-methyl-butyl]-benzoylamino}-2(R)-hydroxy-propionic acid

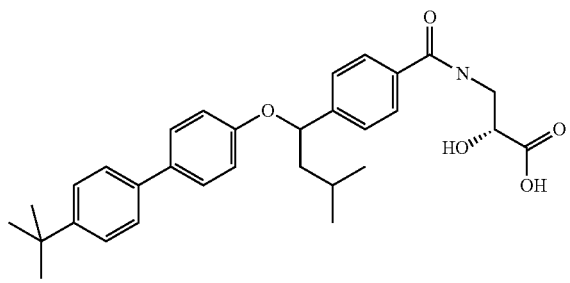 [SMILES: CC(C)CC(Oc1ccc(-c2ccc(C(C)(C)C)cc2)cc1)c1ccc(C(=O)NC[C@@H](O)C(=O)O)cc1]

Step A. 4-[1-(4'-tertbutyl-biphenyl-4-yloxy)-3-methyl-butyl]-benzoic acid

To a solution of racemic 4-(1-hydroxy-3-methyl-butyl)-benzoic acid methyl ester (300 mg, 1.35 mmol) in toluene (14 mL) is added 1,1'-(azodicarbonyl)dipiperidine (ADDP, 512 mg, 2.03 mmol) at 0° C., followed by the addition of tributylphosphine (0.5 mL, 2.03 mmol) and 4'-tert butyl-biphenyl-4-ol (367 mg, 1.62 mmol). The reaction mixture is warmed up to room temperature and stirred overnight. The mixture is loaded on silica gel, eluted with hexanes with a gradient from 0% of ethyl acetate to 50% of ethyl acetate giving 4-[1-(4'-tertbutyl-biphenyl-4-yloxy)-3-methyl-butyl]-benzoic acid methyl ester. The ester product is taken into ethanol (5 mL), treated with sodium hydroxide (5N aqueous, 1 mL) for 3 h at room temperature. The mixture is concentrated, diluted with ethyl acetate, acidified with 5 N HCl (1 mL), extract with ethyl acetate. The organic layers are dried and concentrated giving 4-[1-(4'-tertbutyl-biphenyl-4-yloxy)-3-methyl-butyl]-benzoic acid (400 mg).

Step B. 3-{4-[1-(4'-tert-Butyl-biphenyl-4-yloxy)-3-methyl-butyl]-benzoylamino}-2(R)-hydroxy-propionic acid methyl ester To a mixture of 4-[1-(4'-tertbutyl-biphenyl-4-yloxy)-3-methyl-butyl]-benzoic acid (120 mg) in methylene chloride (3 mL) are added triethyl amine (0.12 mL, 0.87 mmol), DMAP (5 mg), 3-Amino-2(R)-hydroxy-propionic acid methyl ester (67.3 mg, 0.43 mmol) and EDCI (166 mg, 0.87 mmol) at room temperature. The reaction mixture is stirred at room temperature overnight, loaded on silica gel, eluted with eluted with hexanes with a gradient from 0% of ethyl acetate to 100% of ethyl acetate giving 3-{4-[1-(4'-tert-butyl-biphenyl-4-yloxy)-3-methyl-butyl]-benzoylamino}-2(R)-hydroxy-propionic acid methyl ester (60 mg).

Step C. 3-{4-[1-(4'-tert-Butyl-biphenyl-4-yloxy)-3-methyl-butyl]-benzoylamino}-2(R)-hydroxy-propionic acid To a mixture of 3-{4-[1-(4'-tert-butyl-biphenyl-4-yloxy)-3-methyl-butyl]-benzoylamino}-2(R)-hydroxy-propionic acid methyl ester (60 mg, 0.12 mmol) in methanol (2 mL) is added sodium hydroxide (5 N aqueous, 0.5 mL) and stirred for 5 h. The reaction mixture is concentrated and acidified by 5 N HCl (0.5 mL), extracted with ethyl acetate. Combined organic layers are washed with water and brine, dried over sodium sulfate. Concentration gives the title compound (63 mg). MS (ES): 504.3 [M+H]⁺.

Example 132

3-{4-[1-(4'-tert-Butyl-biphenyl-4-yloxy)-3-methyl-butyl]-benzoylamino}-2(S)-hydroxy-propionic acid

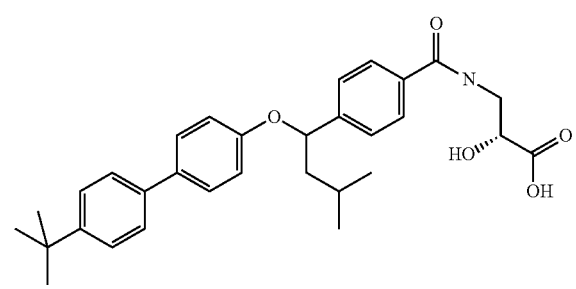 [SMILES: CC(C)CC(Oc1ccc(-c2ccc(C(C)(C)C)cc2)cc1)c1ccc(C(=O)NC[C@@H](O)C(=O)O)cc1]

This compound is made in a substantially similar manner as Example 131 using 3-amino-2(S)-hydroxy-propionic acid methyl ester as reagent in step B. MS (ES): 504.2 [M+H]⁺.

Example 133

3-{4-[1-(4'-Pentyl-biphenyl-4-yloxy)-butyl]-benzoylamino}-propionic acid, Isomer 1

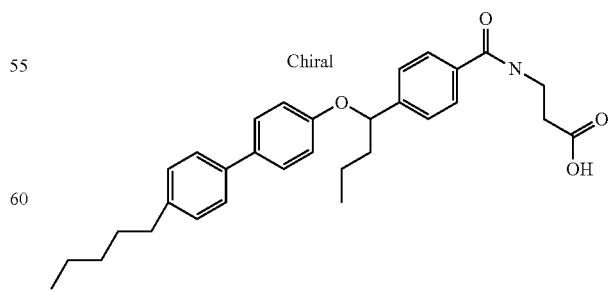

This compound is made in a substantially similar manner as Example 117 using isomer 1 of 3-{4-[1-(4-bromo-phenoxy)-butyl]-benzoylamino}-propionic acid methyl ester and 4-pentylphenylboronic acid as starting materials in step D. MS (ES): 488.3 [M+H]⁺.

Example 134

3-{4-[1-(4'-Isobutyl-biphenyl-4-yloxy)-butyl]-benzoylamino}-propionic acid, Isomer 1

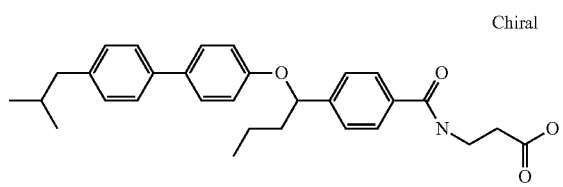 [SMILES: CCCC(Oc1ccc(-c2ccc(CC(C)C)cc2)cc1)c1ccc(C(=O)NCCC(=O)O)cc1]

This compound is made in a substantially similar manner as Example 117 using isomer 1 of 3-{4-[1-(4-bromo-phenoxy)-butyl]-benzoylamino}-propionic acid methyl ester and 4-isobutylphenylbronic acid as starting materials in step D. MS (ES): 472.2 [M−H]⁻.

Example 135

Racemic 3-{4-[1-(6-chloro-pyridin-3-yloxy)-4,4,4-trifluoro-butyl]-benzoylamino}-propionic acid

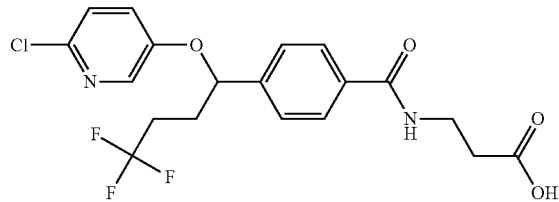 [SMILES: O=C(O)CCNC(=O)c1ccc(C(CCC(F)(F)F)Oc2ccc(Cl)nc2)cc1]

The title compound is prepared in a manner substantially similar to Example 62 starting from 3-{4-[1-(6-chloro-pyridin-3-yloxy)-4,4,4-trifluoro-butyl]-benzoylamino}-propionic acid methyl ester. MS: 429.2 [M−H]⁻.

Example 136

3-{4-[1-(4'-Acetyl-biphenyl-4-yloxy)-butyl]-benzoylamino}-propionic acid, Isomer 1

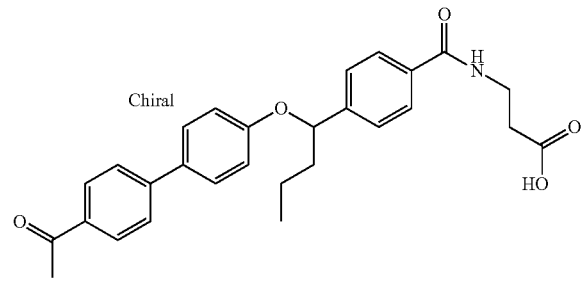 [SMILES: CCCC(Oc1ccc(-c2ccc(C(C)=O)cc2)cc1)c1ccc(C(=O)NCCC(=O)O)cc1]

This compound is made in a substantially similar manner as Example 117 using isomer 1 of 3-{4-[1-(4-bromo-phenoxy)-butyl]-benzoylamino}-propionic acid methyl ester and 4-acetylphenylboronic acid as starting materials in step D. MS (ES): 458.3 [M−H]⁻.

Example 137

3-{4-[1-(3',5'-dichloro-biphenyl-4-yloxy)-butyl]-benzoylamino}-propionic acid, Isomer 1 and

Example 138

3-{4-[1-(3',5'-dichloro-biphenyl-4-yloxy)-butyl]-benzoylamino}-propionic acid, Isomer 2

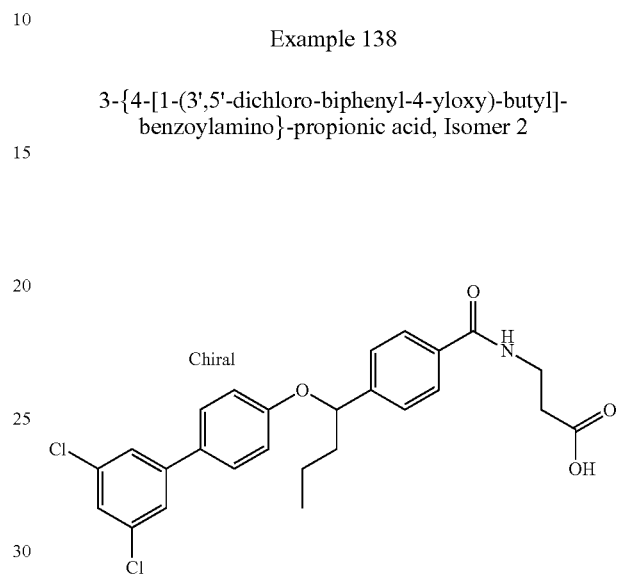

These compounds are made in a manner substantially similar to Example 117 using isomer 1 of 3-{4-[1-(4-bromo-phenoxy)-butyl]-benzoylamino}-propionic acid methyl ester and 3',5'-dichlorophenylboronic acid as starting materials in step D. Isomer 1 MS (ES): 484.2 [M−H]⁻; Isomer 2 MS (ES): 486.2 [M+H]⁺.

Example 139

3-{4-[1-(2',3',4'-trifluoro-biphenyl-4-yloxy)-butyl]-benzoylamino}-propionic acid, Isomer 1

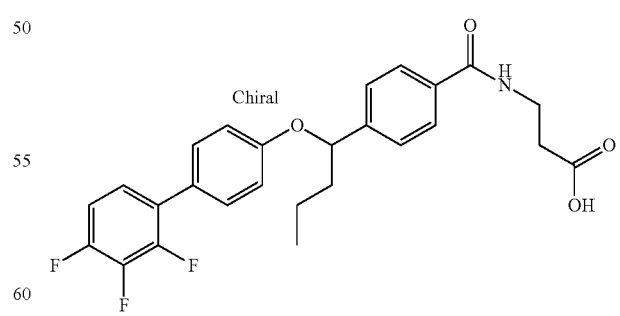

This compound is made in a substantially similar manner as Example 117 using isomer 1 of 3-{4-[1-(4-bromo-phenoxy)-butyl]-benzoylamino}-propionic acid methyl ester and 2',3',4'-trifluorophenylboronic acid as starting materials in step D. MS (ES): 472.2 [M+H]⁺.

Example 140

3-{4-[1-(2',4'-dimethoxy-biphenyl-4-yloxy)-butyl]-benzoylamino}-propionic acid, Isomer 1

Example 141

3-{4-[1-(4'-t-butyl-biphenyl-4-yloxy)-hexyl]-benzoylamino}-propionic acid, Isomer 1 and

Example 142

3-{4-[1-(4'-t-butyl-biphenyl-4-yloxy)-hexyl]-benzoylamino}-propionic acid, Isomer 2

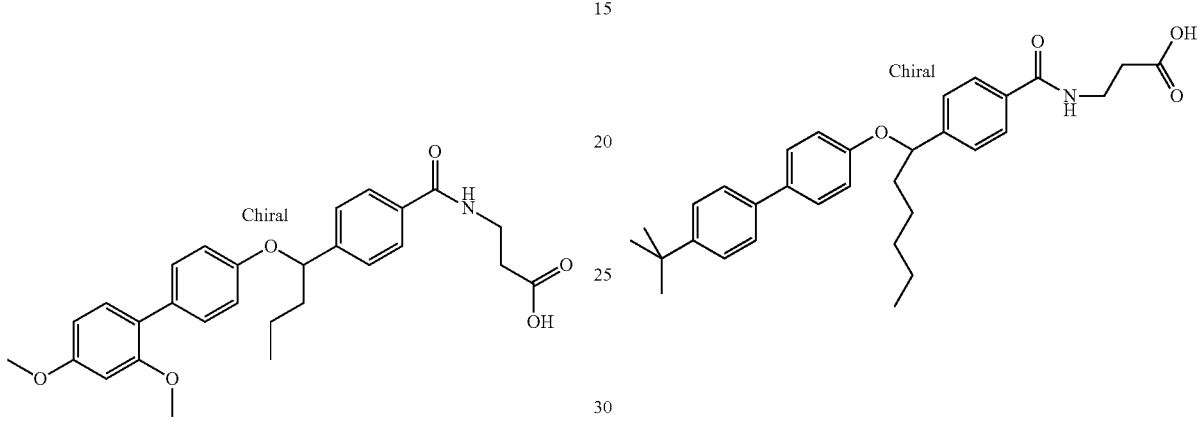

These compounds are made in a manner substantially similar to Example 30 by resolving racemic 3-{4-[1-(4'-t-butyl-biphenyl-4-yloxy)-hexyl]-benzoylamino}-propionic acid methyl ester on Chiralpak AD-H column (4.6×150 mm). Isomer 1 MS (ES): 502.2 [M+H]$^+$; Isomer 2 MS (ES): 502.2 [M+H]$^+$.

This compound is made in a substantially similar manner as Example 117 using isomer 1 of 3-{4-[1-(4-bromo-phenoxy)-butyl]-benzoylamino}-propionic acid methyl ester and 2',4'-dimethoxyphenylboronic acid as starting materials in step D. MS (ES): 478.3 [M+H]$^+$.

Example 143

3-{4-[1-(4'-pentylphenyl-4-yloxy)-hexyl]-benzoylamino}-propionic acid, Isomer 1 and

Example 144

3-{4-[1-(4'-pentylphenyl-4-yloxy)-hexyl]-benzoylamino}-propionic acid, Isomer 2

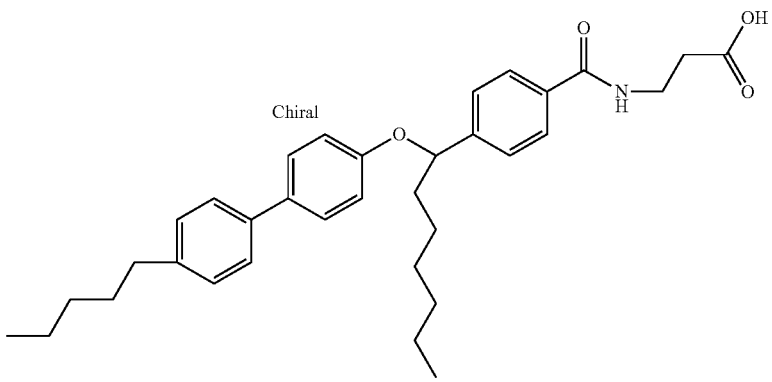 [SMILES: CCCCCCC(Oc1ccc(-c2ccc(CCCCC)cc2)cc1)c1ccc(C(=O)NCCC(=O)O)cc1]

These compounds are made in a manner substantially similar to Example 30 by resolving racemic 3-{4-[1-(4'-pentylphenyl-4-yloxy)-hexyl]-benzoylamino}-propionic acid methyl ester on Chiralpak AD-H column (4.6×150 mm). Isomer 1 MS (ES): 454.2 [M+H]$^+$; Isomer 2 MS (ES): 454.2 [M+H]$^+$.

Example 145

3-(4-{1-[4-(1-Methyl-1-phenyl-ethyl)-phenoxy]-heptyl}-benzoylamino)-propionic acid, Isomer 1 and Example 146

3-(4-{1-[4-(1-Methyl-1-phenyl-ethyl)-phenoxy]-heptyl}-benzoylamino)-propionic acid, Isomer 2

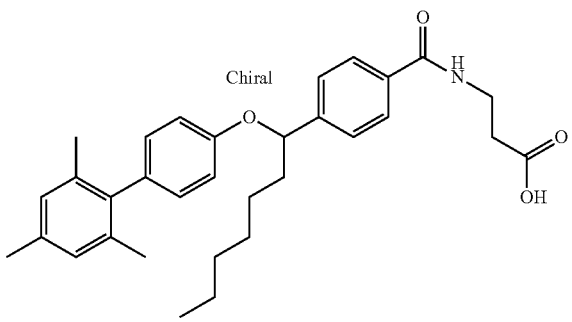 [SMILES: CCCCCCC(Oc1ccc(-c2c(C)cc(C)cc2C)cc1)c1ccc(C(=O)NCCC(=O)O)cc1]

These compounds are made in a manner substantially similar to Example 30 by resolving racemic 3-(4-{1-[4-(1-methyl-1-phenyl-ethyl)-phenoxy]-heptyl}-benzoylamino)-propionic acid methyl ester on Chiralpak AD-H column (4.6×150 mm). Isomer 1 MS (ES): 502.2 [M+H]$^+$. Isomer 2 MS (ES): 502.2 [M+H]$^+$.

Example 147

3-{4-[1-(2',4',6'-trimethyl-biphenyl-4-yloxy)-heptyl]-benzoylamino}-propionic acid, Isomer 1

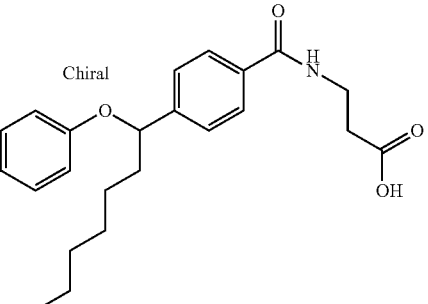

This compound is made in a substantially similar manner as Example 117 using isomer 1 of 3-{4-[1-(4-bromo-phenoxy)-heptyl]-benzoylamino}-propionic acid methyl ester and 2',4',6'-trimethylphenylboronic acid as starting materials in step D. MS (ES): 502.2 [M+H]$^+$.

Example 148

3-{4-[1-(4'-Fluoro-2'-methyl-biphenyl-4-yloxy)-heptyl]-benzoylamino}-propionic acid, Isomer 1

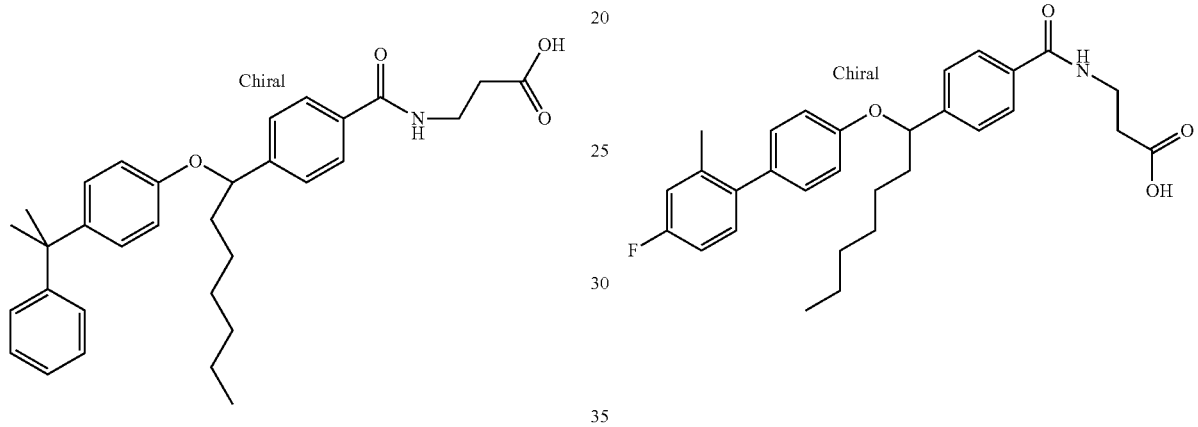

This compound is made in a substantially similar manner as Example 117 using isomer 1 of 3-{4-[1-(4-bromo-phenoxy)-heptyl]-benzoylamino}-propionic acid methyl ester and 4-fluoro-2-methyl-phenylboronic acid as starting materials in step D. MS (ES): 492.3 [M+H]$^+$.

Example 149

3-{4-[1-(4'-Trifluoromethoxy-biphenyl-4-yloxy)-hexyl]-benzoylamino}-propionic acid, Isomer 1

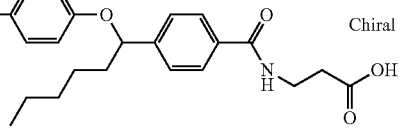

This compound is made in a substantially similar manner to Example 117 using isomer 1 of 3-{4-[1-(4-bromo-phenoxy)-hexyl]-benzoylamino}-propionic acid methyl ester and 4-trifluoromethoxy-phenylboronic acid as starting materials in step D. MS (ES): 530.2 [M+H]+.

Example 150

3-{4-[1-(4'-Fluoro-biphenyl-4-yloxy)-heptyl]-benzoylamino}-propionic acid, Isomer 1

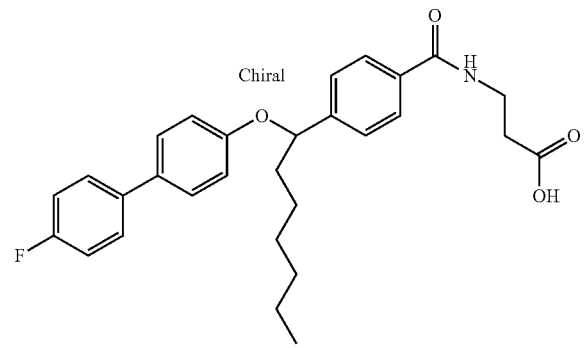 [SMILES: CCCCCCC(Oc1ccc(-c2ccc(F)cc2)cc1)c1ccc(C(=O)NCCC(=O)O)cc1]

This compound is made in a substantially similar manner to Example 117 using isomer 1 of 3-{4-[1-(4-bromo-phenoxy)-heptyl]-benzoylamino}-propionic acid methyl ester and 4-trifluoromethoxy-phenylboronic acid as starting materials in step D. MS (ES): 476.2 [M–H]−.

Example 151

3-{4-[Cyclopropyl-(4'-trifluoromethyl-biphenyl-4-yloxy)-methyl]-benzoylamino}-propionic acid, Isomer 1 and Example 152

3-{4-[Cyclopropyl-(4'-trifluoromethyl-biphenyl-4-yloxy)-methyl]-benzoylamino}-propionic acid, Isomer 2

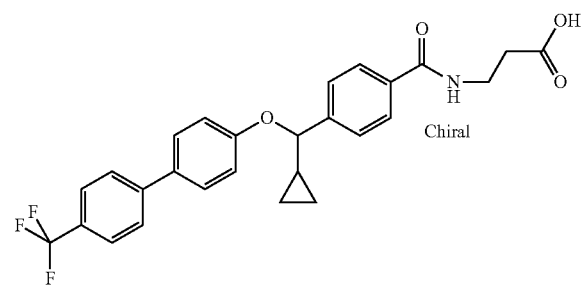 [SMILES: O=C(O)CCNC(=O)c1ccc(C(Oc2ccc(-c3ccc(C(F)(F)F)cc3)cc2)C2CC2)cc1]

These compounds are made by the general method exemplified in Example 30 by resolving racemic 3-{4-[cyclopropyl-(4'-trifluoromethyl-biphenyl-4-yloxy)-methyl]-benzoylamino}-propionic acid methyl ester on Chiralpak AD-H column (4.6×150 mm). Isomer 1 MS (ES): 482.2 [M–H]−; Isomer 2 MS (ES): 482.2 [M–H]−.

Example 153

3-{4-[1-(4'-tert-Butyl-biphenyl-4-yloxy)-4,4,4-trifluoro-butyl]-benzoylamino}-propionic acid, Isomer 1 and Example 154

3-{4-[1-(4'-tert-Butyl-biphenyl-4-yloxy)-4,4,4-trifluoro-butyl]-benzoylamino}-propionic acid, Isomer 2

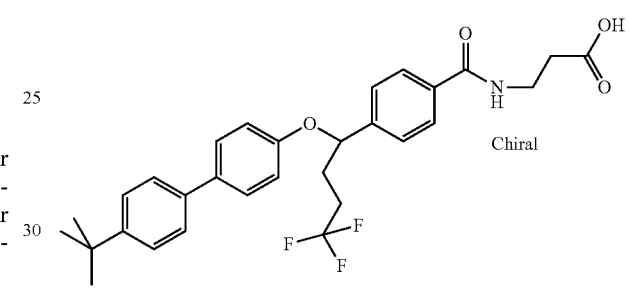

These compounds are made by the general method exemplified in Example 30 by resolving racemic 3-{4-[1-(4'-tert-butyl-biphenyl-4-yloxy)-4,4,4-trifluoro-butyl]-benzoylamino}-propionic acid methyl ester on Chiralpak AD-H column (4.6×150 mm). Isomer 1 MS (ES): 528.3° [M+H]+. Isomer 2 MS (ES): 528.3 [M+H]+.

Example 155

3-{4-[1-(4'-Chloro-biphenyl-4-yloxy)-heptyl]-benzoylamino}-propionic acid, Isomer 1

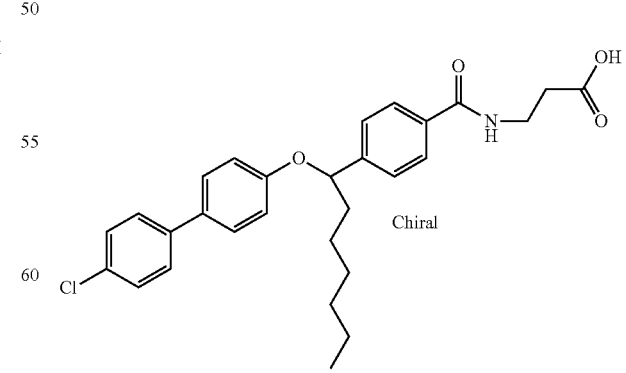

This compound is made in a substantially similar manner to Example 117 using isomer 1 of 3-{4-[1-(4-bromo-phenoxy)-heptyl]-benzoylamino}-propionic acid methyl ester and 4-chlorophenylboronic acid as starting materials in step D. MS (ES): 492.3 [M–H]⁻.

Example 156

3-{4-[1-(4'-tert-Butyl-2-methyl-biphenyl-4-yloxy)-3-methyl-butyl]-3-fluoro-benzoylamino}-propionic acid, Isomer 1 and

Example 157

3-{4-[1-(4'-tert-Butyl-2-methyl-biphenyl-4-yloxy)-3-methyl-butyl]-3-fluoro-benzoylamino}-propionic acid, Isomer 2

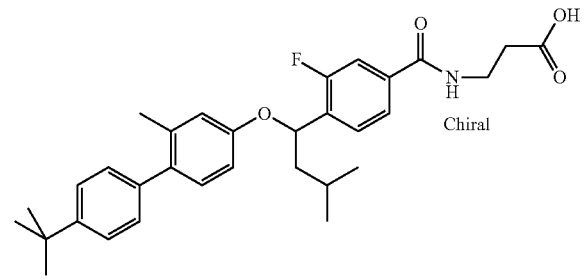 [SMILES: Cc1cc(OC(CC(C)C)c2ccc(C(=O)NCCC(=O)O)cc2F)ccc1-c1ccc(C(C)(C)C)cc1]

These compounds are made by the general method exemplified in Example 30 by resolving racemic 3-{4-[1-(4'-tert-butyl-2-methyl-biphenyl-4-yloxy)-3-methyl-butyl]-3-fluoro-benzoylamino}-propionic acid methyl ester on Chiralpak AD-H column (4.6×150 mm). Isomer 1 MS (ES): 520.2 [M+H]⁺; Isomer 2 MS (ES): 520.2 [M+H]⁺.

Example 158

3-{4-[1-(4'-tert-Butyl-biphenyl-4-yloxy)-heptyl]-3-fluoro-benzoylamino}-propionic acid, Isomer 1 and

Example 159

3-{4-[1-(4'-tert-Butyl-biphenyl-4-yloxy)-heptyl]-3-fluoro-benzoylamino}-propionic acid, Isomer 2

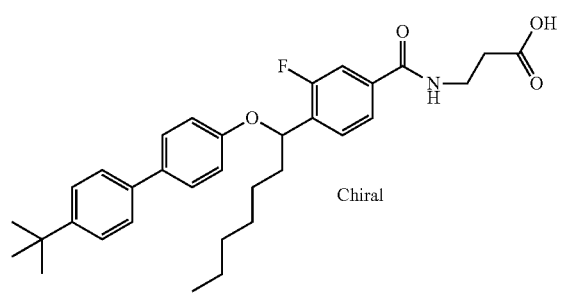 [SMILES: CCCCCCC(Oc1ccc(-c2ccc(C(C)(C)C)cc2)cc1)c1ccc(C(=O)NCCC(=O)O)cc1F]

These compounds are made by the general method exemplified in Example 30 by resolving racemic 3-{4-[1-(4'-tert-butyl-biphenyl-4-yloxy)-heptyl]-3-fluoro-benzoylamino}-propionic acid methyl ester on Chiralpak AD-H column (4.6×150 mm). Isomer 1 MS (ES): 534.2 [M+H]⁺. Isomer 2 MS (ES): 534.2 [M+H]⁺.

Example 160

3-{3-Fluoro-4-[1-(2-methyl-4'-trifluoromethyl-biphenyl-4-yloxy)-heptyl]-benzoylamino}-propionic acid, Isomer 1 and

Example 161

3-{3-Fluoro-4-[1-(2-methyl-4'-trifluoromethyl-biphenyl-4-yloxy)-heptyl]-benzoylamino}-propionic acid, Isomer 2

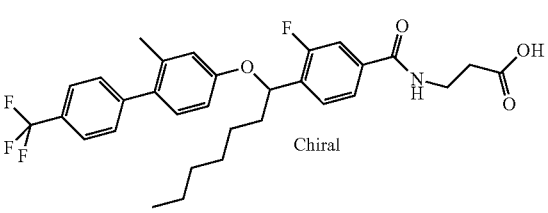 [SMILES: CCCCCCC(Oc1ccc(-c2ccc(C(F)(F)F)cc2)c(C)c1)c1ccc(C(=O)NCCC(=O)O)cc1F]

These compounds are made by the general method exemplified in Example 30 by resolving racemic 3-{3-fluoro-4-[1-(2-methyl-4'-trifluoromethyl-biphenyl-4-yloxy)-heptyl]-benzoylamino}-propionic acid methyl ester on Chiralpak AD-H column (4.6×150 mm). Isomer 1 MS (ES): 560.2 [M+H]⁺; Isomer 2 MS (ES): 560.2 [M+H]⁺.

Example 162

3-{4-[1-(4'-tert-Butyl-biphenyl-4-yloxy)-3-methyl-butyl]-3-fluoro-benzoylamino}-propionic acid, Isomer 1 and

Example 163

3-{4-[1-(4'-tert-Butyl-biphenyl-4-yloxy)-3-methyl-butyl]-3-fluoro-benzoylamino}-propionic acid, Isomer 2

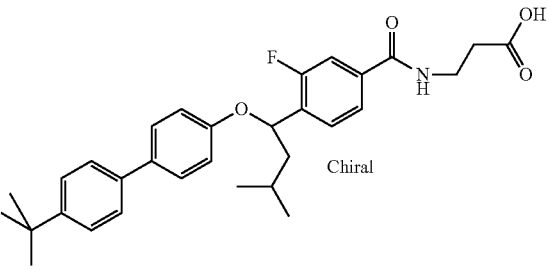 [SMILES: CC(C)CC(Oc1ccc(-c2ccc(C(C)(C)C)cc2)cc1)c1ccc(C(=O)NCCC(=O)O)cc1F]

These compounds are made by the general method exemplified in Example 30 by resolving racemic 3-{4-[1-(4'-tert-butyl-biphenyl-4-yloxy)-3-methyl-butyl]-3-fluoro-benzoylamino}-propionic acid methyl ester on Chiralpak AD-H column (4.6×150 mm). Isomer 1 MS (ES): 506.2 [M+H]⁺; Isomer 2 MS (ES): 506.2 [M+H]⁺.

Example 164

3-{4-[1-(4'-tert-Butyl-2,6-dimethyl-biphenyl-4-yloxy)-heptyl]-benzoylamino}-propionic acid, Isomer 1 and Example 165

3-{4-[1-(4'-tert-Butyl-2,6-dimethyl-biphenyl-4-yloxy)-heptyl]-benzoylamino}-propionic acid, Isomer 2

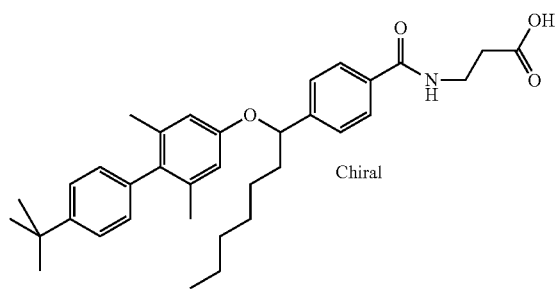 [SMILES: CCCCCCC(Oc1cc(C)c(-c2ccc(C(C)(C)C)cc2)c(C)c1)c1ccc(C(=O)NCCC(=O)O)cc1]

These compounds are made by the general method exemplified in Example 30 by resolving racemic 3-{4-[1-(4'-tert-butyl-2,6-dimethyl-biphenyl-4-yloxy)-heptyl]-benzoylamino}-propionic acid methyl ester on Chiralpak AD-H column (4.6×150 mm). Isomer 1 MS (ES): 544.2 [M+H]⁺. Isomer 2 MS (ES): 544.2 [M+H]⁺.

Example 166

3-{4-[1-(4'-tert-Butyl-2-methyl-biphenyl-4-yloxy)-heptyl]-benzoylamino}-propionic acid, Isomer 1 and Example 167

3-{4-[1-(4'-tert-Butyl-2-methyl-biphenyl-4-yloxy)-heptyl]-benzoylamino}-propionic acid, Isomer 2

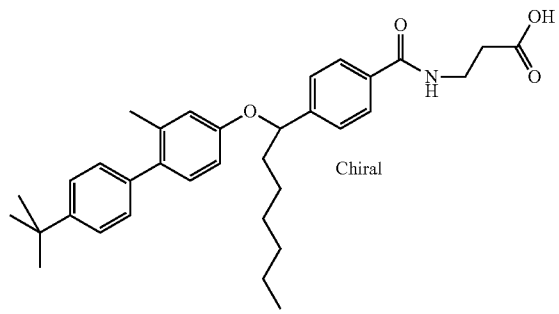 [SMILES: CCCCCCC(Oc1ccc(-c2ccc(C(C)(C)C)cc2)c(C)c1)c1ccc(C(=O)NCCC(=O)O)cc1]

These compounds are made by the general method exemplified in Example 30 by resolving racemic 3-{4-[1-(4'-tert-butyl-2-methyl-biphenyl-4-yloxy)-heptyl]-benzoylamino}-propionic acid methyl ester on Chiralpak AD-H column (4.6×150 mm). Isomer 1 MS (ES): 530.5 [M+H]⁺. Isomer 2 MS (ES): 530.5 [M+H]⁺.

Example 168

3-{4-[1-(2-Methyl-4'-trifluoromethyl-biphenyl-4-yloxy)-heptyl]-benzoylamino}-propionic acid, Isomer 1 and Example 169

3-{4-[1-(2-Methyl-4'-trifluoromethyl-biphenyl-4-yloxy)-heptyl]-benzoylamino}-propionic acid, Isomer 2

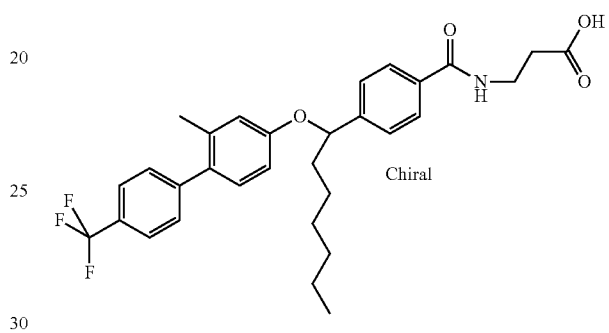

These compounds are made by the general method exemplified in Example 30 by resolving racemic 3-{4-[1-(2-methyl-4'-trifluoromethyl-biphenyl-4-yloxy)-heptyl]-benzoylamino}-propionic acid methyl ester on Chiralpak AD-H column (4.6×150 mm). Isomer 1 MS (ES): 540.3 [M–H]⁻. Isomer 2 MS (ES): 540.3 [M–H]⁻.

Example 170

3-{4-[1-(4'-tert-Butyl-2,6-dimethyl-biphenyl-4-yloxy)-3-methyl-butyl]-benzoylamino}-propionic acid, Isomer 1 and Example 171

3-{4-[1-(4'-tert-Butyl-2,6-dimethyl-biphenyl-4-yloxy)-3-methyl-butyl]-benzoylamino}-propionic acid, Isomer 2

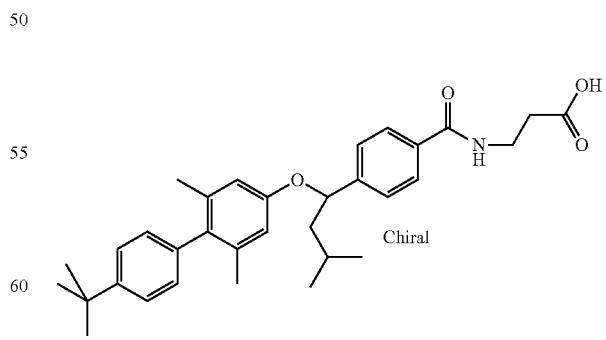

These compounds are made by the general method exemplified in Example 30 by resolving racemic 3-{4-[1-(4'-tert-butyl-2,6-dimethyl-biphenyl-4-yloxy)-3-methyl-butyl]-benzoylamino}-propionic acid methyl ester on Chiralpak AD-H column (4.6×150 mm). Isomer 1 MS (ES): 516.3 [M+H]⁺. Isomer 2 MS (ES): 516.3 [M+H]⁺.

Example 172

3-{4-[1-(4'-Isopropyl-2-methyl-biphenyl-4-yloxy)-heptyl]-benzoylamino}-propionic acid, Isomer 1 and Example 173

3-{4-[1-(4'-Isopropyl-2-methyl-biphenyl-4-yloxy)-heptyl]-benzoylamino}-propionic acid, Isomer 2

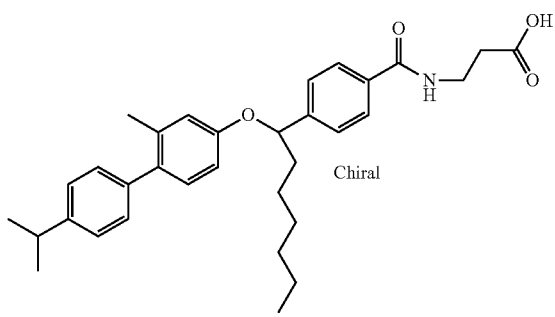 [SMILES: CCCCCCC(Oc1ccc(-c2ccc(C(C)C)cc2)c(C)c1)c1ccc(C(=O)NCCC(=O)O)cc1]

These compounds are made by the general method exemplified in Example 30 by resolving racemic 3-{4-[1-(4'-isopropyl-2-methyl-biphenyl-4-yloxy)-heptyl]-benzoylamino}-propionic acid methyl ester on Chiralpak AD-H column (4.6×150 mm). Isomer 1 MS (ES): 514.2 [M−H]⁻. Isomer 2 MS (ES): 516.3 [M+H]⁺.

Example 174

3-{4-[1-(4'-Fluoro-2-methyl-biphenyl-4-yloxy)-heptyl]-benzoylamino}-propionic acid, Isomer 1 and Example 175

3-{4-[1-(4'-Fluoro-2-methyl-biphenyl-4-yloxy)-heptyl]-benzoylamino}-propionic acid, Isomer 2

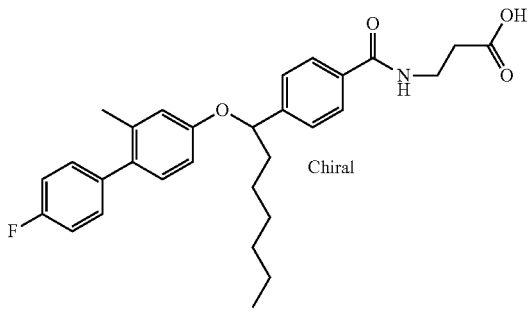 [SMILES: CCCCCCC(Oc1ccc(-c2ccc(F)cc2)c(C)c1)c1ccc(C(=O)NCCC(=O)O)cc1]

These compounds are made by the general method exemplified in Example 30 by resolving racemic 3-{4-[1-(4'-fluoro-2-methyl-biphenyl-4-yloxy)-heptyl]-benzoylamino}- propionic acid methyl ester on Chiralpak AD-H column (4.6×150 mm). Isomer 1 MS (ES): 492.3 [M+H]⁺. Isomer 2 MS (ES): 490.2 [M−H]⁻.

Example 176

3-{4-[1-(4'-Ethyl-2-methyl-biphenyl-4-yloxy)-heptyl]-benzoylamino}-propionic acid, Isomer 1 and Example 177

3-{4-[1-(4'-Ethyl-2-methyl-biphenyl-4-yloxy)-heptyl]-benzoylamino}-propionic acid, Isomer 2

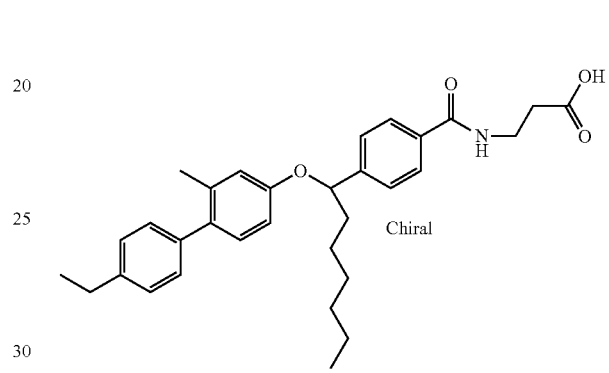

These compounds are made by the general method exemplified in Example 30 by resolving racemic 3-{4-[1-(4'-ethyl-2-methyl-biphenyl-4-yloxy)-heptyl]-benzoylamino}-propionic acid methyl ester on Chiralpak AD-H column (4.6×150 mm). Isomer 1 MS (ES): 502.2 [M+H]⁺; Isomer 2 MS (ES): 502.2 [M+H]⁺.

Example 178

3-{4-[1-(2,6-Dimethyl-biphenyl-4-yloxy)-3-methyl-butyl]-benzoylamino}-propionic acid, Isomer 1 and Example 179

3-{4-[1-(2,6-Dimethyl-biphenyl-4-yloxy)-3-methyl-butyl]-benzoylamino}-propionic acid, Isomer 2

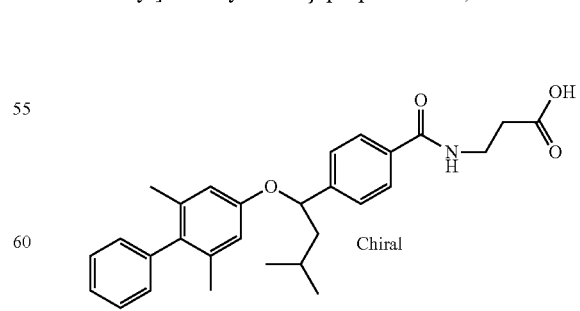

These compounds are made by the general method exemplified in Example 30 by resolving racemic 3-{4-[1-(2,6-dimethyl-biphenyl-4-yloxy)-3-methyl-butyl]-benzoylamino}-propionic acid methyl ester on Chiralcel OJ column (4.6×250 mm). Isomer 1 MS (ES): 458.3 [M−H]⁻; Isomer 2 MS (ES): 458.3 [M−H]⁻.

Example 180

3-{4-[1-(4'-Ethyl-2,6-dimethyl-biphenyl-4-yloxy)-3-methyl-butyl]-benzoylamino}-propionic acid, Isomer 1 and Example 181

3-{4-[1-(4'-Ethyl-2,6-dimethyl-biphenyl-4-yloxy)-3-methyl-butyl]-benzoylamino}-propionic acid, Isomer 2

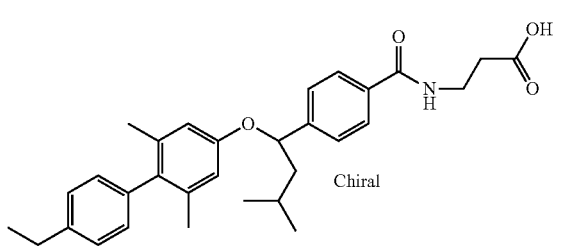 [SMILES: CCc1ccc(-c2c(C)cc(OC(CC(C)C)c3ccc(C(=O)NCCC(=O)O)cc3)cc2C)cc1]

These compounds are made by the general method exemplified in Example 30 by resolving racemic 3-{4-[1-(4'-ethyl-2,6-dimethyl-biphenyl-4-yloxy)-3-methyl-butyl]-benzoylamino}-propionic acid methyl ester on Chiralcel OJ column (4.6×250 mm). Isomer 1 MS (ES): 488.3 [M+H]⁺; Isomer 2 MS (ES): 488.3 [M+H]⁺.

Example 182

3-{4-[1-(4'-tert-Butyl-2-trifluoromethyl-biphenyl-4-yloxy)-3-methyl-butyl]-benzoylamino}-propionic acid, Isomer 1 and Example 183

3-{4-[1-(4'-tert-Butyl-2-trifluoromethyl-biphenyl-4-yloxy)-3-methyl-butyl]-benzoylamino}-propionic acid, Isomer 2

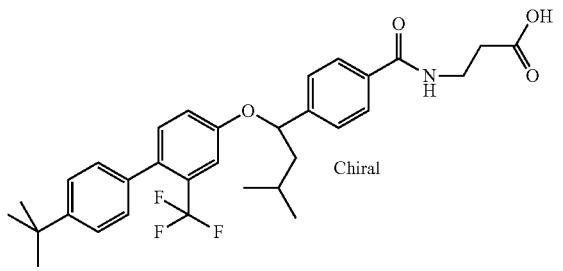 [SMILES: CC(C)CC(Oc1ccc(-c2ccc(C(C)(C)C)cc2)c(C(F)(F)F)c1)c1ccc(C(=O)NCCC(=O)O)cc1]

These compounds are made by the general method exemplified in Example 30 by resolving racemic 3-{4-[1-(4'-tert-butyl-2-trifluoromethyl-biphenyl-4-yloxy)-3-methyl-butyl]-benzoylamino}-propionic acid methyl ester on Chiralpak AD-H column (4.6×150 mm). Isomer 1 MS (ES): 556.3 [M+H]⁺. Isomer 2 MS (ES): 556.3 [M+H]⁺.

Example 184

3-{4-[1-(4'-tert-Butyl-2-trifluoromethyl-biphenyl-4-yloxy)-heptyl]-benzoylamino}-propionic acid, Isomer 1 and Example 185

3-{4-[1-(4'-tert-Butyl-2-trifluoromethyl-biphenyl-4-yloxy)-heptyl]-benzoylamino}propionic acid, Isomer 2

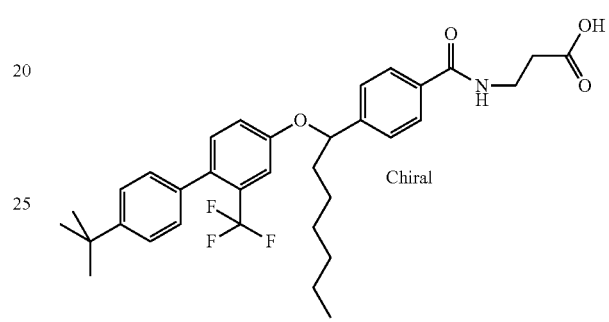

These compounds are made by the general method exemplified in Example 30 by resolving racemic 3-{4-[1-(4'-tert-butyl-2-trifluoromethyl-biphenyl-4-yloxy)-heptyl]-benzoylamino}-propionic acid methyl ester on Chiralpak AD-H column (4.6×150 mm). Isomer 1 MS (ES): 584.2 [M+H]⁺; Isomer 2 MS (ES): 584.2 [M+H]⁺.

Example 186

3-{4-[1-(4'-tert-Butyl-2-trifluoromethyl-biphenyl-4-yloxy)-pentyl]-benzoylamino}-propionic acid, Isomer 1 and Example 187

3-{4-[1-(4'-tert-Butyl-2-trifluoromethyl-biphenyl-4-yloxy)-pentyl]-benzoylamino}-propionic acid, Isomer 2

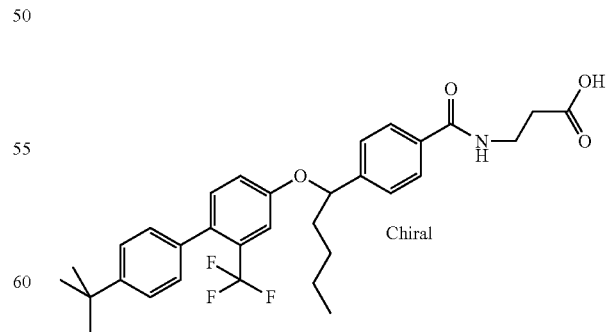

These compounds are made by the general method exemplified in Example 30 by resolving racemic 3-{4-[1-(4'-tert-butyl-2-trifluoromethyl-biphenyl-4-yloxy)-pentyl]-benzoylamino}-propionic acid methyl ester on Chiralpak AD-H column (4.6×150 mm). Isomer 1 MS (ES): 556.3 [M+H]+; Isomer 2 MS (ES): 556.3 [M+H]+.

Example 188

3-{4-[1-(4'-tert-Butyl-2-trifluoromethyl-biphenyl-4-yloxy)-2-methyl-propyl]-benzoylamino}-propionic acid, Isomer 1 and Example 189

3-{4-[1-(4'-tert-Butyl-2-trifluoromethyl-biphenyl-4-yloxy)-2-methyl-propyl]-benzoylamino}-propionic acid, Isomer 2

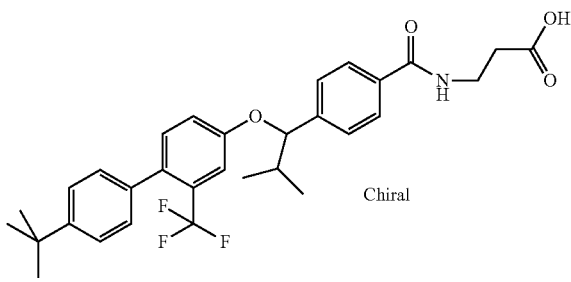 [SMILES: CC(C)C(Oc1ccc(-c2ccc(C(C)(C)C)cc2)c(C(F)(F)F)c1)c1ccc(C(=O)NCCC(=O)O)cc1]

These compounds are made by the general method exemplified in Example 30 by resolving racemic 3-{4-[1-(4'-tert-butyl-2-trifluoromethyl-biphenyl-4-yloxy)-2-methyl-propyl]-benzoylamino}-propionic acid methyl ester on Chiralpak AD-H column (4.6×150 mm). Isomer 1 MS (ES): 542.3 [M+H]+; Isomer 2 MS (ES): 542.3 [M+H]+.

Example 190

3-{4-[1-(2,6-Dimethyl-4'-trifluoromethyl-biphenyl-4-yloxy)-4,4-dimethyl-pentyl]-benzoylamino}-propionic acid, Isomer 1 and Example 191

3-{4-[1-(2,6-Dimethyl-4'-trifluoromethyl-biphenyl-4-yloxy)-4,4-dimethyl-pentyl]-benzoylamino}-propionic acid, Isomer 2

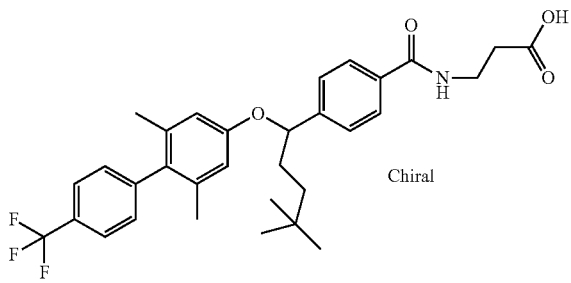 [SMILES: Cc1cc(OC(CCC(C)(C)C)c2ccc(C(=O)NCCC(=O)O)cc2)cc(C)c1-c1ccc(C(F)(F)F)cc1]

These compounds are made by the general method exemplified in Example 30 by resolving racemic 3-{4-[1-(2,6-dimethyl-4'-trifluoromethyl-biphenyl-4-yloxy)-4,4-dimethyl-pentyl]-benzoylamino}-propionic acid methyl ester on Chiralpak AD-H column (4.6×150 mm). Isomer 1 MS (ES): 556.3 [M+H]+; Isomer 2 MS (ES): 556.3 [M+H]+.

Example 192

3-{4-[1-(4'-Isopropyl-2,6-dimethyl-biphenyl-4-yloxy)-4,4-dimethyl-pentyl]-benzoylamino}-propionic acid, Isomer 1 and Example 193

3-{4-[1-(4'-Isopropyl-2,6-dimethyl-biphenyl-4-yloxy)-4,4-dimethyl-pentyl]-benzoylamino}-propionic acid, Isomer 2

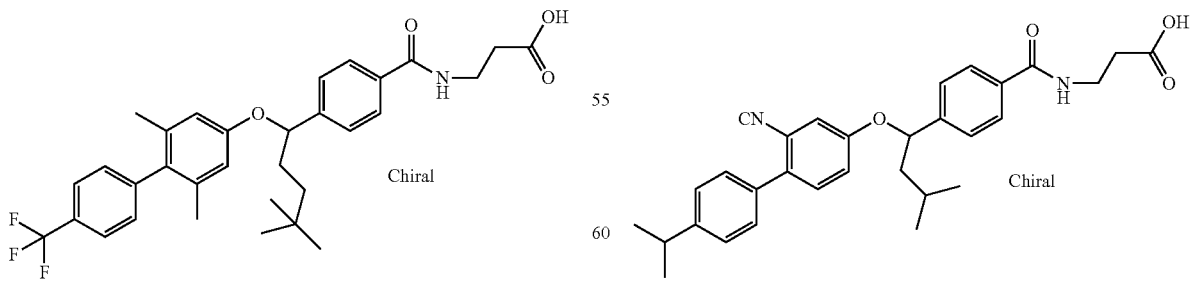

These compounds are made by the general method exemplified in Example 30 by resolving racemic 3-{4-[1-(4'-Isopropyl-2,6-dimethyl-biphenyl-4-yloxy)-4,4-dimethyl-pentyl]-benzoylamino}-propionic acid methyl ester on Chiralpak AD-H column (4.6×150 mm). Isomer 1 MS (ES): 530.5 [M+H]+; Isomer 2 MS (ES): 530.2 [M+H]+.

Example 194

3-{4-[1-(2-Cyano-4'-isopropyl-biphenyl-4-yloxy)-3-methyl-butyl]-benzoylamino}-propionic acid, Isomer 1 and Example 195

3-{4-[1-(2-Cyano-4'-isopropyl-biphenyl-4-yloxy)-3-methyl-butyl]-benzoylamino}-propionic acid, Isomer 2

These compounds are made by the general method exemplified in Example 30 by resolving racemic 3-{4-[1-(2-cyano-4'-isopropyl-biphenyl-4-yloxy)-3-methyl-butyl]-benzoylamino}-propionic acid methyl ester on Chiralpak AD-H column (4.6×150 mm). Isomer 1 MS (ES): 499.2 [M+H]⁺; Isomer 2 MS (ES): 499.2 [M+H]⁺.

Example 196

3-{4-[1-(4'-Isopropyl-2,6-dimethyl-biphenyl-4-yloxy)-2-methyl-propyl]-benzoylamino}-propionic acid, Isomer 1 and Example 197

3-{4-[1-(4'-Isopropyl-2,6-dimethyl-biphenyl-4-yloxy)-2-methyl-propyl]-benzoylamino}-propionic acid, Isomer 2

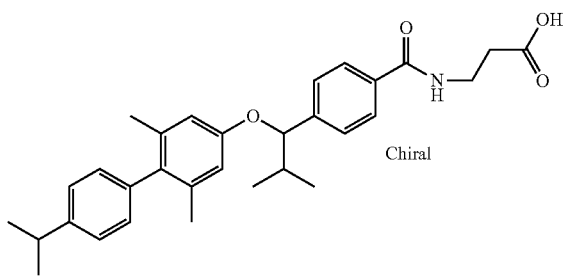 [SMILES: Cc1cc(OC(c2ccc(C(=O)NCCC(=O)O)cc2)C(C)C)cc(C)c1-c1ccc(C(C)C)cc1]

These compounds are made by the general method exemplified in Example 30 by resolving racemic 3-{4-[1-(4'-isopropyl-2,6-dimethyl-biphenyl-4-yloxy)-2-methyl-propyl]-benzoylamino}-propionic acid methyl ester on Chiralpak AD-H column (4.6×150 mm). Isomer 1 MS (ES): 488.3 [M+11]⁺; Isomer 2 MS (ES): 488.3 [M+H]⁺.

Example 198

3-{4-[1-(2-Ethyl-4'-trifluoromethyl-biphenyl-4-yloxy)-heptyl]-benzoylamino}-propionic acid, Isomer 1 and Example 199

3-{4-[1-(2-Ethyl-4'-trifluoromethyl-biphenyl-4-yloxy)-heptyl]-benzoylamino}-propionic acid, Isomer 2

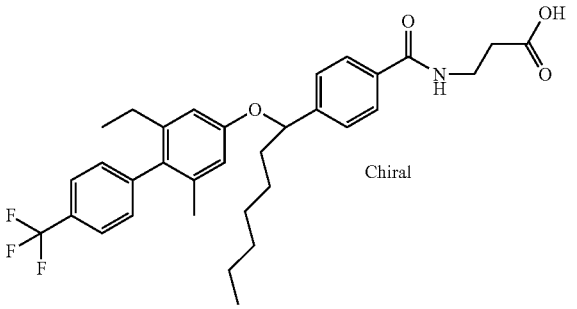 [SMILES: CCCCCCC(Oc1cc(C)c(-c2ccc(C(F)(F)F)cc2)c(CC)c1)c1ccc(C(=O)NCCC(=O)O)cc1]

These compounds are made by the general method exemplified in Example 30 by resolving racemic 3-{4-[1-(2-ethyl-4'-trifluoromethyl-biphenyl-4-yloxy)-heptyl]-benzoylamino}-propionic acid methyl ester on Chiralpak AD-H column (4.6×150 mm). Isomer 1 MS (ES): 556.3 [M+11]⁺; Isomer 2 MS (ES): 556.3 [M+H]⁺.

Example 200

3-{4-[1-(4'-Chloro-2,6-dimethyl-biphenyl-4-yloxy)-4,4-dimethyl-pentyl]-benzoylamino}-propionic acid, Isomer 1 and Example 201

3-{4-[1-(4'-Chloro-2,6-dimethyl-biphenyl-4-yloxy)-4,4-dimethyl-pentyl]-benzoylamino}-propionic acid, Isomer 2

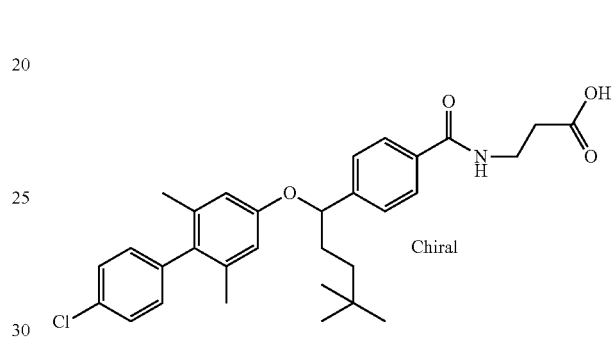

These compounds are made by the general method exemplified in Example 30 by resolving racemic 3-{4-[1-(4'-chloro-2,6-dimethyl-biphenyl-4-yloxy)-4,4-dimethyl-pentyl]-benzoylamino}-propionic acid methyl ester on Chiralpak AD-H column (4.6×150 mm). Isomer 1 MS (ES): 522.2 [M+H]⁺; Isomer 2 MS (ES): 522.2 [M+H]⁺.

Example 202

3-{4-[1-(4'-tert-Butyl-2,6-dimethyl-biphenyl-4-yloxy)-2-methyl-propyl]-benzoylamino}-propionic acid, Isomer 1 and Example 203

3-{4-[1-(4'-tert-Butyl-2,6-dimethyl-biphenyl-4-yloxy)-2-methyl-propyl]-benzoylamino}-propionic acid, Isomer 2

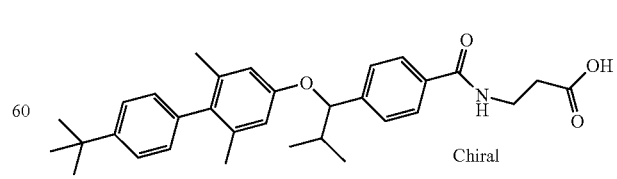

These compounds are made by the general method exemplified in Example 30 by resolving racemic 3-{4-[1-(4'-tert-butyl-2,6-dimethyl-biphenyl-4-yloxy)-2-methyl-propyl]- benzoylamino}-propionic acid methyl ester on Chiralpak AD-H column (4.6×150 mm). MS (ES): 502.2 [M+H]⁺. MS (ES): 502.2 [M+H]⁺.

Example 204

3-{4-[2-Methyl-1-(2-methyl-4'-trifluoromethoxy-biphenyl-4-yloxy)-propyl]-benzoylamino}-propionic acid, Isomer 1 and

Example 205

3-{4-[2-Methyl-1-(2-methyl-4'-trifluoromethoxy-biphenyl-4-yloxy)-propyl]-benzoylamino}-propionic acid, Isomer 2

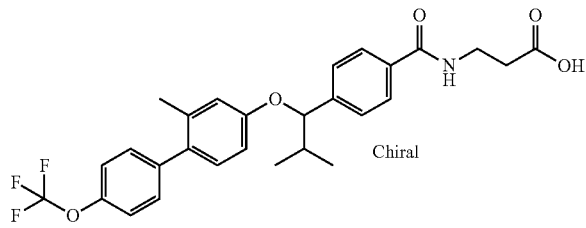 [SMILES: Cc1cc(OC(c2ccc(C(=O)NCCC(=O)O)cc2)C(C)C)ccc1-c1ccc(OC(F)(F)F)cc1]

These compounds are made by the general method exemplified in Example 30 by resolving racemic 3-{4-[2-methyl-1-(2-methyl-4'-trifluoromethoxy-biphenyl-4-yloxy)-propyl]-benzoylamino}-propionic acid methyl ester on Chiralpak AD-H column (4.6×150 mm). Isomer 1 MS (ES): 516.3 [M+H]⁺; Isomer 2 MS (ES): 516.3 [M+H]⁺.

Example 206

3-{4-[1-(2-Chloro-4'-isopropyl-biphenyl-4-yloxy)-3-methyl-butyl]-benzoylamino}-propionic acid, Isomer 1 and

Example 207

3-{4-[1-(2-Chloro-4'-isopropyl-biphenyl-4-yloxy)-3-methyl-butyl]-benzoylamino}-propionic acid, Isomer 2

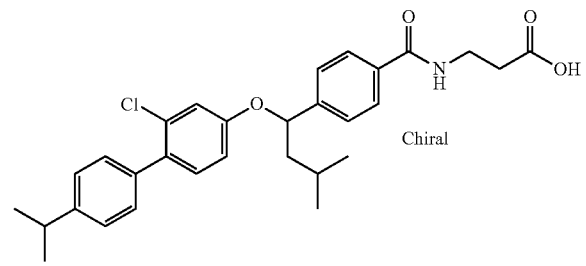 [SMILES: CC(C)CC(Oc1ccc(-c2ccc(C(C)C)cc2)c(Cl)c1)c1ccc(C(=O)NCCC(=O)O)cc1]

These compounds are made by the general method exemplified in Example 30 by resolving racemic 3-{4-[1-(2-chloro-4'-isopropyl-biphenyl-4-yloxy)-3-methyl-butyl]-benzoylamino}-propionic acid methyl ester on Chiralpak AD-H column (4.6×150 mm). Isomer 1 MS (ES): 508.3 [M+H]⁺; Isomer 2 MS (ES): 508.3 [M+H]⁺.

Example 208

3-{4-[1-(2-Chloro-4'-trifluoromethyl-biphenyl-4-yloxy)-3-methyl-butyl]-benzoylamino}-propionic acid, Isomer 1 and

Example 209

3-{4-[1-(2-Chloro-4'-trifluoromethyl-biphenyl-4-yloxy)-3-methyl-butyl]-benzoylamino}-propionic acid, Isomer 2

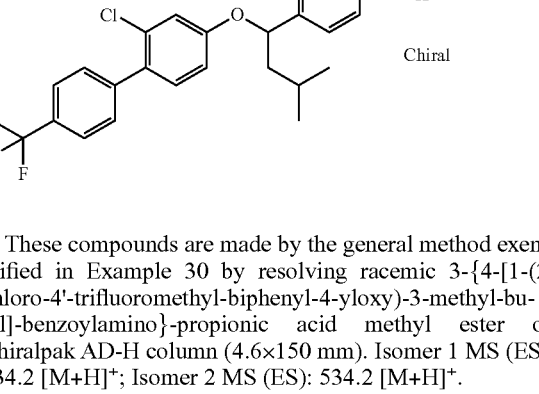

These compounds are made by the general method exemplified in Example 30 by resolving racemic 3-{4-[1-(2-chloro-4'-trifluoromethyl-biphenyl-4-yloxy)-3-methyl-butyl]-benzoylamino}-propionic acid methyl ester on Chiralpak AD-H column (4.6×150 mm). Isomer 1 MS (ES): 534.2 [M+H]⁺; Isomer 2 MS (ES): 534.2 [M+H]⁺.

Example 210

3-{4-[2-Methyl-1-(2-methyl-4'-trifluoromethyl-biphenyl-4-yloxy)-propyl]-benzoylamino}-propionic acid, Isomer 1 and

Example 211

3-{4-[2-Methyl-1-(2-methyl-4'-trifluoromethyl-biphenyl-4-yloxy)-propyl]-benzoylamino}-propionic acid, Isomer 2

These compounds are made by the general method exemplified in Example 30 by resolving racemic 3-{4-[2-Methyl-1-(2-methyl-4'-trifluoromethyl-biphenyl-4-yloxy)-propyl]-benzoylamino}-propionic acid methyl ester on Chiralpak AD-H column (4.6×150 mm). Isomer 1 MS (ES): 500.3 [M+H]+; Isomer 2 MS (ES): 500.3 [M+H]+.

Example 212

3-(4-{3-Methyl-1-[5-methyl-6-(4-trifluoromethyl-phenyl)-pyridin-3-yloxy]-butyl}-benzoylamino)-propionic acid, Isomer 1 and

Example 213

3-(4-{3-Methyl-1-[5-methyl-6-(4-trifluoromethyl-phenyl)-pyridin-3-yloxy]-butyl}-benzoylamino)-propionic acid, Isomer 2

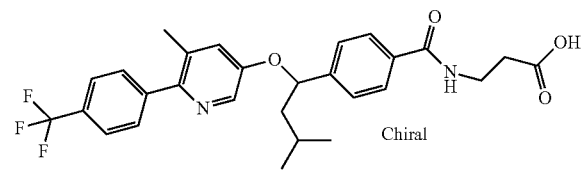 [SMILES: Cc1cc(OC(CC(C)C)c2ccc(C(=O)NCCC(=O)O)cc2)cnc1-c1ccc(C(F)(F)F)cc1]

These compounds are made by the general method exemplified in Example 30 by resolving racemic 3-(4-{3-methyl-1-[5-methyl-6-(4-trifluoromethyl-phenyl)-pyridin-3-yloxy]-butyl}-benzoylamino)-propionic acid methyl ester on Chiralpak AD-H column (4.6×150 mm). Isomer 1 MS (ES): 515.2 [M+H]+; Isomer 2 MS (ES): 515.2 [M+H]+.

Example 214

3-(4-{1-[6-(4-Isopropyl-phenyl)-5-methyl-pyridin-3-yloxy]-3-methyl-butyl}-benzoylamino)-propionic acid, Isomer 1 and

Example 215

3-(4-{1-[6-(4-Isopropyl-phenyl)-5-methyl-pyridin-3-yloxy]-3-methyl-butyl}-benzoylamino)-propionic acid, Isomer 2

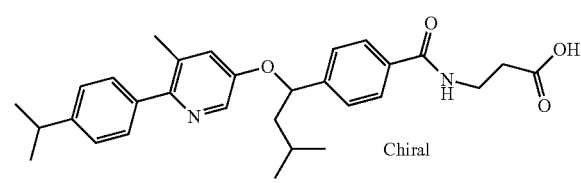 [SMILES: Cc1cc(OC(CC(C)C)c2ccc(C(=O)NCCC(=O)O)cc2)cnc1-c1ccc(C(C)C)cc1]

These compounds are made by the general method exemplified in Example 30 by resolving racemic 3-(4-{1-[6-(4-isopropyl-phenyl)-5-methyl-pyridin-3-yloxy]-3-methyl-butyl}-benzoylamino)-propionic acid methyl ester on Chiralpak AD-H column (4.6×150 mm). Isomer 1 MS (ES): 489.2 [M+H]+; Isomer 2 MS (ES): 489.2 [M+H]+.

Example 216

3-(3-Fluoro-4-{3-methyl-1-[6-(4-trifluoromethyl-phenyl)-pyridin-3-yloxy]-butyl}-benzoylamino)-propionic acid, Isomer 1 and

Example 217

3-(3-Fluoro-4-{3-methyl-1-[6-(4-trifluoromethyl-phenyl)-pyridin-3-yloxy]-butyl}-benzoylamino)-propionic acid, Isomer 2

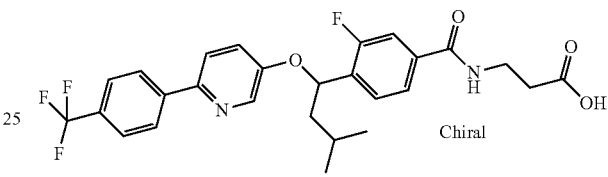

These compounds are made by the general method exemplified in Example 30 by resolving racemic 3-(3-fluoro-4-{3-methyl-1-[6-(4-trifluoromethyl-phenyl)-pyridin-3-yloxy]-butyl}-benzoylamino)-propionic acid methyl ester on Chiralpak AD-H column (4.6×150 mm). Isomer 1 MS (ES): 519.2 [M+H]+. Isomer 2 MS (ES): 519.2 [M+H]+.

Example 218

3-(4-{3-Methyl-1-[4-(5-trifluoromethyl-pyridin-2-yl)-phenoxy]-butyl}-benzoylamino)-propionic acid, Isomer 1 and

Example 219

3-(4-{3-Methyl-1-[4-(5-trifluoromethyl-pyridin-2-yl)-phenoxy]-butyl}-benzoylamino)-propionic acid, Isomer 2

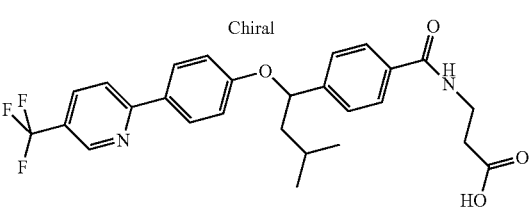 [SMILES: CC(C)CC(Oc1ccc(-c2ccc(C(F)(F)F)cn2)cc1)c1ccc(C(=O)NCCC(=O)O)cc1]

These compounds are made by the general method exemplified in Example 30 by resolving racemic 3-(4-{3-methyl-1-[4-(5-trifluoromethyl-pyridin-2-yl)-phenoxy]-butyl}-benzoylamino)-propionic acid methyl ester on Chiralpak AD-H column (4.6×150 mm). MS (ES): 501.2 [M+H]⁺; MS (ES): 501.2 [M+H]⁺.

Example 220

3-{4-[1-(4-tert-Butyl-phenoxy)-3-methyl-butyl]-benzoylamino}-propionic acid, Isomer 1 and Example 221

3-{4-[1-(4-tert-Butyl-phenoxy)-3-methyl-butyl]-benzoylamino}-propionic acid, Isomer 2

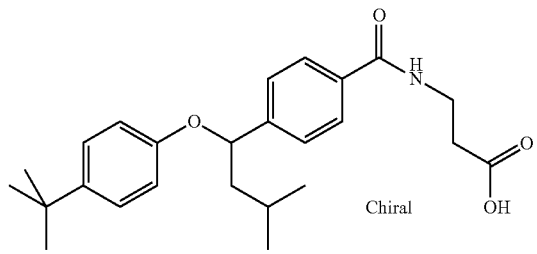 [SMILES: CC(C)CC(Oc1ccc(C(C)(C)C)cc1)c1ccc(C(=O)NCCC(=O)O)cc1]

These compounds are made by the general method exemplified in Example 30 by resolving racemic 3-{4-[1-(4-tert-butyl-phenoxy)-3-methyl-butyl]-benzoylamino}-propionic acid methyl ester on Chiralpak AD-H column (4.6×150 mm). Isomer 1 MS (ES): 412.3 [M+H]⁺. Isomer 2 MS (ES): 412.3 [M+H]⁺.

Example 222

2-Hydroxy-3-{4-[1-(4'-trifluoromethyl-biphenyl-4-yloxy)-heptyl]-benzoylamino}-propionic acid, Isomer 1 and Example 223

2-Hydroxy-3-{4-[1-(4'-trifluoromethyl-biphenyl-4-yloxy)-heptyl]-benzoylamino}-propionic acid, Isomer 2

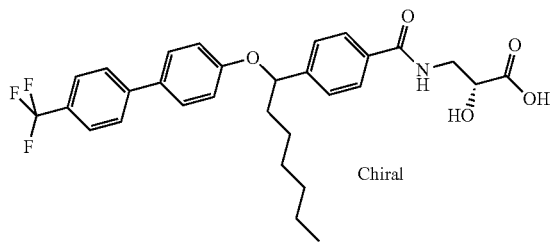 [SMILES: CCCCCCC(Oc1ccc(-c2ccc(C(F)(F)F)cc2)cc1)c1ccc(C(=O)NC[C@@H](O)C(=O)O)cc1]

These compounds are made by the general method exemplified in Example 30 by resolving racemic 2-hydroxy-3-{4-[1-(4'-trifluoromethyl-biphenyl-4-yloxy)-heptyl]-benzoylamino}-propionic acid methyl ester on Chiralpak AD-H column (4.6×150 mm). Isomer 1 MS (ES): 542.3 [M–H]⁻; Isomer 2 MS (ES): 542.3 [M–H]⁻.

Example 224

2-Hydroxy-3-{4-[1-(4'-trifluoromethyl-biphenyl-4-yloxy)-heptyl]-benzoylamino}-propionic acid, Isomer 1 and Example 225

2-Hydroxy-3-{4-[1-(4'-trifluoromethyl-biphenyl-4-yloxy)-heptyl]-benzoylamino}-propionic acid, Isomer 2

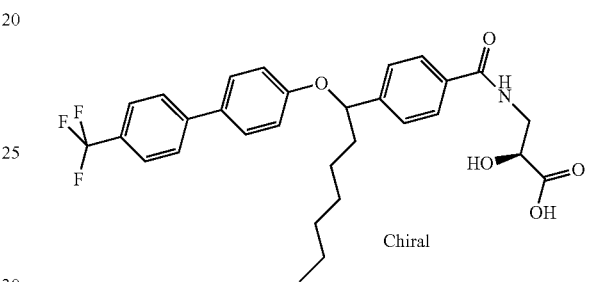

These compounds are made by the general method exemplified in Example 30 by resolving racemic 2-Hydroxy-3-{4-[1-(4'-trifluoromethyl-biphenyl-4-yloxy)-heptyl]-benzoylamino}-propionic acid methyl ester on Chiralpak AD-H column (4.6×150 mm). Isomer 1 MS (ES): 542.3 [M–H]⁻; Isomer 2 MS (ES): 542.3 [M–H]⁻.

Example 226

3-(4-{1-[4-(1,1,3,3-Tetramethyl-butyl)-phenoxy]-heptyl}-benzoylamino)-propionic acid, Isomer 1 and Example 227

3-(4-{1-[4-(1,1,3,3-Tetramethyl-butyl)-phenoxy]-heptyl}-benzoylamino)-propionic acid, Isomer 2

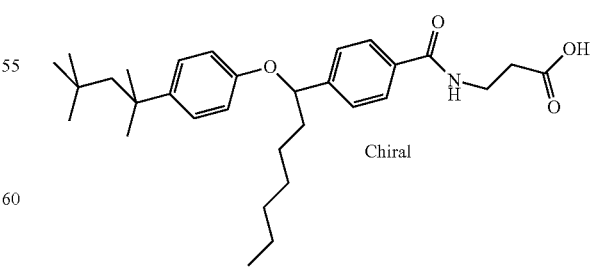

These compounds are made by the general method exemplified in Example 30 by resolving racemic 3-(4-{1-[4-(1,1,3,3-tetramethyl-butyl)-phenoxy]-heptyl}-benzoylamino)- propionic acid methyl ester on Chiralpak AD-H column (4.6× 150 mm). Isomer 1 MS (ES): 496.5 [M+H]⁺; Isomer 2 MS (ES): 496.5 [M+H]⁺.

Example 228

3-{4-[1-(2,2,3,3-Tetrafluoro-2,3-dihydro-benzo[1,4]dioxin-6-yloxy)-heptyl]-benzoylamino}-propionic acid, Isomer 1 and

Example 229

3-{4-[1-(2,2,3,3-Tetrafluoro-2,3-dihydro-benzo[1,4]dioxin-6-yloxy)-heptyl]-benzoylamino}-propionic acid, Isomer 2

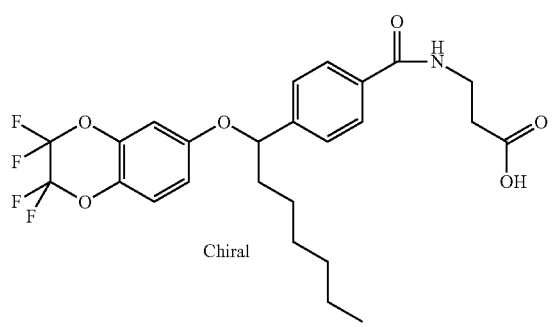 [SMILES: CCCCCCC(Oc1ccc2c(c1)OC(F)(F)C(F)(F)O2)c1ccc(C(=O)NCCC(=O)O)cc1]

These compounds are made by the general method exemplified in Example 30 by resolving racemic 3-{4-[1-(2,2,3,3-tetrafluoro-2,3-dihydro-benzo[1,4]dioxin-6-yloxy)-heptyl]-benzoylamino}-propionic acid methyl ester on Chiralpak AD-H column (4.6×150 mm). Isomer 1 MS (ES): 514.2 [M+H]⁺; Isomer 2 MS (ES): 514.2 [M+H]⁺.

Example 230

3-{4-[1-(2,6-Dimethyl-4'-trifluoromethyl-biphenyl-4-yloxy)-3,3-dimethyl-butyl]-benzoylamino}-propionic acid, Isomer 1 and

Example 231

3-{4-[1-(2,6-Dimethyl-4'-trifluoromethyl-biphenyl-4-yloxy)-3,3-dimethyl-butyl]-benzoylamino}-propionic acid, Isomer 2

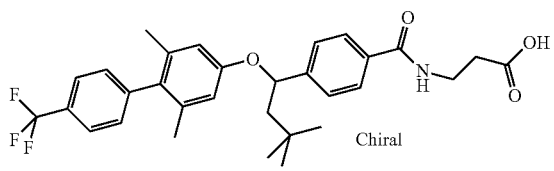 [SMILES: Cc1cc(OC(CC(C)(C)C)c2ccc(C(=O)NCCC(=O)O)cc2)cc(C)c1-c1ccc(C(F)(F)F)cc1]

These compounds are made by the general method exemplified in Example 30 by resolving racemic 3-{4-[1-(2,6-dimethyl-4'-trifluoromethyl-biphenyl-4-yloxy)-3,3-dimethyl-butyl]-benzoylamino}-propionic acid methyl ester on Chiralpak AD-H column (4.6×150 mm). Isomer 1 MS (ES): 540.3 [M−H]⁻; Isomer 2 MS (ES): 542.3 [M+H]⁺.

Example 232

3-{4-[1-(4'-tert-Butyl-2,6-dimethyl-biphenyl-4-yloxy)-3,3-dimethyl-butyl]-benzoylamino}-propionic acid, Isomer 1 and

Example 233

3-{4-[1-(4'-tert-Butyl-2,6-dimethyl-biphenyl-4-yloxy)-3,3-dimethyl-butyl]-benzoylamino}-propionic acid, Isomer 2

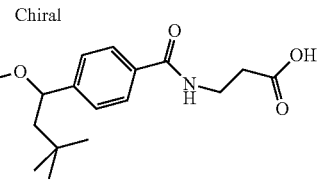

These compounds are made by the general method exemplified in Example 30 by resolving racemic 3-{4-[1-(4'-tert-butyl-2,6-dimethyl-biphenyl-4-yloxy)-3,3-dimethyl-butyl]-benzoylamino}-propionic acid methyl ester on Chiralpak AD-H column (4.6×150 mm). Isomer 1 MS (ES): 528.3 [M−H]⁻; Isomer 2 MS (ES): 528.3 [M−H]⁻.

Example 234

3-{4-[1-(4'-Isopropyl-2,6-dimethyl-biphenyl-4-yloxy)-3,3-dimethyl-butyl]-benzoylamino}-propionic acid, Isomer 1 and

Example 235

3-{4-[1-(4'-Isopropyl-2,6-dimethyl-biphenyl-4-yloxy)-3,3-dimethyl-butyl]-benzoylamino}-propionic acid, Isomer 2

These compounds are made by the general method exemplified in Example 30 by resolving racemic 3-{4-[1-(4'-isopropyl-2,6-dimethyl-biphenyl-4-yloxy)-3,3-dimethyl-butyl]-benzoylamino}-propionic acid methyl ester on

Example 236

3-(4-{3,3-Dimethyl-1-[5-methyl-6-(4-trifluoromethyl-phenyl)-pyridin-3-yloxy]-butyl}-benzoylamino)-propionic acid, Isomer 1 and

Example 237

3-(4-{3,3-Dimethyl-1-[5-methyl-6-(4-trifluoromethyl-phenyl)-pyridin-3-yloxy]-butyl}-benzoylamino)-propionic acid, Isomer 2

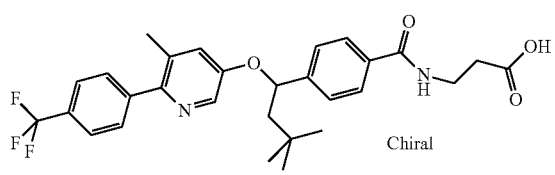 [SMILES: Cc1cc(OC(CC(C)(C)C)c2ccc(C(=O)NCCC(=O)O)cc2)cnc1-c1ccc(C(F)(F)F)cc1]

Chiral

These compounds are made by the general method exemplified in Example 30 by resolving racemic 3-(4-{3,3-dimethyl-1-[5-methyl-6-(4-trifluoromethyl-phenyl)-pyridin-3-yloxy]-butyl}-benzoylamino)-propionic acid methyl ester on Chiralpak AD-H column (4.6×150 mm). Isomer 1 MS (ES): 529.3 [M+H]$^+$; Isomer 2 MS (ES): 529.3 [M+H]$^+$.

Example 238

3-{4-[1-(4'-Isopropyl-2-methoxy-biphenyl-4-yloxy)-3-methyl-butyl]-benzoylamino}-propionic acid, Isomer 1 and

Example 239

3-{4-[1-(4'-Isopropyl-2-methoxy-biphenyl-4-yloxy)-3-methyl-butyl]-benzoylamino}-propionic acid, Isomer 2

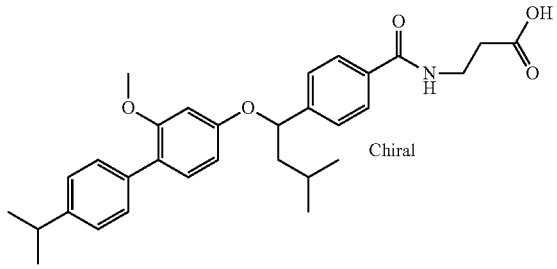 [SMILES: COc1cc(OC(CC(C)C)c2ccc(C(=O)NCCC(=O)O)cc2)ccc1-c1ccc(C(C)C)cc1]

Chiral

These compounds are made by the general method exemplified in Example 30 by resolving racemic 3-{4-[1-(4'-isopropyl-2-methoxy-biphenyl-4-yloxy)-3-methyl-butyl]-benzoylamino}-propionic acid methyl ester on Chiralpak AD-H column (4.6×150 mm). Isomer 1 MS (ES): 504.2 [M+H]$^+$; Isomer 2 MS (ES): 504.2 [M+H]$^+$.

Example 240

3-{4-[1-(4'-Isopropyl-2-methyl-biphenyl-4-yloxy)-3-methyl-butyl]-benzoylamino}-propionic acid, Isomer 1 and

Example 241

3-{4-[1-(4'-Isopropyl-2-methyl-biphenyl-4-yloxy)-3-methyl-butyl]-benzoylamino}-propionic acid, Isomer 2

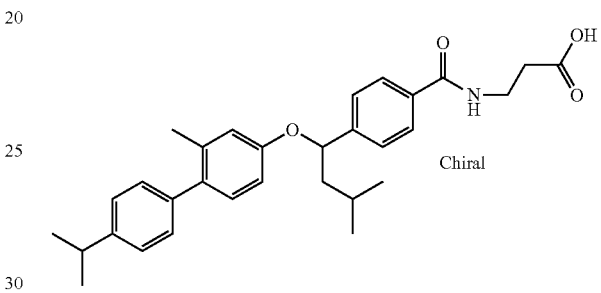

Chiral

These compounds are made by the general method exemplified in Example 30 by resolving racemic 3-{4-[1-(4'-isopropyl-2-methyl-biphenyl-4-yloxy)-3-methyl-butyl]-benzoylamino}-propionic acid methyl ester on Chiralpak AD-H column (4.6×150 mm). Isomer 1 MS (ES): 488.3 [M+H]$^+$; Isomer 2 MS (ES): 488.3 [M+H]$^+$.

Example 242

3-{4-[1-(2,6-Dimethyl-4'-trifluoromethoxy-biphenyl-4-yloxy)-3,3-dimethyl-butyl]-benzoylamino}-propionic acid, Isomer 1 and

Example 243

3-{4-[1-(2,6-Dimethyl-4'-trifluoromethoxy-biphenyl-4-yloxy)-3,3-dimethyl-butyl]-benzoylamino}-propionic acid, Isomer 2

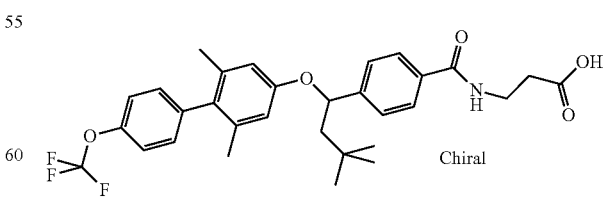

Chiral

These compounds are made by the general method exemplified in Example 30 by resolving racemic 3-{4-[1-(2,6-dimethyl-4'-trifluoromethoxy-biphenyl-4-yloxy)-3,3-dimethyl-butyl]-benzoylamino}-propionic acid methyl ester on Chiralpak AD-H column (4.6×150 mm). Isomer 1 MS (ES): 558.3 [M+H]⁺; Isomer 2 MS (ES): 558.3 [M+H]⁺.

Example 244

3-(4-{1-[2-(tert-Butoxyimino-methyl)-4'-trifluoromethyl-biphenyl-4-yloxy]-3-methyl-butyl}-benzoylamino)-propionic acid, Isomer 1 and Example 245

3-(4-{1-[2-(tert-Butoxyimino-methyl)-4'-trifluoromethyl-biphenyl-4-yloxy]-3-methyl-butyl}-benzoylamino)-propionic acid, Isomer 2

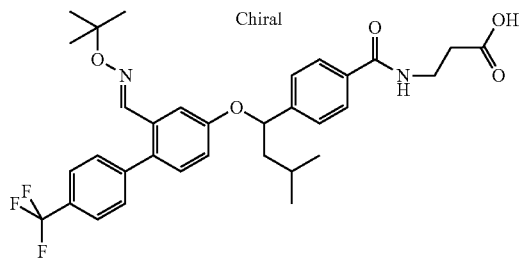 [SMILES: CC(C)CC(Oc1ccc(-c2ccc(C(F)(F)F)cc2)c(/C=N/OC(C)(C)C)c1)c1ccc(C(=O)NCCC(=O)O)cc1]

These compounds are made by the general method exemplified in Example 30 by resolving racemic 3-(4-{1-[2-(tert-butoxyimino-methyl)-4'-trifluoromethyl-biphenyl-4-yloxy]-3-methyl-butyl}-benzoylamino)-propionic acid methyl ester on Chiralpak AD-H column (4.6×150 mm). Isomer 1 MS (ES): 599.2 [M+H]⁺; Isomer 2 MS (ES): 599.2 [M+H]⁺.

Example 246

3-{4-[1-(4'-tert-Butyl-2,6-dimethyl-biphenyl-4-yloxy)-3,3-dimethyl-butyl]-benzoylamino}-2-hydroxy-propionic acid, Isomer 1 and Example 247

3-{4-[1-(4'-tert-Butyl-2,6-dimethyl-biphenyl-4-yloxy)-3,3-dimethyl-butyl]-benzoylamino}-2-hydroxy-propionic acid, Isomer 2

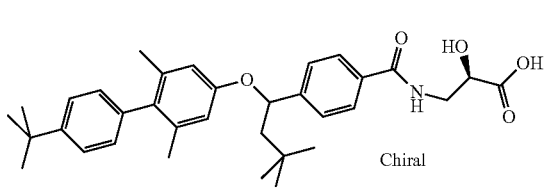 [SMILES: Cc1cc(OC(CC(C)(C)C)c2ccc(C(=O)NC[C@@H](O)C(=O)O)cc2)cc(C)c1-c1ccc(C(C)(C)C)cc1]

These compounds are made by the general method exemplified in Example 30 by resolving racemic 3-{4-[1-(4'-tert-butyl-2,6-dimethyl-biphenyl-4-yloxy)-3,3-dimethyl-butyl]-benzoylamino}-2-hydroxy-propionic acid methyl ester on Chiralpak AD-H column (4.6×150 mm). Isomer 1 MS (ES): 546.3 [M+H]⁺; Isomer 2 MS (ES): 546.3 [M+H]⁺.

Example 248

3-{4-[1-(4'-tert-Butyl-2,6-dimethyl-biphenyl-4-yloxy)-3,3-dimethyl-butyl]-benzoylamino}-2-hydroxy-propionic acid, Isomer 1 and Example 249

3-{4-[1-(4'-tert-Butyl-2,6-dimethyl-biphenyl-4-yloxy)-3,3-dimethyl-butyl]-benzoylamino}-2-hydroxy-propionic acid, Isomer 2

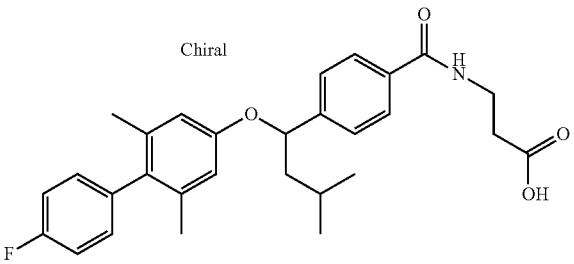 [SMILES: Cc1cc(OC(CC(C)C)c2ccc(C(=O)NCCC(=O)O)cc2)cc(C)c1-c1ccc(F)cc1]

These compounds are made by the general method exemplified in Example 30 by resolving racemic 3-{4-[1-(4'-tert-butyl-2,6-dimethyl-biphenyl-4-yloxy)-3,3-dimethyl-butyl]-benzoylamino}-2-hydroxy-propionic acid ethyl ester on Chiralpak AD-H column (4.6×150 mm). Isomer 1 MS (ES): 546.3 [M+H]⁺; Isomer 2 MS (ES): 546.3 [M+H]⁺.

Example 250

3-{4-[1-(4'-Fluoro-2,6-dimethyl-biphenyl-4-yloxy)-3-methyl-butyl]-benzoylamino}-propionic acid, Isomer 1

This compound is made in a manner substantially similar to Example 117 using isomer 1 of 3-{4-[1-(4-bromo-3,5-dimethyl-phenoxy)-3-methyl-butyl]-benzoylamino}-propionic acid methyl ester and 4-fluorophenylboronic acid as starting materials in step D. MS (ES): 476.2 [M–H]⁻.

Example 251

3-{4-[1-(4'-Fluoro-2,6,2'-trimethyl-biphenyl-4-yloxy)-heptyl]-benzoylamino}-propionic acid, Isomer 1

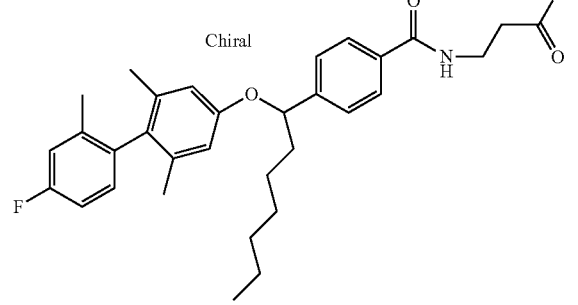

This compound is made in a manner substantially similar to Example 117 using isomer 1 of 3-{4-[1-(4-bromo-3,5-dimethyl-phenoxy)-heptyl]-benzoylamino}-propionic acid methyl ester and 4-fluoro-2-methyl-phenylboronic acid as starting materials in step D. MS (ES): 520.2 [M+H]⁺.

Example 252

3-{4-[1-(4'-Chloro-2,6-dimethyl-biphenyl-4-yloxy)-3-methyl-butyl]-benzoylamino}-propionic acid, Isomer 1

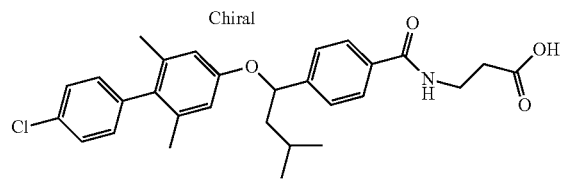 [SMILES: Cc1cc(OC(CC(C)C)c2ccc(C(=O)NCCC(=O)O)cc2)cc(C)c1-c1ccc(Cl)cc1]

This compound is made in a manner substantially similar to Example 117 using isomer 1 of 3-{4-[1-(4-bromo-3,5-dimethyl-phenoxy)-3-methyl-butyl]-benzoylamino}-propi-onic acid methyl ester and 4-chloro-phenylboronic acid as starting materials in step D. MS (ES): 492.3 [M+H]⁺.

Example 253

3-{4-[1-(4'-Isopropyl-2,6-dimethyl-biphenyl-4-yloxy)-3-methyl-butyl]-benzoylamino}-propionic acid, Isomer 1

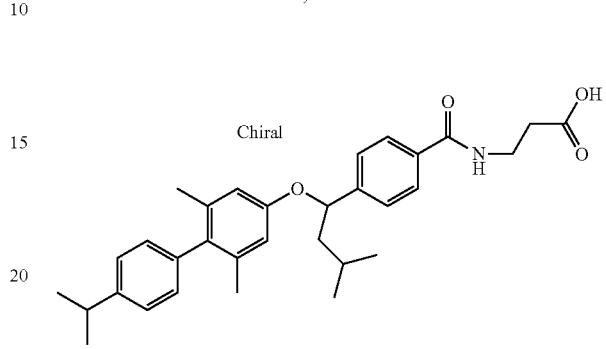

This compound is made in a manner substantially similar to Example 117 using isomer 1 of 3-{4-[1-(4-bromo-3,5-dimethyl-phenoxy)-3-methyl-butyl]-benzoylamino}-propionic acid methyl ester and 4-isopropylphenylboronic acid as starting materials in step D. MS (ES): 502.2 [M+H]⁺.

Example 254

3-{4-[1-(2,6-Dimethyl-4'-trifluoromethyl-biphenyl-4-yloxy)-3-methyl-butyl]-benzoylamino}-propionic acid, Isomer 1 and Example 255

3-{4-[1-(2,6-Dimethyl-4'-trifluoromethyl-biphenyl-4-yloxy)-3-methyl-butyl]-benzoylamino}-propionic acid, Isomer 2

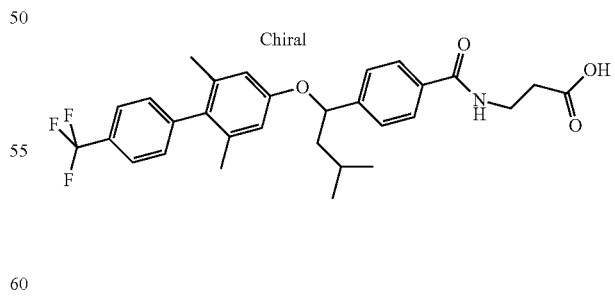

These compounds are made by the general method as exemplified in Example 30 by resolving racemic 3-{4-[1-(2,6-dimethyl-4'-trifluoromethyl-biphenyl-4-yloxy)-3-methyl-butyl]-benzoylamino}-propionic acid methyl ester on Chiral-

Example 256

Racemic 3-{4-[1-(4'-tert-Butyl-biphenyl-4-yloxy)-hexyl]-benzoylamino}-propionic acid

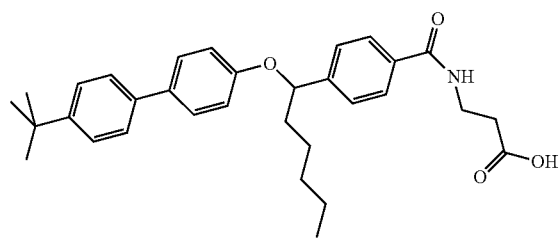 [SMILES: CCCCCC(Oc1ccc(-c2ccc(C(C)(C)C)cc2)cc1)c1ccc(C(=O)NCCC(=O)O)cc1]

This compound is made by the general method exemplified in Example 1 using 4-(1-hydroxy-hexyl)-benzoic acid methyl ester and 4'-tertbutyl-biphenyl-4-ol as starting materials. MS (ES): 502.2 [M+H]$^+$.

Example 257

Racemic 3-{4-[1-(4'-tert-Butyl-biphenyl-4-yloxy)-heptyl]-3-fluoro-benzoylamino}-propionic acid

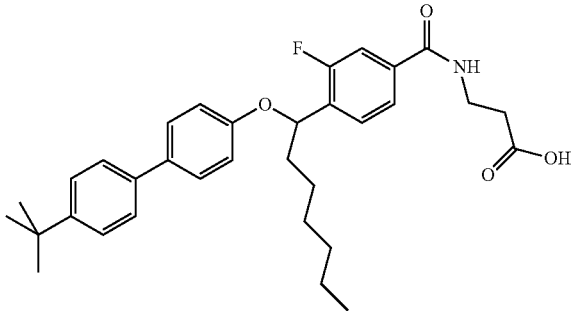 [SMILES: CCCCCCC(Oc1ccc(-c2ccc(C(C)(C)C)cc2)cc1)c1ccc(C(=O)NCCC(=O)O)cc1F]

This compound is made by the general method as exemplified in Example 1 using 3-fluoro-4-(1-hydroxy-heptyl)-benzoic acid methyl ester and 4'-tertbutyl-biphenyl-4-ol as starting materials. MS (ES): 534.2 [M+H]$^+$.

Example 258

Racemic 3-{4-[1-(4'-tert-Butyl-biphenyl-4-yloxy)-3-methyl-butyl]-3-fluoro-benzoylamino}-propionic acid

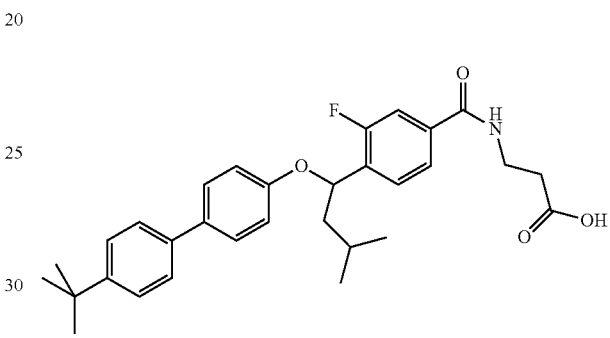

This compound is made by the general method as exemplified in Example 1 using 3-fluoro-4-(1-hydroxy-3-methyl-butyl)-benzoic acid methyl ester and 4'-tertbutyl-biphenyl-4-ol as starting materials. MS (ES): 504.2 [M−H]$^−$.

Example 259

Racemic 3-{4-[1-(4'-2-Cyano-4'-isopropyl-biphenyl-4-yloxy)-3-methyl-butyl]-benzoylamino}-propionic acid

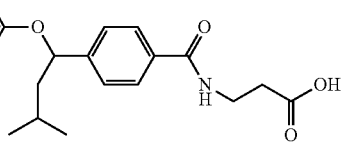

This compound is made by the general method as exemplified in Example 1 using 4-(1-hydroxy-3-methyl-butyl)- benzoic acid methyl ester and 4-hydroxy-4'-isopropyl-biphenyl-2-carbonitrile as starting materials. MS (ES): 499.2 [M+H]⁺.

Example 260

Racemic 3-{4-[1-(4'-Isopropyl-2-trifluoromethyl-biphenyl-4-yloxy)-heptyl]-benzoylamino}-propionic acid

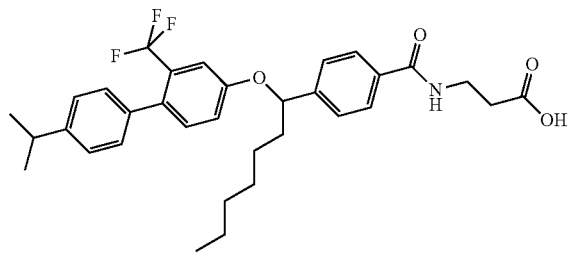 [SMILES: CCCCCCC(Oc1ccc(-c2ccc(C(C)C)cc2)c(C(F)(F)F)c1)c1ccc(C(=O)NCCC(=O)O)cc1]

This compound is made by the general method as exemplified in Example 1 using 4-(1-hydroxy-heptyl)-benzoic acid methyl ester and 4'-isopropyl-2-trifluoromethyl-biphenyl-4-ol as starting materials. MS (ES): 570.2 [M+H]⁺.

Example 261

Racemic 3-{4-[1-(2-Ethyl-4'-trifluoromethyl-biphenyl-4-yloxy)-heptyl]-benzoylamino}-propionic acid

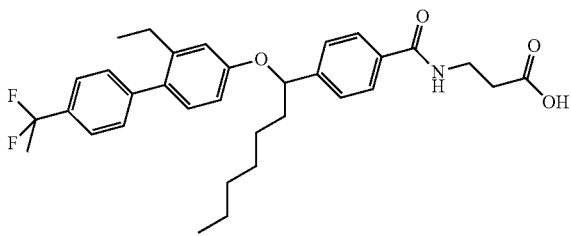 [SMILES: CCCCCCC(Oc1ccc(-c2ccc(C(C)(F)F)cc2)c(CC)c1)c1ccc(C(=O)NCCC(=O)O)cc1]

This compound is made by the general method as exemplified in Example 1 using 4-(1-hydroxy-heptyl)-benzoic acid methyl ester and 2-ethyl-4'-trifluoromethyl-biphenyl-4-ol as starting materials. MS (ES): 556.3 [M+H]⁺.

Example 262

3-[4-(4'-tert-Butyl-2,6-dimethyl-biphenyl-4-yloxymethyl)-benzoylamino]-propionic acid

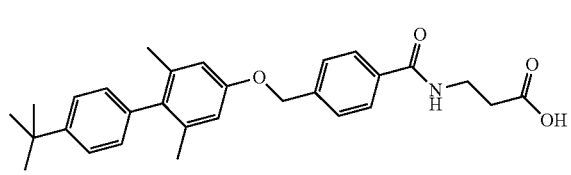 [SMILES: Cc1cc(OCc2ccc(C(=O)NCCC(=O)O)cc2)cc(C)c1-c1ccc(C(C)(C)C)cc1]

This compound is made by the general method as exemplified in Example 1 using 4-hydroxymethyl-benzoic acid methyl ester and 4'-tert-butyl-2,6-dimethyl-biphenyl-4-ol as starting materials. MS (ES): 460.2 [M+H]⁺.

Example 263

3-[4-(4'-tert-Butyl-2,6-dimethyl-biphenyl-4-yloxymethyl)-benzoylamino]-propionic acid

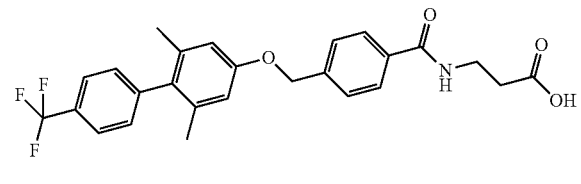 [SMILES: Cc1cc(OCc2ccc(C(=O)NCCC(=O)O)cc2)cc(C)c1-c1ccc(C(F)(F)F)cc1]

This compound is made by the general method as exemplified in Example 1 using 3-(4-hydroxymethyl-benzoic acid methyl ester and 4'-trifluoromethyl-2,6-dimethyl-biphenyl-4-ol as starting materials. MS (ES): 472.2 [M+H]⁺.

Example 264

Racemic 3-{4-[1-(2,6-Dimethyl-4'-trifluoromethyl-biphenyl-4-yloxy)-ethyl]-benzoylamino}-propionic acid

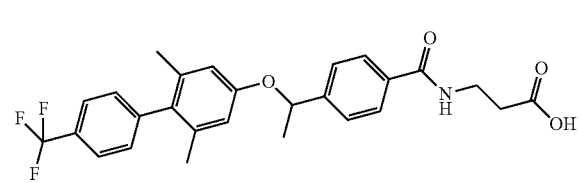 [SMILES: Cc1cc(OC(C)c2ccc(C(=O)NCCC(=O)O)cc2)cc(C)c1-c1ccc(C(F)(F)F)cc1]

This compound is made by the general method as exemplified in Example 1 using 4-(1-hydroxy-ethyl)-benzoic acid methyl ester and 4'-trifluoromethyl-2,6-dimethyl-biphenyl-4-ol as starting materials. MS (ES): 486.2 [M+H]⁺.

Example 265

Racemic 3-{4-[1-(4'-tert-Butyl-2,6-dimethyl-biphenyl-4-yloxy)-ethyl]-benzoylamino}-propionic acid

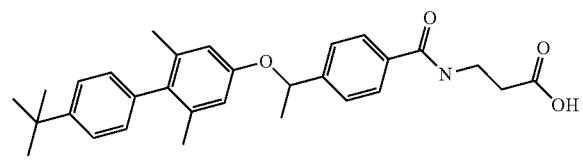 [SMILES: Cc1cc(OC(C)c2ccc(C(=O)NCCC(=O)O)cc2)cc(C)c1-c1ccc(C(C)(C)C)cc1]

This compound is made by the general method as exemplified in Example 1 using 4-(1-hydroxy-ethyl)-benzoic acid methyl ester and 4'-tert-butyl-2,6-dimethyl-biphenyl-4-ol as starting materials. MS (ES): 474.2 [M+H]+.

Example 266

Racemic 3-(3-Fluoro-4-{3-methyl-1-[6-(4-trifluoromethyl-phenyl)-pyridin-3-yloxy]-butyl}-benzoylamino)-propionic acid

This compound is made by the general method as exemplified in Example 1 using 3-fluoro-4-(1-hydroxy-3-methyl-butyl)-benzoic acid methyl ester and 6-(4-trifluoromethyl-phenyl)-pyridin-3-ol as starting materials. MS (ES): 519.2 [M+H]+.

Example 267

Racemic 3-(4-{1-[4-(1,1,3,3-Tetramethyl-butyl)-phenoxy]-heptyl}-benzoylamino)-propionic acid

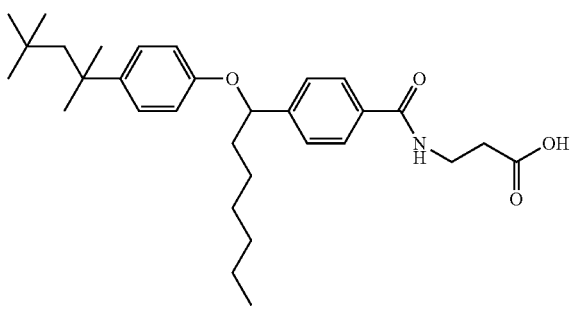 [SMILES: CCCCCCC(Oc1ccc(C(C)(C)CC(C)(C)C)cc1)c1ccc(C(=O)NCCC(=O)O)cc1]

This compound is made by the general method as exemplified in Example 1 using 4-(1-hydroxy-heptyl)-benzoic acid methyl ester and 4-(1,1,3,3-tetramethyl-butyl)-phenol as starting materials. MS (ES): 494.2 [M–H]−.

Example 268

Racemic 3-(4-{3-Methyl-1-[4-(5-trifluoromethyl-pyridin-2-yl)-phenoxy]-butyl}-benzoylamino)-propionic acid

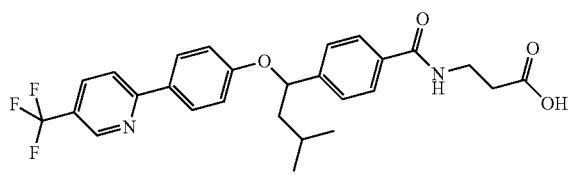 [SMILES: CC(C)CC(Oc1ccc(-c2ccc(C(F)(F)F)cn2)cc1)c1ccc(C(=O)NCCC(=O)O)cc1]

This compound is made by the general method as exemplified in Example 1 using 4-(1-hydroxy-3-methyl-butyl)- benzoic acid methyl ester and 4-(5-trifluoromethyl-pyridin-2-yl)-phenol as starting materials. MS (ES): 499.2 [M–H]−.

Example 269

Racemic 3-{4-[1-(4'-tert-Butyl-2,6-dimethyl-biphenyl-4-yloxy)-3,3-dimethyl-butyl]-benzoylamino}-propionic acid

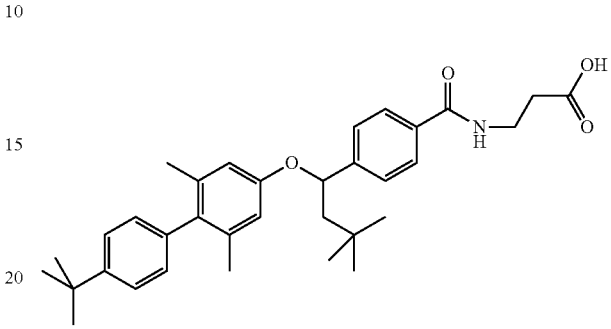

This compound is made by the general method as exemplified in Example 1 using 4-(1-hydroxy-3,3-dimethyl-butyl)-benzoic acid methyl ester and 4'-tert-butyl-2,6-dimethyl-biphenyl-4-ol as starting materials. MS (ES): 530.5 [M+H]+.

Example 270

Racemic 3-{4-[1-(4'-tert-Butyl-2,6-dimethyl-biphenyl-4-yloxy)-3,3-dimethyl-butyl]-benzoylamino}-2-hydroxy-propionic acid

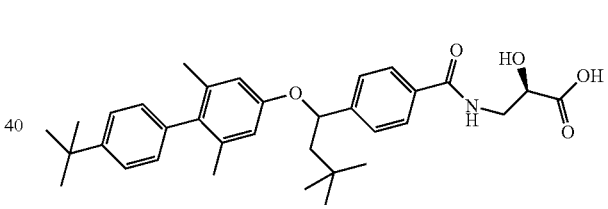

This compound is made by the general method as exemplified in Example 1 using 4-(1-hydroxy-3,3-dimethyl-butyl)-benzoic acid methyl ester and 4'-tert-butyl-2,6-dimethyl-biphenyl-4-ol as starting materials. MS (ES): 546.3 [M+H]+.

Example 271

Racemic 3-{4-[1-(4'-tert-Butyl-2,6-dimethyl-biphenyl-4-yloxy)-3,3-dimethyl-butyl]-benzoylamino}-2-hydroxy-propionic acid

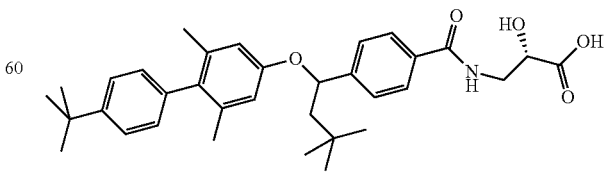

This compound is made by the general method as exemplified in Example 1 using 4-(1-hydroxy-3,3-dimethyl-butyl)-benzoic acid methyl ester and 4'-tert-butyl-2,6-dimethyl-biphenyl-4-ol as starting materials. MS (ES): 546.3 [M+H]⁺.

Example 272

Chiral 3-{4-[1-(2,6-Dimethyl-4'-trifluoromethyl-biphenyl-4-yloxy)-3-methyl-butyl]-benzoylamino}-2-hydroxy-propionic acid, Isomer 1

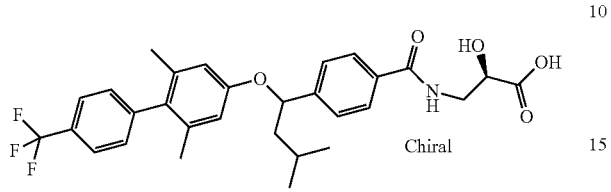

This compound is made by the general method as exemplified in Example 1 using chiral 4-(1-hydroxy-3-methyl-butyl)-benzoic acid methyl ester and 2,6-dimethyl-4'-trifluoromethyl-biphenyl-4-ol as starting materials. MS (ES): 544.2 [M+H]⁺.

Example 273

Chiral 3-{4-[1-(2,6-Dimethyl-4'-trifluoromethyl-biphenyl-4-yloxy)-3-methyl-butyl]-benzoylamino}-2-hydroxy-propionic acid, Isomer 1

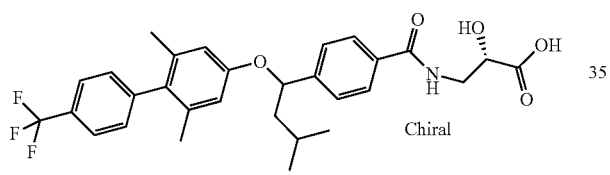

This compound is made by the general method as exemplified in Example 1 using chiral 4-(1-hydroxy-3-methyl-butyl)-benzoic acid methyl ester and 2,6-dimethyl-4'-trifluoromethyl-biphenyl-4-ol as starting materials. MS (ES): 544.2 [M+H]⁺.

Example 274

Racemic 3-{4-[1-(4-Bromo-3-[1,3]dioxan-2-yl-phenoxy)-3-methyl-butyl]-benzoylamino}-propionic acid

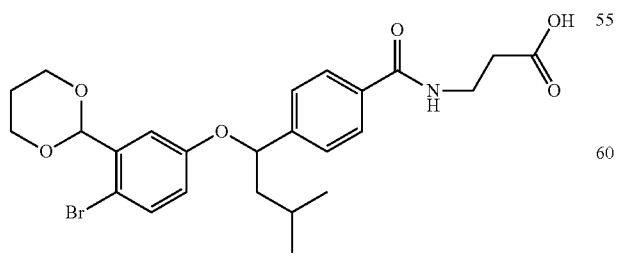

This compound is made by the general method as exemplified in Example 1 using 4-(1-hydroxy-3-methyl-butyl)-benzoic acid methyl ester and 4-bromo-3-[1,3]dioxan-2-yl-phenol as starting materials. MS (ES): 521.3 [M+H]⁺.

Example 275

Racemic 3-{4-[1-(4-tert-Butyl-phenoxy)-3-methyl-butyl]-benzoylamino}-propionic acid

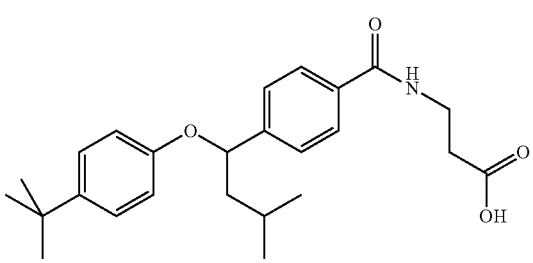 [SMILES: CC(C)CC(Oc1ccc(C(C)(C)C)cc1)c1ccc(C(=O)NCCC(=O)O)cc1]

This compound is made by the general method as exemplified in Example 1 using 4-(1-hydroxy-3-methyl-butyl)-benzoic acid methyl ester and 4-t-butyl-phenol as starting materials. MS (ES): 412.32 [M+H]⁺.

Example 276

Racemic 3-{4-[1-(4'-tert-Butyl-biphenyl-4-yloxy)-3-methyl-butyl]-benzoylamino}-2-hydroxy-propionic acid

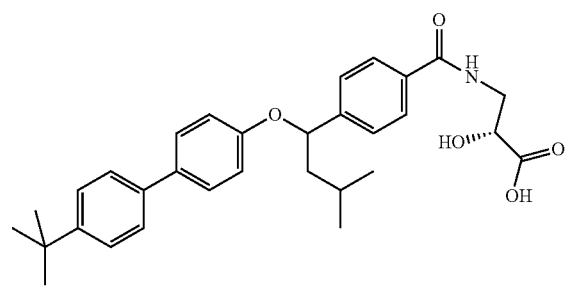 [SMILES: CC(C)CC(Oc1ccc(-c2ccc(C(C)(C)C)cc2)cc1)c1ccc(C(=O)NC[C@@H](O)C(=O)O)cc1]

This compound is made by the general method as exemplified in Example 1 using 4-(1-hydroxy-3-methyl-butyl)- benzoic acid methyl ester and 4'-tertbutyl-biphenol as starting materials. MS (ES): 504.2 [M+H]⁺.

Example 277

Racemic 3-{4-[1-(4'-tert-Butyl-biphenyl-4-yloxy)-3-methyl-butyl]-benzoylamino}-2-hydroxy-propionic acid

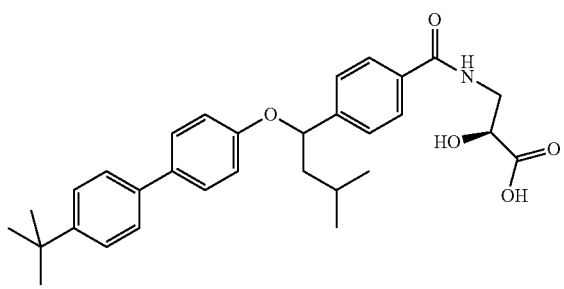 [SMILES: CC(C)CC(Oc1ccc(-c2ccc(C(C)(C)C)cc2)cc1)c1ccc(C(=O)NC[C@H](O)C(=O)O)cc1]

This compound is made by the general method as exemplified in Example 1 using 4-(1-hydroxy-3-methyl-butyl)-benzoic acid methyl ester and 4'-tertbutyl-biphenol as starting materials. MS (ES): 504.2 [M+H]⁺.

Example 278

Racemic 3-{4-[1-(4-Pentyl-phenoxy)-heptyl]-benzoylamino}-propionic acid

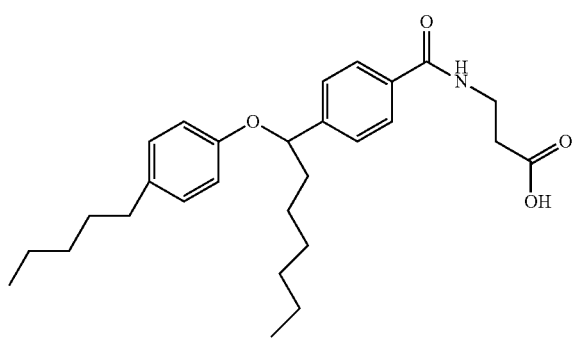 [SMILES: CCCCCCC(Oc1ccc(CCCCC)cc1)c1ccc(C(=O)NCCC(=O)O)cc1]

This compound is made by the general method as exemplified in Example 1 using 4-(1-hydroxy-heptyl)-benzoic acid methyl ester and 4-pentyl-phenol as starting materials. MS (ES): 454.2 [M+H]⁺.

Example 279

Racemic 3-(4-{1-[4-(1-Methyl-1-phenyl-ethyl)-phenoxy]-heptyl}-benzoylamino)-propionic acid

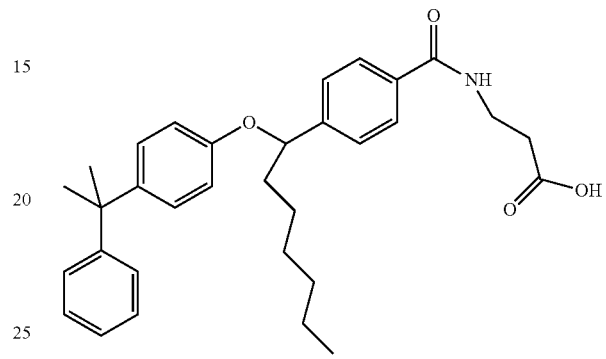

This compound is made by the general method as exemplified in Example 1 using 4-(1-hydroxy-heptyl)-benzoic acid methyl ester and 4-(1-methyl-1-phenyl-ethyl)-phenol as starting materials. MS (ES): 500.3 [M−H]⁻.

Example 280

Racemic 2-Hydroxy-3-{4-[1-(4'-trifluoromethyl-biphenyl-4-yloxy)-heptyl]-benzoylamino}-propionic acid

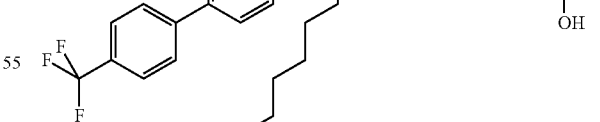

This compound is made by the general method as exemplified in Example 1 using 4-(1-hydroxy-heptyl)-benzoic acid methyl ester and 4-trifluoromethyl-biphenol as starting materials. MS (ES): 542.3 [M−H]−.

Example 281

Racemic 2-Hydroxy-3-{4-[1-(4'-trifluoromethyl-biphenyl-4-yloxy)-heptyl]-benzoylamino}-propionic acid

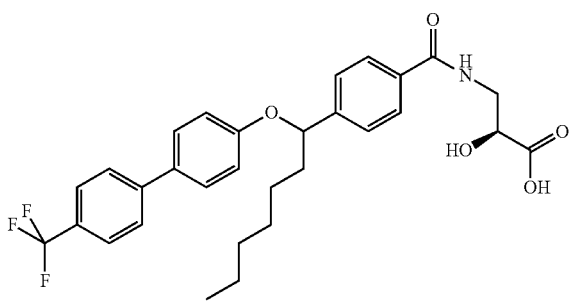 [SMILES: CCCCCCC(Oc1ccc(-c2ccc(C(F)(F)F)cc2)cc1)c1ccc(C(=O)NC[C@H](O)C(=O)O)cc1]

This compound is made by the general method as exemplified in Example 1 using 4-(1-hydroxy-heptyl)-benzoic acid methyl ester and 4-trifluoromethyl-biphenol as starting materials. MS (ES): 542.3 [M−H]−.

Example 282

Racemic 3-{4-[1-(4'-Isopropyl-2-methyl-biphenyl-4-yloxy)-3-methyl-butyl]-benzoylamino}-propionic acid

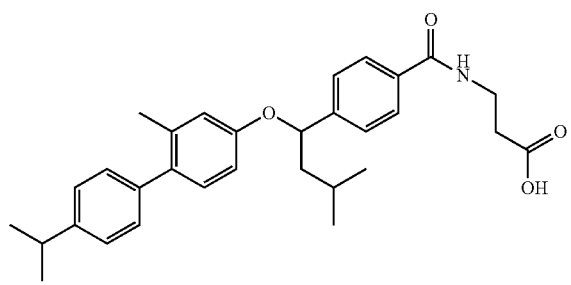 [SMILES: Cc1cc(OC(CC(C)C)c2ccc(C(=O)NCCC(=O)O)cc2)ccc1-c1ccc(C(C)C)cc1]

This compound is made by the general method as exemplified in Example 1 using 4-(1-hydroxy-3-methyl-butyl)-benzoic acid methyl ester and 4'-isopropyl-2-methyl-biphenyl-4-ol as starting materials. MS (ES): 488.3 [M+H]+.

Example 283

Racemic 3-{4-[1-(4-Chloro-3-trifluoromethyl-phenoxy)-heptyl]-benzoylamino}-2-hydroxy-propionic acid

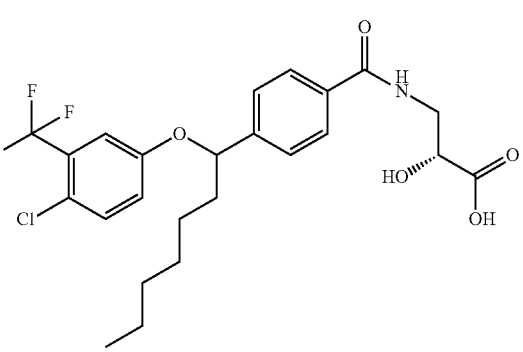

This compound is made by the general method as exemplified in Example 1 using 4-(1-hydroxy-heptyl)-benzoic acid methyl ester and 4-chloro-3-trifluoromethyl-phenol as starting materials. MS (ES): 486.2 [M+H]+.

Example 284

Racemic 3-{4-[1-(3-Chloro-4-methyl-phenoxy)-3-methyl-butyl]-benzoylamino}-propionic acid

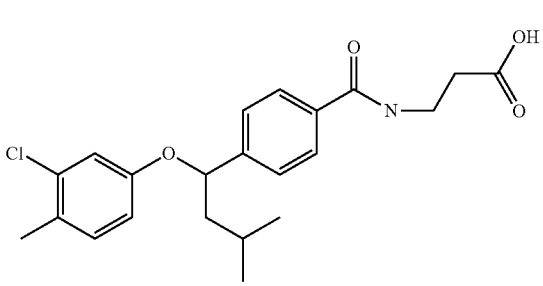 [SMILES: Cc1ccc(OC(CC(C)C)c2ccc(C(=O)NCCC(=O)O)cc2)cc1Cl]

This compound is made by the general method as exemplified in Example 1 using 4-(1-hydroxy-3-methyl-butyl)- benzoic acid methyl ester and 3-chloro-4-methyl-phenol as starting materials. MS (ES): 404.2 [M+H]+.

Example 285

Racemic 3-{4-[1-(2,2,3,3-Tetrafluoro-2,3-dihydro-benzo[1,4]dioxin-6-yloxy)-heptyl]-benzoylamino}-propionic acid

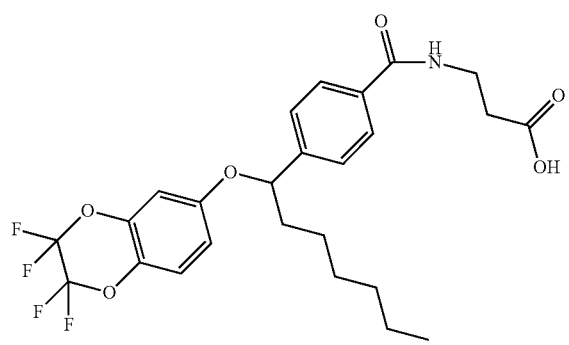 [SMILES: CCCCCCC(Oc1ccc2c(c1)OC(F)(F)C(F)(F)O2)c1ccc(C(=O)NCCC(=O)O)cc1]

This compound is made by the general method as exemplified in Example 1 using 4-(1-hydroxy-heptyl)-benzoic acid methyl ester and 2,2,3,3-tetrafluoro-2,3-dihydro-benzo[1,4]dioxin-6-ol as starting materials. MS (ES): 514.2 [M+H]+.

Example 286

Racemic 3-{4-[Cyclopropyl-(4'-trifluoromethyl-biphenyl-4-yloxy)-methyl]-benzoylamino}-propionic acid

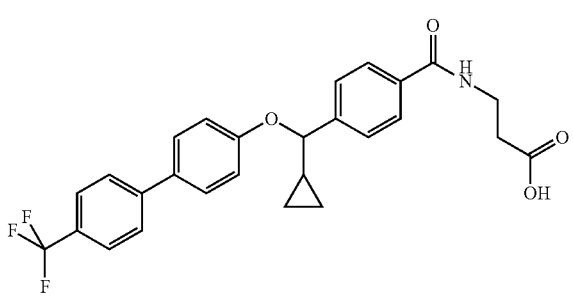 [SMILES: O=C(O)CCNC(=O)c1ccc(C(Oc2ccc(-c3ccc(C(F)(F)F)cc3)cc2)C2CC2)cc1]

This compound is made by the general method as exemplified in Example 1 using 4-(cyclopropyl-hydroxy-methyl)-benzoic acid methyl ester and 4'-trifluoromethyl-biphenyl-4-ol as starting materials. MS (ES): 482.2 [M−H]−.

Example 287

Racemic 3-{4-[1-(4'-Isopropyl-2,6-dimethyl-biphenyl-4-yloxy)-heptyl]-benzoylamino}-propionic acid

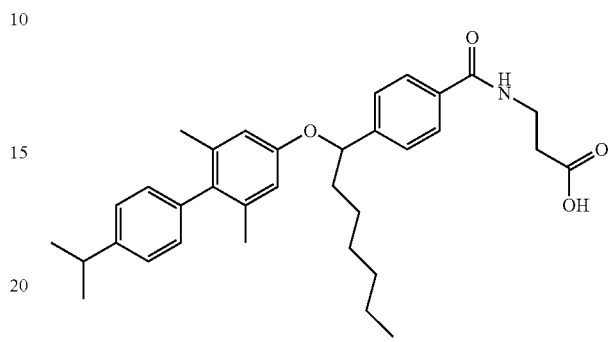

This compound is made by the general method as exemplified in Example 24 using 4-(1-hydroxy-heptyl)-benzoic acid methyl ester and 4-bromo-3,5-dimethylphenol as reagents in step A and 4-isopropylphenyl boronic acid in step C as starting materials. MS (ES): 530.5 [M+H]+.

Example 288

Racemic 3-{4-[1-(4'-Acetyl-2,6-dimethyl-biphenyl-4-yloxy)-heptyl]-benzoylamino}-propionic acid

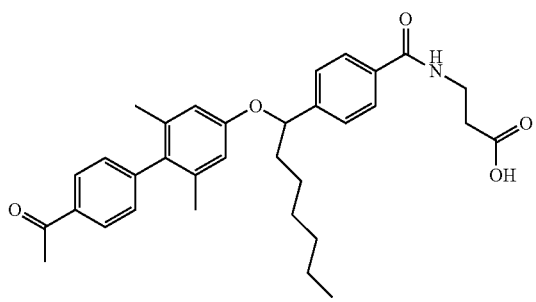 [SMILES: CCCCCCC(Oc1cc(C)c(-c2ccc(C(C)=O)cc2)c(C)c1)c1ccc(C(=O)NCCC(=O)O)cc1]

This compound is made by the general method as exemplified in Example 24 using 4-(1-hydroxy-heptyl)-benzoic acid methyl ester and 4-bromo-3,5-dimethylphenol as reagents in step A and 4-acetylphenyl boronic acid in step C as starting materials. MS (ES): 530.2 [M+H]⁺.

Example 289

Racemic 3-{4-[1-(4'-tert-Butyl-2-methyl-biphenyl-4-yloxy)-heptyl]-benzoylamino}-propionic acid

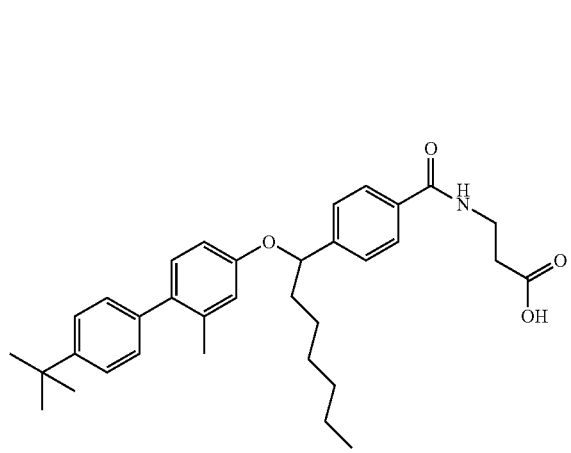 [SMILES: CCCCCCC(Oc1ccc(-c2ccc(C(C)(C)C)cc2)c(C)c1)c1ccc(C(=O)NCCC(=O)O)cc1]

This compound is made by the general method as exemplified in Example 24 using 4-(1-hydroxy-heptyl)-benzoic acid methyl ester and 4-bromo-3-methylphenol as reagents in step A and 4-tertbutylphenyl boronic acid in step C as starting materials. MS (ES): 528.3 [M–H]⁻.

Example 290

Racemic 3-{4-[1-(2-Methyl-4'-trifluoromethyl-biphenyl-4-yloxy)-heptyl]-benzoylamino}-propionic acid

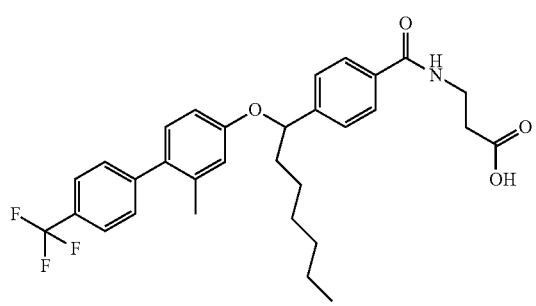 [SMILES: CCCCCCC(Oc1ccc(-c2ccc(C(F)(F)F)cc2)c(C)c1)c1ccc(C(=O)NCCC(=O)O)cc1]

This compound is made by the general method as exemplified in Example 24 using 4-(1-hydroxy-heptyl)-benzoic acid methyl ester and 4-bromo-3-methylphenol as reagents in step A and 4-trifluoromethylphenyl boronic acid in step C as starting materials. MS (ES): 540.3 [M–H]⁻.

Example 291

Racemic 3-(4-{1-[6-(4-Isopropyl-phenyl)-5-methyl-pyridin-3-yloxy]-4,4-dimethyl-pentyl}-benzoylamino)-propionic acid

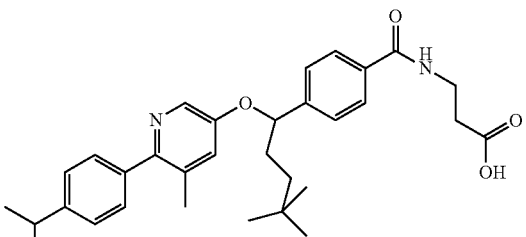

This compound is made by the general method as exemplified in Example 24 using 4-(1-hydroxy-4,4-dimethyl-pentyl)-benzoic acid methyl ester and 6-chloro-5-methyl-pyridin-3-ol as reagents in step A and 4-isopropylphenyl boronic acid in step C as starting materials. MS (ES): 517.3 [M+H]⁺.

Example 292

Racemic 3-(4-{4,4-Dimethyl-1-[5-methyl-6-(4-trifluoromethyl-phenyl)-pyridin-3-yloxy]-pentyl}-benzoylamino)-propionic acid This compound is made by the general method as exemplified in Example 24 using 4-(1-hydroxy-4,4-dimethyl-pentyl)-benzoic acid methyl ester and 6-chloro-5-methyl-pyridin-3-ol as reagents in step A and 4-trifluoromethylphenyl boronic acid in step C as starting materials. MS (ES): 529.3 [M+H]⁺.

Example 293

Racemic 3-(4-{4,4-Dimethyl-1-[5-methyl-6-(4-trifluoromethoxy-phenyl)-pyridin-3-yloxy]-pentyl}-benzoylamino)-propionic acid

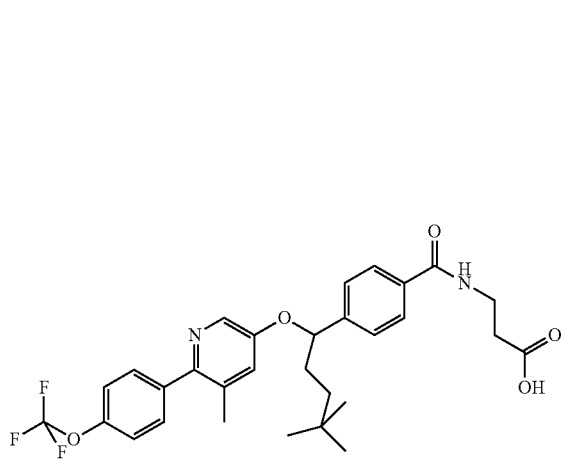 [SMILES: Cc1cc(OC(CCC(C)(C)C)c2ccc(C(=O)NCCC(=O)O)cc2)cnc1-c1ccc(OC(F)(F)F)cc1]

This compound is made by the general method as exemplified in Example 24 using 4-(1-hydroxy-4,4-dimethyl-pentyl)-benzoic acid methyl ester and 6-chloro-5-methyl-pyridin-3-ol as reagents in step A and 4-trifluoromethoxyphenyl boronic acid in step C as starting materials. MS (ES): 545.3 [M+H]⁺.

Example 294

Racemic 3-{4-[1-(2,6-Dimethyl-4'-trifluoromethoxy-biphenyl-4-yloxy)-3,3-dimethyl-butyl]-benzoylamino}-propionic acid

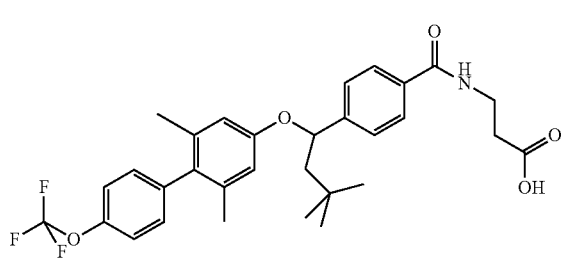 [SMILES: Cc1cc(OC(CC(C)(C)C)c2ccc(C(=O)NCCC(=O)O)cc2)cc(C)c1-c1ccc(OC(F)(F)F)cc1]

This compound is made by the general method as exemplified in Example 24 using 4-(1-hydroxy-3,3-dimethyl-butyl)-benzoic acid methyl ester and 4-bromo-3,5-dimethyl-phenol as reagents in step A and 4-trifluoromethoxyphenyl boronic acid in step C as starting materials. MS (ES): 558.3 [M+H]⁺.

Example 295

Racemic 3-{4-[1-(2,6-Dimethyl-4'-trifluoromethyl-biphenyl-4-yloxy)-3,3-dimethyl-butyl]-benzoylamino}-2-hydroxy-propionic acid

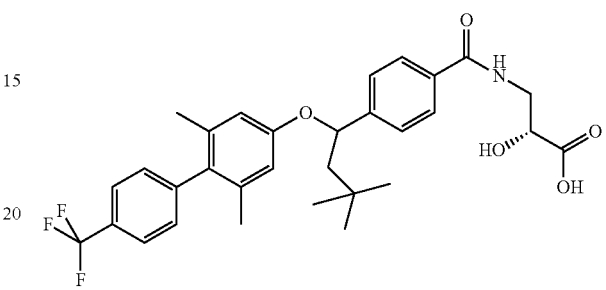

This compound is made by the general method as exemplified in Example 24 using 4-(1-hydroxy-3,3-dimethyl-butyl)-benzoic acid methyl ester and 4-bromo-3,5-dimethyl-phenol as reagents in step A and 4-trifluoromethylphenyl boronic acid in step C as starting materials. MS (ES): 558.3 [M+H]⁺.

Example 296

Racemic 3-{4-[1-(2,6-Dimethyl-4'-trifluoromethyl-biphenyl-4-yloxy)-3,3-dimethyl-butyl]-benzoylamino}-2-hydroxy-propionic acid

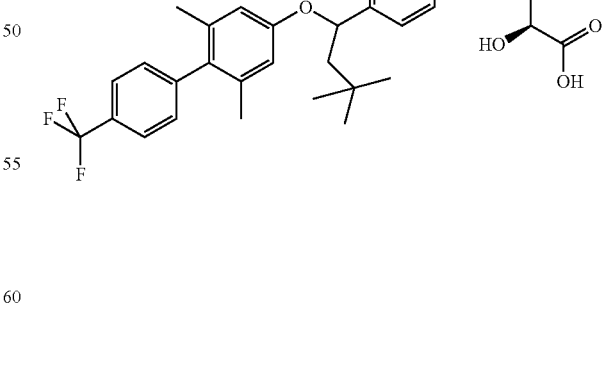

This compound is made by the general method as exemplified in Example 24 using 4-(1-hydroxy-3,3-dimethyl-butyl)-benzoic acid methyl ester and 4-bromo-3,5-dimethylphenol as reagents in step A and 4-trifluoromethylphenyl boronic acid in step C as starting materials. MS (ES): 558.3 [M+H]+.

Example 297

Racemic 2-Hydroxy-3-{4-[1-(4'-isopropyl-2,6-dimethyl-biphenyl-4-yloxy)-3,3-dimethyl-butyl]-benzoylamino}-propionic acid

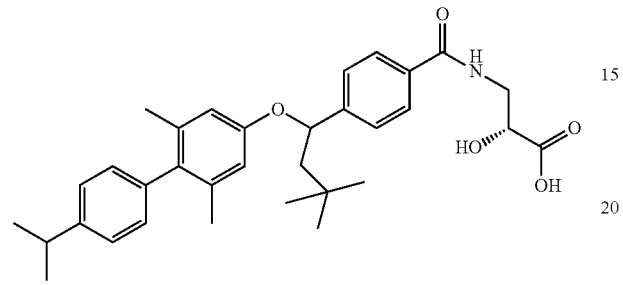

This compound is made by the general method as exemplified in Example 24 using 4-(1-hydroxy-3,3-dimethyl-butyl)-benzoic acid methyl ester and 4-bromo-3,5-dimethylphenol as reagents in step A and 4-trifluoromethylphenyl boronic acid in step C as starting materials. MS (ES): 532.3 [M+H]+.

Example 298

Racemic 3-{4-[1-(4'-Isopropyl-2-methoxy-biphenyl-4-yloxy)-3-methyl-butyl]-benzoylamino}-propionic acid

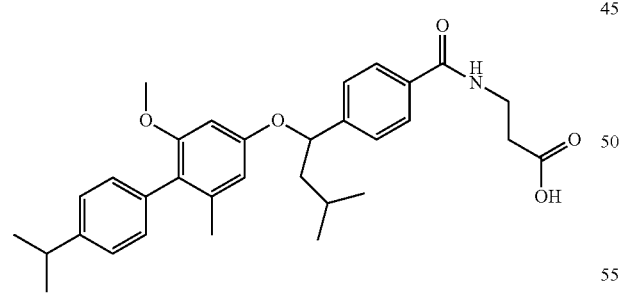

This compound is made by the general method as exemplified in Example 24 using 4-(1-hydroxy-3-methyl-butyl)-benzoic acid methyl ester and 4-bromo-3-methoxy-phenol as reagents in step A and 4-isopropylphenyl boronic acid in step C as starting materials. MS (ES): 504.2 [M+H]+.

Example 299

Racemic 3-{3-Fluoro-4-[1-(2-methyl-4'-trifluoromethyl-biphenyl-4-yloxy)-heptyl]-benzoylamino}-propionic acid

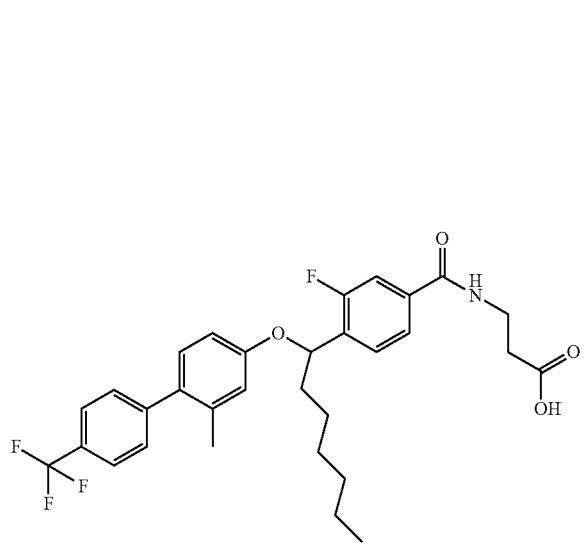

This compound is made by the general method as exemplified in Example 24 using 3-fluoro-4-(1-hydroxy-heptyl)-benzoic acid methyl ester and 4-bromo-3-methylphenol as reagents in step A and 4-trifluoromethylphenyl boronic acid in step C as starting materials. MS (ES): 516.3 [M+H]+.

Example 300

Racemic 3-{4-[1-(4'-tert-Butyl-2-chloro-biphenyl-4-yloxy)-heptyl]-benzoylamino}-propionic acid

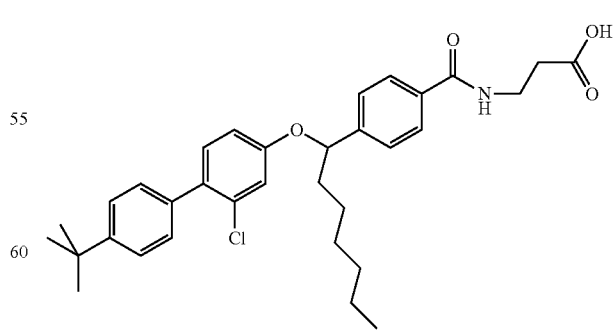

This compound is made by the general method as exemplified in Example 24 using 4-(1-hydroxy-heptyl)-benzoic acid methyl ester and 4-bromo-3-chloro-phenol as reagents in step A and 4-tertbutylphenyl boronic acid in step C as starting materials. MS (ES): 548.3 [M−H]⁻.

Example 301

Racemic 3-{4-[1-(4'-trifluoromethyl-2-chloro-biphenyl-4-yloxy)-heptyl]-benzoylamino}-propionic acid

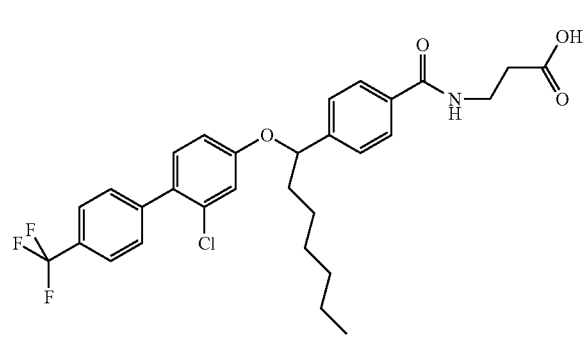 [SMILES: CCCCCCC(Oc1ccc(-c2ccc(C(F)(F)F)cc2)c(Cl)c1)c1ccc(C(=O)NCCC(=O)O)cc1]

This compound is made by the general method as exemplified in Example 24 using 4-(1-hydroxy-heptyl)-benzoic acid methyl ester and 4-bromo-3-chloro-phenol as reagents in step A and 4-trifluoromethylphenyl boronic acid in step C as starting materials. MS (ES): 560.2 [M−H]⁻.

Example 302

Racemic 3-{4-[1-(2',4'-bistrifluoromethyl-2-chloro-biphenyl-4-yloxy)-heptyl]-benzoylamino}-propionic acid

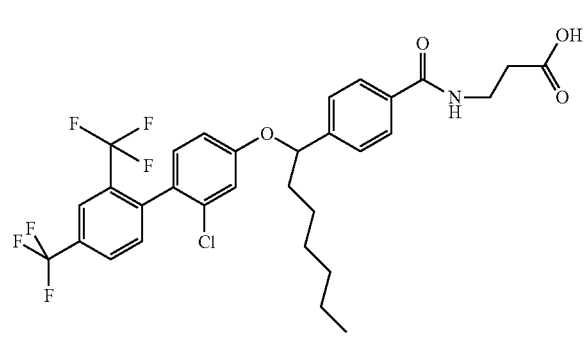 [SMILES: CCCCCCC(Oc1ccc(-c2ccc(C(F)(F)F)cc2C(F)(F)F)c(Cl)c1)c1ccc(C(=O)NCCC(=O)O)cc1]

This compound is made by the general method as exemplified in Example 24 using 4-(1-hydroxy-heptyl)-benzoic acid methyl ester and 4-bromo-3-chloro-phenol as reagents in step A and 2,4-bistrifluoromethylphenyl boronic acid in step C as starting materials. MS (ES): 628.3 [M−H]⁻.

Example 303

Racemic 3-{4-[1-(2,6-Dimethyl-4'-trifluoromethyl-biphenyl-4-yloxy)-3-methyl-butyl]-benzoylamino}-propionic acid

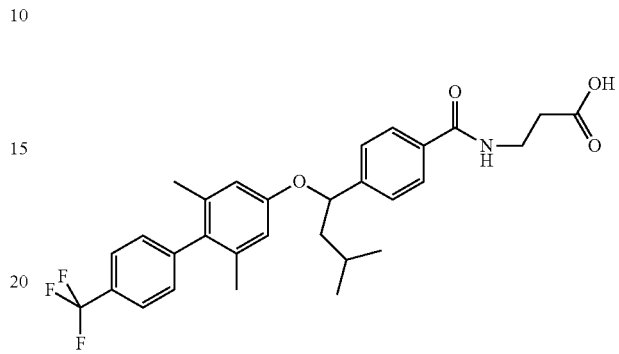

This compound is made by the general method as exemplified in Example 24 using 4-(1-hydroxy-3-methyl-butyl)-benzoic acid methyl ester and 4-bromo-3,5-dimethyl-phenol as reagents in step A and 4-trifluoromethylphenyl boronic acid in step C as starting materials. MS (ES): 526.2 [M−H]⁻.

Example 304

Racemic 3-{4-[1-(4'-tert-Butyl-2,6-dimethyl-biphenyl-4-yloxy)-3-methyl-butyl]-benzoylamino}-propionic acid

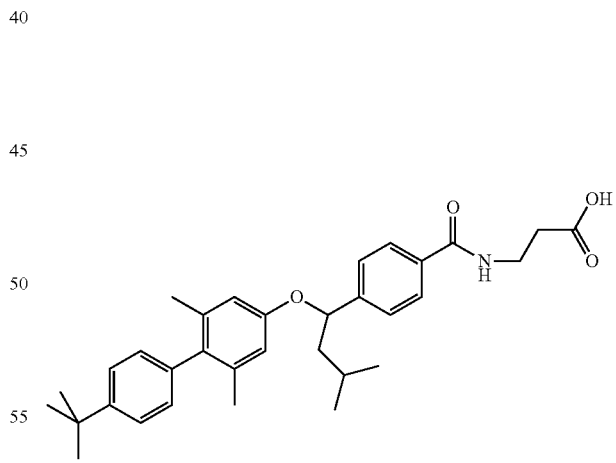

This compound is made by the general method as exemplified in Example 24 using 4-(1-hydroxy-3-methyl-butyl)-benzoic acid methyl ester and 4-bromo-3,5-dimethyl-phenol as reagents in step A and 4-t-butylphenyl boronic acid in step C as starting materials. MS (ES): 516.3 [M+H]+.

Example 305

Racemic 3-{4-[1-(2-Hydroxy-4'-isopropyl-biphenyl-4-yloxy)-3-methyl-butyl]-benzoylamino}-propionic acid

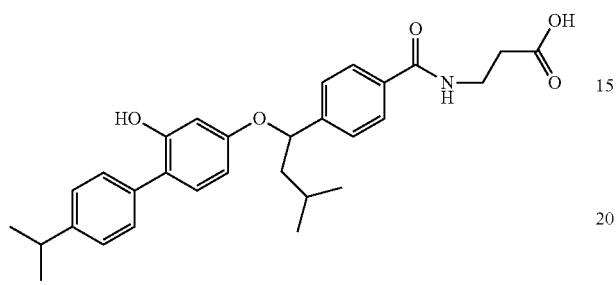

This compound is made by the general method as exemplified in Example 24 using 4-(1-hydroxy-3-methyl-butyl)-benzoic acid methyl ester and 4-bromo-benzene-1,3-diol as reagents in step A and 4-isopropylphenyl boronic acid in step C as starting materials. MS (ES): 490.2 [M+H]+.

Example 306

Racemic 3-{4-[1-(2-[1,3]Dioxan-2-yl-4'-isopropyl-biphenyl-4-yloxy)-3-methyl-butyl]-benzoylamino}-propionic acid

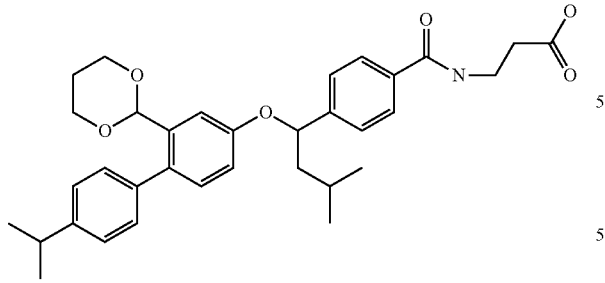

This compound is made by the general method as exemplified in Example 24 using 4-(1-hydroxy-3-methyl-butyl)-benzoic acid methyl ester and 4-bromo-3-[1,3]dioxan-2-yl-phenol as reagents in step A and 4-isopropylphenyl boronic acid in step C as starting materials. MS (ES): 560.2 [M+H]+.

Example 307

Racemic 3-(4-{1-[2-(tert-Butoxyimino-methyl)-4'-isopropyl-biphenyl-4-yloxy]-3-methyl-butyl}-benzoylamino)-propionic acid

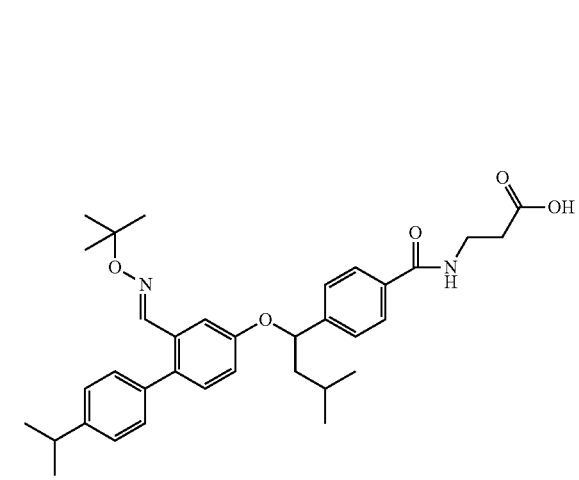 [SMILES: CC(C)CC(Oc1ccc(-c2ccc(C(C)C)cc2)c(/C=N/OC(C)(C)C)c1)c1ccc(C(=O)NCCC(=O)O)cc1]

This compound is made by the general method as exemplified in Example 24 using 4-(1-hydroxy-3-methyl-butyl)-benzoic acid methyl ester and 2-bromo-5-hydroxy-benzaldehyde O-tert-butyl-oxime as reagents in step A and 4-isopropylphenyl boronic acid in step C as starting materials. MS (ES): 573.3 [M+H]+.

Example 308

Racemic 3-(4-{1-[2-(tert-Butoxyimino-methyl)-4'-trifluoromethyl-biphenyl-4-yloxy]-3-methyl-butyl}-benzoylamino)-propionic acid

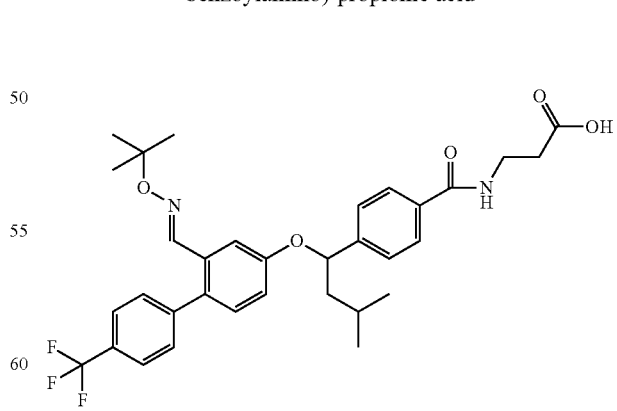

This compound is made by the general method as exemplified in Example 24 using 4-(1-hydroxy-3-methyl-butyl)-benzoic acid methyl ester and 2-bromo-5-hydroxy-benzaldehyde O-tert-butyl-oxime as reagents in step A and 4-trifluoromethylphenyl boronic acid in step C as starting materials. MS (ES): 599.2 [M+H]+.

Example 309

Racemic 3-{4-[1-(2,6-Dimethyl-biphenyl-4-yloxy)-3-methyl-butyl]-benzoylamino}-propionic acid

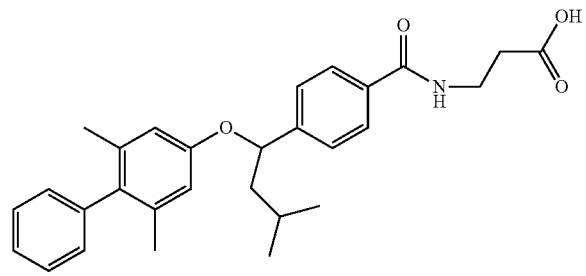 [SMILES: Cc1cc(OC(CC(C)C)c2ccc(C(=O)NCCC(=O)O)cc2)cc(C)c1-c1ccccc1]

This compound is made by the general method as exemplified in Example 24 using 4-(1-hydroxy-3-methyl-butyl)-benzoic acid methyl ester and 4-bromo-3,5-dimethyl-phenol as reagents in step A and phenyl boronic acid in step C as starting materials. MS (ES): 460.2 [M+H]+.

Example 310

Racemic 3-{4-[1-(4'-Ethyl-2,6-dimethyl-biphenyl-4-yloxy)-3-methyl-butyl]-benzoylamino}-propionic acid

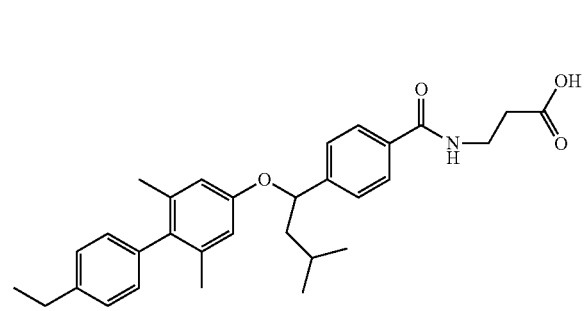 [SMILES: CCc1ccc(-c2c(C)cc(OC(CC(C)C)c3ccc(C(=O)NCCC(=O)O)cc3)cc2C)cc1]

This compound is made by the general method as exemplified in Example 24 using 4-(1-hydroxy-3-methyl-butyl)-benzoic acid methyl ester and 4-bromo-3,5-dimethyl-phenol as reagents in step A and 4-ethyl-phenyl boronic acid in step C as starting materials. MS (ES): 486.2 [M−H]−.

Example 311

Racemic 3-{4-[1-(2-Methyl-4'-trifluoromethoxy-biphenyl-4-yloxy)-heptyl]-benzoylamino}-propionic acid

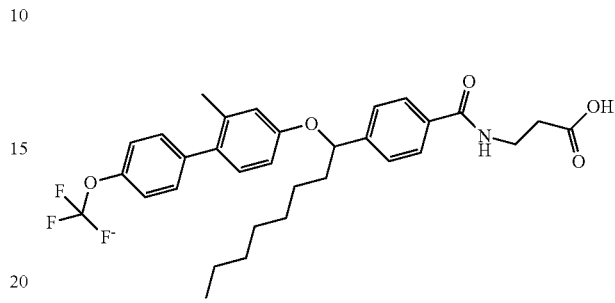

This compound is made by the general method as exemplified in Example 24 using 4-(1-hydroxy-heptyl)-benzoic acid methyl ester and 4-bromo-3-methyl-phenol as reagents in step A and 4-trifluoromethoxy-phenyl boronic acid in step C as starting materials. MS (ES): 556.3 [M−H]−.

Example 312

Racemic 3-{4-[1-(4'-Isopropyl-2-methyl-biphenyl-4-yloxy)-heptyl]-benzoylamino}-propionic acid

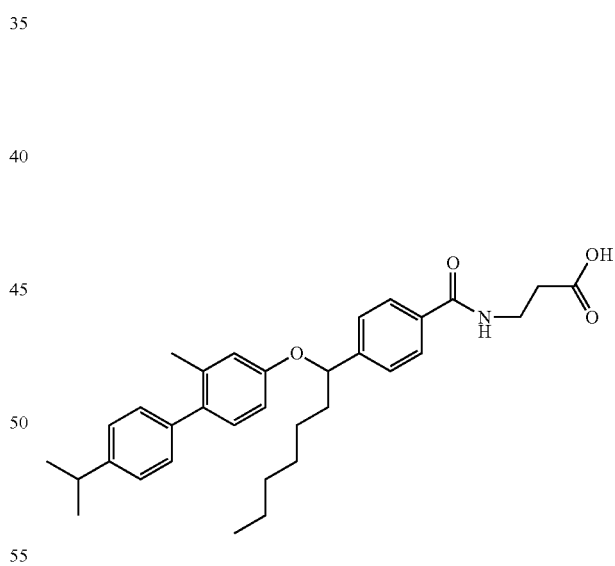

This compound is made by the general method as exemplified in Example 24 using 4-(1-hydroxy-heptyl)-benzoic acid methyl ester and 4-bromo-3-methyl-phenol as reagents in step A and 4-isopropyl-phenyl boronic acid in step C as starting materials. MS (ES): 516.3 [M+H]⁺.

Example 313

Racemic 3-{4-[1-(2,6-Dimethyl-4'-trifluoromethoxy-biphenyl-4-yloxy)-3-methyl-butyl]-benzoylamino}-propionic acid

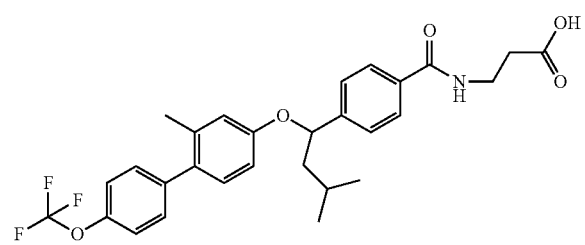 [SMILES: Cc1cc(OC(CC(C)C)c2ccc(C(=O)NCCC(=O)O)cc2)ccc1-c1ccc(OC(F)(F)F)cc1]

This compound is made by the general method as exemplified in Example 24 using 4-(1-hydroxy-3-methyl-butyl)-benzoic acid methyl ester and 4-bromo-3,5-dimethyl-phenol as reagents in step A and 4-trifluoromethoxy-phenyl boronic acid in step C as starting materials. MS (ES): 542.3 [M−H]⁻.

Example 314

Racemic 3-{4-[1-(4'-ethyl-2-methyl-biphenyl-4-yloxy)-heptyl]-benzoylamino}-propionic acid

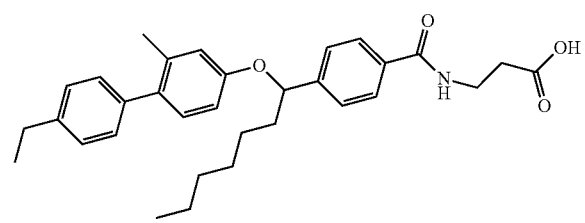 [SMILES: CCCCCCC(Oc1ccc(-c2ccc(CC)cc2)c(C)c1)c1ccc(C(=O)NCCC(=O)O)cc1]

This compound is made by the general method as exemplified in Example 24 using 4-(1-hydroxy-heptyl)-benzoic acid methyl ester and 4-bromo-3-methyl-phenol as reagents in step A and 4-ethyl-phenyl boronic acid in step C as starting materials. MS (ES): 502.2 [M+H]⁺.

Example 315

Racemic 3-{4-[1-(4'-acetyl-2-methyl-biphenyl-4-yloxy)-heptyl]-benzoylamino}-propionic acid

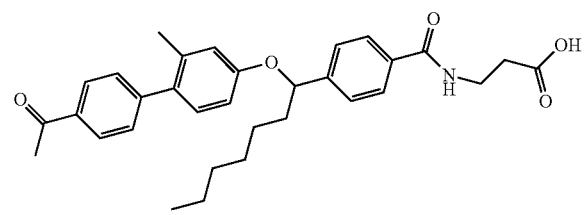 [SMILES: CCCCCCC(Oc1ccc(-c2ccc(C(C)=O)cc2)c(C)c1)c1ccc(C(=O)NCCC(=O)O)cc1]

This compound is made by the general method as exemplified in Example 24 using 4-(1-hydroxy-heptyl)-benzoic acid methyl ester and 4-bromo-3-methyl-phenol as reagents in step A and 4-acetyl-phenyl boronic acid in step C as starting materials. MS (ES): 514.2 [M−H]⁻.

Example 316

Racemic 3-{4-[1-(4'-fluoro-2-methyl-biphenyl-4-yloxy)-heptyl]-benzoylamino}-propionic acid

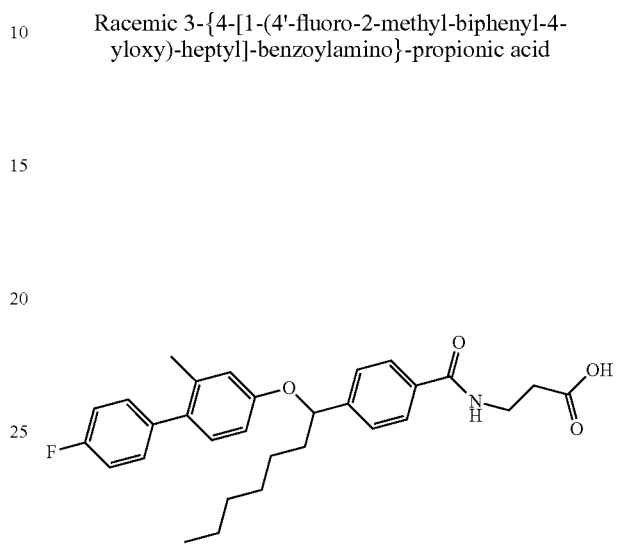

This compound is made by the general method as exemplified in Example 24 using 4-(1-hydroxy-heptyl)-benzoic acid methyl ester and 4-bromo-3-methyl-phenol as reagents in step A and 4-fluoro-phenyl boronic acid in step C as starting materials. MS (ES): 490.2 [M−H]⁻.

Example 317

Racemic 3-{4-[1-(4'-tert-Butyl-2-trifluoromethyl-biphenyl-4-yloxy)-heptyl]-benzoylamino}-propionic acid

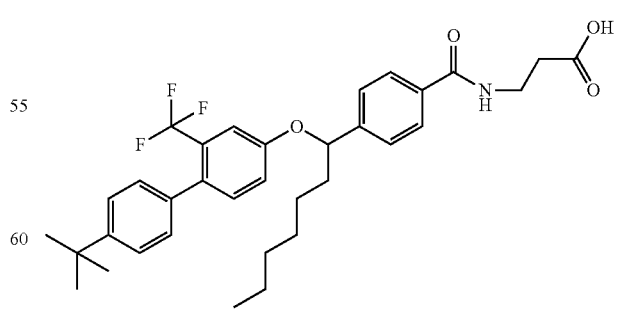

This compound is made by the general method as exemplified in Example 24 using 4-(1-hydroxy-heptyl)-benzoic acid methyl ester and 4-chloro-3-trifluoromethyl-phenol as reagents in step A and 4-tertbutyl-phenyl boronic acid in step C as starting materials. MS (ES): 582.2 [M−H]⁻.

Example 318

Racemic 3-{4-[1-(4'-tert-Butyl-2-trifluoromethyl-biphenyl-4-yloxy)-pentyl]-benzoylamino}-propionic acid

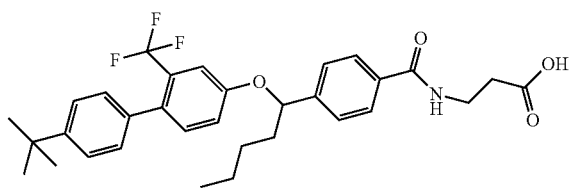 [SMILES: CCCCC(Oc1ccc(-c2ccc(C(C)(C)C)cc2)c(C(F)(F)F)c1)c1ccc(C(=O)NCCC(=O)O)cc1]

This compound is made by the general method as exemplified in Example 24 using 4-(1-hydroxy-pentyl)-benzoic acid methyl ester and 4-chloro-3-trifluoromethyl-phenol as reagents in step A and 4-tertbutyl-phenyl boronic acid in step C as starting materials. MS (ES): 554.2 [M−H]⁻.

Example 319

Racemic 3-{4-[1-(4'-tert-Butyl-2-trifluoromethyl-biphenyl-4-yloxy)-2-methyl-propyl]benzoylamino}-propionic acid

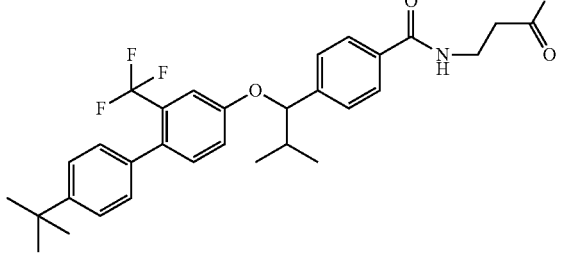

This compound is made by the general method as exemplified in Example 24 using 4-(1-hydroxy-2-methyl-propyl)-benzoic acid methyl ester and 4-chloro-3-trifluoromethyl-phenol as reagents in step A and 4-t-butyl-phenyl boronic acid in step C as starting materials. MS (ES): 540.3 [M−H]⁻.

Example 320

Racemic 3-{4-[1-(4'-tert-Butyl-2-trifluoromethyl-biphenyl-4-yloxy)-3-methyl-butyl]-benzoylamino}-propionic acid

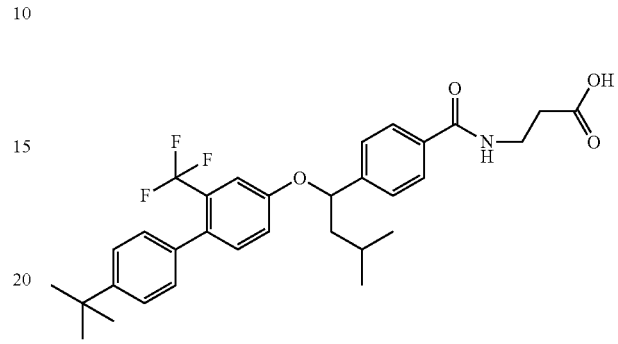

This compound is made by the general method as exemplified in Example 24 using 4-(1-hydroxy-3-methyl-butyl)-benzoic acid methyl ester and 4-chloro-3-trifluoromethyl-phenol as reagents in step A and 4-tertbutyl-phenyl boronic acid in step C as starting materials. MS (ES): 554.2 [M−H]⁻.

Example 321

Racemic 3-{4-[1-(3,5-Dimethyl-4'-trifluoromethyl-biphenyl-4-yloxy)-heptyl]-benzoylamino}-propionic acid

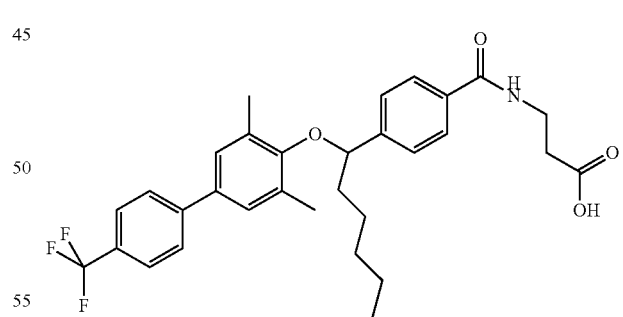

This compound is made by the general method as exemplified in Example 24 using 4-(1-hydroxy-heptyl)-benzoic acid methyl ester and 4-bromo-3,5-dimethyl-phenol as reagents in step A and 4-trifluoromethyl-phenyl boronic acid in step C as starting materials. MS (ES): 554.2 [M−H]⁻.

Example 322

Racemic 3-{4-[1-(4'-Chloro-3,5-dimethyl-biphenyl-4-yloxy)-heptyl]-benzoylamino}-propionic acid

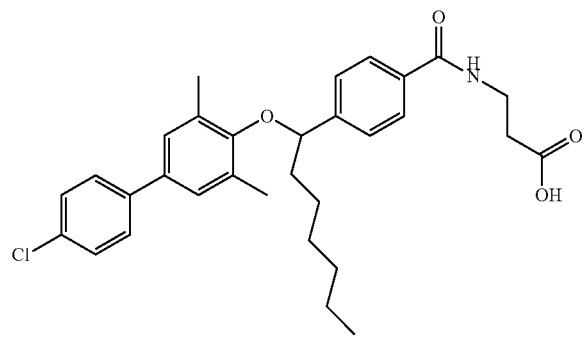

This compound is made by the general method as exemplified in Example 24 using 4-(1-hydroxy-heptyl)-benzoic acid methyl ester and 4-bromo-3,5-dimethyl-phenol as reagents in step A and 4-chloro-phenyl boronic acid in step C as starting materials. MS (ES): 522.2 [M+H]⁺.

Example 323

Racemic 3-{4-[1-(4'-Chloro-3-methyl-biphenyl-4-yloxy)-heptyl]-benzoylamino}-propionic acid

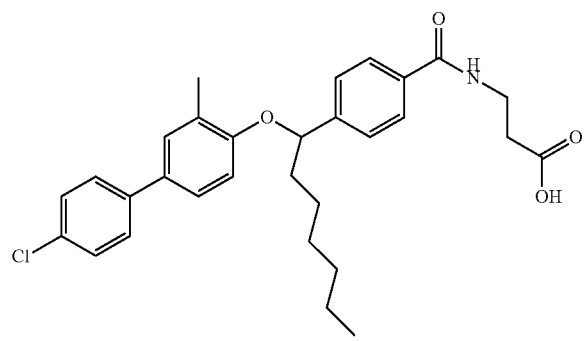

This compound is made by the general method as exemplified in Example 24 using 4-(1-hydroxy-heptyl)-benzoic acid methyl ester and 4-bromo-3-dimethyl-phenol as reagents in step A and 4-chloro-phenyl boronic acid in step C as starting materials. MS (ES): 506.2 [M−H]⁻.

Example 324

Racemic 3-{4-[1-(2,6-Dimethyl-4'-trifluoromethyl-biphenyl-4-yloxy)-3,3-dimethyl-butyl]-benzoylamino}-propionic acid

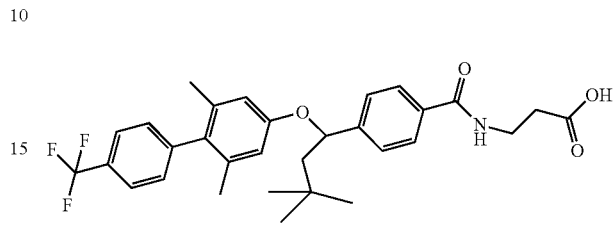

This compound is made by the general method as exemplified in Example 24 using 4-(1-hydroxy-3,3-dimethyl-butyl)-benzoic acid methyl ester and 4-bromo-3,5-dimethyl-phenol as reagents in step A and 4-fluoromethyl-phenyl boronic acid in step C as starting materials. MS (ES): 540.3 [M−H]⁻.

Example 325

Racemic 3-{4-[1-(2,6-Dimethyl-4'-trifluoromethyl-biphenyl-4-yloxy)-4,4-dimethyl-pentyl]-benzoylamino}-propionic acid

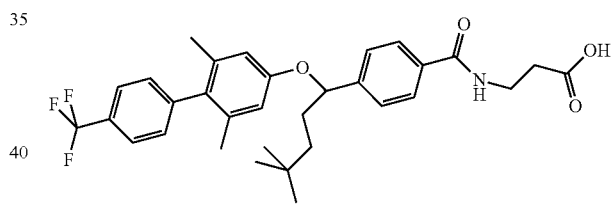

This compound is made by the general method as exemplified in Example 24 using 4-(1-hydroxy-4,4-dimethyl-pentyl)-benzoic acid methyl ester and 4-bromo-3,5-dimethyl-phenol as reagents in step A and 4-fluoromethyl-phenyl boronic acid in step C as starting materials. MS (ES): 554.2 [M−H]⁻.

Example 326

Racemic 3-{4-[1-(2,6-Dimethyl-4'-isopropyl-biphenyl-4-yloxy)-4,4-dimethyl-pentyl]-benzoylamino}-propionic acid

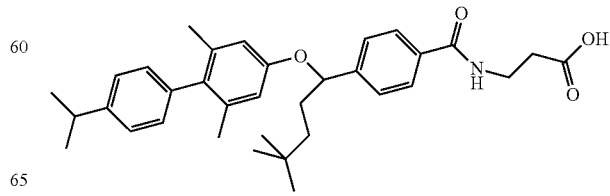

This compound is made by the general method as exemplified in Example 24 using 4-(1-hydroxy-4,4-dimethyl-pentyl)-benzoic acid methyl ester and 4-bromo-3,5-dimethyl-phenol as reagents in step A and 4-isopropyl-phenyl boronic acid in step C as starting materials. MS (ES): 530.2 [M+H]⁺.

Example 327

Racemic 3-{4-[1-(4'-Isopropyl-2,6-dimethyl-biphenyl-4-yloxy)-2-methyl-propyl]-benzoylamino}-propionic acid

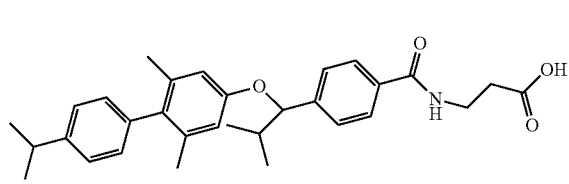 [SMILES: Cc1cc(OC(c2ccc(C(=O)NCCC(=O)O)cc2)C(C)C)cc(C)c1-c1ccc(C(C)C)cc1]

This compound is made by the general method as exemplified in Example 24 using 4-(1-hydroxy-2-methyl-propyl)-benzoic acid methyl ester and 4-bromo-3,5-dimethyl-phenol as reagents in step A and 4-isopropyl-phenyl boronic acid in step C as starting materials. MS (ES): 488.3 [M+H]⁺.

Example 328

Racemic 3-{4-[1-(2,6-Dimethyl-4'-trifluoromethyl-biphenyl-4-yloxy)-2-methyl-propyl]-benzoylamino}-propionic acid

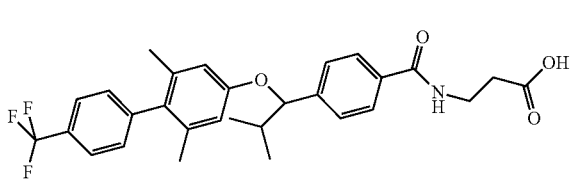 [SMILES: Cc1cc(OC(c2ccc(C(=O)NCCC(=O)O)cc2)C(C)C)cc(C)c1-c1ccc(C(F)(F)F)cc1]

This compound is made by the general method as exemplified in Example 24 using 4-(1-hydroxy-2-methyl-propyl)-benzoic acid methyl ester and 4-bromo-3,5-dimethyl-phenol as reagents in step A and 4-trifluoromethyl-phenyl boronic acid in step C as starting materials. MS (ES): 514.2 [M+H]⁺.

Example 329

Racemic 3-{4-[2-Methyl-1-(2-methyl-4'-trifluoromethyl-biphenyl-4-yloxy)-propyl]-benzoylamino}-propionic acid

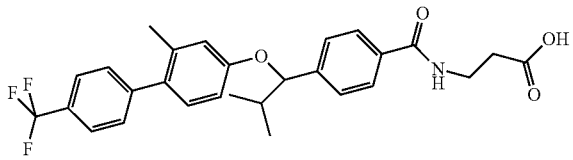 [SMILES: Cc1cc(OC(c2ccc(C(=O)NCCC(=O)O)cc2)C(C)C)ccc1-c1ccc(C(F)(F)F)cc1]

This compound is made by the general method as exemplified in Example 24 using 4-(1-hydroxy-2-methyl-propyl)-benzoic acid methyl ester and 4-bromo-3-methyl-phenol as reagents in step A and 4-trifluoromethyl-phenyl boronic acid in step C as starting materials. MS (ES): 500.3 [M+H]⁺.

Example 330

Racemic 3-{4-[1-(2,6-Dimethyl-4'-chloro-biphenyl-4-yloxy)-4,4-dimethyl-pentyl]-benzoylamino}-propionic acid

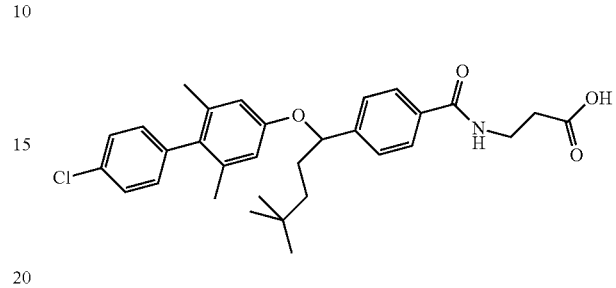

This compound is made by the general method as exemplified in Example 24 using 4-(1-hydroxy-4,4-dimethyl-pentyl)-benzoic acid methyl ester and 4-bromo-3,5-dimethyl-phenol as reagents in step A and 4-chloro-phenyl boronic acid in step C as starting materials. MS (ES): 522.2 [M+H]⁺.

Example 331

Racemic 3-{4-[1-(4'-tert-Butyl-2,6-dimethyl-biphenyl-4-yloxy)-2-methyl-propyl]-benzoylamino}-propionic acid

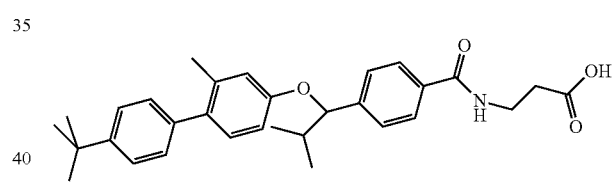

This compound is made by the general method as exemplified in Example 24 using 4-(1-hydroxy-2-methyl-propyl)-benzoic acid methyl ester and 4-bromo-3-methyl-phenol as reagents in step A and 4-tertbutyl-phenyl boronic acid in step C as starting materials. MS (ES): 502.2 [M+H]⁺.

Example 332

Racemic 3-{4-[1-(4'-Isopropyl-2-methyl-biphenyl-4-yloxy)-2-methyl-propyl]-benzoylamino}-propionic acid

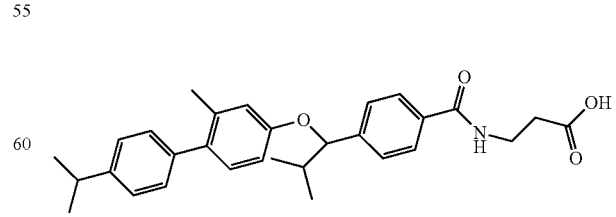

This compound is made by the general method as exemplified in Example 24 using 4-(1-hydroxy-2-methyl-propyl)-benzoic acid methyl ester and 4-bromo-3-methyl-phenol as reagents in step A and 4-isopropyl-phenyl boronic acid in step C as starting materials. MS (ES): 474.2 [M+H]+.

Example 333

Racemic 3-{4-[1-(4'-2,6-Difluoro-4'-trifluoromethyl-biphenyl-4-yloxy)-3-methyl-butyl]-benzoylamino}-propionic acid

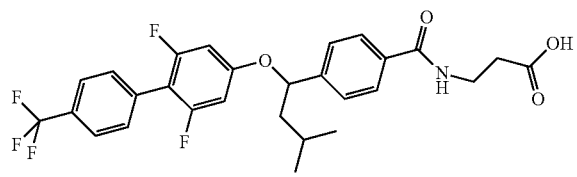 [SMILES: CC(C)CC(Oc1cc(F)c(-c2ccc(C(F)(F)F)cc2)c(F)c1)c1ccc(C(=O)NCCC(=O)O)cc1]

This compound is made by the general method as exemplified in Example 24 using 4-(1-hydroxy-3-methyl-butyl)-benzoic acid methyl ester and 4-bromo-3,5-difluoro-phenol as reagents in step A and 4-trifluoromethyl-phenyl boronic acid in step C as starting materials. MS (ES): 536.2 [M+H]+.

Example 334

Racemic 3-{4-[1-(2,6-Difluoro-4'-isopropyl-biphenyl-4-yloxy)-3-methyl-butyl]-benzoylamino}-propionic acid

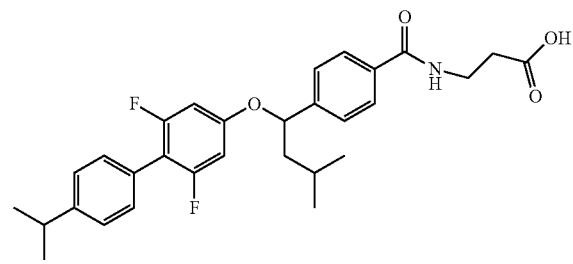 [SMILES: CC(C)CC(Oc1cc(F)c(-c2ccc(C(C)C)cc2)c(F)c1)c1ccc(C(=O)NCCC(=O)O)cc1]

This compound is made by the general method as exemplified in Example 24 using 4-(1-hydroxy-3-methyl-butyl)-benzoic acid methyl ester and 4-bromo-3,5-difluoro-phenol as reagents in step A and 4-isopropyl-phenyl boronic acid in step C as starting materials. MS (ES): 510.2 [M+H]+.

Example 335

Racemic 3-{4-[1-(2-Chloro-4'-isopropyl-biphenyl-4-yloxy)-3-methyl-butyl]-benzoylamino}-propionic acid

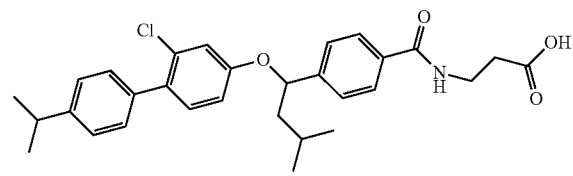 [SMILES: CC(C)CC(Oc1ccc(-c2ccc(C(C)C)cc2)c(Cl)c1)c1ccc(C(=O)NCCC(=O)O)cc1]

This compound is made by the general method as exemplified in Example 24 using 4-(1-hydroxy-3-methyl-butyl)-benzoic acid methyl ester and 4-bromo-3-chloro-phenol as reagents in step A and 4-isopropyl-phenyl boronic acid in step C as starting materials. MS (ES): 508.3 [M+H]+.

Example 336

Racemic 3-{4-[1-(2-Chloro-4'-trifluoromethyl-biphenyl-4-yloxy)-3-methyl-butyl]-benzoylamino}-propionic acid

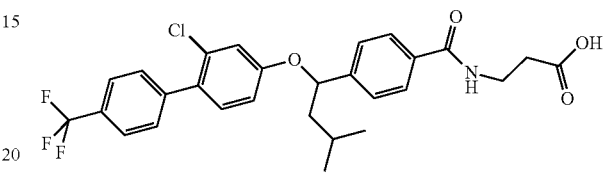

This compound is made by the general method as exemplified in Example 24 using 4-(1-hydroxy-3-methyl-butyl)-benzoic acid methyl ester and 4-bromo-3-chloro-phenol as reagents in step A and 4-trifluoromethyl-phenyl boronic acid in step C as starting materials. MS (ES): 534.2 [M+H]+.

Example 337

Racemic 3-(4-{3-Methyl-1-[5-methyl-6-(4-trifluoromethyl-phenyl)-pyridin-3-yloxy]-butyl}-benzoylamino)-propionic acid

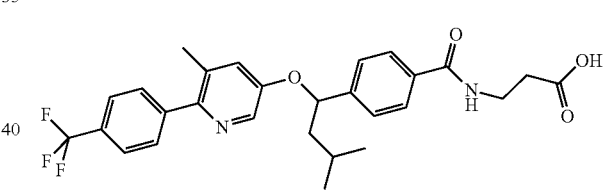

This compound is made by the general method as exemplified in Example 24 using 4-(1-hydroxy-3-methyl-butyl)-benzoic acid methyl ester and 6-chloro-5-methyl-pyridin-3-ol as reagents in step A and 4-trifluoro-phenyl boronic acid in step C as starting materials. MS (ES): 515.2 [M+H]+.

Example 338

Racemic 3-(4-{1-[6-(4-Isopropyl-phenyl)-5-methyl-pyridin-3-yloxy]-3-methyl-butyl}-benzoylamino)-propionic acid

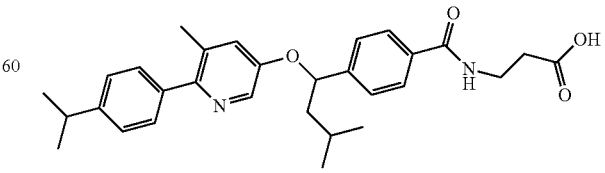

This compound is made by the general method as exemplified in Example 24 using 4-(1-hydroxy-3-methyl-butyl)- benzoic acid methyl ester and 6-chloro-5-methyl-pyridin-3-ol as reagents in step A and 4-isopropyl-phenyl boronic acid in step C as starting materials. MS (ES): 489.2 [M+H]⁺.

Example 339

Racemic 3-{4-[1-(4'-tert-Butyl-biphenyl-3-yloxy)-3-methyl-butyl]-benzoylamino}-propionic acid

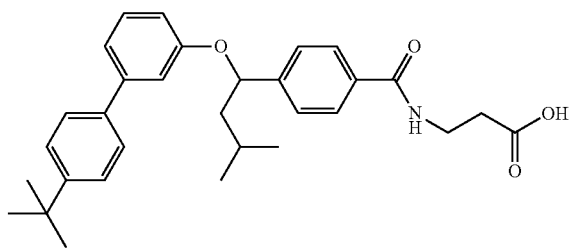

This compound is made by the general method as exemplified in Example 24 using 4-(1-hydroxy-3-methyl-butyl)-benzoic acid methyl ester and 3-bromo-phenol as reagents in step A and 4-tertbutyl-phenyl boronic acid in step C as starting materials. MS (ES): 488.3 [M+H]⁺.

Example 340

Racemic 3-{4-[3-Methyl-1-(4'-trifluoromethyl-biphenyl-3-yloxy)-butyl]-benzoylamino}-propionic acid

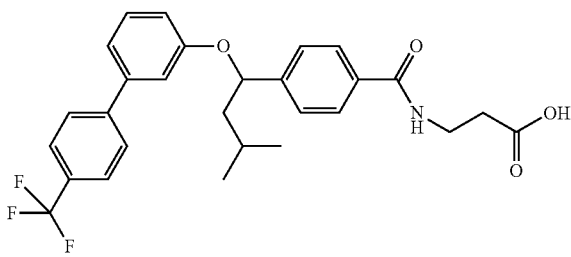 [SMILES: CC(C)CC(Oc1cccc(-c2ccc(C(F)(F)F)cc2)c1)c1ccc(C(=O)NCCC(=O)O)cc1]

This compound is made by the general method as exemplified in Example 24 using 4-(1-hydroxy-3-methyl-butyl)-benzoic acid methyl ester and 3-bromo-phenol as reagents in step A and 4-trifluoromethyl-phenyl boronic acid in step C as starting materials. MS (ES): 500.3 [M+H]⁺.

Example 341

Racemic 3-{4-[1-(4'-Isopropyl-biphenyl-3-yloxy)-3-methyl-butyl]-benzoylamino}-propionic acid

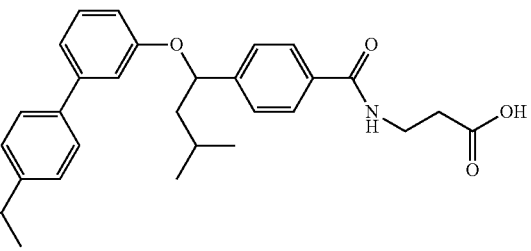

This compound is made by the general method as exemplified in Example 24 using 4-(1-hydroxy-3-methyl-butyl)-benzoic acid methyl ester and 3-bromo-phenol as reagents in step A and 4-isopropyl-phenyl boronic acid in step C as starting materials. MS (ES): 474.2 [M+H]⁺.

Example 342

Racemic 3-{4-[3-Methyl-1-(4'-trifluoromethoxy-biphenyl-3-yloxy)-butyl]-benzoylamino}-propionic acid

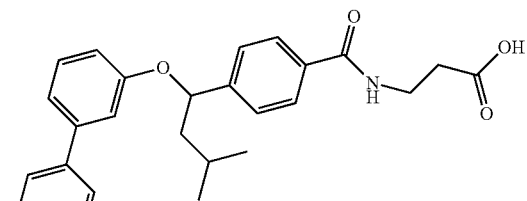

This compound is made by the general method as exemplified in Example 24 using 4-(1-hydroxy-3-methyl-butyl)-benzoic acid methyl ester and 3-bromo-phenol as reagents in step A and 4-trifluoromethoxy-phenyl boronic acid in step C as starting materials. MS (ES): 516.3 [M+H]+.

Example 343

Racemic 3-{4-[3-Methyl-1-(6-methyl-4'-trifluoromethyl-biphenyl-3-yloxy)-butyl]-benzoylamino}-propionic acid

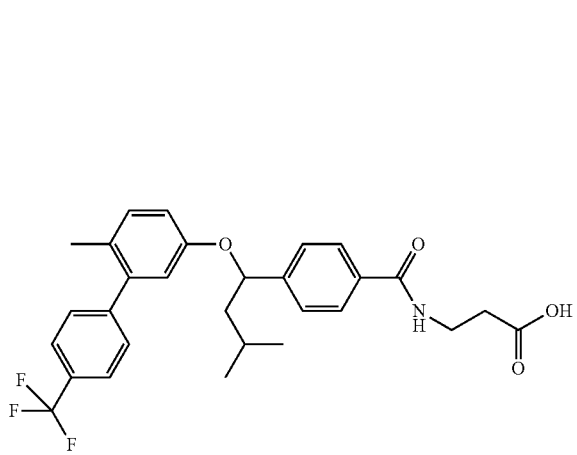 [SMILES: Cc1ccc(OC(CC(C)C)c2ccc(C(=O)NCCC(=O)O)cc2)cc1-c1ccc(C(F)(F)F)cc1]

This compound is made by the general method as exemplified in Example 24 using 4-(1-hydroxy-3-methyl-butyl)-benzoic acid methyl ester and 3-bromo-4-methyl-phenol as reagents in step A and 4-trifluoromethyl-phenyl boronic acid in step C as starting materials. MS (ES): 514.2 [M+H]+.

Example 344

Racemic 3-{4-[1-(4'-tert-Butyl-6-methyl-biphenyl-3-yloxy)-3-methyl-butyl]-benzoylamino}-propionic acid

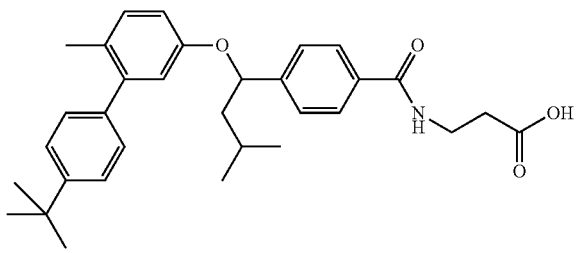 [SMILES: Cc1ccc(OC(CC(C)C)c2ccc(C(=O)NCCC(=O)O)cc2)cc1-c1ccc(C(C)(C)C)cc1]

This compound is made by the general method as exemplified in Example 24 using 4-(1-hydroxy-3-methyl-butyl)-benzoic acid methyl ester and 3-bromo-4-methyl-phenol as reagents in step A and 4-t-butyl-phenyl boronic acid in step C as starting materials. MS (ES): 502.2 [M+H]+.

Example 345

Racemic 3-{4-[1-(4'-2-Hydroxymethyl-4'-isopropyl-biphenyl-4-yloxy)-3-methyl-butyl]-benzoylamino}-propionic acid

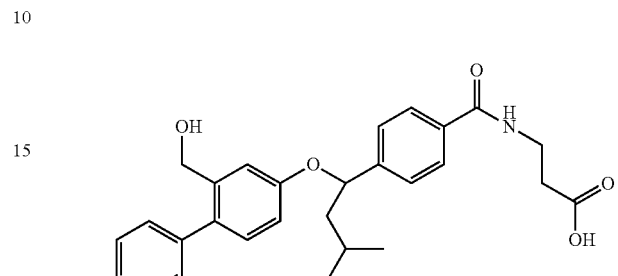

and

Example 346

Racemic 3-{4-[1-(2-Formyl-4'-isopropyl-biphenyl-4-yloxy)-3-methyl-butyl]-benzoylamino}-propionic acid

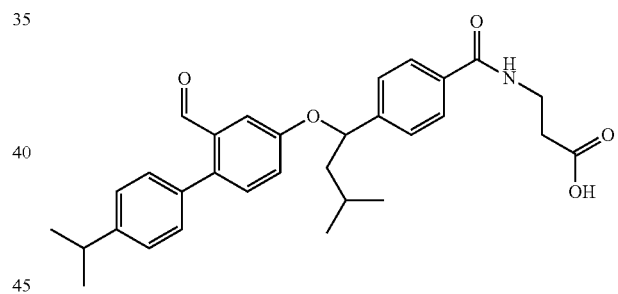

Step A. 4-[1-(4-Bromo-3-[1,3]dioxan-2-yl-phenoxy)-3-methyl-butyl]-benzoic acid methyl ester To a solution of 4-(1-hydroxy-3-methyl-butyl)-benzoic acid methyl ester (1600 mg, 7.21 mmol) in toluene (72 mL) is added 1,1'-(azodicarbonyl)dipiperidine (ADDP, 2728 mg, 10.81 mmol) at 0° C., followed by the additions of tributylphosphine (2.69 mL, 10.81 mmol) and 4-bromo-3-[1,3]dioxan-2-yl-phenol (2240 mg, 8.65 mmol). The reaction mixture is warmed up to room temperature and stirred overnight. The mixture is loaded on silica gel, eluted with hexanes with a gradient from 0% of ethyl acetate to 50% of ethyl acetate giving the titled compound (1000 mg).

Step B. 4-[1-(4-Bromo-3-[1,3]dioxan-2-yl-phenoxy)-3-methyl-butyl]-benzoic acid

To the solution of 4-[1-(4-bromo-3-[1,3]dioxan-2-yl-phenoxy)-3-methyl-butyl]-benzoic acid methyl ester (1000 mg) in methanol (20 mL) is added sodium hydroxide (5 N aqueous, 2 mL) and stirred for 4 h. The reaction mixture is concentrated and acidified by 5 N HCl (2 mL), extracted with ethyl acetate. Combined organic layers are washed with water and brine, dried over sodium sulfate. Concentration gives the title compound (940 mg) as a white solid.

Step C. 3-{4-[1-(4-Bromo-3-[1,3]dioxan-2-yl-phenoxy)-3-methyl-butyl]-benzoylamino}-propionic acid methyl ester To a mixture of 4-[1-(4-bromo-3-[1,3]dioxan-2-yl-phenoxy)-3-methyl-butyl]-benzoic acid (940 mg, 2.09 mmol) in methylene chloride (21 mL) is added triethyl amine (0.88 mL, 6.28 mmol), DMAP (5.0 mg), 3-Amino-propionic acid methyl ester hydrochloride (438 mg, 3.14 mmol) and EDCI (1207 mg, 6.28 mmol) at room temperature. The reaction mixture is stirred at room temperature overnight, loaded on silica gel, eluted with eluted with hexanes with a gradient from 0% of ethyl acetate to 100% of ethyl acetate giving the titled compound (670 mg).

Step D. 3-{4-[1-(2-[1,3]Dioxan-2-yl-4'-Isopropyl-biphenyl-4-yloxy)-3-methyl-butyl]-benzoylamino}-propionic acid methyl ester 3-{4-[1-(4-Bromo-3-[1,3]dioxan-2-yl-phenoxy)-3-methyl-butyl]-benzoylamino}-propionic acid methyl ester (560 mg, 1.05 mmol), potassium Fluoride (183 mg, 3.15 mmol), 4-isopropylphenyl boronic acid (344 mg, 2.1 mmol) and tetrakis(triphenylphosphine)palladium (121 mg, 0.105 mmol) are placed in a flask. After the reaction is purged with $N_2$ for several times, $THF/H_2O$ (20 ml/5 ml) is added. The resulting solution is refluxed overnight, loaded on silica gel, eluted with hexane and ethyl acetate to give the titled compound (570 mg).

Step E. Racemic 3-{4-[1-(2-Formyl-4'-isopropyl-biphenyl-4-yloxy)-3-methyl-butyl]-benzoylamino}-propionic acid methyl ester, and Racemic 3-{4-[1-(2-Formyl-4'-isopropyl-biphenyl-4-yloxy)-3-methyl-butyl]-benzoylamino}-propionic acid 3-{4-[1-(2-[1,3]Dioxan-2-yl-4'-isopropyl-biphenyl-4-yloxy)-3-methyl-butyl]-benzoylamino}-propionic acid methyl ester (570 mg) is taken into THF (10 ml), treated with 5N HCl for 5 h, neutralfied with 5N NaOH, extracted with ethyl actate, dried over $MgSO_4$ and concentrated. The residue is purified by column chromatography to afford 3-{4-[1-(2-formyl-4'-isopropyl-biphenyl-4-yloxy)-3-methyl-butyl]-benzoylamino}-propionic acid methyl ester (36 mg) and 3-{4-[1-(2-formyl-4'-isopropyl-biphenyl-4-yloxy)-3-methyl-butyl]-benzoylamino}-propionic acid (228 mg). MS (ES): 502.2 [M+H]+.

Step F. 3-{4-[1-(2-Hydroxymethyl-4'-isopropyl-biphenyl-4-yloxy)-3-methyl-butyl]-benzoylamino}-propionic acid To the solution of 3-{4-[1-(2-formyl-4'-isopropyl-biphenyl-4-yloxy)-3-methyl-butyl]-benzoylamino}-propionic acid methyl ester (36 mg, 0.07 mmol) in methanol (5 ml) is added $NaBH_4$ (3 mg, 0.07 mmol). After 2 h, the mixture is diluted with ethyl actate, washed with 1N HCl, water, brine, dried over $MgSO_4$, and concentrated. The residue is taken into methanol (20 mL), followed by the addition of sodium hydroxide (5 N aqueous, 1 mL), stirred for 4 h. The reaction mixture is concentrated and acidified by 5 N HCl (1 mL), extracted with ethyl acetate. Combined organic layers are washed with water and brine, dried over sodium sulfate. Concentration gives the title compound (93 mg) as a white solid. MS (ES): 502.2 [M−H]−.

Example 347

Racemic 3-(4-{1-[2-(Hydroxyimino-methyl)-4'-isopropyl-biphenyl-4-yloxy]-3-methyl-butyl}-benzoylamino)-propionic acid

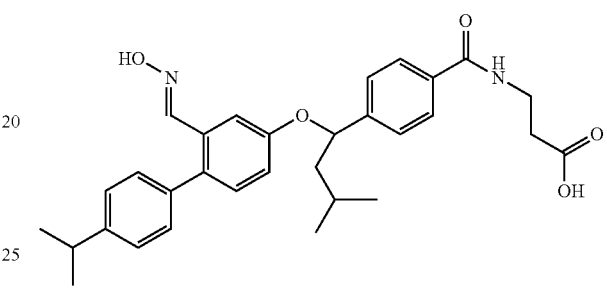

To the solution of 3-{4-[1-(2-formyl-4'-isopropyl-biphenyl-4-yloxy)-3-methyl-butyl]-benzoylamino}-propionic acid (75 mg, 0.15 mmol) in methanol (10 ml) is added hydroxylamine hydrochloride (104 mg, 1.5 mmol). After 4 h, the mixture is diluted with ethyl actate, washed with 1N HCl, water, brine, dried over $MgSO_4$, and concentrated. The residue is purified by column chromatography to afford 38 mg of 3-(4-{1-[2-(hydroxyimino-methyl)-4'-isopropyl-biphenyl-4-yloxy]-3-methyl-butyl}-benzoylamino)-propionic acid methyl ester, which is hydrolyzed by 5N NaOH to afford the titled compound (36 mg). MS (ES): 517.2 [M+H]+.

Example 348

Racemic 3-{4-[1-(4'-Isopropyl-2-morpholin-4-ylmethyl-biphenyl-4-yloxy)-3-methyl-butyl]-benzoylamino}-propionic acid

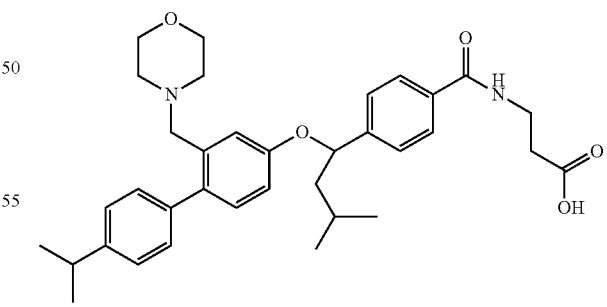

To the solution of 3-{4-[1-(2-formyl-4'-isopropyl-biphenyl-4-yloxy)-3-methyl-butyl]-benzoylamino}-propionic acid (240 mg, 0.48 mmol) and Morpholine (84 mg, 0.96 mmol) in dichloromethane (20 ml) is added $NaBH(OAc)_3$ (143 mg, 0.67 mmol) and acetic acid (58 mg, 0.96 mmol). The resulting mixture is stirred overnight, diluted with ethyl actate, washed with 1N HCl, water, brine, dried over $MgSO_4$, and concentrated. The residue is purified by column chromatography to afford 80 mg of the titled compound as a white solid. MS (ES): 573.5 [M+H]+.

Example 349

3-(4-{3,3-Dimethyl-1-[5-methyl-1-oxy-6-(4-trifluoromethoxy-phenyl)-pyridin-3-yloxy]-butyl}-benzoylamino)-propionic acid

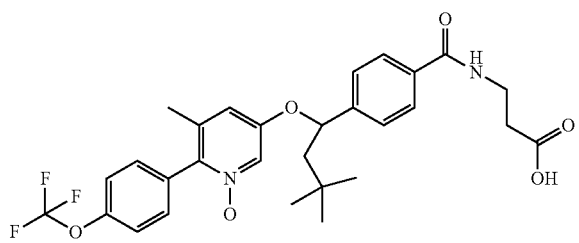

Step A. 4-[1-(6-Chloro-5-methyl-pyridin-3-yloxy)-3,3-dimethyl-butyl]-benzoic acid methyl ester To a solution of 4-(1-hydroxy-3,3-dimethyl-butyl)-benzoic acid methyl ester (450 mg, 1.91 mmol) in toluene (19 mL) is added 1,1'-(azodicarbonyl)dipiperidine (ADDP, 722 mg, 2.86 mmol) at 0° C., followed by the additions of tributylphosphine (0.71 mL, 2.86 mmol) and 6-chloro-5-methyl-pyridin-3-ol (327 mg, 2.29 mmol). The reaction mixture is warmed up to room temperature and stirred overnight. The mixture is loaded on silica gel, eluted with hexanes with a gradient from 0% of ethyl acetate to 50% of ethyl acetate giving the titled compound (440 mg).

Step B. 4-[1-(6-Chloro-5-methyl-pyridin-3-yloxy)-3,3-dimethyl-butyl]-benzoic acid To the solution of 4-[1-(6-chloro-5-methyl-pyridin-3-yloxy)-3,3-dimethyl-butyl]-benzoic acid methyl ester (440 mg) in methanol (30 mL) is added sodium hydroxide (5 N aqueous, 2 mL) and stirred for 5 h. The reaction mixture is concentrated and acidified by 5 N HCl (2 mL), extracted with ethyl acetate. Combined organic layers are washed with water and brine, dried over sodium sulfate. Concentration gives the titled compound (414 mg).

Step C. 3-{4-[1-(6-Chloro-5-methyl-pyridin-3-yloxy)-3,3-dimethyl-butyl]-benzoylamino}-propionic acid methyl ester To a mixture of 4-[1-(6-chloro-5-methyl-pyridin-3-yloxy)-3,3-dimethyl-butyl]-benzoic acid (414 mg, 1.19 mmol) in methylene chloride (12 mL) is added triethyl amine (0.5 mL, 3.6 mmol), DMAP (5.0 mg), 3-Amino-propionic acid methyl ester hydrochloride (250 mg, 1.8 mmol) and EDCI (688 mg, 3.6 mmol) at room temperature. The reaction mixture is stirred at room temperature overnight, loaded on silica gel, eluted with eluted with hexanes with a gradient from 0% of ethyl acetate to 100% of ethyl acetate giving the titled compound (400 mg).

Step D. 3-(4-{3,3-Dimethyl-1-[5-methyl-6-(4-trifluoromethoxy-phenyl)-pyridin-3-yloxy]-butyl}-benzoylamino)-propionic acid methyl ester 3-{4-[1-(6-Chloro-5-methyl-pyridin-3-yloxy)-3,3-dimethyl-butyl]-benzoylamino}-propionic acid methyl ester (200 mg, 0.46 mmol), potassium fluoride (80 mg, 1.38 mmol), 4-trifluoromethoxyphenyl boronic acid (190 mg, 0.92 mmol) and tetrakis(triphenylphosphine)palladium (53 mg, 0.046 mmol) are placed in a flask. After the reaction is purged with $N_2$ for several times, $THF/H_2O$ (20 ml/5 ml) is added. The resulting solution is refluxed overnight, loaded on silica gel, eluted with hexane and ethyl acetate to give the titled compound (220 mg).

Step F. 3-(4-{3,3-Dimethyl-1-[5-methyl-1-oxy-6-(4-trifluoromethoxy-phenyl)-pyridin-3-yloxy]-butyl}-benzoylamino)-propionic acid To the solution of 3-(4-{3,3-Dimethyl-1-[5-methyl-6-(4-trifluoromethoxy-phenyl)-pyridin-3-yloxy]-butyl}-benzoylamino)-propionic acid methyl ester (200 mg, 0.36 mmol) in chloroform (20 mL) is added the solution of mCPBA (247 mg, 1.43 mmol) in chloroform (10 ml) dropwise. The resulting mixture is stirred overnight. $K_2CO_3$ (200 mg) and MeOH (1 ml) are added. The mixture is stirred for 30 min, filtrated. The solid residue is washed with dichloromethane/MeOH (9/1). The filtrate is concentrated and purified by column chromatography to afford 3-(4-{3,3-dimethyl-1-[5-methyl-1-oxy-6-(4-trifluoromethoxy-phenyl)-pyridin-3-yloxy]-butyl}-benzoylamino)-propionic acid methyl ester (80 mg), which is hydrolyzed by sodium hydroxide (5 N aqueous, 1 mL) giving the title compound (55 mg). MS (ES): 561.3 [M+H]+.

Example 350

2-Hydroxy-3-{4-[1-(4'-isopropyl-2,6-dimethyl-biphenyl-4-yloxy)-2-methyl-propyl]-benzoylamino}-propionic acid, Isomer 1

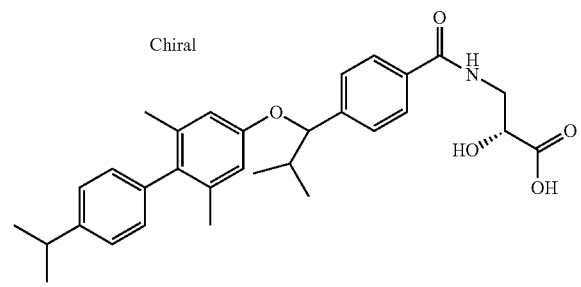 [SMILES: Cc1cc(OC(c2ccc(C(=O)NC[C@@H](O)C(=O)O)cc2)C(C)C)cc(C)c1-c1ccc(C(C)C)cc1]

Step A. 4-[1-(4-Bromo-3,5-dimethyl-phenoxy)-2-methyl-propyl]-benzoic acid methyl ester To a solution of 4-(1-hydroxy-2-methyl-propyl)-benzoic acid methyl ester (5000 mg, 24.04 mmol) in toluene (240 mL) is added 1,1'-(azodicarbonyl)dipiperidine (ADDP, 9098 mg, 36.06 mmol) at 0° C., followed by the additions of tributylphosphine (8.98 mL, 36.06 mmol) and 4-bromo-3,5-dimethyl-phenol (5798 mg, 28.85 mmol). The reaction mixture is warmed up to room temperature and stirred overnight. The mixture is loaded on silica gel, eluted with hexanes with a gradient from 0% of ethyl acetate to 50% of ethyl acetate giving the titled compound (5540 mg).

Step B. 4-[1-(4-Bromo-3,5-dimethyl-phenoxy)-2-methyl-propyl]-benzoic acid methyl ester, isomers 1 and 2

The racemic 4-[1-(4-bromo-3,5-dimethyl-phenoxy)-2-methyl-propyl]-benzoic acid methyl ester was resolved on a Chiralcel OJ-H column (4.6×150 mm). Eluted with Methanol/DMEA (98/2) and concentrated the fractions to provide a purified enantiomer ester (isomer 1, 98.4% ee, isomer 2, >99% ee).

Step C. 4-[1-(4'-Isopropyl-2,6-dimethyl-biphenyl-4-yloxy)-2-methyl-propyl]-benzoic acid methyl ester, isomer 1

Isomer 1 of 4-[1-(4-bromo-3,5-dimethyl-phenoxy)-2-methyl-propyl]-benzoic acid methyl ester (500 mg, 1.28 mmol), potassium fluoride (223 mg, 3.84 mmol), 4-isopropylphenyl boronic acid (419 mg, 2.56 mmol) and tetrakis-(triphenylphosphine)palladium (148 mg, 0.128 mmol) are placed in a flask. After the reaction is purged with $N_2$ for several times, THF/$H_2O$ (20 ml/5 ml) is added. The resulting solution is refluxed overnight, loaded on silica gel, eluted with hexane and ethyl acetate to give the titled compound (510 mg).

Step D. 4-[1-(4'-Isopropyl-2,6-dimethyl-biphenyl-4-yloxy)-2-methyl-propyl]-benzoic acid, isomers 1

To the solution of isomer 1 of 4-[1-(4'-isopropyl-2,6-dimethyl-biphenyl-4-yloxy)-2-methyl-propyl]-benzoic acid methyl ester (510 mg) in methanol (10 mL) is added sodium hydroxide (5 N aqueous, 2 mL) and stirred for 4 h. The reaction mixture is concentrated and acidified by 5 N HCl (2 mL), extracted with ethyl acetate. Combined organic layers are washed with water and brine, dried over sodium sulfate. Concentration gives the title compound (450 mg) as a white solid.

Step E. 2-Hydroxy-3-{4-[1-(4'-isopropyl-2,6-dimethyl-biphenyl-4-yloxy)-2-methyl-propyl]-benzoylamino}-propionic acid methyl ester, isomer 1

To a mixture of 4-[1-(4'-isopropyl-2,6-dimethyl-biphenyl-4-yloxy)-2-methyl-propyl]-benzoic acid (150 mg, 0.36 mmol) in methylene chloride (4 mL) is added triethyl amine (0.15 mL, 1.08 mmol), DMAP (5.0 mg), 3-Amino-2-hydroxy-propionic acid methyl ester (83 mg, 0.54 mmol) and EDCI (208 mg, 1.08 mmol) at room temperature. The reaction mixture is stirred at room temperature overnight, loaded on silica gel, eluted with eluted with hexanes with a gradient from 0% of ethyl acetate to 100% of ethyl acetate giving the titled compound (150 mg).

Step F. 2-Hydroxy-3-{4-[1-(4'-isopropyl-2,6-dimethyl-biphenyl-4-yloxy)-2-methyl-propyl]-benzoylamino}-propionic acid, isomer 1

To the solution of isomer 1 of 2-Hydroxy-3-{4-[1-(4'-isopropyl-2,6-dimethyl-biphenyl-4-yloxy)-2-methyl-propyl]-benzoylamino}-propionic acid methyl ester (150 mg) in methanol (10 mL) is added sodium hydroxide (5 N aqueous, 1 mL) and stirred for 4 h. The reaction mixture is concentrated and acidified by 5 N HCl (1 mL), extracted with ethyl acetate. Combined organic layers are washed with water and brine, dried over sodium sulfate. Concentration gives the title compound (93 mg) as a white solid. MS (ES): 504.2 $[M+H]^+$.

The following compounds are made in a manner substantially similar to Example 350 using appropriate starting materials:

Example 351

2-Hydroxy-3-{4-[1-(4'-isopropyl-2,6-dimethyl-biphenyl-4-yloxy)-2-methyl-propyl]-benzoylamino}-propionic acid, Isomer 2

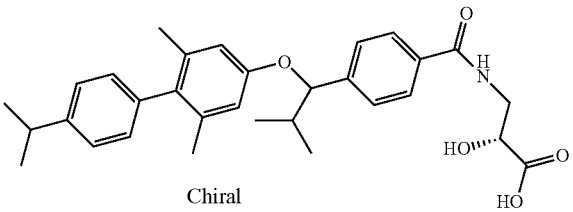 [SMILES: Cc1cc(OC(c2ccc(C(=O)NC[C@@H](O)C(=O)O)cc2)C(C)C)cc(C)c1-c1ccc(C(C)C)cc1]

MS (ES): 504.2 $[M+H]^+$.

Example 352

2-Hydroxy-3-{4-[1-(4'-isopropyl-2,6-dimethyl-biphenyl-4-yloxy)-2-methyl-propyl]-benzoylamino}-propionic acid, Isomer 1

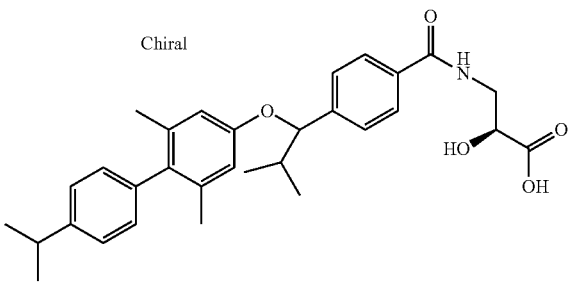 [SMILES: Cc1cc(OC(c2ccc(C(=O)NC[C@H](O)C(=O)O)cc2)C(C)C)cc(C)c1-c1ccc(C(C)C)cc1]

MS (ES): 504.2 $[M+H]^+$.

Example 353

2-Hydroxy-3-{4-[1-(4'-isopropyl-2,6-dimethyl-biphenyl-4-yloxy)-2-methyl-propyl]-benzoylamino}-propionic acid, Isomer 2

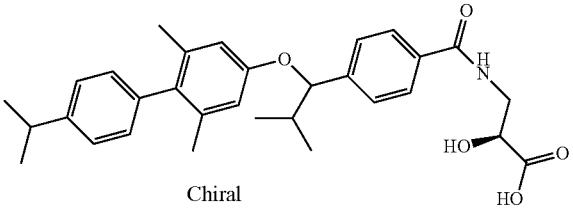 [SMILES: Cc1cc(OC(c2ccc(C(=O)NC[C@H](O)C(=O)O)cc2)C(C)C)cc(C)c1-c1ccc(C(C)C)cc1]

MS (ES): 504.2 $[M+H]^+$.

Example 354

3-{4-[1-(2,6-Dimethyl-4'-trifluoromethyl-biphenyl-4-yloxy)-2-methyl-propyl]-benzoylamino}-2-hydroxy-propionic acid, Isomer 1

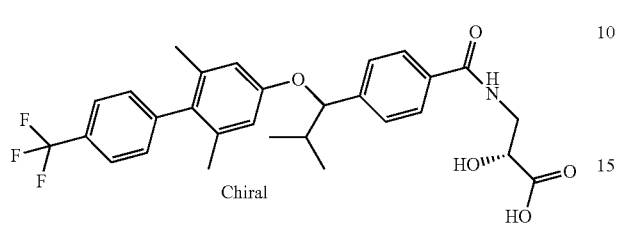

MS (ES): 530.2 [M+H]⁺.

Example 355

3-{4-[1-(2,6-Dimethyl-4'-trifluoromethyl-biphenyl-4-yloxy)-2-methyl-propyl]-benzoylamino}-2-hydroxy-propionic acid, Isomer 2

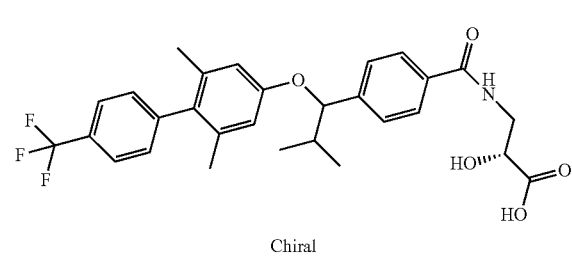 [SMILES: Cc1cc(OC(c2ccc(C(=O)NC[C@@H](O)C(=O)O)cc2)C(C)C)cc(C)c1-c1ccc(C(F)(F)F)cc1]

MS (ES): 530.2 [M+H]⁺.

Example 356

3-{4-[1-(2,6-Dimethyl-4'-trifluoromethyl-biphenyl-4-yloxy)-2-methyl-propyl]-benzoylamino}-2-hydroxy-propionic acid, Isomer 1

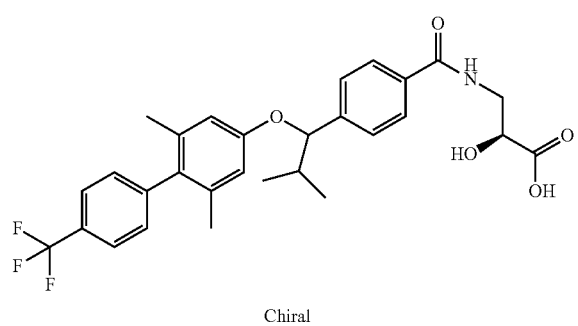 [SMILES: Cc1cc(OC(c2ccc(C(=O)NC[C@H](O)C(=O)O)cc2)C(C)C)cc(C)c1-c1ccc(C(F)(F)F)cc1]

MS (ES): 530.2 [M+H]⁺.

Example 357

3-{4-[1-(2,6-Dimethyl-4'-trifluoromethyl-biphenyl-4-yloxy)-2-methyl-propyl]-benzoylamino}-2-hydroxy-propionic acid, Isomer 2

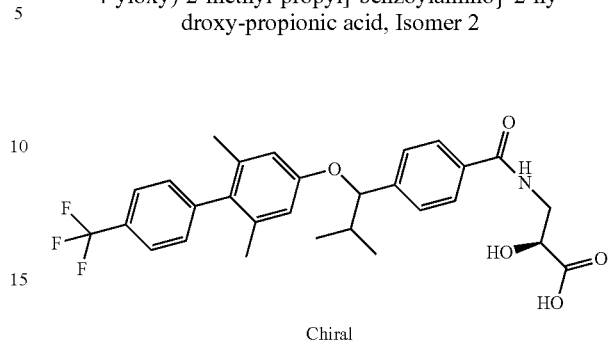

MS (ES): 530.2 [M+H]⁺.

Example 358

Racemic 3-{4-[1-(2,6-dimethyl-4'-trifluoromethyl-biphenyl-4-ylsulfanyl)-5,5,5-trifluoro-pentyl]-benzoylamino}-propionic acid

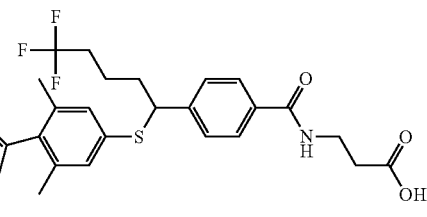

Step A. Racemic 4-[1-(4-Bromo-3,5-dimethyl-phenylsulfanyl)-5,5,5-trifluoro-pentyl]-benzoic acid methyl ester A solution of the 4-bromo-3,5-dimethyl-benzenethiol (0.572 g, 2.26 mmol) and (R,S) 4-(5,5,5-trifluoro-1-hydroxy-pentyl)-benzoic acid methyl ester (0.500 g, 1.81 mmol) in toluene (10 mL) is degassed and filled with nitrogen three times. Tributylphosphine (0.670 mL, 2.72 mmol) is added to the reaction mixture under nitrogen at 0° C., followed by addition of 1,1'-(azodicarbonyl)-dipiperidine (0.685 g, 2.72 mmol). The reaction mixture is allowed to warm to room temperature and stirred overnight, the mixture is concentrated and purified by flash column chromatography (0.424 g, 0.89 mmol).

Step B. Racemic 4-[1-(4-Bromo-3,5-dimethyl-phenylsulfanyl)-5,5,5-trifluoro-pentyl]-benzoic acid Racemic 4-[1-(4-bromo-3,5-dimethyl-phenylsulfanyl)-5,5,5-trifluoro-pentyl]-benzoic acid methyl ester (0.424 g, 0.890 mmol) is dissolved in the tetrahydrofuran (2.5 mL) and sodium hydroxide (2.5 mL, 5N) is added. The reaction is monitored by HPLC, and upon complete conversion, the reaction is neutralized with hydrochloric acid (2.5 mL, 5N) and diluted with diethyl ether and water. The two phases are separated, and the organic layer is washed, dried, and concentrated. The title compound (0.380 g, 0.826 mmol) is used without further purification.

Step C. Racemic 3-{4-[1-(4-Bromo-3,5-dimethyl-phenylsulfanyl)-5,5,5-trifluoro-pentyl]-benzoylamino}-propionic acid ethyl ester Racemic 4-[1-(4-bromo-3,5-dimethyl-phenylsulfanyl)-5,5,5-trifluoro-pentyl]-benzoic acid (0.190 g, 0.410 mmol), 2-chloro-4,6-dimethoxy-1,3,5-triazine (0.0747 g, 0.430 mmol) and 4-methylmorpholine (0.050 mL, 0.430 mmol) are combined in anhydrous dichloromethane (2.0 mL) under nitrogen. The reaction is allowed to stir under nitrogen at room temperature overnight. The beta alanine ethyl ester hydrochloride (0.0695 g, 0.450 mmol) and 4-methylmorpholine (0.100 mL, 0.860 mmol) is added to the reaction mixture and allowed to stir at room temperature. Some water (<10% volume) is added to help solubility. The reaction is monitored by HPLC, and upon complete consumption of the acid, the reaction is diluted with dichloromethane. The reaction is diluted with water and rinsed with 1N hydrochloric acid. Upon acidification, the two layers are separated. The organic layer is washed with brine, dried over anhydrous sodium sulfate, and concentrated. Flash column chromatography gave the title compound (0.200 g, 0.360 mmol).

Step D. Racemic 3-{4-[1-(2,6-Dimethyl-4'-trifluoromethyl-biphenyl-4-ylsulfanyl)-5,5,5-trifluoro-pentyl]-benzoylamino}-propionic acid ethyl ester To a solution of racemic 3-{4-[1-(4-bromo-3,5-dimethyl-phenylsulfanyl)-5,5,5-trifluoro-pentyl]-benzoylamino}-propionic acid ethyl ester (0.200 g, 0.360 mmol) in toluene (2 mL) is added palladium tetrakis triphenylphosphine (0.0267 g, 0.020 mmol), 4-trifluoromethyl phenyl boronic acid (0.135 g, 0.720 mmol), and potassium fluoride (0.0416 g, 0.720 mmol). The reaction is purged with nitrogen three times and heated to reflux under nitrogen. At reflux, water (1.0 mL) is added to the reaction and the reaction is allowed to reflux under nitrogen. The reaction is monitored by HPLC, and upon completion, allowed to cool to room temperature. The reaction is diluted with ethyl acetate and celite is added, followed by water. This mixture is then filtered through a pad of celite. The solution is poured into a separatory funnel and the organic layer is washed with water and brine. The organic layer is dried over anhydrous sodium sulfate and concentrated. The product is purified by flash column chromatography (0.150 g, 0.240 mmol).

Step E. Racemic 3-[4-{1-(2,6-Dimethyl-4'-trifluoromethyl-biphenyl-4-ylsulfanyl)-5,5,5-trifluoro-pentyl]-benzoylamino}-propionic acid Racemic 3-[4-{1-(2,6-dimethyl-4'-trifluoromethyl-biphenyl-4-ylsulfanyl)-5,5,5-trifluoro-pentyl]-benzoylamino}-propionic acid ethyl ester (0.150 g, 0.240 mmol) is dissolved in tetrahydrofuran (1.0 mL) and sodium hydroxide (1.0 mL, 5N) is added. The reaction is monitored by HPLC, and upon complete conversion, the reaction is neutralized with hydrochloric acid (1.0 mL, 5N) and diluted with diethyl ether and water. The two phases are separated, and the organic layer is washed, dried, and concentrated. The title compound is used without further purification. MS (ES): 596.3 [M−H]⁻.

Example 359

Racemic 3-{4-[1-(2,4,6-tri-t-butyl-phenoxy)-5,5,5-trifluoro-pentyl]-benzoylamino}-propionic acid

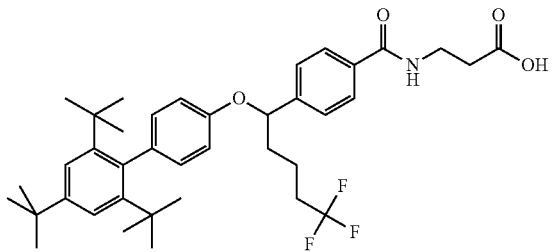 [SMILES: CC(C)(C)c1cc(C(C)(C)C)c(-c2ccc(OC(CCCC(F)(F)F)c3ccc(C(=O)NCCC(=O)O)cc3)cc2)c(C(C)(C)C)c1]

Step A. Racemic 4-[1-(4-Bromo-phenoxy)-5,5,5-trifluoro-pentyl]-benzoic acid methyl ester A solution of the 4-bromo-phenol (2.36 g, 13.61 mmol) and (R,S) 4-(5,5,5-trifluoro-1-hydroxy-pentyl)-benzoic acid methyl ester (3.00 g, 10.89 mmol) in toluene (50 mL) is degassed and filled with nitrogen three times. Tributylphosphine (4.03 mL, 16.34 mmol) is added to the reaction mixture under nitrogen at 0° C., followed by addition of 1,1'-(azodicarbonyl)-dipiperidine (4.12 g, 16.34 mmol). The reaction mixture is allowed to warm to room temperature and stirred overnight; the mixture is concentrated and purified by flash column chromatography (3.0 g, 6.96 mmol).

Step B. Racemic 4-[1-(4-Bromo-phenoxy)-5,5,5-trifluoro-pentyl]-benzoic acid

Racemic 4-[1-(4-bromo-phenoxy)-5,5,5-trifluoro-pentyl]-benzoic acid methyl ester (7.80 g, 18.1 mmol) is dissolved in the tetrahydrofuran (75 mL) and sodium hydroxide (25 mL, 5N) is added. The reaction is heated to reflux under nitrogen. The reaction is monitored by HPLC, and upon complete conversion, the reaction is neutralized with hydrochloric acid (25 mL, 5N) and diluted with diethyl ether and water. The two phases are separated, and the organic layer is washed, dried, and concentrated. The title compound (7.46 g, 16.24 mmol) is used without further purification.

Step C. Racemic 3-{4-[1-(4-Bromo-phenoxy)-5,5,5-trifluoro-pentyl]-benzoylamino}-propionic acid methyl ester Racemic 4-[1-(4-bromo-phenoxy)-5,5,5-trifluoro-pentyl]-benzoic acid (7.46 g, 17.89 mmol), 2-chloro-4,6-dimethoxy-1,3,5-triazine (3.23 g, 18.43 mmol) and 4-methylmorpholine (2.07 mL, 18.78 mmol) are combined in anhydrous dichloromethane (100 mL) under nitrogen. The reaction is allowed to stir under nitrogen at room temperature overnight. Beta alanine methyl ester hydrochloride (2.76 g, 19.68 mmol) and 4-methylmorpholine (4.14 mL, 37.56 mmol) is added to the reaction mixture and allowed to stir at room temperature. Some water (<10% volume) is added to help solubility. The reaction is monitored by HPLC, and upon complete consumption of the acid, the reaction is diluted with dichloromethane. The reaction is diluted with water and rinsed with 1N hydrochloric acid. Upon acidification, the two layers are separated. The organic layer is washed with brine, dried over anhydrous sodium sulfate, and concentrated. Flash column chromatography gave the title compound (7.07 g, 14.1 mmol).

Step D. Racemic 3-(4-{5,5,5-Trifluoro-1-[4-(4,4,5,5-tetramethyl-[1,3,2]dioxaborolan-2-yl)-phenoxy]-pentyl}-benzoylamino)-propionic acid methyl ester To a solution of racemic 3-{4-[1-(4-bromo-phenoxy)-5,5,5-trifluoro-pentyl]-benzoylamino}-propionic acid methyl ester (2.20 g, 4.38 mmol) in dimethyl sulfoxide (15 mL) is added [1,1'-bis(diphenylphosphino)ferrocene]dichloropalladium(II), complex with dichloromethane (1:1) (0.178 g, 0.022 mmol), bis(pinnocalado)diborane (2.22 g, 8.76 mmol), and potassium acetate (0.860 g, 8.76 mmol). The reaction is purged with nitrogen three times and heated to reflux under nitrogen. The reaction is monitored by HPLC, and upon completion, allowed to cool to room temperature. The reaction is diluted with ethyl acetate and celite is added, followed by water. This mixture is then filtered through a pad of celite. The solution is poured into a separatory funnel and the organic layer is washed with water and brine. The organic layer is dried over anhydrous sodium sulfate and concentrated. The product is purified by flash column chromatography (1.78 g, 3.24 mmol).

Step E. Racemic 3-{4-[1-(2,4,6-tri-t-butyl-phenoxy)-5,5,5-trifluoro-pentyl]-benzoylamino}-propionic acid methyl ester To a solution of racemic 3-(4-{5,5,5-Trifluoro-1-[4-(4,4,5,5-tetramethyl-[1,3,2]dioxaborolan-2-yl)-phenoxy]-pentyl}-benzoylamino)-propionic acid methyl ester (0.300 g, 0.550 mmol) in toluene (3.0 mL) is added palladium tetrakis triphenylphosphine (0.0316 g, 0.030 mmol), 2-bromo-1,3,5-tri-tert-butyl-benzene (0.353 g, 1.09 mmol), and potassium fluoride (0.063 g, 1.09 mmol). The reaction is purged with nitrogen three times and heated to reflux under nitrogen. At reflux, water (1.0 mL) is added to the reaction and the reaction is allowed to reflux under nitrogen. The reaction is monitored by HPLC, and upon completion, allowed to cool to room temperature. The reaction is diluted with ethyl acetate and celite is added, followed by water. This mixture is then filtered through a pad of celite. The solution is poured into a separatory funnel and the organic layer is washed with water and brine. The organic layer is dried over anhydrous sodium sulfate and concentrated. The product is purified by flash column chromatography (0.333 g, 0.500 mmol).

Step F. Racemic 3-{4-[1-(2,4,6-tri-t-butyl-phenoxy)-5,5,5-trifluoro-pentyl]-benzoylamino}-propionic acid Racemic 3-{4-[1-(2,4,6-tri-t-butyl-phenoxy)-5,5,5-trifluoro-pentyl]-benzoylamino}-propionic acid methyl ester (0.333 g, 0.500 mmol) is dissolved in tetrahydrofuran (3.0 mL) and sodium hydroxide (3.0 mL, 5N) is added. The reaction is monitored by HPLC, and upon complete conversion, the reaction is neutralized with hydrochloric acid (3.0 mL, 5N) and diluted with diethyl ether and water. The two phases are separated, and the organic layer is washed, dried, and concentrated. The title compound is used without further purification. MS (ES): 652.2 [M−H]⁻.

Example 360

3-(4-{5,5,5-trifluoro-1-[5-methyl-6-(4-trifluoromethyl-phenyl)-pyridin-3-yloxy]-pentyl}-benzoylamino)-propionic acid, Isomer 1 and Example 361

3-(4-{5,5,5-trifluoro-1-[5-methyl-6-(4-trifluoromethyl-phenyl)-pyridin-3-yloxy]-pentyl}-benzoylamino)-propionic acid, Isomer 2

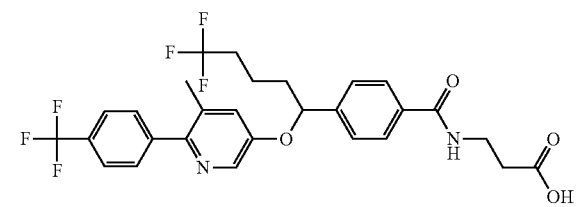 [SMILES: Cc1cc(OC(CCCC(F)(F)F)c2ccc(C(=O)NCCC(=O)O)cc2)cnc1-c1ccc(C(F)(F)F)cc1]

The title compounds are prepared in a manner substantially similar to Example 1 starting from 4-(5,5,5-trifluoro-1-hydroxy-pentyl)-benzoic acid methyl ester and 5-methyl-6-(4-trifluoromethyl-phenyl)-pyridin-3-ol (Preparation 34). The isomers are resolved by methods described herein or known to one skilled in the art. Isomer 1 MS: 567.3 [M−H]⁻; Isomer 2 MS: 567.3 [M−H]⁻.

Example 362

Racemic 3-(4-{1-[6-(4-trifluoromethyl-phenyl)-pyridin-3-yloxy]-pentyl}-benzoylamino)-propionic acid

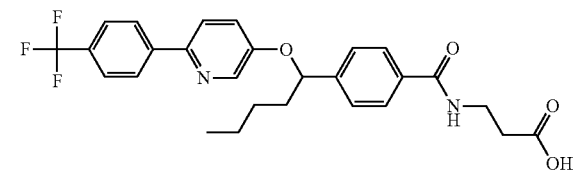 [SMILES: CCCCC(Oc1ccc(-c2ccc(C(F)(F)F)cc2)nc1)c1ccc(C(=O)NCCC(=O)O)cc1]

The title compound is prepared in a manner substantially similar to Example 62 starting from 3-{4-[1-(6-chloro-pyridin-3-yloxy)-pentyl]-benzoylamino}-propionic acid methyl ester and 4-trifluoromethyl phenyl boronic acid. MS: 499.2 [M–H]⁻.

Example 363

Racemic 3-{4-[1-(4'-tert-butyl-2,6-dimethyl-biphenyl-4-ylsulfanyl)-5,5,5-trifluoro-pentyl]-benzoylamino}-propionic acid

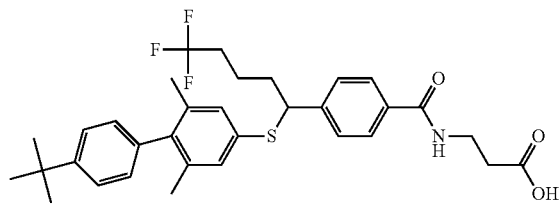 [SMILES: Cc1cc(SC(CCCC(F)(F)F)c2ccc(C(=O)NCCC(=O)O)cc2)cc(C)c1-c1ccc(C(C)(C)C)cc1]

The title compound is prepared in a manner substantially similar to Example 358 starting from 3-{4-[1-(4-bromo-3,5-dimethyl-phenylsulfanyl)-5,5,5-trifluoro-pentyl]-benzoylamino}-propionic acid methyl ester and 4-tert-butyl phenyl boronic acid. MS: 584.2 [M–H]⁻.

Example 364

Racemic 3-{4-[1-(4-bromo-3,5-dimethyl-phenylsulfanyl)-5,5,5-trifluoro-pentyl]-benzoylamino}-propionic acid

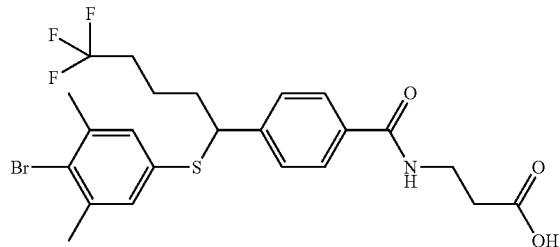 [SMILES: Cc1cc(SC(CCCC(F)(F)F)c2ccc(C(=O)NCCC(=O)O)cc2)cc(C)c1Br]

The title compound is prepared in a manner substantially similar to Example 358 starting from 3-{4-[1-(4-bromo-3,5-dimethyl-phenylsulfanyl)-5,5,5-trifluoro-pentyl]-benzoylamino}-propionic acid methyl ester. MS: 531.2 [M–H]⁻.

Example 365

Racemic 3-(4-{5,5,5-trifluoro-1-[5-methyl-6-(4-trifluoromethyl-phenyl)-pyridin-3-yloxy]-pentyl}-benzoylamino)-propionic acid

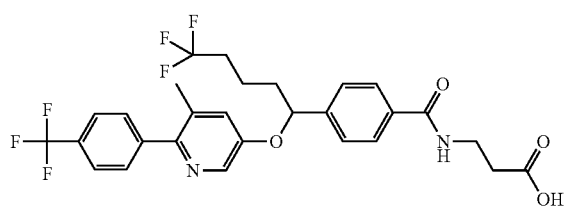 [SMILES: Cc1cc(OC(CCCC(F)(F)F)c2ccc(C(=O)NCCC(=O)O)cc2)cnc1-c1ccc(C(F)(F)F)cc1]

The title compound is prepared in a manner substantially similar to Example 1 starting from 4-(5,5,5-trifluoro-1-hydroxy-pentyl)-benzoic acid methyl ester and 5-methyl-6-(4-trifluoromethyl-phenyl)-pyridin-3-ol (Preparation 34). MS: 567.3 [M–H]⁻.

Example 366

Racemic 3-(4-{4,4,4-trifluoro-1-[5-methyl-6-(4-trifluoromethyl-phenyl)-pyridin-3-yloxy]-butyl}-benzoylamino)-propionic acid

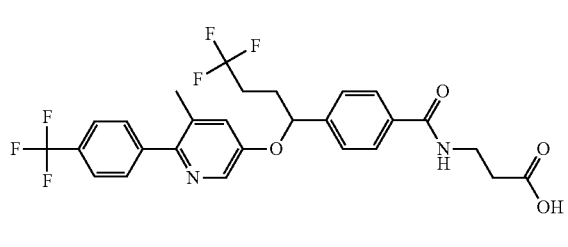 [SMILES: Cc1cc(OC(CCC(F)(F)F)c2ccc(C(=O)NCCC(=O)O)cc2)cnc1-c1ccc(C(F)(F)F)cc1]

The title compound is prepared in a manner substantially similar to Example 1 starting from 3-[4-(4,4,4-trifluoro-1-hydroxy-butyl)-benzoylamino]-propionic acid methyl ester and 5-methyl-6-(4-trifluoromethyl-phenyl)-pyridin-3-ol (Preparation 34). MS: 553.3 [M−H]⁻.

Example 367

3-{4-[1-(2,6-dimethyl-4'-trifluoromethyl-biphenyl-4-ylsulfanyl)-3-methyl-butyl]-benzoylamino}-propionic acid, Isomer 1 and Example 368

3-{4-[1-(2,6-dimethyl-4'-trifluoromethyl-biphenyl-4-ylsulfanyl)-3-methyl-butyl]-benzoylamino}-propionic acid, Isomer 2

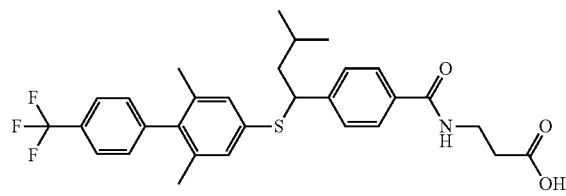 [SMILES: Cc1cc(SC(CC(C)C)c2ccc(C(=O)NCCC(=O)O)cc2)cc(C)c1-c1ccc(C(F)(F)F)cc1]

The title compound is prepared in a manner substantially similar to Example 358 starting from enantiomerically purified 3-{4-[1-(4-bromo-3,5-dimethyl-phenylsulfanyl)-3-methyl-butyl]-benzoylamino}-propionic acid methyl ester and 4-trifluoromethyl phenyl boronic acid. Isomer 1 MS: 542.2 [M−H]⁻; Isomer 2 MS: 542.2 [M−H]⁻.

Example 369

3-{4-[1-(4'-tert-butyl-2,6-dimethyl-biphenyl-4-ylsulfanyl)-3-methyl-butyl]-benzoylamino}-propionic acid, Isomer 1 and Example 370

3-{4-[1-(4'-tert-butyl-2,6-dimethyl-biphenyl-4-ylsulfanyl)-3-methyl-butyl]-benzoylamino}-propionic acid, Isomer 2

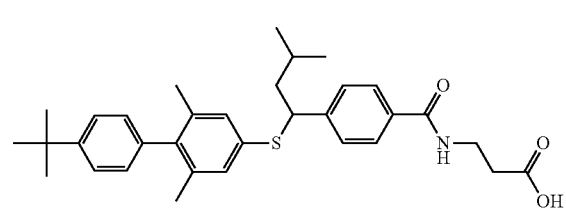 [SMILES: Cc1cc(SC(CC(C)C)c2ccc(C(=O)NCCC(=O)O)cc2)cc(C)c1-c1ccc(C(C)(C)C)cc1]

The title compound is prepared in a manner substantially similar to Example 367 starting from 3-{4-[1-(4-bromo-3,5-dimethyl-phenylsulfanyl)-3-methyl-butyl]-benzoylamino}-propionic acid methyl ester and 4-tert-butyl phenyl boronic acid. Isomer 1 MS: 530.2 [M−H]⁻; Isomer 2 MS: 530.2 [M−H]⁻.

Example 371

3-{4-[1-(4'-tert-butyl-2,6-dimethyl-biphenyl-4-ylsulfanyl)-4,4,4-trifluoro-butyl]-benzoylamino}-propionic acid, Isomer 1 and Example 372

3-{4-[1-(4'-tert-butyl-2,6-dimethyl-biphenyl-4-ylsulfanyl)-4,4,4-trifluoro-butyl]-benzoylamino}-propionic acid, Isomer 2

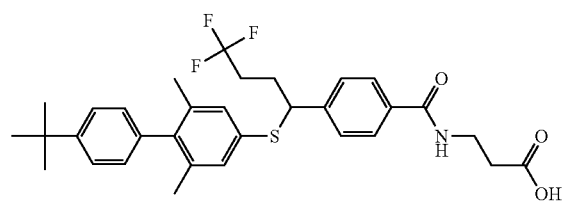 [SMILES: Cc1cc(SC(CCC(F)(F)F)c2ccc(C(=O)NCCC(=O)O)cc2)cc(C)c1-c1ccc(C(C)(C)C)cc1]

The title compounds are prepared in a manner substantially similar to Example 367 starting from 3-{4-[1-(4-bromo-3,5-dimethyl-phenylsulfanyl)-4,4,4-trifluoro-butyl]-benzoylamino}-propionic acid methyl ester and 4-tert-butyl phenyl boronic acid. Isomer 1 MS: 570.2 [M−H]⁻; Isomer 2 MS: 570.2 [M−H]⁻.

Example 373

3-{4-[1-(4-bromo-3,5-dimethyl-phenylsulfanyl)-4,4,4-trifluoro-butyl]-benzoylamino}-propionic acid, Isomer 1 and Example 374

3-{4-[1-(4-bromo-3,5-dimethyl-phenylsulfanyl)-4,4,4-trifluoro-butyl]-benzoylamino}-propionic acid, Isomer 2

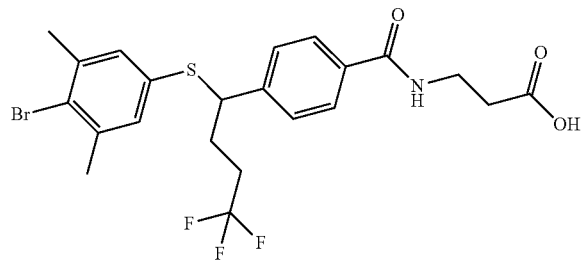 [SMILES: Cc1cc(SC(CCC(F)(F)F)c2ccc(C(=O)NCCC(=O)O)cc2)cc(C)c1Br]

The title compounds are prepared in a manner substantially similar to Example 358 starting from 3-{4-[1-(4-bromo-3,5-dimethyl-phenylsulfanyl)-4,4,4-trifluoro-butyl]-benzoylamino}-propionic acid methyl ester. Isomer 1 MS: 517.3 [M−H]⁻; Isomer 2 MS: 517.3 [M−H]⁻.

Example 375

3-{4-[1-(4-bromo-3,5-dimethyl-phenylsulfanyl)-3-methyl-butyl]-benzoylamino}-propionic acid, Isomer 1 and

Example 376

3-{4-[1-(4-bromo-3,5-dimethyl-phenylsulfanyl)-3-methyl-butyl]-benzoylamino}-propionic acid, Isomer 2

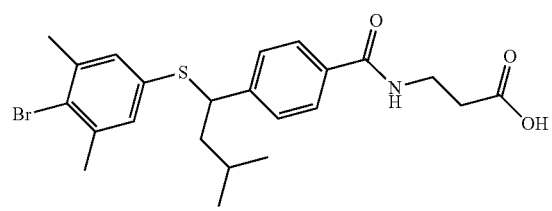 [SMILES: Cc1cc(SC(CC(C)C)c2ccc(C(=O)NCCC(=O)O)cc2)cc(C)c1Br]

The title compounds are prepared in a manner substantially similar to Example 358 starting from enantiomers of 3-{4-[1-(4-bromo-3,5-dimethyl-phenylsulfanyl)-3-methyl-butyl]-benzoylamino}-propionic acid methyl ester. Isomer 1 MS: 477.2 [M−H]⁻; Isomer 2 MS: 477.2 [M−H]⁻.

Example 377

3-{4-[1-(2,6-dimethyl-4'-trifluoromethyl-biphenyl-4-yloxy)-5,5,5-trifluoro-pentyl]-benzoylamino}-propionic acid, Isomer 1 and

Example 378

3-{4-[1-(2,6-dimethyl-4'-trifluoromethyl-biphenyl-4-yloxy)-5,5,5-trifluoro-pentyl]-benzoylamino}-propionic acid, Isomer 2

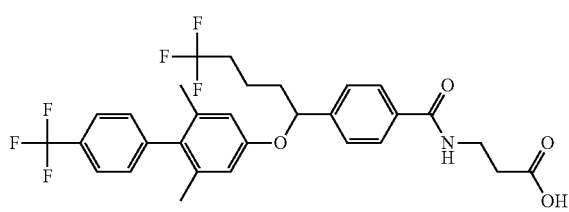 [SMILES: Cc1cc(OC(CCCC(F)(F)F)c2ccc(C(=O)NCCC(=O)O)cc2)cc(C)c1-c1ccc(C(F)(F)F)cc1]

The title compounds are prepared in a manner substantially similar to Example 1 starting from 4-(6,6,6-trifluoro-1-hydroxy-hexyl)-benzoic acid methyl ester and 4'-tert-butyl-2,6-dimethyl-biphenyl-4-ol. The isomers are resolved by methods described herein or known to one skilled in the art. Isomer 1 MS: 580.2 [M−H]⁻; Isomer 2 MS: 580.2 [M−H]⁻.

Example 379

3-{4-[4,4,4-trifluoro-1-(4'-isopropyl-2,6-dimethyl-biphenyl-4-yloxy)-butyl]-benzoylamino}-propionic acid, Isomer 1 and

Example 380

3-{4-[4,4,4-trifluoro-1-(4'-isopropyl-2,6-dimethyl-biphenyl-4-yloxy)-butyl]-benzoylamino}-propionic acid, Isomer 2

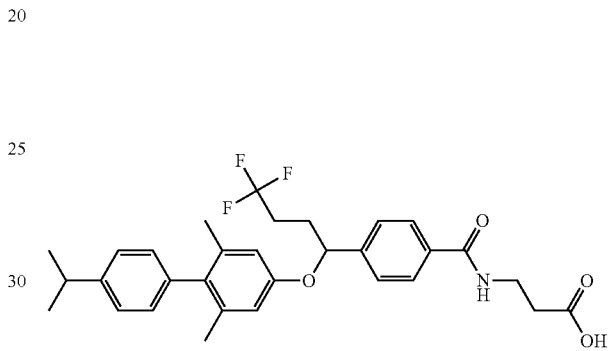

The title compounds are prepared in a manner substantially similar to Example 128 starting from enantiomers of 3-{4-[1-(4-bromo-3,5-dimethyl-phenoxy)-4,4,4-trifluoro-butyl]-benzoylamino}-propionic acid methyl ester and 4-isopropyl phenyl boronic acid. Isomer 1 MS: 540.2 [M−H]⁻, Isomer 2 MS: 540.2 [M−H]⁻.

Example 381

Racemic 3-{4-[1-(2,6-dimethyl-4'-trifluoromethyl-biphenyl-4-ylsulfanyl)-4,4,4-trifluoro-butyl]-benzoylamino}-propionic acid

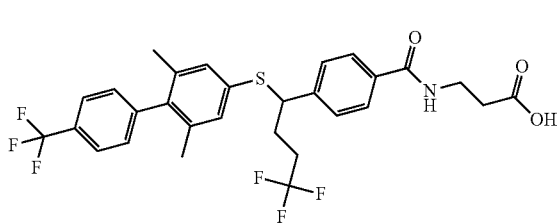 [SMILES: Cc1cc(SC(CCC(F)(F)F)c2ccc(C(=O)NCCC(=O)O)cc2)cc(C)c1-c1ccc(C(F)(F)F)cc1]

The title compound is prepared in a manner substantially similar to Example 358 starting from 3-{4-[1-(4-bromo-3,5-dimethyl-phenylsulfanyl)-4,4,4-trifluoro-butyl]-benzoylamino}-propionic acid methyl ester and 4-trifluoromethyl phenyl boronic acid. MS: 582.3 [M–H]⁻.

Example 382

Racemic 3-{4-[1-(4'-tert-butyl-2,6-dimethyl-biphenyl-4-ylsulfanyl)-4,4,4-trifluoro-butyl]-benzoylamino}-propionic acid

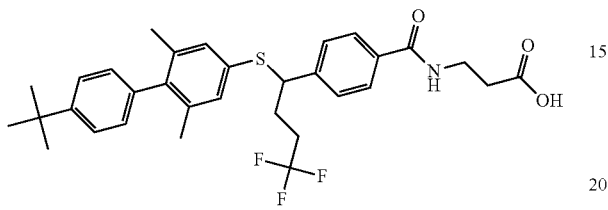

The title compound is prepared in a manner substantially similar to Example 358 starting from 3-{4-[1-(4-bromo-3,5-dimethyl-phenylsulfanyl)-4,4,4-trifluoro-butyl]-benzoylamino}-propionic acid methyl ester and 4-tert-butyl phenyl boronic acid. MS: 570.2 [M–H]⁻.

Example 383

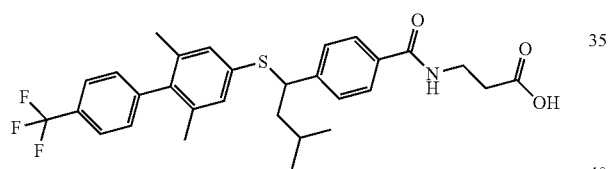

The title compound is prepared in a manner substantially similar to Example 358 starting from 3-{4-[1-(4-bromo-3,5-dimethyl-phenylsulfanyl)-3-methyl-butyl]-benzoylamino}-propionic acid methyl ester and 4-trifluoromethyl phenyl boronic acid. MS: 542.2 [M–H]⁻.

Example 384

Racemic 3-{4-[1-(4'-tert-butyl-2,6-dimethyl-biphenyl-4-ylsulfanyl)-3-methyl-butyl]-benzoylamino}-propionic acid

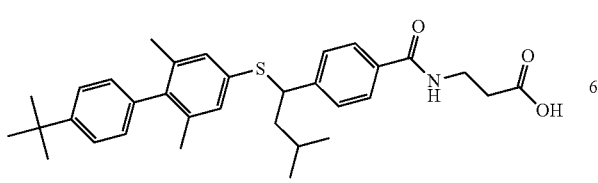

The title compound is prepared in a manner substantially similar to Example 358 starting from 3-{4-[1-(4-bromo-3,5- dimethyl-phenylsulfanyl)-3-methyl-butyl]-benzoylamino}-propionic acid methyl ester and 4-tert-butyl phenyl boronic acid. MS: 530.2 [M–H]⁻.

Example 385

Racemic 3-{4-[1-(4-bromo-3,5-dimethyl-phenylsulfanyl)-4,4,4-trifluoro-butyl]-benzoylamino}-propionic acid

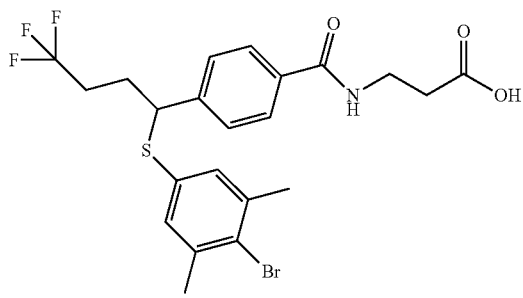 [SMILES: Cc1cc(SC(CCC(F)(F)F)c2ccc(C(=O)NCCC(=O)O)cc2)cc(C)c1Br]

The title compound is prepared in a manner substantially similar to Example 358 starting from 3-{4-[1-(4-bromo-3,5-dimethyl-phenylsulfanyl)-4,4,4-trifluoro-butyl]-benzoylamino}-propionic acid methyl ester. MS: 517.3 [M–H]⁻.

Example 386

Racemic 3-{4-[1-(4-bromo-3,5-dimethyl-phenylsulfanyl)-3-methyl-butyl]-benzoylamino}-propionic acid

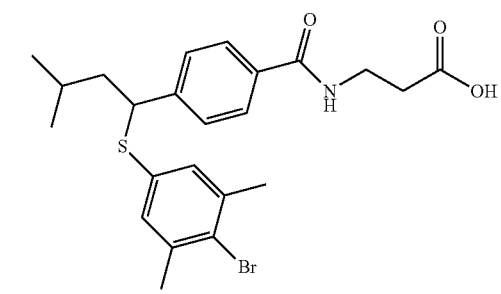 [SMILES: Cc1cc(SC(CC(C)C)c2ccc(C(=O)NCCC(=O)O)cc2)cc(C)c1Br]

The title compound is prepared in a manner substantially similar to Example 358 starting from 3-{4-[1-(4-bromo-3,5- dimethyl-phenylsulfanyl)-3-methyl-butyl]-benzoylamino}-propionic acid methyl ester. MS: 477.2 [M–H]⁻.

Example 387

3-{4-[1-(2,6-dimethyl-4'-trifluoromethyl-biphenyl-4-yloxy)-heptyl]-benzoylamino}-propionic acid, Isomer 1 and Example 388

3-{4-[1-(2,6-dimethyl-4'-trifluoromethyl-biphenyl-4-yloxy)-heptyl]-benzoylamino}-propionic acid, Isomer 2

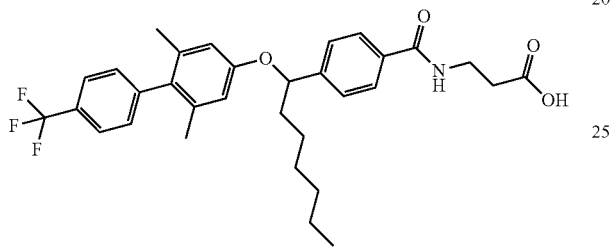

The title compounds are prepared in a manner substantially similar to Example 1 starting from 4-(1-hydroxy-heptyl)-benzoic acid methyl ester and 4'-tert-butyl-2,6-dimethyl-biphenyl-4-ol. The isomers are resolved by methods described herein or known to one skilled in the art. Isomer 1 MS: 554.3 [M–H]⁻; Isomer 2 MS: 554.3 [M–H]⁻.

Example 389

3-{4-[3-methyl-1-(2,2',4'-trichloro-biphenyl-4-yloxy)-butyl]-benzoylamino}-propionic acid, Isomer 1 and Example 390

3-{4-[3-methyl-1-(2,2',4'-trichloro-biphenyl-4-yloxy)-butyl]-benzoylamino}-propionic acid, isomer 2

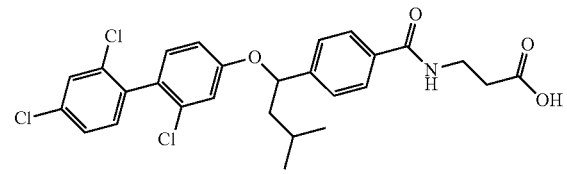 [SMILES: CC(C)CC(Oc1ccc(-c2ccc(Cl)cc2Cl)c(Cl)c1)c1ccc(C(=O)NCCC(=O)O)cc1]

The title compounds are prepared in a manner substantially similar to Example 24 starting from 3-{4-[1-(4-bromo-3-chloro-phenoxy)-3-methyl-butyl]-benzoylamino}-propionic acid methyl ester and 2,4-dichlorophenyl boronic acid. The isomers are resolved by methods described herein or known to one skilled in the art. Isomer 1 MS: 533.2 [M–H]⁻; Isomer 2 MS: 533.2 [M–H]⁻.

Example 391

3-{4-[1-(2,6-dimethyl-4'-trifluoromethyl-biphenyl-4-yloxy)-4,4,4-trifluoro-butyl]-benzoylamino}-propionic acid, Isomer 1 and Example 392

3-{4-[1-(2,6-dimethyl-4'-trifluoromethyl-biphenyl-4-yloxy)-4,4,4-trifluoro-butyl]-benzoylamino}-propionic acid, Isomer 2

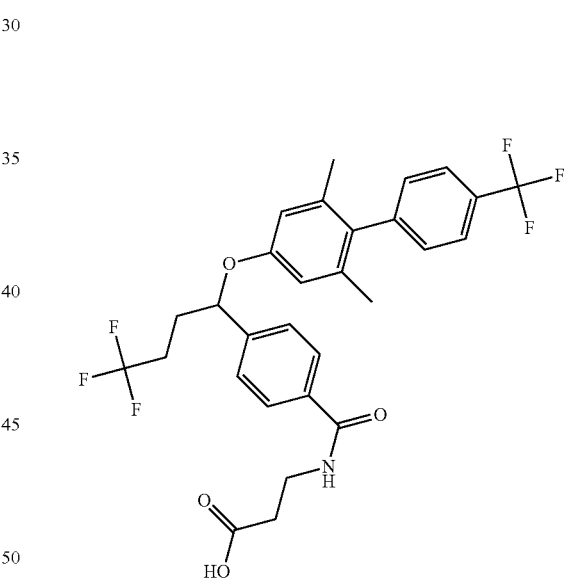

The title compounds are prepared in a manner substantially similar to Example 1 starting from 4-(4,4,4-trifluoro-1-hydroxy-butyl)-benzoic acid methyl ester and 2,6-dimethyl-4'-trifluoromethyl-biphenyl-4-ol. The isomers are resolved by methods described herein or known to one skilled in the art. Isomer 1 MS: 566.3 [M−H]⁻; Isomer 2 MS: 566.3 [M−H]⁻.

Example 393

3-{4-[1-(4'-tert-butyl-2,6-dimethyl-biphenyl-4-yloxy)-4,4,4-trifluoro-butyl]-benzoylamino}-propionic acid, Isomer 1 and

Example 394

3-{4-[1-(4'-tert-butyl-2,6-dimethyl-biphenyl-4-yloxy)-4,4,4-trifluoro-butyl]-benzoylamino}-propionic acid, Isomer 2

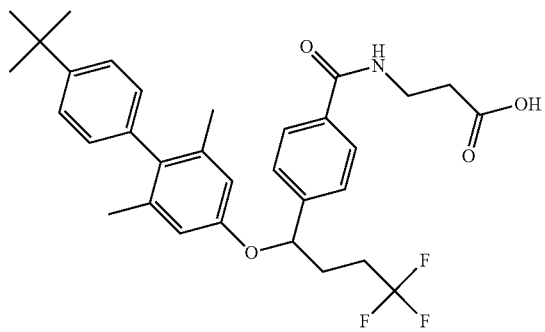 [SMILES: Cc1cc(OC(CCC(F)(F)F)c2ccc(C(=O)NCCC(=O)O)cc2)cc(C)c1-c1ccc(C(C)(C)C)cc1]

The title compounds are prepared in a manner substantially similar to Example 1 starting from 4-(4,4,4-trifluoro-1-hydroxy-butyl)-benzoic acid methyl ester and 4'-tert-butyl-2,6-dimethyl-biphenyl-4-ol. The isomers are resolved by methods described herein or known to one skilled in the art. Isomer 1 MS: 554.2 [M−H]⁻; Isomer 2 MS: 554.2 [M−H]⁻.

Example 395

3-{4-[5,5,5-trifluoro-1-(4'-isopropyl-2,6-dimethyl-biphenyl-4-yloxy)-pentyl]-benzoylamino}-propionic acid, Isomer 1 and

Example 396

3-{4-[5,5,5-trifluoro-1-(4'-isopropyl-2,6-dimethyl-biphenyl-4-yloxy)-pentyl]-benzoylamino}-propionic acid, Isomer 2

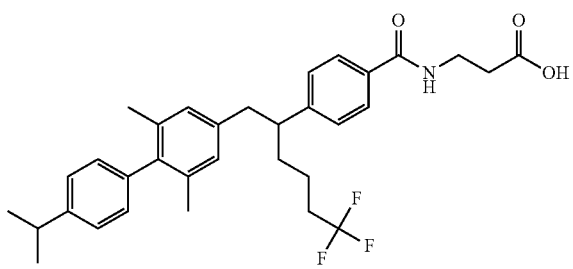 [SMILES: Cc1cc(CC(CCCC(F)(F)F)c2ccc(C(=O)NCCC(=O)O)cc2)cc(C)c1-c1ccc(C(C)C)cc1]

The title compounds are prepared in a manner substantially similar to Example 128 starting from 3-{4-[1-(4-bromo-3,5-dimethyl-phenoxy)-5,5,5-trifluoro-pentyl]-benzoylamino}-propionic acid methyl ester and 4-isopropyl phenyl boronic acid. Isomer 1 MS: 554.2 [M−H]⁻; Isomer 2 MS: 554.2 [M−H]⁻.

Example 397

Racemic 3-{4-[5,5,5-trifluoro-1-(4'-isopropyl-2,6-dimethyl-biphenyl-4-yloxy)-pentyl]-benzoylamino}-propionic acid

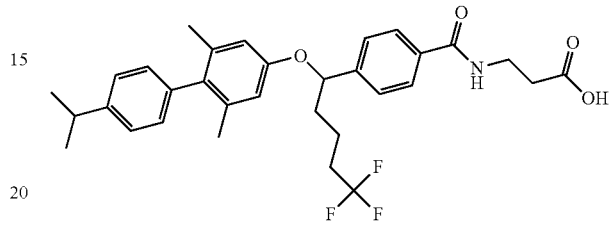

The title compound is prepared in a manner substantially similar to Example 128 starting from 3-{4-[1-(4-bromo-3,5-dimethyl-phenoxy)-5,5,5-trifluoro-pentyl]-benzoylamino}-propionic acid methyl ester and 4-isopropyl phenyl boronic acid. MS: 554.2 [M−H]⁻.

Example 398

3-{4-[1-(2,6-dimethyl-4'-trifluoromethyl-biphenyl-4-yloxy)-5-methyl-hexyl]-benzoylamino}-propionic acid, Isomer 1 and

Example 399

3-{4-[1-(2,6-dimethyl-4'-trifluoromethyl-biphenyl-4-yloxy)-5-methyl-hexyl]-benzoylamino}-propionic acid, Isomer 2

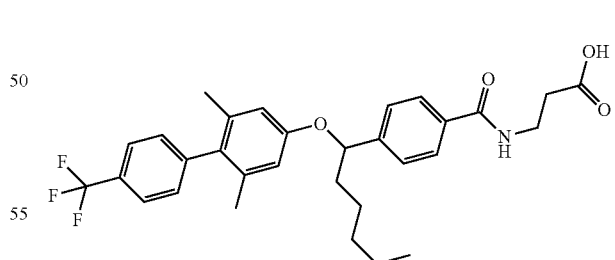

The title compounds are prepared in a manner substantially similar to Example 1 starting from 4-(1-hydroxy-5-methyl-hexyl)-benzoic acid methyl ester and 2,6-dimethyl-4'-trifluoromethyl-biphenyl-4-ol. The isomers are resolved by methods described herein or known to one skilled in the art. Isomer 1 MS: 554.2 [M–H]⁻; Isomer 2 MS:554.2 [M–H]⁻.

Example 400

3-{4-[5-methyl-1-(4'-trifluoromethyl-biphenyl-4-yloxy)-hexyl]-benzoylamino}-propionic acid, Isomer 1 and Example 401

3-{4-[5-methyl-1-(4'-trifluoromethyl-biphenyl-4-yloxy)-hexyl]-benzoylamino}-propionic acid, Isomer 2

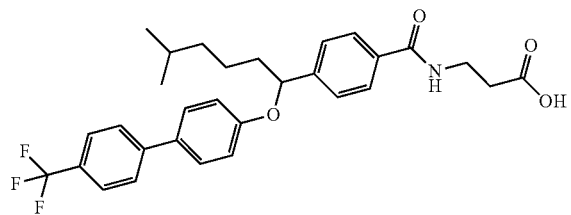 [SMILES: CC(C)CCCC(Oc1ccc(-c2ccc(C(F)(F)F)cc2)cc1)c1ccc(C(=O)NCCC(=O)O)cc1]

The title compounds are prepared in a manner substantially similar to Example 1 starting from 4-(1-hydroxy-5-methyl-hexyl)-benzoic acid methyl ester and 4'-trifluoromethyl-biphenyl-4-ol. The isomers are resolved by methods described herein or known to one skilled in the art. Isomer 1 MS: 526.2 [M–H]⁻; Isomer 2 MS: 526.2 [M–H]⁻.

Example 402

3-(4-{1-[6-(4-tert-butyl-phenyl)-pyridin-3-yloxy]-5-methyl-hexyl}-benzoylamino)-propionic acid, Isomer 1 and Example 403

3-(4-{1-[6-(4-tert-butyl-phenyl)-pyridin-3-yloxy]-5-methyl-hexyl}-benzoylamino)-propionic acid, Isomer 2

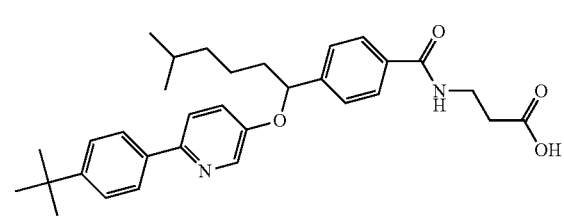 [SMILES: CC(C)CCCC(Oc1ccc(-c2ccc(C(C)(C)C)cc2)nc1)c1ccc(C(=O)NCCC(=O)O)cc1]

The title compounds are prepared in a manner substantially similar to Example 62 starting from 3-{4-[1-(6-chloro-pyridin-3-yloxy)-5-methyl-hexyl]-benzoylamino}-propionic acid methyl ester and 4-tert-butyl phenyl boronic acid. Isomer 1 MS: 515.2 [M–H]⁻; Isomer 2 MS: 515.2 [M–H]⁻.

Example 404

Racemic 3-(4-{5-methyl-1-[6-(4-trifluoromethyl-phenyl)-pyridin-3-yloxy]-hexyl}-benzoylamino)-propionic acid

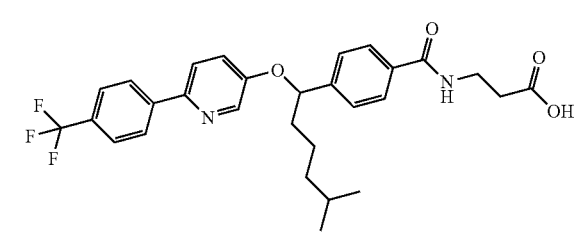 [SMILES: CC(C)CCCC(Oc1ccc(-c2ccc(C(F)(F)F)cc2)nc1)c1ccc(C(=O)NCCC(=O)O)cc1]

The title compound is prepared in a manner substantially similar to Example 62 starting from 3-{4-[1-(6-chloro-pyridin-3-yloxy)-5-methyl-hexyl]-benzoylamino}-propionic acid methyl ester and 4-trifluoromethyl phenyl boronic acid. MS: 527.2 [M–H]⁻.

Example 405

Racemic 3-{4-[1-(6-chloro-pyridin-3-yloxy)-5-methyl-hexyl]-benzoylamino}-propionic acid

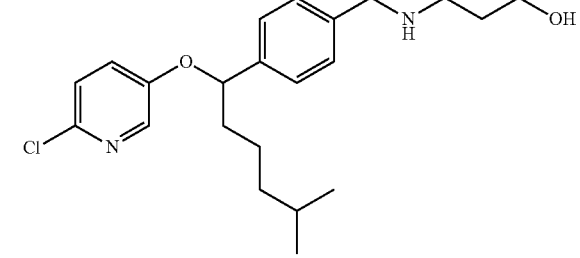

The title compound is prepared in a manner substantially similar to Example 62 starting from 3-{4-[1-(6-chloro-pyridin-3-yloxy)-5-methyl-hexyl]-benzoylamino}-propionic acid methyl ester. MS: 417.3 [M–H]⁻.

Example 406

Racemic 3-{4-[1-(2,6-dimethyl-4'-trifluoromethyl-biphenyl-4-yloxy)-5-methyl-hexyl]-benzoylamino}-propionic acid

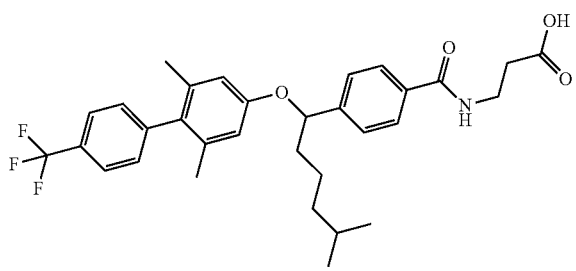 [SMILES: Cc1cc(OC(CCCC(C)C)c2ccc(C(=O)NCCC(=O)O)cc2)cc(C)c1-c1ccc(C(F)(F)F)cc1]

The title compound is prepared in a manner substantially similar to Example 1 starting from 4-(1-hydroxy-5-methyl-hexyl)-benzoic acid methyl ester and 2,6-dimethyl-4'-trifluoromethyl-biphenyl-4-ol. MS: 554.2 [M–H]⁻.

Example 407

Racemic 3-(4-{1-[6-(4-tert-butyl-phenyl)-pyridin-3-yloxy]-5-methyl-hexyl}-benzoylamino)-propionic acid

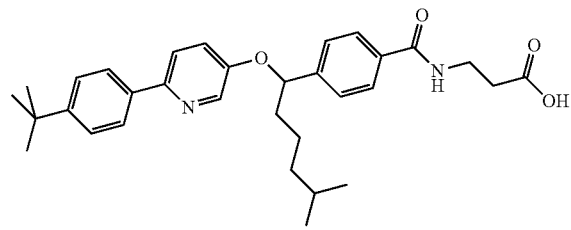 [SMILES: CC(C)CCCC(Oc1ccc(-c2ccc(C(C)(C)C)cc2)nc1)c1ccc(C(=O)NCCC(=O)O)cc1]

The title compound is prepared in a manner substantially similar to Example 62 starting from 3-{4-[1-(6-chloro-pyri-din-3-yloxy)-5-methyl-hexyl]-benzoylamino}-propionic acid methyl ester and 4-tert-butyl phenyl boronic acid. MS: 515.2 [M–H]⁻.

Example 408

Racemic 3-{4-[5-methyl-1-(4'-trifluoromethyl-biphenyl-4-yloxy)-hexyl]-benzoylamino}-propionic acid

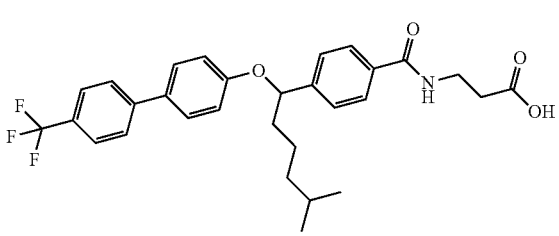 [SMILES: CC(C)CCCC(Oc1ccc(-c2ccc(C(F)(F)F)cc2)cc1)c1ccc(C(=O)NCCC(=O)O)cc1]

The title compound is prepared in a manner substantially similar to Example 1 starting from 4-(1-hydroxy-5-methyl-hexyl)-benzoic acid methyl ester and 4'-trifluoromethyl-biphenyl-4-ol. MS: 526.2 [M–H]⁻.

Example 409

Racemic 3-{4-[1-(4'-tert-butyl-biphenyl-4-yloxy)-5-methyl-hexyl]-benzoylamino}-propionic acid

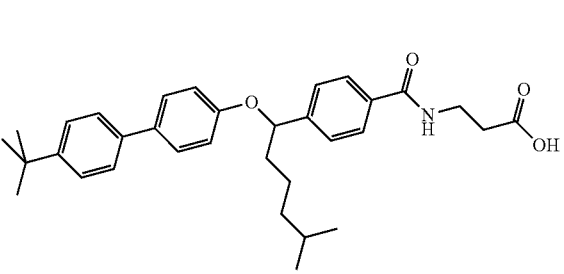 [SMILES: CC(C)CCCC(Oc1ccc(-c2ccc(C(C)(C)C)cc2)cc1)c1ccc(C(=O)NCCC(=O)O)cc1]

The title compound is prepared in a manner substantially similar to Example 1 starting from 4-(1-hydroxy-5-methyl-hexyl)-benzoic acid methyl ester and 4'-tert-butyl-biphenyl-4-ol. MS: 514.2 [M–H]⁻.

Example 410

3-(4-{1-[6-(4-tert-butyl-phenyl)-pyridin-3-yloxy]-5,5,5-trifluoro-pentyl}-benzoylamino)-propionic acid, Isomer 1 and Example 411

3-(4-{1-[6-(4-tert-butyl-phenyl)-pyridin-3-yloxy]-5,5,5-trifluoro-pentyl}-benzoylamino)-propionic acid, Isomer 2

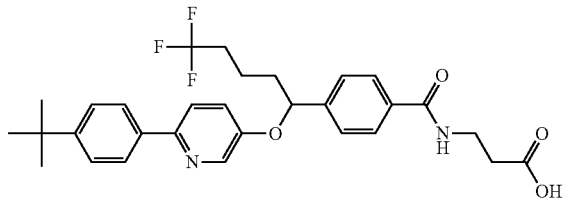 [SMILES: CC(C)(C)c1ccc(-c2ccc(OC(CCCC(F)(F)F)c3ccc(C(=O)NCCC(=O)O)cc3)cn2)cc1]

The title compounds are prepared in a manner substantially similar to Example 62 starting from 4-[1-(6-chloro-pyridin-3-yloxy)-5,5,5-trifluoro-pentyl]-benzoic acid methyl ester and 4-tert-butyl phenyl boronic acid. Isomer 1 MS: 541.3 [M–H]⁻; Isomer 2 MS: 541.3 [M–H]⁻.

Example 412

3-(4-{1-[6-(4-tert-butyl-phenyl)-pyridin-3-yloxy]-4,4,4-trifluoro-butyl}-benzoylamino)-propionic acid, Isomer 1 and Example 413

3-(4-{1-[6-(4-tert-butyl-phenyl)-pyridin-3-yloxy]-4,4,4-trifluoro-butyl}-benzoylamino)-propionic acid, Isomer 2

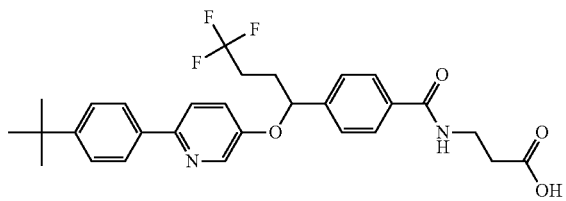 [SMILES: CC(C)(C)c1ccc(-c2ccc(OC(CCC(F)(F)F)c3ccc(C(=O)NCCC(=O)O)cc3)cn2)cc1]

The title compounds are prepared in a manner substantially similar to Example 62 starting from 4-[1-(6-chloro-pyridin-3-yloxy)-4,4,4-trifluoro-butyl]-benzoic acid methyl ester and 4-tert-butyl phenyl boronic acid. Isomer 1 MS: 527.2 [M–H]⁻; Isomer 2 MS: 527.2 [M–H]⁻.

Example 414

Racemic 3-{4-[(4'-tert-butyl-2,6-dimethyl-biphenyl-4-yloxy)-cyclohexyl-methyl]-benzoylamino}-propionic acid

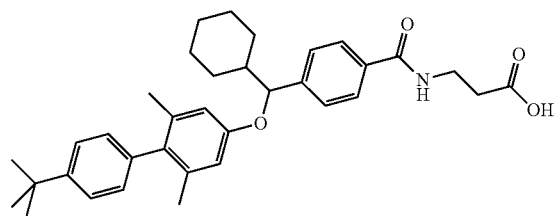 [SMILES: Cc1cc(OC(c2ccc(C(=O)NCCC(=O)O)cc2)C2CCCCC2)cc(C)c1-c1ccc(C(C)(C)C)cc1]

The title compound is prepared in a manner substantially similar to Example 1 starting from 4-(cyclohexyl-hydroxy-methyl)-benzoic acid methyl ester and 4'-tert-butyl-biphenyl-4-ol. MS: 540.3 [M–H]⁻.

Example 415

Racemic 3-{4-[1-(4'-tert-butyl-2,6-dimethyl-biphenyl-4-yloxy)-4,4,4-trifluoro-butyl]-benzoylamino}-propionic acid

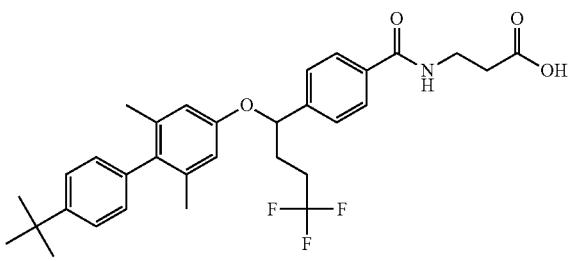 [SMILES: Cc1cc(OC(CCC(F)(F)F)c2ccc(C(=O)NCCC(=O)O)cc2)cc(C)c1-c1ccc(C(C)(C)C)cc1]

The title compound is prepared in a manner substantially similar to Example 1 starting from 4-(4,4,4-trifluoro-1-hydroxy-butyl)-benzoic acid methyl ester and 4'-tert-butyl-biphenyl-4-ol. MS: 554.2 [M−H]⁻.

Example 416

3-{4-[4,4,4-trifluoro-1-(4'-trifluoromethyl-biphenyl-4-yloxy)-butyl]-benzoylamino}-propionic acid, Isomer 1 and Example 417

3-{4-[4,4,4-trifluoro-1-(4'-trifluoromethyl-biphenyl-4-yloxy)-butyl]-benzoylamino}-propionic acid, Isomer 2

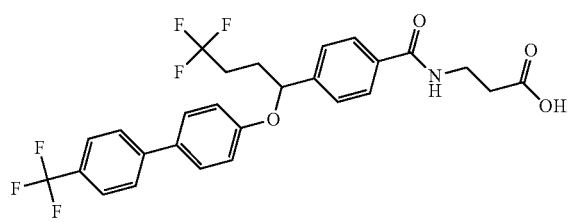 [SMILES: O=C(O)CCNC(=O)c1ccc(C(CCC(F)(F)F)Oc2ccc(-c3ccc(C(F)(F)F)cc3)cc2)cc1]

The title compounds are prepared in a manner substantially similar to Example 1 starting from 4-(4,4,4-trifluoro-1-hydroxy-butyl)-benzoic acid methyl ester and 4'-trifluoromethyl-biphenyl-4-ol. The isomers are resolved by methods described herein or known to one skilled in the art. Isomer 1 MS: 538.3 [M−H]⁻; Isomer 2 MS: 538.3 [M−H]⁻.

Example 418

Racemic 3-(4-{4,4,4-trifluoro-1-[6-(4-isopropyl-phenyl)-pyridin-3-yloxy]-butyl}-benzoylamino)-propionic acid

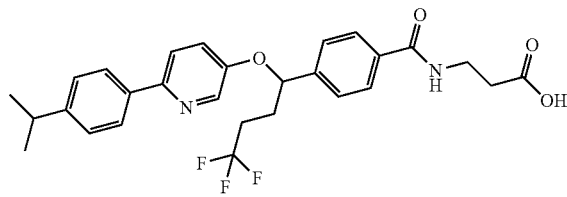 [SMILES: CC(C)c1ccc(-c2ccc(OC(CCC(F)(F)F)c3ccc(C(=O)NCCC(=O)O)cc3)cn2)cc1]

The title compound is prepared in a manner substantially similar to Example 62 starting from 4-[1-(6-chloro-pyridin-3-yloxy)-4,4,4-trifluoro-butyl]-benzoic acid methyl ester and 4-isopropyl phenyl boronic acid. MS: 513.2 [M−H]⁻.

Example 419

Racemic 3-(4-{5,5,5-trifluoro-1-[6-(4-trifluoromethyl-phenyl)-pyridin-3-yloxy]-pentyl}-benzoylamino)-propionic acid

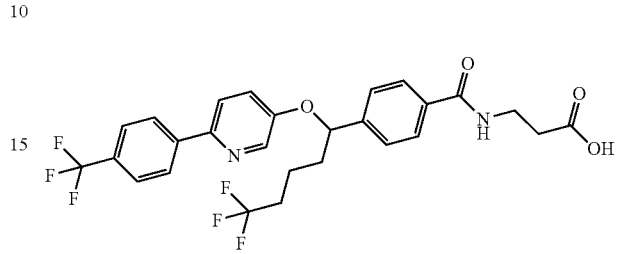

The title compound is prepared in a manner substantially similar to Example 62 starting from 4-[1-(6-chloro-pyridin-3-yloxy)-5,5,5-trifluoro-pentyl]-benzoic acid methyl ester and 4-trifluoromethyl phenyl boronic acid. MS: 553.3 [M−H]⁻.

Example 420

Racemic 3-(4-{[6-(4-tert-butyl-phenyl)-pyridin-3-yloxy]-cyclohexyl-methyl}-benzoylamino)-propionic acid

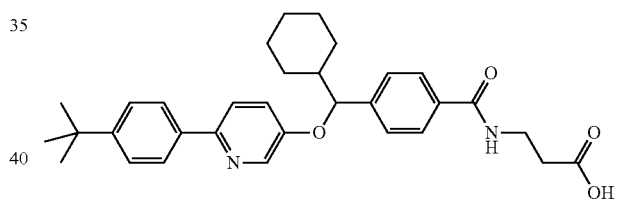

The title compound is prepared in a manner substantially similar to Example 62 starting from 4-[(6-chloro-pyridin-3-yloxy)-cyclohexyl-methyl]-benzoic acid methyl ester and 4-tert-butyl phenyl boronic acid. MS: 513.2 [M−H]⁻.

Example 421

Racemic 3-(4-{5,5,5-trifluoro-1-[6-(4-isopropyl-phenyl)-pyridin-3-yloxy]-pentyl}-benzoylamino)-propionic acid

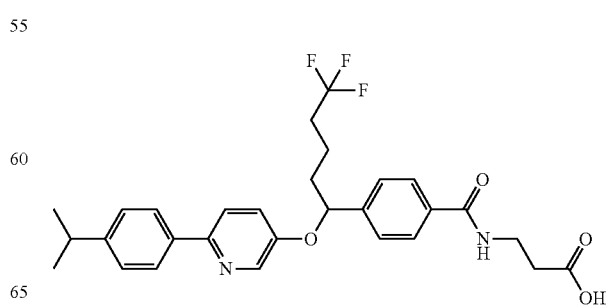

The title compound is prepared in a manner substantially similar to Example 62 starting from 4-[1-(6-chloro-pyridin-3-yloxy)-5,5,5-trifluoro-pentyl]-benzoic acid methyl ester and 4-isopropyl phenyl boronic acid. MS: 527.2 [M–H]⁻.

Example 422

Racemic 3-{4-[1-(2,6-dimethyl-4'-trifluoromethyl-biphenyl-4-yloxy)-4,4,4-trifluoro-butyl]-benzoylamino}-propionic acid

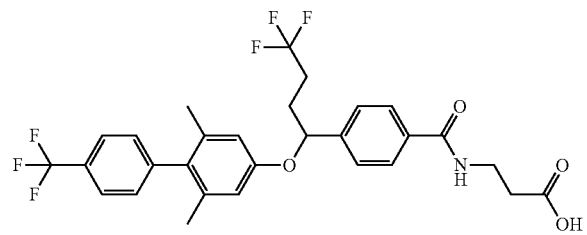 [SMILES: Cc1cc(OC(CCC(F)(F)F)c2ccc(C(=O)NCCC(=O)O)cc2)cc(C)c1-c1ccc(C(F)(F)F)cc1]

The title compound is prepared in a manner substantially similar to Example 128 starting from 3-{4-[1-(4-bromo-3,5-dimethyl-phenoxy)-4,4,4-trifluoro-butyl]-benzoylamino}-propionic acid methyl ester and 4-trifluoromethyl phenyl boronic acid. MS: 566.2 [M–H]⁻.

Example 423

Racemic 3-(4-{cyclohexyl-[6-(4-isopropyl-phenyl)-pyridin-3-yloxy]-methyl}-benzoylamino)-propionic acid

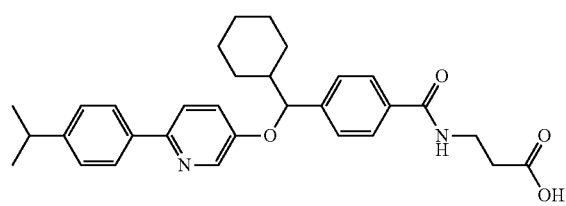 [SMILES: Cc1cc(OC(c2ccc(C(=O)NCCC(=O)O)cc2)C2CCCCC2)cc(C)c1-c1ccc(C(C)C)cc1]

The title compound is prepared in a manner substantially similar to Example 62 starting from 4-[(6-chloro-pyridin-3-yloxy)-cyclohexyl-methyl]-benzoic acid methyl ester and 4-isopropyl phenyl boronic acid. MS: 499.2 [M–H]⁻.

Example 424

Racemic 3-{4-[cyclohexyl-(4'-isopropyl-2,6-dimethyl-biphenyl-4-yloxy)-methyl]-benzoylamino}-propionic acid

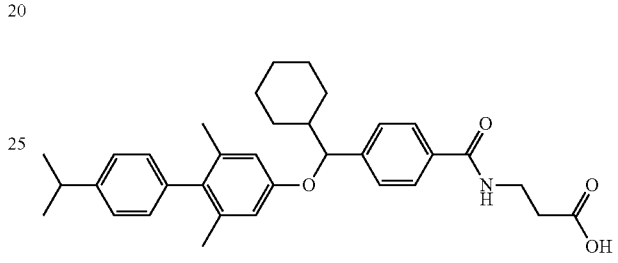

The title compound is prepared in a manner substantially similar to Example 128 starting from 3-{4-[(4-bromo-3,5-dimethyl-phenoxy)-cyclohexyl-methyl]-benzoylamino}-propionic acid methyl ester and 4-isopropyl phenyl boronic acid. MS: 526.2 [M–H]⁻.

Example 425

Racemic 3-{4-[4,4,4-trifluoro-1-(4'-isopropyl-2,6-dimethyl-biphenyl-4-yloxy)-butyl]-benzoylamino}-propionic acid

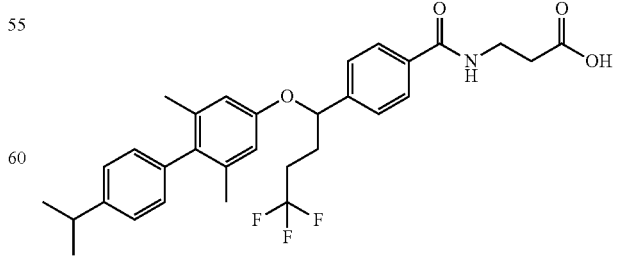

The title compound is prepared in a manner substantially similar to Example 128 starting from 3-{4-[(4-bromo-3,5- dimethyl-phenoxy)-4,4,4-trifluoro-butyl]-benzoylamino}-propionic acid methyl ester and 4-isopropyl phenyl boronic acid. MS: 540.3 [M–H]⁻.

Example 426

3-{4-[cyclohexyl-(4'-trifluoromethyl-biphenyl-4-yloxy)-methyl]-benzoylamino}-propionic acid, Isomer 1 and

Example 427

3-{4-[cyclohexyl-(4'-trifluoromethyl-biphenyl-4-yloxy)-methyl]-benzoylamino}-propionic acid, Isomer 2

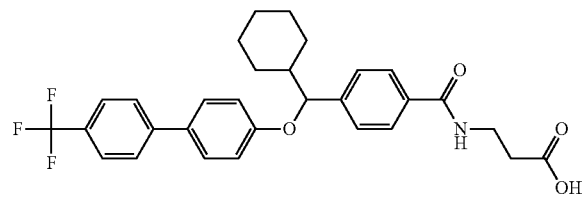 [SMILES: O=C(O)CCNC(=O)c1ccc(C(Oc2ccc(-c3ccc(C(F)(F)F)cc3)cc2)C2CCCCC2)cc1]

The title compound is prepared in a manner substantially similar to Example 128 starting from 3-{4-[(4-bromo-phenoxy)-cyclohexyl-methyl]-benzoylamino}-propionic acid methyl ester and 4-trifluoromethyl phenyl boronic acid. The isomers are resolved by methods described herein or known to one skilled in the art. Isomer 1 MS: 524.3 [M–H]⁻; Isomer 2 MS: 524.3 [M–H]⁻.

Example 428

3-{4-[5,5,5-trifluoro-1-(4'-isopropyl-biphenyl-4-yloxy)-pentyl]-benzoylamino}-propionic acid, Isomer 1 and

Example 429

3-{4-[5,5,5-trifluoro-1-(4'-isopropyl-biphenyl-4-yloxy)-pentyl]-benzoylamino}-propionic acid, Isomer 2

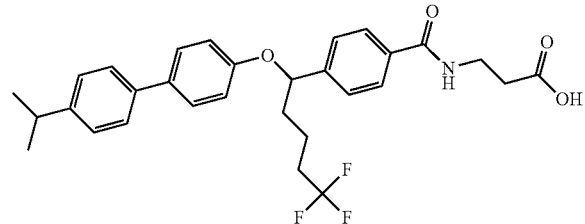 [SMILES: CC(C)c1ccc(-c2ccc(OC(CCCC(F)(F)F)c3ccc(C(=O)NCCC(=O)O)cc3)cc2)cc1]

The title compound is prepared in a manner substantially similar to Example 128 starting from 3-{4-[1-(4-bromo-phenoxy)-5,5,5-trifluoro-pentyl]-benzoylamino}-propionic acid methyl ester and 4-isopropyl phenyl boronic acid. The isomers are resolved by methods described herein or known to one skilled in the art. Isomer 1 MS: 526.2 [M–H]⁻; Isomer 2 MS: 526.2 [M–H]⁻.

Example 430

Racemic 3-{4-[(4'-tert-butyl-biphenyl-4-yloxy)-cyclohexyl-methyl]-benzoylamino}-propionic acid

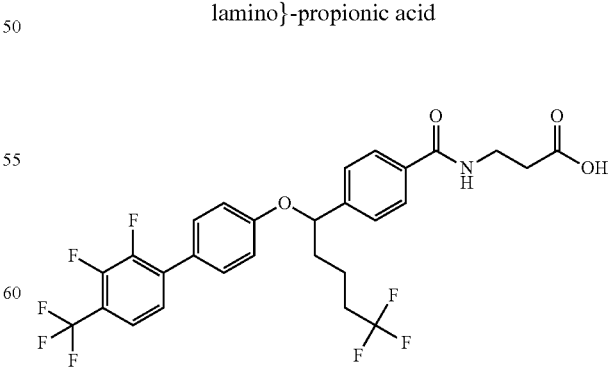

The title compound is prepared in a manner substantially similar to Example 128 starting from 3-{4-[(4-bromo-phenoxy)-cyclohexyl-methyl]-benzoylamino}-propionic acid methyl ester and 4-tert-butyl phenyl boronic acid. MS: 512.3 [M–H]⁻.

Example 431

Racemic 3-{4-[5,5,5-trifluoro-1-(2'-3'-fluoro-4'-trifluoromethyl-biphenyl-4-yloxy)-pentyl]-benzoylamino}-propionic acid The title compound is prepared in a manner substantially similar to Example 359 starting from 3-(4-{5,5,5-trifluoro-1-[4-(4,4,5,5-tetramethyl-[1,3,2]dioxaborolan-2-yl)-phenoxy]-pentyl}-benzoylamino)-propionic acid methyl ester and 1-bromo-2,3-difluoro-4-trifluoromethyl-benzene. MS: 588.3 [M−H]⁻.

Example 432

Racemic 3-{4-[cyclohexyl-(4'-trifluoromethyl-biphenyl-4-yloxy)-methyl]-benzoylamino}-propionic acid

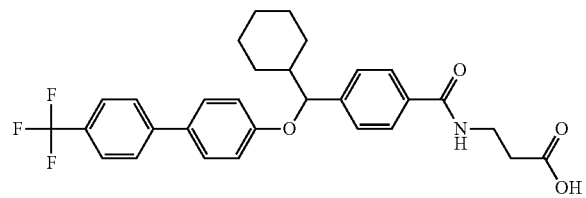 [SMILES: O=C(O)CCNC(=O)c1ccc(C(Oc2ccc(-c3ccc(C(F)(F)F)cc3)cc2)C2CCCCC2)cc1]

The title compound is prepared in a manner substantially similar to Example 128 starting from 3-{4-[(4-bromo-phenoxy)-cyclohexyl-methyl]-benzoylamino}-propionic acid methyl ester and 4-trifluoromethyl phenyl boronic acid. MS: 524.3 [M−H]⁻.

Example 433

Racemic 3-{4-[5,5,5-trifluoro-1-(4'-isopropyl-biphenyl-4-yloxy)-pentyl]-benzoylamino}-propionic acid

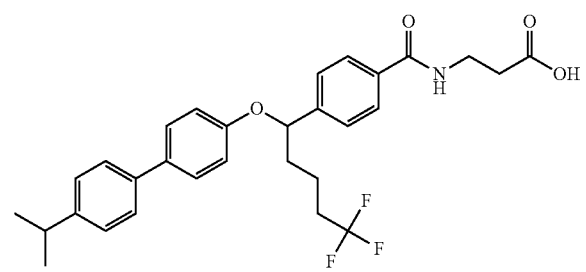 [SMILES: CC(C)c1ccc(-c2ccc(OC(CCCC(F)(F)F)c3ccc(C(=O)NCCC(=O)O)cc3)cc2)cc1]

The title compound is prepared in a manner substantially similar to Example 128 starting from 3-{4-[1-(4-bromo-phenoxy)-5,5,5-trifluoro-pentyl]-benzoylamino}-propionic acid methyl ester and 4-isopropyl phenyl boronic acid. MS: 526.2 [M−H]⁻.

Example 434

Racemic 3-{4-[1-(4'-ethyl-biphenyl-4-yloxy)-5,5,5-trifluoro-pentyl]-benzoylamino}-propionic acid

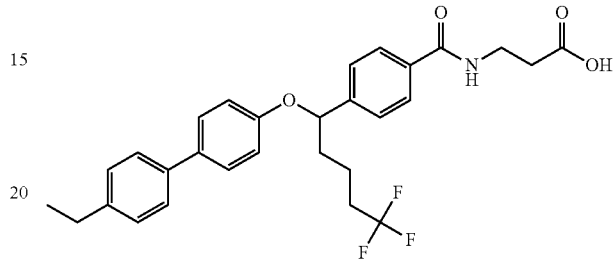

The title compound is prepared in a manner substantially similar to Example 128 starting from 3-{4-[1-(4-bromo-phenoxy)-5,5,5-trifluoro-pentyl]-benzoylamino}-propionic acid methyl ester and 4-ethyl phenyl boronic acid. MS: 572.3 [M−H]⁻.

Example 435

Racemic 3-{4-[5,5,5-trifluoro-1-(3'-fluoro-4'-trifluoromethyl-biphenyl-4-yloxy)-pentyl]-benzoylamino}-propionic acid

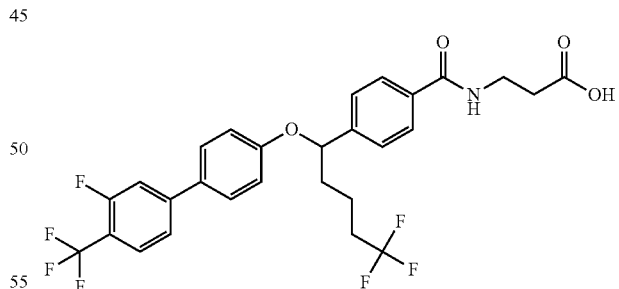

The title compound is prepared in a manner substantially similar to Example 359 starting from 3-(4-{5,5,5-trifluoro-1-[4-(4,4,5,5-tetramethyl-[1,3,2]dioxaborolan-2-yl)-phenoxy]-pentyl}-benzoylamino)-propionic acid methyl ester and 4-bromo-2-fluoro-1-trifluoromethyl-benzene. MS: 570.2 [M−H]⁻.

Example 436

Racemic 3-{4-[1-(2,4,6-triisopropyl-phenoxy)-5,5,5-trifluoro-pentyl]-benzoylamino}-propionic acid

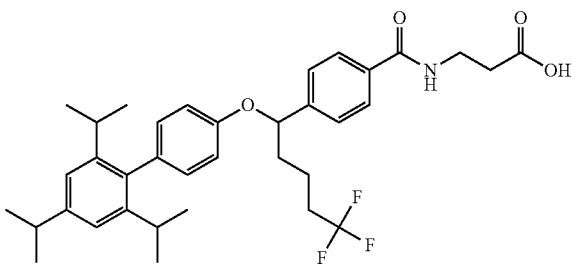 [SMILES: CC(C)c1cc(C(C)C)c(-c2ccc(OC(CCCC(F)(F)F)c3ccc(C(=O)NCCC(=O)O)cc3)cc2)c(C(C)C)c1]

The title compound is prepared in a manner substantially similar to Example 359 starting from 3-(4-{5,5,5-trifluoro-1-[4-(4,4,5,5-tetramethyl-[1,3,2]dioxaborolan-2-yl)-phenoxy]-pentyl}-benzoylamino)-propionic acid methyl ester and 2-bromo-1,3,5-triisopropyl-benzene. MS: 610.2 [M−H]⁻.

Example 437

Racemic 3-{4-[1-(2,3,4,5,6-pentamethyl-phenoxy)-5,5,5-trifluoro-pentyl]-benzoylamino}-propionic acid

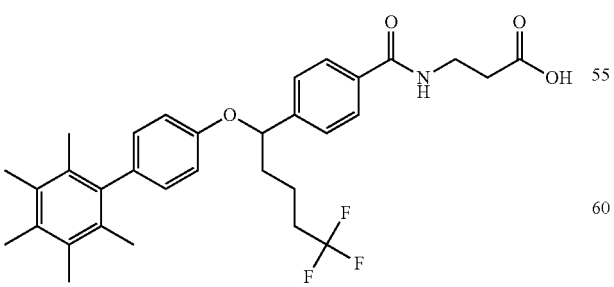

The title compound is prepared in a manner substantially similar to Example 359 starting from 3-(4-{5,5,5-trifluoro-1-[4-(4,4,5,5-tetramethyl-[1,3,2]dioxaborolan-2-yl)-phenoxy]-pentyl}-benzoylamino)-propionic acid methyl ester and 1-bromo-2,3,4,5,6-pentamethyl-benzene. MS: 554.2 [M−H]⁻.

Example 438

Racemic 3-{4-[1-(2,4,6-tri-t-butyl-phenoxy)-5,5,5-trifluoro-pentyl]-benzoylamino}-propionic acid

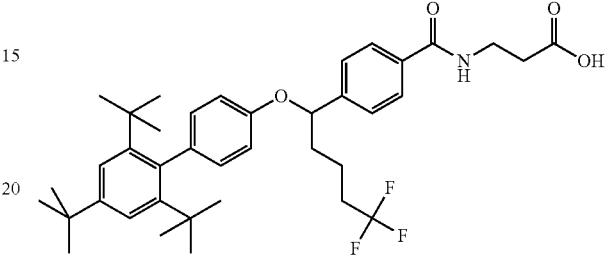

The title compound is prepared in a manner substantially similar to Example 359 starting from 3-(4-{5,5,5-trifluoro-1-[4-(4,4,5,5-tetramethyl-[1,3,2]dioxaborolan-2-yl)-phenoxy]-pentyl}-benzoylamino)-propionic acid methyl ester and 2-bromo-1,3,5-tri-tert-butyl-benzene. MS: 652.2 [M−H]⁻.

Example 439

Racemic 3-{4-[1-(3,5-dimethyl-phenoxy)-5,5,5-trifluoro-pentyl]-benzoylamino}-propionic acid

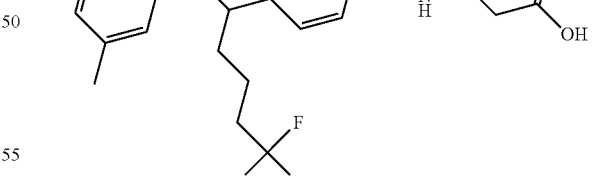

The title compound is prepared in a manner substantially similar to Example 128 starting from 3-{4-[1-(4-bromo-phenoxy)-5,5,5-trifluoro-pentyl]-benzoylamino}-propionic acid methyl ester. MS: 436.2 [M–H]⁻.

Example 440

3-{4-[1-(4'-tert-butyl-2,6-dimethyl-biphenyl-4-yloxy)-5,5,5-trifluoro-pentyl]-benzoylamino}-propionic acid, Isomer 1 and Example 441

3-{4-[1-(4'-tert-butyl-2,6-dimethyl-biphenyl-4-yloxy)-5,5,5-trifluoro-pentyl]-benzoylamino}-propionic acid, isomer 2

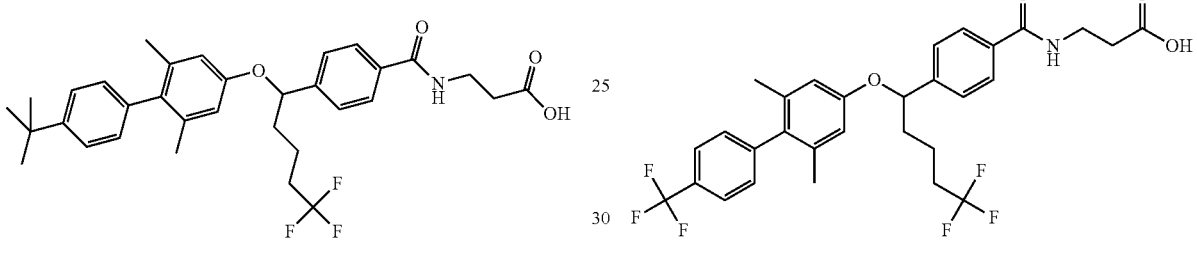

The title compounds are prepared in a manner substantially similar to Example 128 starting from 3-{4-[1-(4-bromo-3,5-dimethyl-phenoxy)-5,5,5-trifluoro-pentyl]-benzoylamino}-propionic acid methyl ester and 4-tert-butyl phenyl boronic acid. Isomer 1 MS: 568.2 [M–H]⁻; Isomer 2 MS: 568.2 [M–H]⁻.

Example 442

Racemic 3-{4-[1-(4-ethyl-3,5-dimethyl-phenoxy)-5,5,5-trifluoro-pentyl]-benzoylamino}-propionic acid The title compound is prepared in a manner substantially similar to Example 128 starting from 3-{4-[1-(4-bromo-3,5-dimethyl-phenoxy)-5,5,5-trifluoro-pentyl]-benzoylamino}-propionic acid methyl ester and ethyl boronic acid. MS: 464.2 [M–H]⁻.

Example 443

Racemic 3-{4-[1-(2,6-dimethyl-4'-trifluoromethyl-biphenyl-4-yloxy)-5,5,5-trifluoro-pentyl]-benzoylamino}-propionic acid

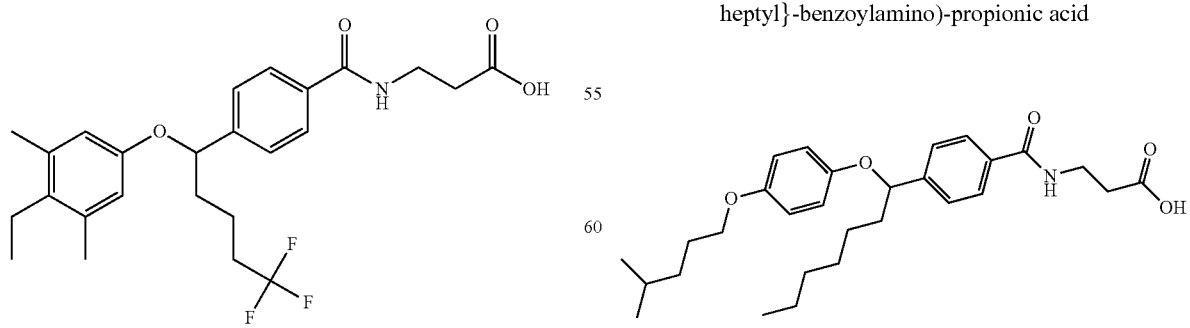

The title compound is prepared in a manner substantially similar to Example 128 starting from 3-{4-[1-(4-bromo-3,5-dimethyl-phenoxy)-5,5,5-trifluoro-pentyl]-benzoylamino}-propionic acid methyl ester and 4-trifluoromethyl phenyl boronic acid. MS: 580.3 [M–H]⁻.

Example 444

Racemic 3-(4-{1-[4-(4-methyl-pentyloxy)-phenoxy]-heptyl}-benzoylamino)-propionic acid The title compound is prepared in a manner substantially similar to Example 92 starting from 3-{4-[1-(4-hydroxy-phenoxy)-heptyl]-benzoylamino}-propionic acid methyl ester and 1-bromo-4-methyl-pentane. MS: 484.2 [M−H]⁻.

Example 445

Racemic 3-{4-[1-(4-pentyloxy-phenoxy)-heptyl]-benzoylamino}-propionic acid

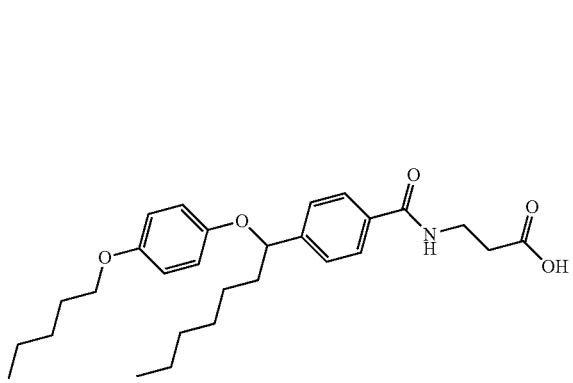 [SMILES: CCCCCCC(Oc1ccc(OCCCCC)cc1)c1ccc(C(=O)NCCC(=O)O)cc1]

The title compound is prepared in a manner substantially similar to Example 92 starting from 3-{4-[1-(4-hydroxy-phenoxy)-heptyl]-benzoylamino}-propionic acid methyl ester and 1-bromo-pentane. MS: 468.2 [M−H]⁻.

Example 446

3-{4-[5,5,5-trifluoro-1-(4'-trifluoromethyl-biphenyl-4-yloxy)-pentyl]-benzoylamino}-propionic acid, Isomer 1 and Example 447

3-{4-[5,5,5-trifluoro-1-(4'-trifluoromethyl-biphenyl-4-yloxy)-pentyl]-benzoylamino}-propionic acid, Isomer 2

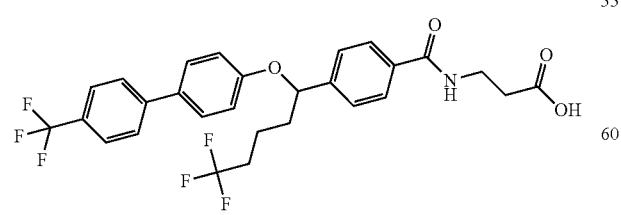

The title compound is prepared in a manner substantially similar to Example 128 starting from 3-{4-[1-(4-bromo-phenoxy)-5,5,5-trifluoro-pentyl]-benzoylamino}-propionic acid methyl ester and 4-trifluoromethyl phenyl boronic acid. Isomer 1 MS: 552.2 [M−H]⁻; Isomer 2 MS: 552.2

Example 448

Racemic 3-{4-[1-(4'-tert-butyl-2,6-dimethyl-biphenyl-4-yloxy)-5,5,5-trifluoro-pentyl]-benzoylamino}-propionic acid

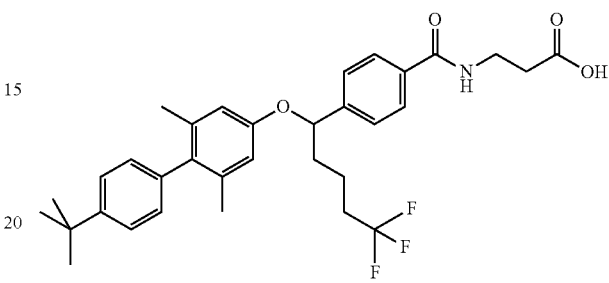

The title compound is prepared in a manner substantially similar to Example 128 starting from 3-{4-[1-(4-bromo-3,5-dimethyl-phenoxy)-5,5,5-trifluoro-pentyl]-benzoylamino}-propionic acid methyl ester and 4-tert-butyl phenyl boronic acid. MS: 568.2 [M−H]⁻.

Example 449

Racemic 3-{4-[1-(4-bromo-3,5-dimethyl-phenoxy)-5,5,5-trifluoro-pentyl]-benzoylamino}-propionic acid

The title compound is prepared in a manner substantially similar to Example 128 starting from 3-{4-[1-(4-bromo-3,5- dimethyl-phenoxy)-5,5,5-trifluoro-pentyl]-benzoylamino}-propionic acid methyl ester. MS: 516 [M–H]⁻.

Example 450

3-{4-[1-(4'-tert-butyl-biphenyl-4-yloxy)-5,5,5-trifluoro-pentyl]-benzoylamino}-propionic acid, Isomer 1 and Example 451

3-{4-[1-(4'-tert-butyl-biphenyl-4-yloxy)-5,5,5-trifluoro-pentyl]-benzoylamino}-propionic acid, Isomer 2

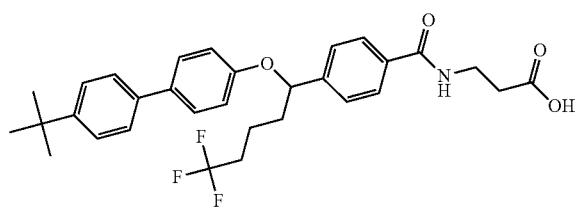 [SMILES: CC(C)(C)c1ccc(-c2ccc(OC(CCCC(F)(F)F)c3ccc(C(=O)NCCC(=O)O)cc3)cc2)cc1]

The title compounds are prepared in a manner substantially similar to Example 128 starting from 3-{4-[1-(4-bromo-phenoxy)-5,5,5-trifluoro-pentyl]-benzoylamino}-propionic acid methyl ester and 4-tert-butyl phenyl boronic acid. Isomer 1 MS: 540.3 [M–H]⁻; Isomer 2 MS: 540.3 [M–H]⁻.

Example 452

3-(4-{1-[6-(4-trifluoromethyl-phenyl)-pyridin-3-yloxy]-hexyl}-benzoylamino)-propionic acid, Isomer 1 and Example 453

3-(4-{1-[6-(4-trifluoromethyl-phenyl)-pyridin-3-yloxy]-hexyl}-benzoylamino)-propionic acid, Isomer 2

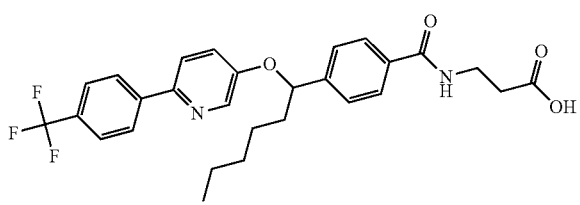 [SMILES: CCCCCC(Oc1ccc(-c2ccc(C(F)(F)F)cc2)nc1)c1ccc(C(=O)NCCC(=O)O)cc1]

The title compounds are prepared in a manner substantially similar to Example 62 starting from 3-{4-[1-(6-chloro-pyridin-3-yloxy)-hexyl]-benzoylamino}-propionic acid methyl ester and 4-trifluoromethyl phenyl boronic acid. Isomer 1 MS: 513.3 [M–H]⁻; Isomer 2 MS: 513.3 [M–H]⁻.

Example 454

3-(4-{1-[6-(4-trifluoromethyl-phenyl)-pyridin-3-yloxy]-pentyl}-benzoylamino)-propionic acid, Isomer 1 and Example 455

3-(4-{1-[6-(4-trifluoromethyl-phenyl)-pyridin-3-yloxy]-pentyl}-benzoylamino)-propionic acid, Isomer 2

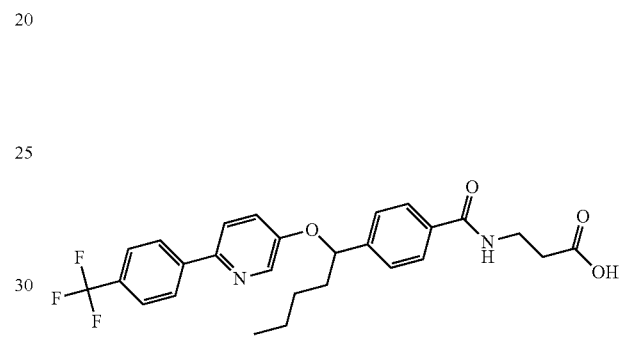

The title compounds are prepared in a manner substantially similar to Example 62 starting from 3-{4-[1-(6-chloro-pyridin-3-yloxy)-pentyl]-benzoylamino}-propionic acid methyl ester and 4-trifluoromethyl phenyl boronic acid. Isomer 1 MS: 499.2 [M–H]⁻; Isomer 2 MS: 499.2 [M–H]⁻.

Example 456

Racemic 3-{4-[5,5,5-trifluoro-1-(4'-trifluoromethyl-biphenyl-4-yloxy)-pentyl]-benzoylamino}-propionic acid The title compound is prepared in a manner substantially similar to Example 128 starting from 3-{4-[1-(4-bromo-phenoxy)-5,5,5-trifluoro-pentyl]-benzoylamino}-propionic acid methyl ester and 4-trifluoromethyl phenyl boronic acid. MS: 552.2 [M–H]⁻.

Example 457

Racemic 3-{4-[1-(4'-tert-butyl-biphenyl-4-yloxy)-5,5,5-trifluoro-pentyl]-benzoylamino}-propionic acid

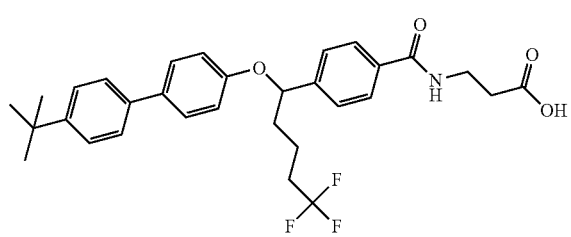 [SMILES: CC(C)(C)c1ccc(-c2ccc(OC(CCCC(F)(F)F)c3ccc(C(=O)NCCC(=O)O)cc3)cc2)cc1]

The title compound is prepared in a manner substantially similar to Example 128 starting from 3-{4-[1-(4-bromo-phenoxy)-5,5,5-trifluoro-pentyl]-benzoylamino}-propionic acid methyl ester and 4-tert-butyl phenyl boronic acid. MS: 540.3 [M–H]⁻.

Example 458

Racemic 3-{4-[1-(4-bromo-phenoxy)-5,5,5-trifluoro-pentyl]-benzoylamino}-propionic acid

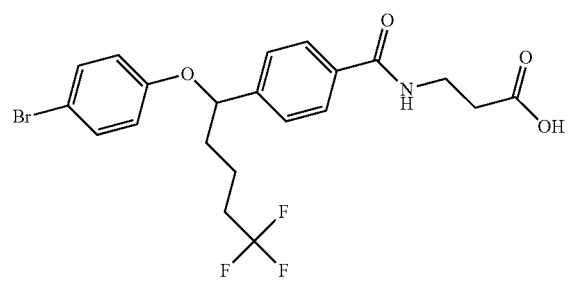 [SMILES: O=C(O)CCNC(=O)c1ccc(C(CCCC(F)(F)F)Oc2ccc(Br)cc2)cc1]

The title compound is prepared in a manner substantially similar to Example 128 starting from 3-{4-[1-(4-bromo-phenoxy)-5,5,5-trifluoro-pentyl]-benzoylamino}-propionic acid methyl ester. MS: 488 [M–H]⁻.

Example 459

Racemic 3-{4-[1-(4-hydroxy-phenoxy)-heptyl]-benzoylamino}-propionic acid

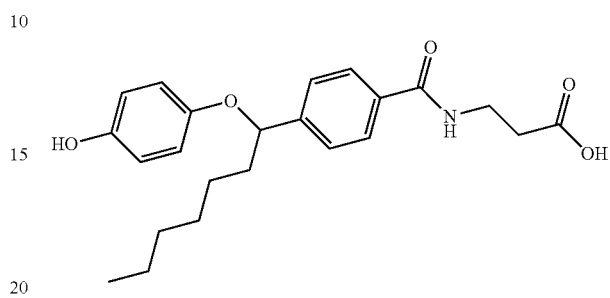

The title compound is prepared in a manner substantially similar to Example 92 starting from 3-{4-[1-(4-hydroxy-phenoxy)-heptyl]-benzoylamino}-propionic acid methyl ester. MS: 398.3 [M–H]⁻.

Example 460

3-{4-[1-(2,6-Dimethyl-4'-trifluoromethyl-biphenyl-4-yloxy)-2-methyl-propyl]-benzoylamino}-propionic acid, isomer 1

Example 461

3-{4-[1-(2,6-Dimethyl-4'-trifluoromethyl-biphenyl-4-yloxy)-2-methyl-propyl]-benzoylamino}-propionic acid, isomer 1

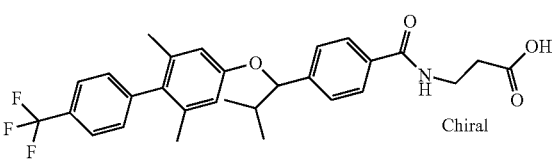 [SMILES: Cc1cc(OC(c2ccc(C(=O)NCCC(=O)O)cc2)C(C)C)cc(C)c1-c1ccc(C(F)(F)F)cc1]

The racemic 3-{4-[1-(2,6-Dimethyl-4'-trifluoromethyl-biphenyl-4-yloxy)-2-methyl-propyl]-benzoylamino}-propionic acid is resolved on a Chiralpak OJ-H column (0.46×15 cm) with a flow rate of 0.6 mL/min. and detection at 250 nm. Elute with Methanol and concentrate the fractions to provide a purified enantiomer ester isomer 1 (100% ee) and enantiomer ester isomer 2 (99.3% ee). Hydrolysis of the purified enantiomer of the ester provided the title compound as a white solid. The structure was confirmed by proton NMR.

Example 462

3-{4-[1-(2,6-Dimethyl-4'-trifluoromethoxy-biphenyl-4-yloxy)-heptyl]-benzoylamino}-propionic acid, isomer 1

Example 463

3-{4-[1-(2,6-Dimethyl-4'-trifluoromethoxy-biphenyl-4-yloxy)-heptyl]-benzoylamino}-propionic acid, isomer 1

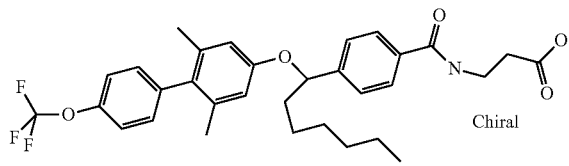 [SMILES: CCCCCCC(Oc1cc(C)c(-c2ccc(OC(F)(F)F)cc2)c(C)c1)c1ccc(C(=O)NCCC(=O)O)cc1]

The racemic 3-{4-[1-(2,6-Dimethyl-4'-trifluoromethoxy-biphenyl-4-yloxy)-heptyl]-benzoylamino}-propionic acid is resolved on a Chiralpak OJ-H column (0.46×15 cm) with a flow rate of 0.6 mL/min. and detection at 250 nm. Elute with Methanol and concentrate the fractions to provide a purified enantiomer ester isomer 1 (100% ee) and enantiomer ester isomer 2 (99.2% ee). Hydrolysis of the purified enantiomer of the ester provided the title compound as a white solid. The structure was confirmed by proton NMR.

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients.

The present pharmaceutical compositions are prepared by known procedures using well-known and readily available ingredients. In making the formulations of the present invention, the active ingredient (Formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

There is increasing evidence that glucagon plays an important role in glucose homeostasis. Compounds of Formula I are effective as antagonists or inverse agonists of the glucagon receptor, and thus inhibit the activity of the glucagon receptor. More particularly, these compounds are selective antagonists or inverse agonists of the glucagon receptor. As selective antagonists or inverse agonists, the compounds of Formula I are useful in the treatment of diseases, disorders, or conditions responsive to the inactivation of the glucagon receptor, including but not limited to diabetic and other glucagon related disorder. It is postulated that selective antagonists or inverse agonists of the glucagon receptor will lower plasma glucose levels and thus prevent or treat diabetic and other glucagon related metabolic disorders.

PHARMACOLOGICAL METHODS

In the following section binding assays as well as functional assays useful for evaluating the efficiency of the compounds of the invention are described.

Binding of compounds to the glucagon receptor may be determined in a competition binding assay using the cloned human glucagon receptor, and selectivity against the hGlp1 receptor. Antagonism may be determined as the ability of the compounds to inhibit the amount of cAMP formed in in the assay in the presence of 5 nM glucagon.

Glucagon Receptor (hGlucR) Binding Assay

The receptor binding assay used cloned human glucagon receptor (Lok S, Kuijper J L, Jelinek L J, Kramer J M, Whitmore T E, Sprecher C A, Mathewes S, Grant F J, Biggs S H, Rosenberg G B, et al. Gene 140 (2), 203-209 (1994)) isolated from 293HEK membranes. The hGlucR cDNA was subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA was transfected into 293 HEK cells and selected with 200 ug/mL Hygromycin.

Crude plasma membranes are prepared using cells from suspension culture. The cells are lysed on ice in hypotonic buffer containing 25 mM Tris HCL, pH 7.5, 1 mM MgCl2, DNAse1, 20 u/mL, and Roche Complete Inhibitors-without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots at −80 degree C. freezer until needed.

Glucagon is radioiodinated by I-125-lactoperoxidase procedure and purified by reversed phase HPLC at Perkin-Elmer/NEN (NEX207). The specific activity is 2200 Ci/mmol. Kd determination is performed by homologous competition instead of saturation binding due to high propanol content in the I-125 glucagon material. The Kd is estimated to be 3 nM and is used to calculate Ki values for all compounds tested.

The binding assays are carried out using a Scintillation Proximity Assay (Amersham) with WGA beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon is dissolved in 0.01 N HCl at 1 mg/mL and immediately frozen at −80 degrees C. in 30 ul aliquots. The glucagon aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 ul assay binding buffer or cold glucagon (NSB at 1 uM final). 50 ul of I-125 glucagon (0.15 nM final in reaction), 50 ul of membranes (300 ug/well), and 40 ul of WGA beads (150 ugs/well) are added, covered, and mixed end over end. Plates are read with a MicroBeta after 14 hours of settling time at room temp.

Results are calculated as a percent of specific I-125-glucagon binding in the presence of compound. The absolute EC50 dose of compound is derived by non-linear regression of percent specific binding of I-125-glucagon vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Like-Peptide 1 (Glp1-R) Receptor Binding Assay

The receptor binding assay used cloned human glucagon-like peptide 1 receptor (hGlp1-R). (Graziano M P, Hey P J, Borkowski D, Chicchi G G, Strader C D, Biochem Biophys Res Commun. 1993 Oct. 15; 196(1):141-6) isolated from 293HEK membranes. The hGlp1-R cDNA was subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA was transfected into 293 HEK cells and selected with 200 ug/mL Hygromycin.

Crude plasma membrane is prepared using cells from suspension culture. The cells are lysed on ice in hypotonic buffer containing 25 mM Tris HCl, pH 7.5, 1 mM MgCl2, DNAse, 20 u/mL, and Roche Complete Inhibitors without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots in −80 degree C. freezer until use.

Glucagaon-like peptide 1 (Glp-1) is radioiodinated by the I-125-lactoperoxidase procedure and purified by reversed phase HPLC at Perkin-Elmer/NEN (NEX308). The specific activity is 2200 Ci/mmol. Kd determination is performed by homologous competition instead of saturation binding due to high propanol content in the I-125 Glp-1 material. The Kd is estimated to be 3 nM and is used to calculate Ki values for all compounds tested.

The binding assays are carried out using a Scintillation Proximity Assay (Amersham) with wheat germ agglutinin (WGA) beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon-like peptide 1 is dissolved in PBS at 1 mg/mL and immediately frozen at −80 degrees C. in 30 ul aliquots. The glucagon-like peptide aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 ul assay binding buffer or cold glucagon-like peptide 1 (NSB at 1 uM final). 50 ul of I-125 glucagon-like peptide 1 (0.15 nM final in reaction), 50 ul of membranes (600 ug/well), and 40 ul of WGA beads (150 ugs/well) are added, covered, and mixed end over end. Plates are read with a MicroBeta after 14 hours of settling time at room temp.

Results are calculated as a percent of specific I-125-glucagon-like peptide 1 binding in the presence of compound. The absolute EC50 dose of compound is derived by non-linear regression of percent specific binding of I-125-glucagon-like peptide 1 vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Stimulated cAMP Functional Antagonist Assay

The cAMP functional assay uses the same cloned human glucagon receptor cell line isolated for the hGlucR binding assay described above. Cells are stimulated with a mixture of an EC80 dose of glucagon in the presence of compound. The cAMP generated within the cell is quantitated using an Amplified Luminescent Proximity Homogeneous Assay, Alpha Screen, from Perkin Elmer (6760625R).

Briefly, cAMP within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinylated cAMP-Donor bead complex occurs and decreases the signal.

Glucagon is dissolved in 0.01 N HCl at 1 mg/mL and immediately frozen at −80 degrees C. in 30 ul aliquots. The glucagon aliquot is diluted and used in the functional assay within an hour. Cells are harvested from sub-confluent tissue culture dishes with Enzyme-Free Cell Dissociation Solution, (Specialty Media 5-004-B). The cells are pelleted at low speed and washed 3 times with assay buffer [25 mM Hepes in HBSS—with Mg and Ca (GIBCO, 14025-092) with 0.1% Fatty Acid Free BSA (ICN)] then diluted to a final concentration of 250,000 cells per mL. Compounds are serially diluted into DMSO then diluted into assay buffer with a 3× concentration of glucagon and 3% DMSO. The EC80 of glucagon is pre-determined from a full glucagon dose response and represents the dose at which glucagons produces an 80% of the maximal glucagon response. A mixture of biotinylated cAMP (1 unit/well final) from the Alpha Screen Kit and 3×IBMX (1500 uM) is prepared in Assay Buffer.

The functional assay is performed in 96 well, low-volume, white, polystyrene Costar Plates (3688). The biotinylated cAMP/IBMX mixture, 0.02 mLs, is placed into each well, followed by addition of 0.02 mLs of glucagon dose response, cAMP standard curve, or compound/glucagon mixtures. The reaction is started by addition of 0.02 mLs of cells (5000/well final). After 60 minutes at room temperature, the reaction is stopped by the addition of 0.03 mLs of Lysis Buffer [10 mM Hepes, pH 7.4, 1% NP40, and 0.01% fatty acid free BSA (ICN) containing 1 unit each/well of Acceptor and Donor beads from the Alpha Screen Kit]. Lysis Buffer addition is performed under a green light to prevent bleaching of the detection beads. The plates are wrapped in foil and left to equilibrate overnight at room temperature. The plates are read on a Packard Fusion™-□Instrument.

Alpha screen units are converted to pmoles cAMP generated per well based upon the cAMP standard curve. The pmoles cAMP produced in the presence of compound are converted to % of a maximal response with the EC80 dose of glucagon alone. With each experiment, the dose of glucagon needed to produce a 50% response of pmoles cAMP is determined. This EC50 dose is used to normalize results to a Kb using a modified Cheng-Prusoff equation (Cheng Y., Prusoff W. H., Biochem. Pharmacol. 22, 3099-3108, 1973), where $Kb=(EC50\ compound)/[1+(pM\ glucagon\ used/EC50\ in\ pM\ for\ glucagon\ dose\ response)]$.

The compounds according to the invention preferably have a Ki value of no greater than 50 µM as determined by the Glucagon Receptor (hGlucR) Binding Assay disclosed herein. More preferably, the compounds according to the invention have a Ki value of less than 5 µM, preferably of less than 500 nM and even more preferred of less than 100 nM as determined by the Glucagon Receptor (hGlucR) Binding Assay disclosed herein. Generally, the compounds according to the invention show a higher affinity for the glucagon receptor compared to the GLP-1 receptor, and preferably have a higher binding affinity to the glucagon receptor than to the GLP-1 receptor.

The results are given below for the indicated compound.

TABLE 1

| Example | Ki (nM) |
| --- | --- |
| 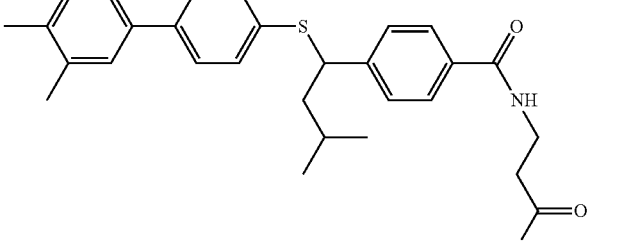 Example #25 | 265 |
| 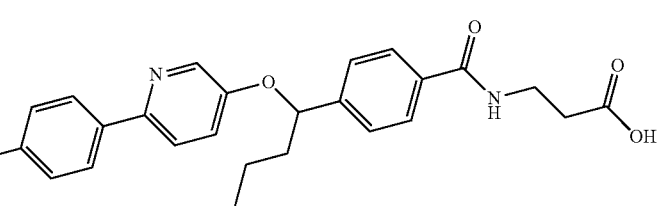 Example #77 | 254 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I

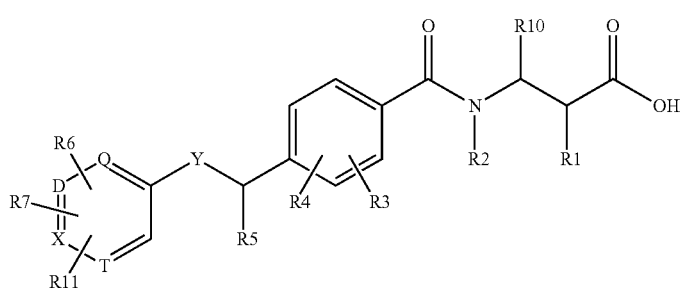

(I)

or a pharmaceutically acceptable salt thereof wherein:
Y is —O— or —S—;
Q, D, X, and T independently represent carbon (substituted with hydrogen or the optional substituents as indicated herein), or nitrogen (optionally substituted with oxygen),
provided that no more than two of Q, D, X, and T are nitrogen;
R1 is —H, —OH, or -halogen;
R2 is —H or —($C_1$-$C_3$) alkyl (optionally substituted with 1 to 3 halogens);
R3 and R4 are independently
—H, -halogen, —CN, —OH, —($C_1$-$C_7$) alkoxy, —($C_1$-$C_7$) alkyl (optionally substituted with 1 to 3 halogens), or —($C_2$-$C_7$) alkenyl;
R5 is selected from the group consisting of
—H, —($C_1$-$C_{12}$) alkyl (optionally substituted with 1 to 3 halogens), —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, —($C_2$-$C_{12}$) alkenyl, —($C_3$-$C_{12}$)cycloalkenyl, -heterocycloalkyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, and -heteroaryl-($C_2$-$C_{12}$)alkynyl, and wherein —($C_1$-$C_{12}$)alkyl, —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, -heterocycloalkyl, —($C_2$-$C_{12}$)alkenyl, —($C_3$-$C_{12}$)cycloalkenyl,
-aryl-($C_2$-$C_{10}$)alkenyl, -heteroaryl-($C_2$-$C_{10}$)alkenyl, —($C_2$-$C_{12}$)alkynyl, —($C_3$-$C_{12}$) cycloalkynyl, -aryl-($C_2$-$C_{12}$)alkynyl, -heteroaryl-($C_2$-$C_{12}$)alkynyl, are each optionally substituted with from one to three substituents each independently selected from the group consisting of -hydrogen, -hydroxy, -cyano, -nitro, -halo, -oxo, —($C_1$-$C_7$)alkyl (optionally substituted with 1 to 3 halogens), —($C_1$-$C_7$)alkyl-C(O)OR12, —($C_1$-$C_7$)alkoxy, —($C_3$-$C_7$)cycloalkyl, —C(O)R12, —C(O)OR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;
R6 and R7 are independently at each occurrence selected from the group consisting of
—H, -halogen, -hydroxy, —CN, —($C_1$-$C_7$) alkoxy, —($C_2$-$C_7$)alkenyl, —($C_1$-$C_{10}$)alkyl (optionally substituted with 1 to 3 halogens), —($C_3$-$C_{12}$)cycloalkyl, tert-butoxyiminomethyl, 1,3-dioxan-2-yl, hydroxymethyl, formyl, hydroxyiminomethyl, morphylino-4-yl-methyl, 4-methylpentyloxy, and pentyloxy; provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X; wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence selected from the group consisting of
-hydrogen, -hydroxy, —CN, -nitro, -halo, —($C_1$-$C_7$) alkyl (optionally substituted with 1 to 3 halogens), —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, —O($C_2$-$C_7$)alkenyl, and —S(O)$_2$N(R12)$_2$; and wherein —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, and —O($C_2$-$C_7$) alkenyl are each optionally substituted with from one to three substituents independently selected from the group consisting of -hydrogen, -hydroxy, -cyano, -nitro, -halo, -oxo, —($C_1$-$C_7$)alkyl, —($C_1$-$C_7$)alkyl-C(O)OR12, —($C_1$-$C_7$)alkoxyl, —($C_3$-$C_7$)cycloalkyl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N (R12)$_2$;
R10 is selected from the group consisting of
—H, halogen, —($C_1$-$C_{12}$)alkyl (optionally substituted with 1 to 3 halogens), -cycloalkyl, -aryl, -aryl-($C_1$-$C_7$) alkyl, -heteroaryl, -heteroaryl —($C_1$-$C_7$)alkyl, —($C_2$-$C_{12}$)alkenyl, —($C_3$-$C_{12}$)cycloalkenyl, -aryl-($C_2$-$C_{10}$) alkenyl, -heteroaryl-($C_2$-$C_{10}$)alkenyl, —($C_2$-$C_{12}$) alkynyl, —($C_3$-$C_{12}$)cycloalkynyl, -aryl-($C_2$-$C_{12}$) alkynyl, and -heteroaryl-($C_2$-$C_{12}$)alkynyl;

R11 is independently at each occurrence selected from the group consisting of
—H, -halogen,

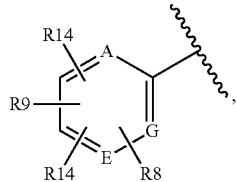

wherein the zig-zag mark shows the point of attachment to the parent molecule, wherein A, G, and E independently represent carbon (substituted with hydrogen or the optional substituents as indicated herein) or nitrogen, provided that no more than two of A, G, and E are nitrogen;
provided however that wherein A is nitrogen, then R8, R9, and R14 are not attached to A, and provided that wherein G is nitrogen, then R8, R9, and R14 are not attached to G, and provided that wherein E is nitrogen, then R8, R9, and R14 are not attached to E,

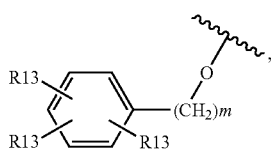

wherein the zig-zag mark shows the point of attachment to the parent molecule, wherein m is an integer of 0, 1, 2, or 3, and when m is 0 then $(CH_2)_m$ is a bond, and

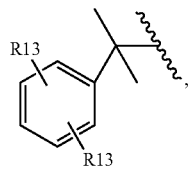

wherein the zig-zag mark shows the point of attachment to the parent molecule,
provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;
R12 is independently at each occurrence selected from the group consisting of
-hydrogen, —($C_1$-$C_7$) alkyl (optionally substituted with 1 to 3 halogens), and -aryl;
R13 is independently at each occurrence selected from the group consisting of
-hydrogen, -halogen, —($C_1$-$C_7$) alkyl (optionally substituted with 1 to 3 halogens), phenyl, and —($C_2$-$C_7$) alkenyl; and
R14 is independently at each occurrence
—H, halogen, or —($C_1$-$C_7$) alkyl (optionally substituted with 1 to 3 halogens), provided the compound is not 3-{4-[1-(4'-tert-butyl-2,6-dimethyl-biphenyl-4-yloxy)-4,4,4-trifluoro-butyl]-benzoylamino}-propionic acid.

2. A compound of Formula I, as claimed in claim 1, or a pharmaceutically acceptable salt thereof, wherein:
Y is —O— or —S—;
Q, D, X, and T independently represent carbon (substituted with hydrogen or the optional substituents as indicated herein), or nitrogen, provided that no more than two of Q, D, X, and T are nitrogen;
R1 is —H, —OH, or -halogen;
R2 is —H or —($C_1$-$C_3$) alkyl (optionally substituted with 1 to 3 halogens);
R3 and R4 are independently
—H, -halogen, —CN, —($C_1$-$C_7$) alkoxy, —($C_1$-$C_7$) alkyl (optionally substituted with 1 to 3 halogens), or —($C_2$-$C_7$)alkenyl;
R5 is selected from the group consisting of
—($C_1$-$C_{12}$) alkyl (optionally substituted with 1 to 3 halogens), —($C_3$-$C_{12}$)cycloalkyl, -phenyl, -phenyl-phenyl-($C_1$-$C_{12}$)alkyl, —($C_2$-$C_{12}$)alkenyl, —($C_3$-$C_{12}$)cycloalkenyl, -heterocycloalkyl, —($C_2$-$C_{12}$) alkynyl, and —($C_3$-$C_{12}$)cycloalkynyl, and wherein —($C_1$-$C_{12}$)alkyl, —($C_3$-$C_{12}$)cycloalkyl, -phenyl, -phenyl-phenyl-($C_1$-$C_{12}$)alkyl, -heterocycloalkyl, —($C_2$-$C_{12}$)alkenyl, —($C_3$-$C_{12}$)cycloalkenyl, —($C_2$-$C_{12}$)alkynyl, and —($C_3$-$C_{12}$) cycloalkynyl, are each optionally substituted with from one to three substituents each independently selected from the group consisting of -hydrogen, -hydroxy, -cyano, -nitro, -halo, -oxo, —($C_1$-$C_7$)alkyl (optionally substituted with 1 to 3 halogens);
R6 and R7 are independently at each occurrence selected from the group consisting of
—H, -halogen, -hydroxy, —CN, —($C_1$-$C_7$) alkoxy, —($C_2$-$C_7$)alkenyl, —($C_1$-$C_{10}$)alkyl (optionally substituted with 1 to 3 halogens), —($C_3$-$C_{12}$)cycloalkyl, tert-butoxyiminomethyl, 1,3-dioxan-2-yl, hydroxymethyl, formyl, hydroxyiminomethyl, morphylino-4-yl-methyl, 4-methylpentyloxy, and pentyloxy; provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;
wherein R6 and R7 may optionally form a six membered ring with the atoms to which they are attached, and the ring so formed may optionally contain up to two oxygens, and further the ring so formed may optionally be substituted with up to four halogens;
R8 and R9 are independently at each occurrence selected from the group consisting of
-hydrogen, -hydroxy, —CN, -nitro, -halo, —($C_1$-$C_7$) alkyl (optionally substituted with 1 to 3 halogens), —($C_1$-$C_7$)alkoxy, —($C_3$-$C_7$)cycloalkyl, —C(O)R12, —C(O)OR12, —OC(O)R12, —OS(O)$_2$R12, —N(R12)$_2$, —NR12C(O)R12, —NR12SO$_2$R12, —SR12, —S(O)R12, —S(O)$_2$R12, —O($C_2$-$C_7$)alkenyl, and —S(O)$_2$N(R12)$_2$; and wherein —($C_1$-$C_7$) alkyl, —($C_1$-$C_7$)alkoxy, —($C_3$-$C_7$)cycloalkyl, and —O($C_2$-$C_7$)alkenyl are each optionally substituted with from one to three substituents independently selected from the group consisting of -hydrogen, -hydroxy, -cyano, -nitro, -halo, -oxo, and —($C_1$-$C_7$) alkyl;
R10 is selected from the group consisting of
—H, halogen, and —($C_1$-$C_{12}$)alkyl (optionally substituted with 1 to 3 halogens);

R11 is independently at each occurrence selected from the group consisting of
—H, -halogen,

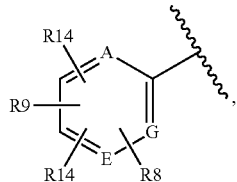

wherein the zig-zag mark shows the point of attachment to the parent molecule, wherein A, G, and E independently represent carbon (substituted with hydrogen or the optional substituents as indicated herein) or nitrogen, provided that no more than two of A, G, and E are nitrogen;
provided however that wherein A is nitrogen, then R8, R9, and R14 are not attached to A, and provided that wherein G is nitrogen, then R8, R9, and R14 are not attached to G, and provided that wherein E is nitrogen, then R8, R9, and R14 are not attached to E,

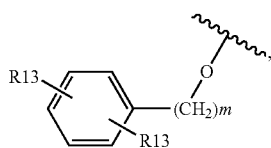

wherein the zig-zag mark shows the point of attachment to the parent molecule, wherein m is an integer of 0, 1, 2, or 3, and when m is 0 then $(CH_2)_m$ is a bond, and

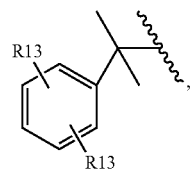

wherein the zig-zag mark shows the point of attachment to the parent molecule,
provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;
R12 is independently at each occurrence selected from the group consisting of
-hydrogen, and —$(C_1$-$C_7)$ alkyl (optionally substituted with 1 to 3 halogens);
R13 is independently at each occurrence selected from the group consisting of
-hydrogen, -halogen, —$(C_1$-$C_7)$ alkyl (optionally substituted with 1 to 3 halogens), phenyl, and —$(C_2$-$C_7)$ alkenyl; and
R14 is independently at each occurrence
—H, halogen, or —$(C_1$-$C_7)$ alkyl (optionally substituted with 1 to 3 halogens).

3. A compound of Formula I, as claimed in claim 2, or a pharmaceutically acceptable salt thereof, wherein:

Y is —O—, or —S—;
Q, D, X, and T independently represent carbon (substituted with hydrogen or the optional substituents as indicated herein);
R1 is —H, —OH, or -halogen;
R2 is —H;
R3 and R4 are independently —H, -halogen, or —$(C_1$-$C_7)$ alkyl (optionally substituted with 1 to 3 halogens);
R5 is selected from the group consisting of
—$(C_1$-$C_{12})$ alkyl (optionally substituted with 1 to 3 halogens), and
—$(C_3$-$C_{12})$cycloalkyl (optionally substituted with 1 to 3 halogens);
R6 and R7 are independently at each occurrence selected from the group consisting of
—H, -halogen, -hydroxy, —CN, —$(C_1$-$C_7)$ alkoxy, —$(C_2$-$C_7)$alkenyl, —$(C_1$-$C_{10})$alkyl (optionally substituted with 1 to 3 halogens), —$(C_3$-$C_{12})$cycloalkyl, tert-butoxyiminomethyl, 1,3-dioxan-2-yl, hydroxymethyl, formyl, hydroxyiminomethyl, morphylino-4-yl-methyl, 4-methylpentyloxy, and pentyloxy; provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;
R8 and R9 are independently at each occurrence selected from the group consisting of
-hydrogen, -halogen, —$(C_1$-$C_7)$alkyl (optionally substituted with 1 to 3 halogens), —$(C_1$-$C_7)$alkoxy, —$(C_3$-$C_7)$cycloalkyl, —C(O)R12, —C(O)OR12, —OC(O)R12, —OS(O)$_2$R12, —SR12, —S(O)R12, —S(O)$_2$R12, and —O($C_2$-$C_7)$alkenyl;
R10 is —H;
R11 is independently at each occurrence selected from the group consisting of —H, -halogen, and

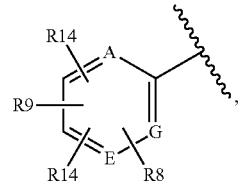

wherein the zig-zag mark shows the point of attachment to the parent molecule, wherein A, G, and E independently represent carbon (substituted with hydrogen or the optional substituents as indicated herein);
R12 is independently at each occurrence selected from the group consisting of
-hydrogen, and —$(C_1$-$C_7)$ alkyl (optionally substituted with 1 to 3 halogens);
and
R14 is independently at each occurrence
—H, halogen, or —$(C_1$-$C_7)$ alkyl (optionally substituted with 1 to 3 halogens).

4. A compound or salt of claim 1, wherein Y is —O— or —S—; R1 is hydrogen or —OH; R2 is hydrogen; R3 and R4 are independently hydrogen or halogen; R5 is methyl, ethyl, propyl, isopropyl, butyl, pentyl, hexyl, octyl, 3,3-dimethylbutyl, 2-methylpropyl, 4-methylpentyl, 2,2-dimethylpropyl, 3-trifluoropropyl, 4-trifluorobutyl, cyclohexyl, or 4-bromophenyl; R6 and R7 are independently hydrogen, methyl, ethyl, 1,1,3,3-tetramethylbutyl, tert-butyl, cyclohexyl, pentyl, isopropoxy, chloro, fluoro, bromo, hydroxy, trifluoromethyl, —CN, methoxy, tertbutoxyiminomethyl, 1,3-dioxan-2-yl, hydroxymethyl, formyl, hydroxyiminomethyl, morpholino-4-yl-methyl, 4-methylpentyloxy, and pentyloxy, and wherein R6 and R7 combine to form, with the phenyl to which they are attached, a fused benzodioxin moiety; R8 and R9 are independently hydrogen, fluoro, chloro, methyl, ethyl, pentyl, isopropyl, tert-butyl, trifluoromethyl, acetyl, 2-methylpropyl, methoxy, cyclohexyl, allyloxy, or trifluoromethoxy; R10 is hydrogen; R11 is hydrogen, halogen, phenyl (substituted, independently at each occurrence, once with R8, once with R9, and twice with R14), pyridinyl (substituted, independently at each occurrence, once with R8, once with R9, and twice with R14), or benzoxy (substituted twice with R13); R13 is hydrogen, trifluoromethyl, tertbutyl, isopropyl, chloro, fluoro, bromo, methyl, ethyl, or phenyl, T is —CH—, —CR6-, or N; X is —CH— or —CR11-; D is —CH—, —CR6-, —CR11-, or N; and Q is —CH—, —CR6-, or N; R14 is hydrogen, bromo, fluoro, methyl, tert-butyl, or isopropyl.

5. A compound or salt of claim 1, wherein Y is —O—.

6. A compound or salt of claim 1, wherein Y is —S—.

7. The compound or salt of claim 5 wherein R1, R2, R3, R4, and R10 are —H.

8. The compound or salt of claim 7 wherein D, X, Q, and T are carbon (substituted with hydrogen or the optional substituents as indicated herein).

9. The compound or salt of claim 7 wherein D is nitrogen, and T, Q, and X are carbon (substituted with hydrogen or the optional substituents as indicated herein).

10. The compound or salt of claim 7 wherein R6 and R7 are independently hydrogen or methyl.

11. The compound or salt of claim 10 wherein X is carbon substituted with R11.

12. The compound or salt of claim 11 wherein A, G, and E are carbon (substituted with hydrogen or the optional substituents as indicated herein).

13. The compound or salt of claim 12 wherein R5 is —($C_1$-$C_{12}$) alkyl (optionally substituted with 1 to 3 halogens), —($C_3$-$C_{12}$)cycloalkyl, —($C_2$-$C_{12}$)alkenyl, —($C_3$-$C_{12}$)cycloalkenyl, -heterocycloalkyl, —($C_2$-$C_{12}$)alkynyl, or —($C_3$-$C_{12}$)cycloalkynyl.

14. The compound or salt of claim 12 wherein R5 is —($C_1$-$C_{12}$) alkyl (optionally substituted with 1 to 3 halogens), or —($C_3$-$C_{12}$)cycloalkyl.

15. A compound of claim 1 selected from the group consisting of:

Racemic 3-{4-[1-(4'-Trifluoromethyl-biphenyl-4-yloxy)-propyl]-benzoylamino}-propionic acid;
Racemic 3-{4-[3-Methyl-1-(4'-trifluoromethyl-biphenyl-4-yloxy)-butyl]-benzoylamino}-propionic acid;
Racemic 3-{4-[1-(4-tert-Butyl-phenoxy)-3-methyl-butyl]-benzoylamino}-propionic acid;
Racemic 3-{4-[1-(4'-tert-Butyl-biphenyl-4-yloxy)-4,4,4-trifluoro-butyl]-benzoylamino}-propionic acid;
Racemic 3-{4-[4,4,4-Trifluoro-1-(4'-trifluoromethyl-biphenyl-4-yloxy)-butyl]-benzoylamino}-propionic acid;
Racemic 3-{4-[4-(4-Bromo-phenyl)-(4'-tert-butyl-biphenyl-4-yloxy)-methyl]-benzoylamino}-propionic acid;
Racemic 3-{4-[2-Methyl-1-(4'-trifluoromethyl-biphenyl-4-yloxy)-propyl]-benzoylamino}-propionic acid;
Racemic 3-{4-[1-(4'-tert-Butyl-biphenyl-4-yloxy)-propyl]-benzoylamino}-propionic acid;
Racemic 3-{4-[1-(4'-tert-Butyl-biphenyl-4-yloxy)-heptyl]-benzoylamino}-propionic acid;
Racemic 3-{4-[1-(4'-tert-Butyl-biphenyl-4-yloxy)-3-methyl-butyl]-benzoylamino}-propionic acid;
Racemic 3-{4-[1-(4-Cyclohexyl-phenoxy)-hexyl]-benzoylamino}-propionic acid;
Racemic 3-{4-[1-(4-Benzyloxy-phenoxy)-hexyl]-benzoylamino}-propionic acid;
Racemic 3-[4-(1-Phenoxy-hexyl)-benzoylamino]-propionic acid;
Racemic 3-{4-[1-(4'-Trifluoromethyl-biphenyl-4-yloxy)-heptyl]-benzoylamino}-propionic acid;
Racemic 3-{4-[1-(4'-Trifluoromethyl-biphenyl-4-ylsulfanyl)-heptyl]-benzoylamino}-propionic acid;
Racemic 3-{4-[1-(4'-Trifluoromethyl-biphenyl-4-yloxy)-pentyl]-benzoylamino}-propionic acid;
Racemic 3-{4-[1-(4'-tert-Butyl-biphenyl-4-yloxy)-pentyl]-benzoylamino}-propionic acid;
Racemic 3-{4-[1-(4'-Trifluoromethyl-biphenyl-4-yloxy)-butyl]-benzoylamino}-propionic acid;
Racemic 3-{4-[1-(4'-tert-Butyl-biphenyl-4-yloxy)-butyl]-benzoylamino}-propionic acid;
Racemic 3-{4-[3-Methyl-1-(4'-trifluoromethyl-biphenyl-4-ylsulfanyl)-butyl]-benzoylamino}-propionic acid;
Racemic 3-{4-[1-(4'-Trifluoromethyl-biphenyl-4-yloxy)-nonyl]-benzoylamino}-propionic acid;
Racemic 3-(4-{3-Methyl-1-[4-(6-trifluoromethyl-pyridin-3-yl)-phenoxy]-butyl}-benzoylamino)-propionic acid;
Racemic 3-(4-{2-Methyl-1-[4-(6-trifluoromethyl-pyridin-3-yl)-phenoxy]-propyl}-benzoylamino)-propionic acid;
Racemic 3-(4-{1-[4'-trifluoromethoxy-biphenyl-4-ylsulfanyl]-3-methyl-butyl}-benzoylamino)-propionic acid;
Racemic 3-{4-[1-(3',4'-dimethyl-biphenyl-4-ylsulfanyl)-3-methyl-butyl]-benzoylamino}-propionic acid;
Racemic 3-{4-[1-(4'-cyano-biphenyl-4-ylsulfanyl)-3-methyl-butyl]-benzoylamino}-propionic acid;
Racemic 3-{4-[1-(4'-Isobutyl-biphenyl-4-ylsulfanyl)-3-methyl-butyl]-benzoylamino}-propionic acid;
Racemic 3-(4-{1-[4-(6-Methoxy-pyridin-3-yl)-phenylsulfanyl]-3-methyl-butyl}-benzoylamino)-propionic acid;
Racemic 3-{4-[1-(4'-Ethyl-biphenyl-4-yloxy)-heptyl]-benzoylamino}-propionic acid;
3-{4-[1-(4-Benzyloxy-phenoxy)-hexyl]-benzoylamino}-propionic acid, Isomer 1;
3-{4-[1-(4-Benzyloxy-phenoxy)-hexyl]-benzoylamino}-propionic acid, Isomer 2;
3-{4-[3-Methyl-1-(4'-trifluoromethyl-biphenyl-4-yloxy)-butyl]-benzoylamino}-propionic acid, Isomer 1;
3-{4-[3-Methyl-1-(4'-trifluoromethyl-biphenyl-4-yloxy)-butyl]-benzoylamino}-propionic acid, Isomer 2;
3-{4-[1-(4'-Trifluoromethyl-biphenyl-4-yloxy)-propyl]-benzoylamino}-propionic acid, Isomer 1;
3-{4-[1-(4'-Trifluoromethyl-biphenyl-4-yloxy)-propyl]-benzoylamino}-propionic acid, Isomer 2;
3-{4-[1-(4'-tert-Butyl-biphenyl-4-yloxy)-propyl]-benzoylamino}-propionic acid, Isomer 1;
3-{4-[1-(4'-tert-Butyl-biphenyl-4-yloxy)-propyl]-benzoylamino}-propionic acid, Isomer 2;
3-{4-[1-(4'-tert-Butyl-biphenyl-4-yloxy)-heptyl]-benzoylamino}-propionic acid, Isomer 1;
3-{4-[1-(4'-tert-Butyl-biphenyl-4-yloxy)-heptyl]-benzoylamino}-propionic acid, Isomer 2;
3-{4-[1-(4'-tert-Butyl-biphenyl-4-yloxy)-3-methyl-butyl]-benzoylamino}-propionic acid, Isomer 1;
3-{4-[1-(4'-tert-Butyl-biphenyl-4-yloxy)-3-methyl-butyl]-benzoylamino}-propionic acid, Isomer 2;
3-{4-[1-(4'-Trifluoromethyl-biphenyl-4-ylsulfanyl)-heptyl]-benzoylamino}-propionic acid, Isomer 1;

3-{4-[1-(4'-Trifluoromethyl-biphenyl-4-ylsulfanyl)-heptyl]-benzoylamino}-propionic acid, Isomer 2;
3-{4-[1-(4'-tert-Butyl-biphenyl-4-yloxy)-pentyl]-benzoylamino}-propionic acid, Isomer 1;
3-{4-[1-(4'-tert-Butyl-biphenyl-4-yloxy)-pentyl]-benzoylamino}-propionic acid, Isomer 2;
3-{4-[2-Methyl-1-(4'-trifluoromethyl-biphenyl-4-yloxy)-propyl]-benzoylamino}-propionic acid, Isomer 1;
3-{4-[2-Methyl-1-(4'-trifluoromethyl-biphenyl-4-yloxy)-propyl]-benzoylamino}-propionic acid, Isomer 2;
3-{4-[1-(4'-Trifluoromethyl-biphenyl-4-yloxy)-pentyl]-benzoylamino}-propionic acid, Isomer 1;
3-{4-[1-(4'-Trifluoromethyl-biphenyl-4-yloxy)-pentyl]-benzoylamino}-propionic acid, Isomer 2;
3-{4-[1-(4'-Trifluoromethyl-biphenyl-4-yloxy)-butyl]-benzoylamino}-propionic acid, Isomer 1;
3-{4-[1-(4'-Trifluoromethyl-biphenyl-4-yloxy)-butyl]-benzoylamino}-propionic acid, Isomer 2;
3-{4-[1-(4'-tert-Butyl-biphenyl-4-yloxy)-butyl]-benzoylamino}-propionic acid, Isomer 1;
3-{4-[1-(4'-tert-Butyl-biphenyl-4-yloxy)-butyl]-benzoylamino}-propionic acid, Isomer 2;
3-(4-{1-[4'-(1-Fluoro-1-methyl-ethyl)-biphenyl-4-ylsulfanyl]-3-methyl-butyl}-benzoylamino)-propionic acid, Isomer 1;
3-(4-{1-[4'-(1-Fluoro-1-methyl-ethyl)-biphenyl-4-ylsulfanyl]-3-methyl-butyl}-benzoylamino)-propionic acid, Isomer 2;
3-(4-{3-Methyl-1-[4-(6-trifluoromethyl-pyridin-3-yl)-phenoxy]-butyl}-benzoylamino)-propionic acid, Isomer 1;
3-(4-{3-Methyl-1-[4-(6-trifluoromethyl-pyridin-3-yl)-phenoxy]-butyl}-benzoylamino)-propionic acid, Isomer 2;
3-{4-[1-(4'-Trifluoromethyl-biphenyl-4-yloxy)-nonyl]-benzoylamino}-propionic acid, Isomer 1;
3-{4-[1-(4'-Trifluoromethyl-biphenyl-4-yloxy)-nonyl]-benzoylamino}-propionic acid, Isomer 2;
3-{4-[1-(4'-Ethyl-biphenyl-4-yloxy)-heptyl]-benzoylamino}-propionic acid, Isomer 1;
3-{4-[1-(4'-Ethyl-biphenyl-4-yloxy)-heptyl]-benzoylamino}-propionic acid, Isomer 2;
3-(4-{1-[6-(4-tert-Butyl-phenyl)-pyridin-3-yloxy]-4,4-dimethyl-pentyl}-benzoylamino)-propionic acid, Isomer 1;
Racemic 3-(4-{1-[6-(4-Trifluoromethyl-phenyl)-pyridin-3-yloxy]-heptyl}-benzoylamino)-propionic acid;
Racemic 3-(4-{4,4,4-Trifluoro-1-[6-(4-trifluoromethyl-phenyl)-pyridin-3-yloxy]-butyl}-benzoylamino)-propionic acid;
Racemic 3-(4-{3-Methyl-1-[6-(4-trifluoromethyl-phenyl)-pyridin-3-yloxy]-butyl}-benzoylamino)-propionic acid;
Racemic 3-(4-{4,4-Dimethyl-1-[6-(4-trifluoromethyl-phenyl)-pyridin-3-yloxy]-pentyl}-benzoylamino)-propionic acid;
Racemic 3-(4-{1-[6-(4-Trifluoromethyl-phenyl)-pyridin-3-yl]-butoxy}-benzoylamino)-propionic acid;
Racemic 3-(4-{1-[6-(4-tert-Butyl-phenyl)-pyridin-3-yloxy]-4,4,4-trifluoro-butyl}-benzoylamino)-propionic acid;
Racemic 3-(4-{1-[6-(4-tert-Butyl-phenyl)-pyridin-3-yloxy]-3-methyl-butyl}-benzoylamino)-propionic acid;
3-(4-{1-[6-(4-tert-Butyl-phenyl)-pyridin-3-yloxy]-4,4-dimethyl-pentyl}-benzoylamino)-propionic acid, Isomer 2;
3-(4-{1-[6-(4-Trifluoromethyl-phenyl)-pyridin-3-yloxy]-heptyl}-benzoylamino)-propionic acid, Isomer 1;
3-(4-{1-[6-(4-Trifluoromethyl-phenyl)-pyridin-3-yloxy]-heptyl}-benzoylamino)-propionic acid, Isomer 2;
3-(4-{4,4,4-Trifluoro-1-[6-(4-trifluoromethyl-phenyl)-pyridin-3-yloxy]-butyl}-benzoylamino)-propionic acid, Isomer 1;
3-(4-{4,4,4-Trifluoro-1-[6-(4-trifluoromethyl-phenyl)-pyridin-3-yloxy]-butyl}-benzoylamino)-propionic acid, Isomer 2;
3-(4-{1-[6-(4-tert-Butyl-phenyl)-pyridin-3-yloxy]-butyl}-benzoylamino)-propionic acid, Isomer 1;
3-(4-{1-[6-(4-tert-Butyl-phenyl)-pyridin-3-yloxy]-butyl}-benzoylamino)-propionic acid, Isomer 2;
Racemic 3-(4-{1-[6-(4-Isobutyl-phenyl)-pyridin-3-yloxy]-butyl}-benzoylamino)-propionic acid;
Racemic 3-{4-[1-(3'-Trifluoromethyl-biphenyl-4-ylsulfanyl)-heptyl]-benzoylamino}-propionic acid;
Racemic 3-{4-[1-(4'-Acetyl-biphenyl-4-ylsulfanyl)-heptyl]-benzoylamino}-propionic acid;
Racemic 3-{4-[1-(3',4'-dimethyl-biphenyl-4-ylsulfanyl)-heptyl]-benzoylamino}-propionic acid;
Racemic 3-{4-[1-(4'-methylsulfonyl-biphenyl-4-ylsulfanyl)-heptyl]-benzoylamino}-propionic acid;
Racemic 3-{4-[1-(2',3'-dimethyl-biphenyl-4-ylsulfanyl)-heptyl]-benzoylamino}-propionic acid;
Racemic 3-{4-[1-(2',6'-dimethyl-biphenyl-4-ylsulfanyl)-heptyl]-benzoylamino}-propionic acid;
Racemic 3-{4-[1-(3'-isopropyl-biphenyl-4-ylsulfanyl)-heptyl]-benzoylamino}-propionic acid;
Racemic 3-{4-[1-(3'-acetyl-biphenyl-4-ylsulfanyl)-heptyl]-benzoylamino}-propionic acid;
Racemic 3-{4-[1-(4'-pentyl-biphenyl-4-ylsulfanyl)-heptyl]-benzoylamino}-propionic acid;
Racemic 3-{4-[1-(4'-cyclohexyl-biphenyl-4-ylsulfanyl)-heptyl]-benzoylamino}-propionic acid;
Racemic 3-{4-[1-(4-Allyloxy-phenoxy)-heptyl]-benzoylamino}-propionic acid;
Racemic 3-{4-[1-(2,2,3,3-Tetrafluoro-2,3-dihydro-benzo[1,4]dioxin-6-yloxy)-heptyl]-benzoylamino}-propionic acid;
Racemic 3-(4-{1-[4-(4-Trifluoromethyl-phenoxy)-phenoxy]-heptyl}-benzoylamino)-propionic acid;
Racemic 3-{4-[1-(4-Pentyl-phenoxy)-heptyl]-benzoylamino}-propionic acid;
Racemic 3-(4-{1-[4-(4-tert-Butyl-benzyloxy)-phenoxy]-heptyl}-benzoylamino)-propionic acid;
Racemic 3-(4-{1-[4-(3,5-bistrifluoromethyl-benzyloxy)-phenoxy]-heptyl}-benzoylamino)-propionic acid;
Racemic 3-(4-{1-[4-(4-isopropyl-benzyloxy)-phenoxy]-heptyl}-benzoylamino)-propionic acid;
Racemic 3-(4-{1-[4-(4-chloro-benzyloxy)-phenoxy]-heptyl}-benzoylamino)-propionic acid;
Racemic 3-(4-{1-[4-(4-ethyl-benzyloxy)-phenoxy]-heptyl}-benzoylamino)-propionic acid;
Racemic 3-(4-{1-[4-(4-bromo-benzyloxy)-phenoxy]-heptyl}-benzoylamino)-propionic acid;
Racemic 3-(4-{1-[4-(4-fluoro-benzyloxy)-phenoxy]-heptyl}-benzoylamino)-propionic acid;
Racemic 3-(4-{1-[4-(4-trifluoromethyl-benzyloxy)-phenoxy]-heptyl}-benzoylamino)-propionic acid;
Racemic 3-(4-{1-[4-(4-phenyl-benzyloxy)-phenoxy]-heptyl}-benzoylamino)-propionic acid;
Racemic 3-(4-{1-[4-(3-chloro-benzyloxy)-phenoxy]-heptyl}-benzoylamino)-propionic acid;
Racemic 3-(4-{1-[4-(3,4-dimethyl-benzyloxy)-phenoxy]-heptyl}-benzoylamino)-propionic acid;

Racemic 3-(4-{1-[4-(4-isopropxyphenoxy]-heptyl}-benzoylamino)-propionic acid;
Racemic 3-{4-[1-(3',5'-bistrifluoromethyl-biphenyl-4-yloxy)-heptyl]-benzoylamino}-propionic acid;
Racemic 3-{4-[1-(4'-tert-Butyl-biphenyl-4-yloxy)-4,4-dimethyl-pentyl]-benzoylamino}-propionic acid;
Racemic 3-{4-[1-(4'-trifluoromethyl-biphenyl-4-yloxy)-4,4-dimethyl-pentyl]-benzoylamino}-propionic acid;
Racemic 3-{4-[1-(4'-tert-Butyl-biphenyl-4-yloxy)-2-methyl-propyl]-benzoylamino}-propionic acid;
Racemic 3-{4-[1-(4'-trifluoromethyl-biphenyl-4-yloxy)-hexyl]-benzoylamino}-propionic acid;
3-{4-[1-(3',5'-bistrifluoromethyl-biphenyl-4-yloxy)-heptyl]-benzoylamino}-propionic acid, Isomer 1;
3-{4-[1-(3',5'-bistrifluoromethyl-biphenyl-4-yloxy)-heptyl]-benzoylamino}-propionic acid, Isomer 2;
3-{4-[1-(4-tert-Butyl-phenoxy)-3-methyl-butyl]-benzoylamino}-propionic acid, Isomer 1;
3-{4-[1-(4-tert-Butyl-phenoxy)-3-methyl-butyl]-benzoylamino}-propionic acid, Isomer 2;
3-{4-[1-(4'-tertbutyl-biphenyl-4-yloxy)-2-methyl-propyl]-benzoylamino}-propionic acid, Isomer 1;
3-{4-[1-(4'-tertbutyl-biphenyl-4-yloxy)-2-methyl-propyl]-benzoylamino}-propionic acid, Isomer 2;
3-{4-[1-(4'-trifluoromethyl-biphenyl-4-yloxy)-4,4-dimethyl-pentyl]-benzoylamino}-propionic acid, Isomer 1;
3-{4-[1-(4'-trifluoromethyl-biphenyl-4-yloxy)-4,4-dimethyl-pentyl]-benzoylamino}-propionic acid, Isomer 2;
3-{4-[1-(4'-Trifluoromethoxy-biphenyl-4-yloxy)-heptyl]-benzoylamino}-propionic acid, Isomer 1;
3-{4-[1-(4'-Trifluoromethoxy-biphenyl-4-yloxy)-heptyl]-benzoylamino}-propionic acid, Isomer 2;
3-{4-[1-(4'-Trifluoromethyl-biphenyl-4-yloxy)-heptyl]-benzoylamino}-propionic acid, Isomer 1;
3-{4-[1-(4'-Trifluoromethyl-biphenyl-4-yloxy)-heptyl]-benzoylamino}-propionic acid, Isomer 2;
3-{4-[1-(2,2,3,3-Tetrafluoro-2,3-dihydro-benzo[1,4]dioxin-6-yloxy)-heptyl]-benzoylamino}-propionic acid, Isomer 1;
3-{4-[1-(2,2,3,3-Tetrafluoro-2,3-dihydro-benzo[1,4]dioxin-6-yloxy)-heptyl]-benzoylamino}-propionic acid, Isomer 2;
3-(4-{1-[4-(4-Trifluoromethyl-phenoxy)-phenoxy]-heptyl}-benzoylamino)-propionic acid, Isomer 1;
3-(4-{1-[4-(4-Trifluoromethyl-phenoxy)-phenoxy]-heptyl}-benzoylamino)-propionic acid, Isomer 2;
3-{4-[1-(4'-Trifluoromethyl-biphenyl-4-yloxy)-hexyl]-benzoylamino}-propionic acid, Isomer 1;
3-{4-[1-(4'-Trifluoromethyl-biphenyl-4-yloxy)-hexyl]-benzoylamino}-propionic acid, Isomer 2;
3-(4-{1-[4'-isopropyl-biphenyl-4-ylsulfanyl]-butyl}-benzoylamino)-propionic acid, Isomer 1;
Racemic 3-{4-[1-(2,6-Dimethyl-4'-trifluoromethoxy-biphenyl-4-yloxy)-heptyl]-benzoylamino}-propionic acid;
Racemic 3-{4-[1-(2,6-Dimethyl-4'-trifluoromethyl-biphenyl-4-yloxy)-heptyl]-benzoylamino}-propionic acid;
Racemic 3-{4-[1-(2,6-Dimethyl-4'-tertbutyl-biphenyl-4-yloxy)-heptyl]-benzoylamino}-propionic acid;
3-{4-[1-(4'-tert-Butyl-biphenyl-4-yloxy)-3-methyl-butyl]-benzoylamino}-2(R)-hydroxy-propionic acid;
3-{4-[1-(4'-tert-Butyl-biphenyl-4-yloxy)-3-methyl-butyl]-benzoylamino}-2(S)-hydroxy-propionic acid;
3-{4-[1-(4'-Pentyl-biphenyl-4-yloxy)-butyl]-benzoylamino}-propionic acid, Isomer 1;
3-{4-[1-(4'-Isobutyl-biphenyl-4-yloxy)-butyl]-benzoylamino}-propionic acid, Isomer 1;
Racemic 3-{4-[1-(6-chloro-pyridin-3-yloxy)-4,4,4-trifluoro-butyl]-benzoylamino}-propionic acid;
3-{4-[1-(4'-Acetyl-biphenyl-4-yloxy)-butyl]-benzoylamino}-propionic acid, Isomer 1;
3-{4-[1-(3',5'-dichloro-biphenyl-4-yloxy)-butyl]-benzoylamino}-propionic acid, Isomer 1;
3-{4-[1-(3',5'-dichloro-biphenyl-4-yloxy)-butyl]-benzoylamino}-propionic acid, Isomer 2;
3-{4-[1-(2',3',4'-trifluoro-biphenyl-4-yloxy)-butyl]-benzoylamino}-propionic acid, Isomer 1;
3-{4-[1-(2',4'-dimethoxy-biphenyl-4-yloxy)-butyl]-benzoylamino}-propionic acid, Isomer 1;
3-{4-[1-(4'-t-butyl-biphenyl-4-yloxy)-hexyl]-benzoylamino}-propionic acid, Isomer 1;
3-{4-[1-(4'-t-butyl-biphenyl-4-yloxy)-hexyl]-benzoylamino}-propionic acid, Isomer 2;
3-{4-[1-(4'-pentylphenyl-4-yloxy)-hexyl]-benzoylamino}-propionic acid, Isomer 1;
3-{4-[1-(4'-pentylphenyl-4-yloxy)-hexyl]-benzoylamino}-propionic acid, Isomer 2;
3-(4-{1-[4-(1-Methyl-1-phenyl-ethyl)-phenoxy]-heptyl}-benzoylamino)-propionic acid, Isomer 1;
3-(4-{1-[4-(1-Methyl-1-phenyl-ethyl)-phenoxy]-heptyl}-benzoylamino)-propionic acid, Isomer 2;
3-{4-[1-(2',4',6'-trimethyl-biphenyl-4-yloxy)-heptyl]-benzoylamino}-propionic acid, Isomer 1;
3-{4-[1-(4'-Fluoro-2'-methyl-biphenyl-4-yloxy)-heptyl]-benzoylamino}-propionic acid, Isomer 1;
3-{4-[1-(4'-Trifluoromethoxy-biphenyl-4-yloxy)-hexyl]-benzoylamino}-propionic acid, Isomer 1;
3-{4-[1-(4'-Fluoro-biphenyl-4-yloxy)-heptyl]-benzoylamino}-propionic acid, Isomer 1;
3-{4-[Cyclopropyl-(4'-trifluoromethyl-biphenyl-4-yloxy)-methyl]-benzoylamino}-propionic acid, Isomer 1;
3-{4-[Cyclopropyl-(4'-trifluoromethyl-biphenyl-4-yloxy)-methyl]-benzoylamino}-propionic acid, Isomer 2;
3-{4-[1-(4'-tert-Butyl-biphenyl-4-yloxy)-4,4,4-trifluoro-butyl]-benzoylamino}-propionic acid, Isomer 1;
3-{4-[1-(4'-tert-Butyl-biphenyl-4-yloxy)-4,4,4-trifluoro-butyl]-benzoylamino}-propionic acid, Isomer 2;
3-{4-[1-(4'-Chloro-biphenyl-4-yloxy)-heptyl]-benzoylamino}-propionic acid, Isomer 1;
3-{4-[1-(4'-tert-Butyl-2-methyl-biphenyl-4-yloxy)-3-methyl-butyl]-3-fluoro-benzoylamino}-propionic acid, Isomer 1;
3-{4-[1-(4'-tert-Butyl-2-methyl-biphenyl-4-yloxy)-3-methyl-butyl]-3-fluoro-benzoylamino}-propionic acid, Isomer 2;
3-{4-[1-(4'-tert-Butyl-biphenyl-4-yloxy)-heptyl]-3-fluoro-benzoylamino}-propionic acid, Isomer 1;
3-{4-[1-(4'-tert-Butyl-biphenyl-4-yloxy)-heptyl]-3-fluoro-benzoylamino}-propionic acid, Isomer 2;
3-{3-Fluoro-4-[1-(2-methyl-4'-trifluoromethyl-biphenyl-4-yloxy)-heptyl]-benzoylamino}-propionic acid, Isomer 1;
3-{3-Fluoro-4-[1-(2-methyl-4'-trifluoromethyl-biphenyl-4-yloxy)-heptyl]-benzoylamino}-propionic acid, Isomer 2;
3-{4-[1-(4'-tert-Butyl-biphenyl-4-yloxy)-3-methyl-butyl]-3-fluoro-benzoylamino}-propionic acid, Isomer 1;
3-{4-[1-(4'-tert-Butyl-biphenyl-4-yloxy)-3-methyl-butyl]-3-fluoro-benzoylamino}-propionic acid, Isomer 2;
3-{4-[1-(4'-tert-Butyl-2,6-dimethyl-biphenyl-4-yloxy)-heptyl]-benzoylamino}-propionic acid, Isomer 1;

3-{4-[1-(4'-tert-Butyl-2,6-dimethyl-biphenyl-4-yloxy)-heptyl]-benzoylamino}-propionic acid, Isomer 2;
3-{4-[1-(4'-tert-Butyl-2-methyl-biphenyl-4-yloxy)-heptyl]-benzoylamino}-propionic acid, Isomer 1;
3-{4-[1-(4'-tert-Butyl-2-methyl-biphenyl-4-yloxy)-heptyl]-benzoylamino}-propionic acid, Isomer 2;
3-{4-[1-(2-Methyl-4'-trifluoromethyl-biphenyl-4-yloxy)-heptyl]-benzoylamino}-propionic acid, Isomer 1;
3-{4-[1-(2-Methyl-4'-trifluoromethyl-biphenyl-4-yloxy)-heptyl]-benzoylamino}-propionic acid, Isomer 2;
3-{4-[1-(4'-tert-Butyl-2,6-dimethyl-biphenyl-4-yloxy)-3-methyl-butyl]-benzoylamino}-propionic acid, Isomer 1;
3-{4-[1-(4'-tert-Butyl-2,6-dimethyl-biphenyl-4-yloxy)-3-methyl-butyl]-benzoylamino}-propionic acid, Isomer 2;
3-{4-[1-(4'-Isopropyl-2-methyl-biphenyl-4-yloxy)-heptyl]-benzoylamino}-propionic acid, Isomer 1;
3-{4-[1-(4'-Isopropyl-2-methyl-biphenyl-4-yloxy)-heptyl]-benzoylamino}-propionic acid, Isomer 2;
3-{4-[1-(4'-Fluoro-2-methyl-biphenyl-4-yloxy)-heptyl]-benzoylamino}-propionic acid, Isomer 1;
3-{4-[1-(4'-Fluoro-2-methyl-biphenyl-4-yloxy)-heptyl]-benzoylamino}-propionic acid, Isomer 2;
3-{4-[1-(4'-Ethyl-2-methyl-biphenyl-4-yloxy)-heptyl]-benzoylamino}-propionic acid, Isomer 1;
3-{4-[1-(4'-Ethyl-2-methyl-biphenyl-4-yloxy)-heptyl]-benzoylamino}-propionic acid, Isomer 2;
3-{4-[1-(2,6-Dimethyl-biphenyl-4-yloxy)-3-methyl-butyl]-benzoylamino}-propionic acid, Isomer 1;
3-{4-[1-(2,6-Dimethyl-biphenyl-4-yloxy)-3-methyl-butyl]-benzoylamino}-propionic acid, Isomer 2;
3-{4-[1-(4'-Ethyl-2,6-dimethyl-biphenyl-4-yloxy)-3-methyl-butyl]-benzoylamino}-propionic acid, Isomer 1;
3-{4-[1-(4'-Ethyl-2,6-dimethyl-biphenyl-4-yloxy)-3-methyl-butyl]-benzoylamino}-propionic acid, Isomer 2;
3-{4-[1-(4'-tert-Butyl-2-trifluoromethyl-biphenyl-4-yloxy)-3-methyl-butyl]-benzoylamino}-propionic acid, Isomer 1;
3-{4-[1-(4'-tert-Butyl-2-trifluoromethyl-biphenyl-4-yloxy)-3-methyl-butyl]-benzoylamino}-propionic acid, Isomer 2;
3-{4-[1-(4'-tert-Butyl-2-trifluoromethyl-biphenyl-4-yloxy)-heptyl]-benzoylamino}-propionic acid, Isomer 1;
3-{4-[1-(4'-tert-Butyl-2-trifluoromethyl-biphenyl-4-yloxy)-heptyl]-benzoylamino}-propionic acid, Isomer 2;
3-{4-[1-(4'-tert-Butyl-2-trifluoromethyl-biphenyl-4-yloxy)-pentyl]-benzoylamino}-propionic acid, Isomer 1;
3-{4-[1-(4'-tert-Butyl-2-trifluoromethyl-biphenyl-4-yloxy)-pentyl]-benzoylamino}-propionic acid, Isomer 2;
3-{4-[1-(4'-tert-Butyl-2-trifluoromethyl-biphenyl-4-yloxy)-2-methyl-propyl]-benzoylamino}-propionic acid, Isomer 1;
3-{4-[1-(4'-tert-Butyl-2-trifluoromethyl-biphenyl-4-yloxy)-2-methyl-propyl]-benzoylamino}-propionic acid, Isomer 2;
3-{4-[1-(2,6-Dimethyl-4'-trifluoromethyl-biphenyl-4-yloxy)-4,4-dimethyl-pentyl]-benzoylamino}-propionic acid, Isomer 1;
3-{4-[1-(2,6-Dimethyl-4'-trifluoromethyl-biphenyl-4-yloxy)-4,4-dimethyl-pentyl]-benzoylamino}-propionic acid, Isomer 2;
3-{4-[1-(4'-Isopropyl-2,6-dimethyl-biphenyl-4-yloxy)-4,4-dimethyl-pentyl]-benzoylamino}-propionic acid, Isomer 1;
3-{4-[1-(4'-Isopropyl-2,6-dimethyl-biphenyl-4-yloxy)-4,4-dimethyl-pentyl]-benzoylamino}-propionic acid, Isomer 2;
3-{4-[1-(2-Cyano-4'-isopropyl-biphenyl-4-yloxy)-3-methyl-butyl]-benzoylamino}-propionic acid, Isomer 1;
3-{4-[1-(2-Cyano-4'-isopropyl-biphenyl-4-yloxy)-3-methyl-butyl]-benzoylamino}-propionic acid, Isomer 2;
3-{4-[1-(4'-Isopropyl-2,6-dimethyl-biphenyl-4-yloxy)-2-methyl-propyl]-benzoylamino}-propionic acid, Isomer 1;
3-{4-[1-(4'-Isopropyl-2,6-dimethyl-biphenyl-4-yloxy)-2-methyl-propyl]-benzoylamino}-propionic acid, Isomer 2;
3-{4-[1-(2-Ethyl-4'-trifluoromethyl-biphenyl-4-yloxy)-heptyl]-benzoylamino}-propionic acid, Isomer 1;
3-{4-[1-(2-Ethyl-4'-trifluoromethyl-biphenyl-4-yloxy)-heptyl]-benzoylamino}-propionic acid, Isomer 2;
3-{4-[1-(4'-Chloro-2,6-dimethyl-biphenyl-4-yloxy)-4,4-dimethyl-pentyl]-benzoylamino}-propionic acid, Isomer 1;
3-{4-[1-(4'-Chloro-2,6-dimethyl-biphenyl-4-yloxy)-4,4-dimethyl-pentyl]-benzoylamino}-propionic acid, Isomer 2; 2398902, TC6-A07480-162-B 3-{4-[1-(4'-tert-Butyl-2,6-dimethyl-biphenyl-4-yloxy)-2-methyl-propyl]-benzoylamino}-propionic acid, Isomer 1;
3-{4-[1-(4'-tert-Butyl-2,6-dimethyl-biphenyl-4-yloxy)-2-methyl-propyl]-benzoylamino}-propionic acid, Isomer 2;
3-{4-[2-Methyl-1-(2-methyl-4'-trifluoromethoxy-biphenyl-4-yloxy)-propyl]-benzoylamino}-propionic acid, Isomer 1;
3-{4-[2-Methyl-1-(2-methyl-4'-trifluoromethoxy-biphenyl-4-yloxy)-propyl]-benzoylamino}-propionic acid, Isomer 2;
3-{4-[1-(2-Chloro-4'-isopropyl-biphenyl-4-yloxy)-3-methyl-butyl]-benzoylamino}-propionic acid, Isomer 1;
3-{4-[1-(2-Chloro-4'-isopropyl-biphenyl-4-yloxy)-3-methyl-butyl]-benzoylamino}-propionic acid, Isomer 2;
3-{4-[1-(2-Chloro-4'-trifluoromethyl-biphenyl-4-yloxy)-3-methyl-butyl]-benzoylamino}-propionic acid, Isomer 1;
3-{4-[1-(2-Chloro-4'-trifluoromethyl-biphenyl-4-yloxy)-3-methyl-butyl]-benzoylamino}-propionic acid, Isomer 2;
3-{4-[2-Methyl-1-(2-methyl-4'-trifluoromethyl-biphenyl-4-yloxy)-propyl]-benzoylamino}-propionic acid, Isomer 1;
3-{4-[2-Methyl-1-(2-methyl-4'-trifluoromethyl-biphenyl-4-yloxy)-propyl]-benzoylamino}-propionic acid, Isomer 2;
3-(4-{3-Methyl-1-[5-methyl-6-(4-trifluoromethyl-phenyl)-pyridin-3-yloxy]-butyl}-benzoylamino)-propionic acid, Isomer 1;
3-(4-{3-Methyl-1-[5-methyl-6-(4-trifluoromethyl-phenyl)-pyridin-3-yloxy]-butyl}-benzoylamino)-propionic acid, Isomer 2;
3-(4-{1-[6-(4-Isopropyl-phenyl)-5-methyl-pyridin-3-yloxy]-3-methyl-butyl}-benzoylamino)-propionic acid, Isomer 1;
3-(4-{1-[6-(4-Isopropyl-phenyl)-5-methyl-pyridin-3-yloxy]-3-methyl-butyl}-benzoylamino)-propionic acid, Isomer 2;

3-(3-Fluoro-4-{3-methyl-1-[6-(4-trifluoromethyl-phenyl)-pyridin-3-yloxy]-butyl}-benzoylamino)-propionic acid, Isomer 1;
3-(3-Fluoro-4-{3-methyl-1-[6-(4-trifluoromethyl-phenyl)-pyridin-3-yloxy]-butyl}-benzoylamino)-propionic acid, Isomer 2;
3-(4-{3-Methyl-1-[4-(5-trifluoromethyl-pyridin-2-yl)-phenoxy]-butyl}-benzoylamino)-propionic acid, Isomer 1;
3-(4-{3-Methyl-1-[4-(5-trifluoromethyl-pyridin-2-yl)-phenoxy]-butyl}-benzoylamino)-propionic acid, Isomer 2;
3-{4-[1-(4-tert-Butyl-phenoxy)-3-methyl-butyl]-benzoylamino}-propionic acid, Isomer 1;
3-{4-[1-(4-tert-Butyl-phenoxy)-3-methyl-butyl]-benzoylamino}-propionic acid, Isomer 2;
2-Hydroxy-3-{4-[1-(4'-trifluoromethyl-biphenyl-4-yloxy)-heptyl]-benzoylamino}-propionic acid, Isomer 1;
2-Hydroxy-3-{4-[1-(4'-trifluoromethyl-biphenyl-4-yloxy)-heptyl]-benzoylamino}-propionic acid, Isomer 2;
2-Hydroxy-3-{4-[1-(4'-trifluoromethyl-biphenyl-4-yloxy)-heptyl]-benzoylamino}-propionic acid, Isomer 1;
2-Hydroxy-3-{4-[1-(4'-trifluoromethyl-biphenyl-4-yloxy)-heptyl]-benzoylamino}-propionic acid, Isomer 2;
3-(4-{1-[4-(1,1,3,3-Tetramethyl-butyl)-phenoxy]-heptyl}-benzoylamino)-propionic acid, Isomer 1;
3-(4-{1-[4-(1,1,3,3-Tetramethyl-butyl)-phenoxy]-heptyl}-benzoylamino)-propionic acid, Isomer 2;
3-{4-[1-(2,2,3,3-Tetrafluoro-2,3-dihydro-benzo[1,4]dioxin-6-yloxy)-heptyl]-benzoylamino}-propionic acid, Isomer 1;
3-{4-[1-(2,2,3,3-Tetrafluoro-2,3-dihydro-benzo[1,4]dioxin-6-yloxy)-heptyl]-benzoylamino}-propionic acid, Isomer 2;
3-{4-[1-(2,6-Dimethyl-4'-trifluoromethyl-biphenyl-4-yloxy)-3,3-dimethyl-butyl]-benzoylamino}-propionic acid, Isomer 1;
3-{4-[1-(2,6-Dimethyl-4'-trifluoromethyl-biphenyl-4-yloxy)-3,3-dimethyl-butyl]-benzoylamino}-propionic acid, Isomer 2;
3-{4-[1-(4'-tert-Butyl-2,6-dimethyl-biphenyl-4-yloxy)-3,3-dimethyl-butyl]-benzoylamino}-propionic acid, Isomer 1;
3-{4-[1-(4'-tert-Butyl-2,6-dimethyl-biphenyl-4-yloxy)-3,3-dimethyl-butyl]-benzoylamino}-propionic acid, Isomer 2;
3-{4-[1-(4'-Isopropyl-2,6-dimethyl-biphenyl-4-yloxy)-3,3-dimethyl-butyl]-benzoylamino}-propionic acid, Isomer 1;
3-{4-[1-(4'-Isopropyl-2,6-dimethyl-biphenyl-4-yloxy)-3,3-dimethyl-butyl]-benzoylamino}-propionic acid, Isomer 2;
3-(4-{3,3-Dimethyl-1-[5-methyl-6-(4-trifluoromethyl-phenyl)-pyridin-3-yloxy]-butyl}-benzoylamino)-propionic acid, Isomer 1;
3-(4-{3,3-Dimethyl-1-[5-methyl-6-(4-trifluoromethyl-phenyl)-pyridin-3-yloxy]-butyl}-benzoylamino)-propionic acid, Isomer 2;
3-{4-[1-(4'-Isopropyl-2-methoxy-biphenyl-4-yloxy)-3-methyl-butyl]-benzoylamino}-propionic acid, Isomer 1;
3-{4-[1-(4'-Isopropyl-2-methoxy-biphenyl-4-yloxy)-3-methyl-butyl]-benzoylamino}-propionic acid, Isomer 2;
3-{4-[1-(4'-Isopropyl-2-methyl-biphenyl-4-yloxy)-3-methyl-butyl]-benzoylamino}-propionic acid, Isomer 1;
3-{4-[1-(4'-Isopropyl-2-methyl-biphenyl-4-yloxy)-3-methyl-butyl]-benzoylamino}-propionic acid, Isomer 2;
3-{4-[1-(2,6-Dimethyl-4'-trifluoromethoxy-biphenyl-4-yloxy)-3,3-dimethyl-butyl]-benzoylamino}-propionic acid, Isomer 1;
3-{4-[1-(2,6-Dimethyl-4'-trifluoromethoxy-biphenyl-4-yloxy)-3,3-dimethyl-butyl]-benzoylamino}-propionic acid, Isomer 2;
3-(4-{1-[2-(tert-Butoxyimino-methyl)-4'-trifluoromethyl-biphenyl-4-yloxy]-3-methyl-butyl}-benzoylamino)-propionic acid, Isomer 1;
3-(4-{1-[2-(tert-Butoxyimino-methyl)-4'-trifluoromethyl-biphenyl-4-yloxy]-3-methyl-butyl}-benzoylamino)-propionic acid, Isomer 2;
3-{4-[1-(4'-tert-Butyl-2,6-dimethyl-biphenyl-4-yloxy)-3,3-dimethyl-butyl]-benzoylamino}-2-hydroxy-propionic acid, Isomer 1;
3-{4-[1-(4'-tert-Butyl-2,6-dimethyl-biphenyl-4-yloxy)-3,3-dimethyl-butyl]-benzoylamino}-2-hydroxy-propionic acid, Isomer 2;
3-{4-[1-(4'-tert-Butyl-2,6-dimethyl-biphenyl-4-yloxy)-3,3-dimethyl-butyl]-benzoylamino}-2-hydroxy-propionic acid, Isomer 1;
3-{4-[1-(4'-tert-Butyl-2,6-dimethyl-biphenyl-4-yloxy)-3,3-dimethyl-butyl]-benzoylamino}-2-hydroxy-propionic acid, Isomer 2;
3-{4-[1-(4'-Fluoro-2,6-dimethyl-biphenyl-4-yloxy)-3-methyl-butyl]-benzoylamino}-propionic acid, Isomer 1;
3-{4-[1-(4'-Fluoro-2,6,2'-trimethyl-biphenyl-4-yloxy)-heptyl]-benzoylamino}-propionic acid, Isomer 1;
3-{4-[1-(4'-Chloro-2,6-dimethyl-biphenyl-4-yloxy)-3-methyl-butyl]-benzoylamino}-propionic acid, Isomer 1;
3-{4-[1-(4'-Isopropyl-2,6-dimethyl-biphenyl-4-yloxy)-3-methyl-butyl]-benzoylamino}-propionic acid, Isomer 1;
3-{4-[1-(2,6-Dimethyl-4'-trifluoromethyl-biphenyl-4-yloxy)-3-methyl-butyl]-benzoylamino}-propionic acid, Isomer 1;
3-{4-[1-(2,6-Dimethyl-4'-trifluoromethyl-biphenyl-4-yloxy)-3-methyl-butyl]-benzoylamino}-propionic acid, Isomer 2;
Racemic 3-{4-[1-(4'-tert-Butyl-biphenyl-4-yloxy)-hexyl]-benzoylamino}-propionic acid;
Racemic 3-{4-[1-(4'-tert-Butyl-biphenyl-4-yloxy)-heptyl]-3-fluoro-benzoylamino}-propionic acid;
Racemic 3-{4-[1-(4'-tert-Butyl-biphenyl-4-yloxy)-3-methyl-butyl]-3-fluoro-benzoylamino}-propionic acid;
Racemic 3-{4-[1-(2-Cyano-4'-isopropyl-biphenyl-4-yloxy)-3-methyl-butyl}-benzoylamino]-propionic acid;
Racemic 3-{4-[1-(4'-Isopropyl-2-trifluoromethyl-biphenyl-4-yloxy)-heptyl]-benzoylamino}-propionic acid;
Racemic 3-{4-[1-(2-Ethyl-4'-trifluoromethyl-biphenyl-4-yloxy)-heptyl]-benzoylamino}-propionic acid;
3-[4-(4'-tert-Butyl-2,6-dimethyl-biphenyl-4-yloxymethyl)-benzoylamino]-propionic acid;
3-[4-(4'-tert-Butyl-2,6-dimethyl-biphenyl-4-yloxymethyl)-benzoylamino]-propionic acid;
Racemic 3-{4-[1-(2,6-Dimethyl-4'-trifluoromethyl-biphenyl-4-yloxy)-ethyl]-benzoylamino}-propionic acid;

Racemic 3-{4-[1-(4'-tert-Butyl-2,6-dimethyl-biphenyl-4-yloxy)-ethyl]-benzoylamino}-propionic acid;
Racemic 3-(3-Fluoro-4-{3-methyl-1-[6-(4-trifluoromethyl-phenyl)-pyridin-3-yloxy]-butyl}-benzoylamino)-propionic acid;
Racemic 3-(4-{1-[4-(1,1,3,3-Tetramethyl-butyl)-phenoxy]-heptyl}-benzoylamino)-propionic acid;
Racemic 3-(4-{3-Methyl-1-[4-(5-trifluoromethyl-pyridin-2-yl)-phenoxy]-butyl}-benzoylamino)-propionic acid;
Racemic 3-{4-[1-(4'-tert-Butyl-2,6-dimethyl-biphenyl-4-yloxy)-3,3-dimethyl-butyl]-benzoylamino}-propionic acid;
Racemic 3-{4-[1-(4'-tert-Butyl-2,6-dimethyl-biphenyl-4-yloxy)-3,3-dimethyl-butyl]-benzoylamino}-2-hydroxy-propionic acid;
Racemic 3-{4-[1-(4'-tert-Butyl-2,6-dimethyl-biphenyl-4-yloxy)-3,3-dimethyl-butyl]-benzoylamino}-2-hydroxy-propionic acid;
Chiral 3-{4-[1-(2,6-Dimethyl-4'-trifluoromethyl-biphenyl-4-yloxy)-3-methyl-butyl]-benzoylamino}-2-hydroxy-propionic acid, Isomer 1;
Chiral 3-{4-[1-(2,6-Dimethyl-4'-trifluoromethyl-biphenyl-4-yloxy)-3-methyl-butyl]-benzoylamino}-2-hydroxy-propionic acid, Isomer 1;
Racemic 3-{4-[1-(4-Bromo-3-[1,3]dioxan-2-yl-phenoxy)-3-methyl-butyl]-benzoylamino}-propionic acid;
Racemic 3-{4-[1-(4-tert-Butyl-phenoxy)-3-methyl-butyl]-benzoylamino}-propionic acid;
Racemic 3-{4-[1-(4'-tert-Butyl-biphenyl-4-yloxy)-3-methyl-butyl]-benzoylamino}-2-hydroxy-propionic acid;
Racemic 3-{4-[1-(4'-tert-Butyl-biphenyl-4-yloxy)-3-methyl-butyl]-benzoylamino}-2-hydroxy-propionic acid;
Racemic 3-{4-[1-(4-Pentyl-phenoxy)-heptyl]-benzoylamino}-propionic acid;
Racemic 3-(4-{1-[4-(1-Methyl-1-phenyl-ethyl)-phenoxy]-heptyl}-benzoylamino)-propionic acid;
Racemic 2-Hydroxy-3-{4-[1-(4'-trifluoromethyl-biphenyl-4-yloxy)-heptyl]-benzoylamino}-propionic acid;
Racemic 2-Hydroxy-3-{4-[1-(4'-trifluoromethyl-biphenyl-4-yloxy)-heptyl]-benzoylamino}-propionic acid;
Racemic 3-{4-[1-(4'-Isopropyl-2-methyl-biphenyl-4-yloxy)-3-methyl-butyl]-benzoylamino}-propionic acid;
Racemic 3-{4-[1-(4-Chloro-3-trifluoromethyl-phenoxy)-heptyl]-benzoylamino}-2-hydroxy-propionic acid;
Racemic 3-{4-[1-(3-Chloro-4-methyl-phenoxy)-3-methyl-butyl]-benzoylamino}-propionic acid;
Racemic 3-{4-[1-(2,2,3,3-Tetrafluoro-2,3-dihydro-benzo[1,4]dioxin-6-yloxy)-heptyl]-benzoylamino}-propionic acid;
Racemic 3-{4-[Cyclopropyl-(4'-trifluoromethyl-biphenyl-4-yloxy)-methyl]-benzoylamino}-propionic acid;
Racemic 3-{4-[1-(4'-Isopropyl-2,6-dimethyl-biphenyl-4-yloxy)-heptyl]-benzoylamino}-propionic acid;
Racemic 3-{4-[1-(4'-Acetyl-2,6-dimethyl-biphenyl-4-yloxy)-heptyl]-benzoylamino}-propionic acid;
Racemic 3-{4-[1-(4'-tert-Butyl-2-methyl-biphenyl-4-yloxy)-heptyl]-benzoylamino}-propionic acid;
Racemic 3-{4-[1-(2-Methyl-4'-trifluoromethyl-biphenyl-4-yloxy)-heptyl]-benzoylamino}-propionic acid;
Racemic 3-(4-{1-[6-(4-Isopropyl-phenyl)-5-methyl-pyridin-3-yloxy]-4,4-dimethyl-pentyl}-benzoylamino)-propionic acid;
Racemic 3-(4-{4,4-Dimethyl-1-[5-methyl-6-(4-trifluoromethyl-phenyl)-pyridin-3-yloxy]-pentyl}-benzoylamino)-propionic acid;
Racemic 3-(4-{4,4-Dimethyl-1-[5-methyl-6-(4-trifluoromethoxy-phenyl)-pyridin-3-yloxy]-pentyl}-benzoylamino)-propionic acid;
Racemic 3-{4-[1-(2,6-Dimethyl-4'-trifluoromethoxy-biphenyl-4-yloxy)-3,3-dimethyl-butyl]-benzoylamino}-propionic acid;
Racemic 3-{4-[1-(2,6-Dimethyl-4'-trifluoromethyl-biphenyl-4-yloxy)-3,3-dimethyl-butyl]-benzoylamino}-2-hydroxy-propionic acid;
Racemic 3-{4-[1-(2,6-Dimethyl-4'-trifluoromethyl-biphenyl-4-yloxy)-3,3-dimethyl-butyl]-benzoylamino}-2-hydroxy-propionic acid;
Racemic 2-Hydroxy-3-{4-[1-(4'-isopropyl-2,6-dimethyl-biphenyl-4-yloxy)-3,3-dimethyl-butyl]-benzoylamino}-propionic acid;
Racemic 3-{4-[1-(4'-Isopropyl-2-methoxy-biphenyl-4-yloxy)-3-methyl-butyl]-benzoylamino]-propionic acid;
Racemic 3-{3-Fluoro-4-[1-(2-methyl-4'-trifluoromethyl-biphenyl-4-yloxy)-heptyl]-benzoylamino}-propionic acid;
Racemic 3-{4-[1-(4'-tert-Butyl-2-chloro-biphenyl-4-yloxy)-heptyl]-benzoylamino}-propionic acid;
Racemic 3-{4-[1-(4'-trifluoromethyl-2-chloro-biphenyl-4-yloxy)-heptyl]-benzoylamino}-propionic acid;
Racemic 3-{4-[1-(2',4'-bistrifluoromethyl-2-chloro-biphenyl-4-yloxy)-heptyl]-benzoylamino}-propionic acid;
Racemic 3-{4-[1-(2,6-Dimethyl-4'-trifluoromethyl-biphenyl-4-yloxy)-3-methyl-butyl]-benzoylamino}-propionic acid;
Racemic 3-{4-[1-(4'-tert-Butyl-2,6-dimethyl-biphenyl-4-yloxy)-3-methyl-butyl]-benzoylamino}-propionic acid;
Racemic 3-{4-[1-(2-Hydroxy-4'-isopropyl-biphenyl-4-yloxy)-3-methyl-butyl]-benzoylamino}-propionic acid;
Racemic 3-{4-[1-(2-[1,3]Dioxan-2-yl-4'-isopropyl-biphenyl-4-yloxy)-3-methyl-butyl]-benzoylamino}-propionic acid;
Racemic 3-(4-{1-[2-(tert-Butoxyimino-methyl)-4'-isopropyl-biphenyl-4-yloxy]-3-methyl-butyl}-benzoylamino)-propionic acid;
Racemic 3-(4-{1-[2-(tert-Butoxyimino-methyl)-4'-trifluoromethyl-biphenyl-4-yloxy]-3-methyl-butyl}-benzoylamino)-propionic acid;
Racemic 3-{4-[1-(2,6-Dimethyl-biphenyl-4-yloxy)-3-methyl-butyl]-benzoylamino}-propionic acid;
Racemic 3-{4-[1-(4'-Ethyl-2,6-dimethyl-biphenyl-4-yloxy)-3-methyl-butyl]-benzoylamino}-propionic acid;
Racemic 3-{4-[1-(2-Methyl-4'-trifluoromethoxy-biphenyl-4-yloxy)-heptyl]-benzoylamino}-propionic acid;
Racemic 3-{4-[1-(4'-Isopropyl-2-methyl-biphenyl-4-yloxy)-heptyl]-benzoylamino}-propionic acid;
Racemic 3-{4-[1-(2,6-Dimethyl-4'-trifluoromethoxy-biphenyl-4-yloxy)-3-methyl-butyl]-benzoylamino}-propionic acid;
Racemic 3-{4-[1-(4'-ethyl-2-methyl-biphenyl-4-yloxy)-heptyl]-benzoylamino}-propionic acid;
Racemic 3-{4-[1-(4'-acetyl-2-methyl-biphenyl-4-yloxy)-heptyl]-benzoylamino}-propionic acid;
Racemic 3-{4-[1-(4'-fluoro-2-methyl-biphenyl-4-yloxy)-heptyl]-benzoylamino}-propionic acid;
Racemic 3-{4-[1-(4'-tert-Butyl-2-trifluoromethyl-biphenyl-4-yloxy)-heptyl]-benzoylamino}-propionic acid;
Racemic 3-{4-[1-(4'-tert-Butyl-2-trifluoromethyl-biphenyl-4-yloxy)-pentyl]-benzoylamino}-propionic acid;
Racemic 3-{4-[1-(4'-tert-Butyl-2-trifluoromethyl-biphenyl-4-yloxy)-2-methyl-propyl]-benzoylamino}-propionic acid;

Racemic 3-{4-[1-(4'-tert-Butyl-2-trifluoromethyl-biphenyl-4-yloxy)-3-methyl-butyl]-benzoylamino}-propionic acid;
Racemic 3-{4-[1-(3,5-Dimethyl-4'-trifluoromethyl-biphenyl-4-yloxy)-heptyl]-benzoylamino}-propionic acid;
Racemic 3-{4-[1-(4'-Chloro-3,5-dimethyl-biphenyl-4-yloxy)-heptyl]-benzoylamino}-propionic acid;
Racemic 3-{4-[1-(4'-Chloro-3-methyl-biphenyl-4-yloxy)-heptyl]-benzoylamino}-propionic acid;
Racemic 3-{4-[1-(2,6-Dimethyl-4'-trifluoromethyl-biphenyl-4-yloxy)-3,3-dimethyl-butyl]-benzoylamino}-propionic acid;
Racemic 3-{4-[1-(2,6-Dimethyl-4'-trifluoromethyl-biphenyl-4-yloxy)-4,4-dimethyl-pentyl]-benzoylamino}-propionic acid;
Racemic 3-{4-[1-(2,6-Dimethyl-4'-isopropyl-biphenyl-4-yloxy)-4,4-dimethyl-pentyl]-benzoylamino}-propionic acid;
Racemic 3-{4-[1-(4'-Isopropyl-2,6-dimethyl-biphenyl-4-yloxy)-2-methyl-propyl]-benzoylamino}-propionic acid;
Racemic 3-{4-[1-(2,6-Dimethyl-4'-trifluoromethyl-biphenyl-4-yloxy)-2-methyl-propyl]-benzoylamino}-propionic acid;
Racemic 3-{4-[2-Methyl-1-(2-methyl-4'-trifluoromethyl-biphenyl-4-yloxy)-propyl]-benzoylamino}-propionic acid;
Racemic 3-{4-[1-(2,6-Dimethyl-4'-chloro-biphenyl-4-yloxy)-4,4-dimethyl-pentyl]-benzoylamino}-propionic acid;
Racemic 3-{4-[1-(4'-tert-Butyl-2,6-dimethyl-biphenyl-4-yloxy)-2-methyl-propyl]-benzoylamino}-propionic acid;
Racemic 3-{4-[1-(4'-Isopropyl-2-methyl-biphenyl-4-yloxy)-2-methyl-propyl]-benzoylamino}-propionic acid;
Racemic 3-{4-[1-(2,6-Difluoro-4'-trifluoromethyl-biphenyl-4-yloxy)-3-methyl-butyl]-benzoylamino}-propionic acid;
Racemic 3-{4-[1-(2,6-Difluoro-4'-isopropyl-biphenyl-4-yloxy)-3-methyl-butyl]-benzoylamino}-propionic acid;
Racemic 3-{4-[1-(2-Chloro-4'-isopropyl-biphenyl-4-yloxy)-3-methyl-butyl]-benzoylamino}-propionic acid;
Racemic 3-{4-[1-(2-Chloro-4'-trifluoromethyl-biphenyl-4-yloxy)-3-methyl-butyl]-benzoylamino}-propionic acid;
Racemic 3-(4-{3-Methyl-1-[5-methyl-6-(4-trifluoromethyl-phenyl)-pyridin-3-yloxy]-butyl}-benzoylamino)-propionic acid;
Racemic 3-(4-{1-[6-(4-Isopropyl-phenyl)-5-methyl-pyridin-3-yloxy]-3-methyl-butyl}-benzoylamino)-propionic acid;
Racemic 3-{4-[1-(4'-tert-Butyl-biphenyl-3-yloxy)-3-methyl-butyl]-benzoylamino}-propionic acid;
Racemic 3-{4-[3-Methyl-1-(4'-trifluoromethyl-biphenyl-3-yloxy)-butyl]-benzoylamino}-propionic acid;
Racemic 3-{4-[1-(4'-Isopropyl-biphenyl-3-yloxy)-3-methyl-butyl]-benzoylamino}-propionic acid;
Racemic 3-{4-[3-Methyl-1-(4'-trifluoromethoxy-biphenyl-3-yloxy)-butyl]-benzoylamino}-propionic acid;
Racemic 3-{4-[3-Methyl-1-(6-methyl-4'-trifluoromethyl-biphenyl-3-yloxy)-butyl]-benzoylamino}-propionic acid;
Racemic 3-{4-[1-(4'-tert-Butyl-6-methyl-biphenyl-3-yloxy)-3-methyl-butyl]-benzoylamino}-propionic acid;
Racemic 3-{4-[1-(2-Hydroxymethyl-4'-isopropyl-biphenyl-4-yloxy)-3-methyl-butyl]-benzoylamino}-propionic acid;
Racemic 3-{4-[1-(2-Formyl-4'-isopropyl-biphenyl-4-yloxy)-3-methyl-butyl]-benzoylamino}-propionic acid;
Racemic 3-(4-{1-[2-(Hydroxyimino-methyl)-4'-isopropyl-biphenyl-4-yloxy]-3-methyl-butyl}-benzoylamino)-propionic acid;
Racemic 3-{4-[1-(4'-Isopropyl-2-morpholin-4-ylmethyl-biphenyl-4-yloxy)-3-methyl-butyl]-benzoylamino}-propionic acid;
3-(4-{3,3-Dimethyl-1-[5-methyl-1-oxy-6-(4-trifluoromethoxy-phenyl)-pyridin-3-yloxy]-butyl}-benzoylamino)-propionic acid;
2-Hydroxy-3-{4-[1-(4'-isopropyl-2,6-dimethyl-biphenyl-4-yloxy)-2-methyl-propyl]-benzoylamino}-propionic acid, Isomer 1;
2-Hydroxy-3-{4-[1-(4'-isopropyl-2,6-dimethyl-biphenyl-4-yloxy)-2-methyl-propyl]-benzoylamino}-propionic acid, Isomer 2;
2-Hydroxy-3-{4-[1-(4'-isopropyl-2,6-dimethyl-biphenyl-4-yloxy)-2-methyl-propyl]-benzoylamino}-propionic acid, Isomer 1;
2-Hydroxy-3-{4-[1-(4'-isopropyl-2,6-dimethyl-biphenyl-4-yloxy)-2-methyl-propyl]-benzoylamino}-propionic acid, Isomer 2;
3-{4-[1-(2,6-Dimethyl-4'-trifluoromethyl-biphenyl-4-yloxy)-2-methyl-propyl]-benzoylamino}-2-hydroxy-propionic acid, Isomer 1;
3-{4-[1-(2,6-Dimethyl-4'-trifluoromethyl-biphenyl-4-yloxy)-2-methyl-propyl]-benzoylamino}-2-hydroxy-propionic acid, Isomer 2;
3-{4-[1-(2,6-Dimethyl-4'-trifluoromethyl-biphenyl-4-yloxy)-2-methyl-propyl]-benzoylamino}-2-hydroxy-propionic acid, Isomer 1;
3-{4-[1-(2,6-Dimethyl-4'-trifluoromethyl-biphenyl-4-yloxy)-2-methyl-propyl]-benzoylamino}-2-hydroxy-propionic acid, Isomer 2;
Racemic 3-{4-[1-(2,6-dimethyl-4'-trifluoromethyl-biphenyl-4-ylsulfanyl)-5,5,5-trifluoro-pentyl]-benzoylamino}-propionic acid;
Racemic 3-{4-[1-(2,4,6-tri-t-butyl-phenoxy)-5,5,5-trifluoro-pentyl]-benzoylamino}-propionic acid;
3-(4-{5,5,5-trifluoro-1-[5-methyl-6-(4-trifluoromethyl-phenyl)-pyridin-3-yloxy]-pentyl}-benzoylamino)-propionic acid, Isomer 1;
3-(4-{5,5,5-trifluoro-1-[5-methyl-6-(4-trifluoromethyl-phenyl)-pyridin-3-yloxy]-pentyl}-benzoylamino)-propionic acid, Isomer 2;
Racemic 3-{4-[1-(2,6-dimethyl-4'-trifluoromethyl-biphenyl-4-ylsulfanyl)-5,5,5-trifluoro-pentyl]-benzoylamino}-propionic acid;
Racemic 3-{4-[1-(4'-tert-butyl-2,6-dimethyl-biphenyl-4-ylsulfanyl)-5,5,5-trifluoro-pentyl]-benzoylamino}-propionic acid;
Racemic 3-{4-[1-(4-bromo-3,5-dimethyl-phenylsulfanyl)-5,5,5-trifluoro-pentyl]-benzoylamino}-propionic acid;
Racemic 3-(4-{5,5,5-trifluoro-1-[5-methyl-6-(4-trifluoromethyl-phenyl)-pyridin-3-yloxy]-pentyl}-benzoylamino)-propionic acid;
Racemic 3-(4-{4,4,4-trifluoro-1-[5-methyl-6-(4-trifluoromethyl-phenyl)-pyridin-3-yloxy]-butyl}-benzoylamino)-propionic acid;
3-{4-[1-(2,6-dimethyl-4'-trifluoromethyl-biphenyl-4-ylsulfanyl)-3-methyl-butyl]-benzoylamino}-propionic acid, Isomer 1;

3-{4-[1-(2,6-dimethyl-4'-trifluoromethyl-biphenyl-4-yl-sulfanyl)-3-methyl-butyl]-benzoylamino}-propionic acid, Isomer 2;
3-{4-[1-(4'-tert-butyl-2,6-dimethyl-biphenyl-4-ylsulfanyl)-3-methyl-butyl]-benzoylamino}-propionic acid, Isomer 1;
3-{4-[1-(4'-tert-butyl-2,6-dimethyl-biphenyl-4-ylsulfanyl)-3-methyl-butyl]-benzoylamino}-propionic acid, Isomer 2;
3-{4-[1-(4'-tert-butyl-2,6-dimethyl-biphenyl-4-ylsulfanyl)-4,4,4-trifluoro-butyl]-benzoylamino}-propionic acid, Isomer 1;
3-{4-[1-(4'-tert-butyl-2,6-dimethyl-biphenyl-4-ylsulfanyl)-4,4,4-trifluoro-butyl]-benzoylamino}-propionic acid, Isomer 2;
3-{4-[1-(4-bromo-3,5-dimethyl-phenylsulfanyl)-4,4,4-trifluoro-butyl]-benzoylamino}-propionic acid, Isomer 1;
3-{4-[1-(4-bromo-3,5-dimethyl-phenylsulfanyl)-4,4,4-trifluoro-butyl]-benzoylamino}-propionic acid, Isomer 2;
3-{4-[1-(4-bromo-3,5-dimethyl-phenylsulfanyl)-3-methyl-butyl]-benzoylamino}-propionic acid, Isomer 1;
3-{4-[1-(4-bromo-3,5-dimethyl-phenylsulfanyl)-3-methyl-butyl]-benzoylamino}-propionic acid, Isomer 2;
3-{4-[1-(2,6-dimethyl-4'-trifluoromethyl-biphenyl-4-yloxy)-5,5,5-trifluoro-pentyl]-benzoylamino}-propionic acid, Isomer 1;
3-{4-[1-(2,6-dimethyl-4'-trifluoromethyl-biphenyl-4-yloxy)-5,5,5-trifluoro-pentyl]-benzoylamino}-propionic acid, Isomer 2;
3-{4-[4,4,4-trifluoro-1-(4'-isopropyl-2,6-dimethyl-biphenyl-4-yloxy)-butyl]-benzoylamino}-propionic acid, Isomer 1;
3-{4-[4,4,4-trifluoro-1-(4'-isopropyl-2,6-dimethyl-biphenyl-4-yloxy)-butyl]-benzoylamino}-propionic acid, Isomer 2;
Racemic 3-{4-[1-(2,6-dimethyl-4'-trifluoromethyl-biphenyl-4-ylsulfanyl)-4,4,4-trifluoro-butyl]-benzoylamino}-propionic acid;
Racemic 3-{4-[1-(4'-tert-butyl-2,6-dimethyl-biphenyl-4-ylsulfanyl)-4,4,4-trifluoro-butyl]-benzoylamino}-propionic acid;
Racemic 3-{4-[1-(2,6-dimethyl-4'-trifluoromethyl-biphenyl-4-ylsulfanyl)-3-methyl-butyl]-benzoylamino}-propionic acid
Racemic 3-{4-[1-(4'-tert-butyl-2,6-dimethyl-biphenyl-4-ylsulfanyl)-3-methyl-butyl]-benzoylamino}-propionic acid;
Racemic 3-{4-[1-(4-bromo-3,5-dimethyl-phenylsulfanyl)-4,4,4-trifluoro-butyl]-benzoylamino}-propionic acid;
Racemic 3-{4-[1-(4-bromo-3,5-dimethyl-phenylsulfanyl)-3-methyl-butyl]-benzoylamino}-propionic acid;
3-{4-[1-(2,6-dimethyl-4'-trifluoromethyl-biphenyl-4-yloxy)-heptyl]-benzoylamino}-propionic acid, Isomer 1;
3-{4-[1-(2,6-dimethyl-4'-trifluoromethyl-biphenyl-4-yloxy)-heptyl]-benzoylamino}-propionic acid, Isomer 2;
3-{4-[3-methyl-1-(2,2',4'-trichloro-biphenyl-4-yloxy)-butyl]-benzoylamino}-propionic acid, Isomer 1;
3-{4-[3-methyl-1-(2,2',4'-trichloro-biphenyl-4-yloxy)-butyl]-benzoylamino}-propionic acid, isomer 2;
3-{4-[1-(2,6-dimethyl-4'-trifluoromethyl-biphenyl-4-yloxy)-4,4,4-trifluoro-butyl]-benzoylamino}-propionic acid, Isomer 1;
3-{4-[1-(2,6-dimethyl-4'-trifluoromethyl-biphenyl-4-yloxy)-4,4,4-trifluoro-butyl]-benzoylamino}-propionic acid, Isomer 2;
3-{4-[5,5,5-trifluoro-1-(4'-isopropyl-2,6-dimethyl-biphenyl-4-yloxy)-pentyl]-benzoylamino}-propionic acid, Isomer 1;
3-{4-[5,5,5-trifluoro-1-(4'-isopropyl-2,6-dimethyl-biphenyl-4-yloxy)-pentyl]-benzoylamino}-propionic acid, Isomer 2;
Racemic 3-{4-[5,5,5-trifluoro-1-(4'-isopropyl-2,6-dimethyl-biphenyl-4-yloxy)-pentyl]-benzoylamino}-propionic acid;
3-{4-[1-(2,6-dimethyl-4'-trifluoromethyl-biphenyl-4-yloxy)-5-methyl-hexyl]-benzoylamino}-propionic acid, Isomer 1;
3-{4-[1-(2,6-dimethyl-4'-trifluoromethyl-biphenyl-4-yloxy)-5-methyl-hexyl]-benzoylamino}-propionic acid, Isomer 2;
3-{4-[5-methyl-1-(4'-trifluoromethyl-biphenyl-4-yloxy)-hexyl]-benzoylamino}-propionic acid, Isomer 1;
3-{4-[5-methyl-1-(4'-trifluoromethyl-biphenyl-4-yloxy)-hexyl]-benzoylamino}-propionic acid, Isomer 2;
3-(4-{1-[6-(4-tert-butyl-phenyl)-pyridin-3-yloxy]-5-methyl-hexyl}-benzoylamino)-propionic acid, Isomer 1;
3-(4-{1-[6-(4-tert-butyl-phenyl)-pyridin-3-yloxy]-5-methyl-hexyl}-benzoylamino)-propionic acid, Isomer 2;
Racemic 3-(4-{5-methyl-1-[6-(4-trifluoromethyl-phenyl)-pyridin-3-yloxy]-hexyl}-benzoylamino)-propionic acid;
Racemic 3-{4-[1-(6-chloro-pyridin-3-yloxy)-5-methyl-hexyl]-benzoylamino}-propionic acid;
Racemic 3-{4-[1-(2,6-dimethyl-4'-trifluoromethyl-biphenyl-4-yloxy)-5-methyl-hexyl]-benzoylamino}-propionic acid;
Racemic 3-(4-{1-[6-(4-tert-butyl-phenyl)-pyridin-3-yloxy]-5-methyl-hexyl}-benzoylamino)-propionic acid;
Racemic 3-{4-[5-methyl-1-(4'-trifluoromethyl-biphenyl-4-yloxy)-hexyl]-benzoylamino}-propionic acid;
Racemic 3-{4-[1-(4'-tert-butyl-biphenyl-4-yloxy)-5-methyl-hexyl]-benzoylamino}-propionic acid;
3-(4-{1-[6-(4-tert-butyl-phenyl)-pyridin-3-yloxy]-5,5,5-trifluoro-pentyl}-benzoylamino)-propionic acid, Isomer 1;
3-(4-{1-[6-(4-tert-butyl-phenyl)-pyridin-3-yloxy]-5,5,5-trifluoro-pentyl}-benzoylamino)-propionic acid, Isomer 2;
3-(4-{1-[6-(4-tert-butyl-phenyl)-pyridin-3-yloxy]-4,4,4-trifluoro-butyl}-benzoylamino)-propionic acid, Isomer 1;
3-(4-{1-[6-(4-tert-butyl-phenyl)-pyridin-3-yloxy]-4,4,4-trifluoro-butyl}-benzoylamino)-propionic acid, Isomer 2;
Racemic 3-{4-[(4'-tert-butyl-2,6-dimethyl-biphenyl-4-yloxy)-cyclohexyl-methyl]-benzoylamino}-propionic acid;
3-{4-[4,4,4-trifluoro-1-(4'-trifluoromethyl-biphenyl-4-yloxy)-butyl]-benzoylamino}-propionic acid, Isomer 1;
3-{4-[4,4,4-trifluoro-1-(4'-trifluoromethyl-biphenyl-4-yloxy)-butyl]-benzoylamino}-propionic acid, Isomer 2;
Racemic 3-(4-{4,4,4-trifluoro-1-[6-(4-isopropyl-phenyl)-pyridin-3-yloxy]-butyl}-benzoylamino)-propionic acid;
Racemic 3-(4-{5,5,5-trifluoro-1-[6-(4-trifluoromethyl-phenyl)-pyridin-3-yloxy]-pentyl}-benzoylamino)-propionic acid;

Racemic 3-(4-{[6-(4-tert-butyl-phenyl)-pyridin-3-yloxy]-cyclohexyl-methyl}-benzoylamino)-propionic acid;

Racemic 3-(4-{5,5,5-trifluoro-1-[6-(4-isopropyl-phenyl)-pyridin-3-yloxy]-pentyl}-benzoylamino)-propionic acid;

Racemic 3-{4-[1-(2,6-dimethyl-4'-trifluoromethyl-biphenyl-4-yloxy)-4,4,4-trifluoro-butyl]-benzoylamino}-propionic acid;

Racemic 3-(4-{cyclohexyl-[6-(4-isopropyl-phenyl)-pyridin-3-yloxy]-methyl}-benzoylamino)-propionic acid;

Racemic 3-{4-[cyclohexyl-(4'-isopropyl-2,6-dimethyl-biphenyl-4-yloxy)-methyl]-benzoylamino}-propionic acid;

Racemic 3-{4-[4,4,4-trifluoro-1-(4'-isopropyl-2,6-dimethyl-biphenyl-4-yloxy)-butyl}-benzoylamino]-propionic acid;

3-{4-[cyclohexyl-(4'-trifluoromethyl-biphenyl-4-yloxy)-methyl]-benzoylamino}-propionic acid, Isomer 1;

3-{4-[cyclohexyl-(4'-trifluoromethyl-biphenyl-4-yloxy)-methyl]-benzoylamino}-propionic acid, Isomer 2;

3-{4-[5,5,5-trifluoro-1-(4'-isopropyl-biphenyl-4-yloxy)-pentyl}-benzoylamino]-propionic acid, Isomer 1;

3-{4-[5,5,5-trifluoro-1-(4'-isopropyl-biphenyl-4-yloxy)-pentyl}-benzoylamino]-propionic acid, Isomer 2;

Racemic 3-{4-[(4'-tert-butyl-biphenyl-4-yloxy)-cyclohexyl-methyl]-benzoylamino}-propionic acid;

Racemic 3-{4-[5,5,5-trifluoro-1-(2'-3'-fluoro-4'-trifluoromethyl-biphenyl-4-yloxy)-pentyl}-benzoylamino]-propionic acid;

Racemic 3-{4-[cyclohexyl-(4'-trifluoromethyl-biphenyl-4-yloxy)-methyl]-benzoylamino}-propionic acid;

Racemic 3-{4-[5,5,5-trifluoro-1-(4'-isopropyl-biphenyl-4-yloxy)-pentyl}-benzoylamino]-propionic acid;

Racemic 3-{4-[1-(4'-ethyl-biphenyl-4-yloxy)-5,5,5-trifluoro-pentyl}-benzoylamino]-propionic acid;

Racemic 3-{4-[5,5,5-trifluoro-1-(3'-fluoro-4'-trifluoromethyl-biphenyl-4-yloxy)-pentyl}-benzoylamino]-propionic acid;

Racemic 3-{4-[1-(2,4,6-triisopropyl-phenoxy)-5,5,5-trifluoro-pentyl}-benzoylamino]-propionic acid;

Racemic 3-{4-[1-(2,3,4,5,6-pentamethyl-phenoxy)-5,5,5-trifluoro-pentyl}-benzoylamino]-propionic acid;

Racemic 3-{4-[1-(2,4,6-tri-t-butyl-phenoxy)-5,5,5-trifluoro-pentyl]-benzoylamino}-propionic acid;

Racemic 3-{4-[1-(3,5-dimethyl-phenoxy)-5,5,5-trifluoro-pentyl]-benzoylamino}-propionic acid;

3-{4-[1-(4'-tert-butyl-2,6-dimethyl-biphenyl-4-yloxy)-5,5,5-trifluoro-pentyl]-benzoylamino}-propionic acid, Isomer 1;

3-{4-[1-(4'-tert-butyl-2,6-dimethyl-biphenyl-4-yloxy)-5,5,5-trifluoro-pentyl]-benzoylamino}-propionic acid, isomer 2;

Racemic 3-{4-[1-(4-ethyl-3,5-dimethyl-phenoxy)-5,5,5-trifluoro-pentyl]-benzoylamino}-propionic acid;

Racemic 3-{4-[1-(2,6-dimethyl-4'-trifluoromethyl-biphenyl-4-yloxy)-5,5,5-trifluoro-pentyl]-benzoylamino}-propionic acid;

Racemic 3-(4-{1-[4-(4-methyl-pentyloxy)-phenoxy]-heptyl}-benzoylamino)-propionic acid;

Racemic 3-{4-[1-(4-pentyloxy-phenoxy)-heptyl]-benzoylamino}-propionic acid;

3-{4-[5,5,5-trifluoro-1-(4'-trifluoromethyl-biphenyl-4-yloxy)-pentyl]-benzoylamino}-propionic acid, Isomer 1;

3-{4-[5,5,5-trifluoro-1-(4'-trifluoromethyl-biphenyl-4-yloxy)-pentyl]-benzoylamino}-propionic acid, Isomer 2;

Racemic 3-{4-[1-(4'-tert-butyl-2,6-dimethyl-biphenyl-4-yloxy)-5,5,5-trifluoro-pentyl]-benzoylamino}-propionic acid;

Racemic 3-{4-[1-(4-bromo-3,5-dimethyl-phenoxy)-5,5,5-trifluoro-pentyl]-benzoylamino}-propionic acid;

3-{4-[1-(4'-tert-butyl-biphenyl-4-yloxy)-5,5,5-trifluoro-pentyl]-benzoylamino}-propionic acid, Isomer 1;

3-{4-[1-(4'-tert-butyl-biphenyl-4-yloxy)-5,5,5-trifluoro-pentyl]-benzoylamino}-propionic acid, Isomer 2;

3-(4-{1-[6-(4-trifluoromethyl-phenyl)-pyridin-3-yloxy]-hexyl}-benzoylamino)-propionic acid, Isomer 1;

3-(4-{1-[6-(4-trifluoromethyl-phenyl)-pyridin-3-yloxy]-hexyl}-benzoylamino)-propionic acid, Isomer 2;

3-(4-{1-[6-(4-trifluoromethyl-phenyl)-pyridin-3-yloxy]-pentyl}-benzoylamino)-propionic acid, Isomer 1;

3-(4-{1-[6-(4-trifluoromethyl-phenyl)-pyridin-3-yloxy]-pentyl}-benzoylamino)-propionic acid, Isomer 2;

Racemic 3-{4-[5,5,5-trifluoro-1-(4'-trifluoromethyl-biphenyl-4-yloxy)-pentyl]-benzoylamino}-propionic acid;

Racemic 3-{4-[1-(4'-tert-butyl-biphenyl-4-yloxy)-5,5,5-trifluoro-pentyl]-benzoylamino}-propionic acid;

Racemic 3-{4-[1-(4-bromo-phenoxy)-5,5,5-trifluoro-pentyl]-benzoylamino}-propionic acid;

Racemic 3-{4-[1-(4-hydroxy-phenoxy)-heptyl]-benzoylamino}-propionic acid;

Racemic 3-(4-{1-[6-(4-trifluoromethyl-phenyl)-pyridin-3-yloxy]-pentyl}-benzoylamino)-propionic acid;

3-{4-[1-(2,6-Dimethyl-4'-trifluoromethyl-biphenyl-4-yloxy)-2-methyl-propyl]-benzoylamino}-propionic acid, isomer 1;

3-{4-[1-(2,6-Dimethyl-4'-trifluoromethyl-biphenyl-4-yloxy)-2-methyl-propyl]-benzoylamino}-propionic acid, isomer 1;

3-{4-[1-(2,6-Dimethyl-4'-trifluoromethoxy-biphenyl-4-yloxy)-heptyl]-benzoylamino}-propionic acid, isomer 1; and 3-{4-[1-(2,6-Dimethyl-4'-trifluoromethoxy-biphenyl-4-yloxy)-heptyl]-benzoylamino}-propionic acid, isomer 1, or a pharmaceutically acceptable salt thereof.

16. A pharmaceutical composition which comprises a compound or salt of claim 1 and a pharmaceutically acceptable carrier.

17. A compound of claim 1 of the formula

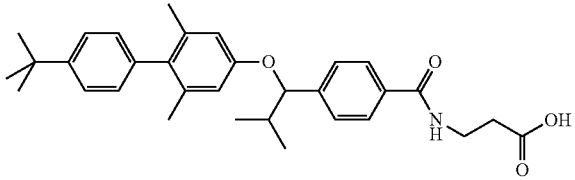 [SMILES: Cc1cc(OC(c2ccc(C(=O)NCCC(=O)O)cc2)C(C)C)cc(C)c1-c1ccc(C(C)(C)C)cc1]

or a pharmaceutically acceptable salt thereof.

18. A compound of claim 17 which is 3-{4-[1-(4'-tert-Butyl-2,6-dimethyl-biphenyl-4-yloxy)-2-methyl-propyl]-benzoylamino}-propionic acid, Isomer 1, or is 3-{4-[1-(4'-tert-Butyl-2,6-dimethyl-biphenyl-4-yloxy)-2-methyl-propyl]-benzoylamino}-propionic acid, Isomer 1, or a pharmaceutically acceptable salt thereof.

* * * * *